US009012186B2

(12) United States Patent
Cann et al.

(10) Patent No.: US 9,012,186 B2
(45) Date of Patent: Apr. 21, 2015

(54) HEMICELLULOSE-DEGRADING ENZYMES

(75) Inventors: Isaac K. O. Cann, Savoy, IL (US);
Shinichi Kiyonari, Urbana, IL (US);
Dylan Dodd, Champaign, IL (US);
Yejun Han, Urbana, IL (US); Roderick I. Mackie, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 487 days.

(21) Appl. No.: 13/266,762

(22) PCT Filed: Apr. 27, 2010

(86) PCT No.: PCT/US2010/032589
§ 371 (c)(1),
(2), (4) Date: Jan. 13, 2012

(87) PCT Pub. No.: WO2010/129287
PCT Pub. Date: Nov. 11, 2010

(65) Prior Publication Data
US 2012/0135474 A1   May 31, 2012

Related U.S. Application Data

(60) Provisional application No. 61/173,174, filed on Apr. 27, 2009, provisional application No. 61/245,619, filed on Sep. 24, 2009.

(51) Int. Cl.
| | | |
|---|---|---|
| *C12P 19/14* | (2006.01) | |
| *C12N 9/00* | (2006.01) | |
| *C12N 9/42* | (2006.01) | |
| *C12N 1/20* | (2006.01) | |
| *C12N 15/00* | (2006.01) | |
| *C07H 21/04* | (2006.01) | |

(52) U.S. Cl.
CPC ............... *C12N 9/2434* (2013.01); *C12P 19/14* (2013.01)

(58) Field of Classification Search
None
See application file for complete search history.

(56) References Cited

U.S. PATENT DOCUMENTS

| | | |
|---|---|---|
| 5,871,730 A | 2/1999 | Brzezinski et al. |
| 5,935,836 A | 8/1999 | Vehmaanpera et al. |
| 5,997,913 A | 12/1999 | Fowler et al. |
| 6,031,155 A | 2/2000 | Cameron-Mills et al. |
| 6,121,034 A | 9/2000 | Laroche et al. |
| 6,294,366 B1 | 9/2001 | Farrington et al. |
| 6,682,923 B1 | 1/2004 | Bentzien et al. |
| 2004/0053238 A1 | 3/2004 | Hseu et al. |
| 2004/0102619 A1 | 5/2004 | Dunn-Coleman et al. |
| 2005/0164355 A1 | 7/2005 | Vlasenko et al. |
| 2005/0210548 A1 | 9/2005 | Yaver et al. |
| 2006/0019301 A1 | 1/2006 | Hansen et al. |
| 2007/0154987 A1 | 7/2007 | Kita et al. |
| 2007/0214517 A1 | 9/2007 | Alexandrov et al. |
| 2007/0238155 A1 | 10/2007 | Gusakov et al. |
| 2008/0167214 A1 | 7/2008 | Teter et al. |
| 2008/0194005 A1 | 8/2008 | Emalfarb et al. |
| 2008/0268526 A1 | 10/2008 | Maiyuran et al. |
| 2008/0293109 A1 | 11/2008 | Berka et al. |
| 2008/0293115 A1 | 11/2008 | Taylor et al. |
| 2008/0299613 A1 | 12/2008 | Merino et al. |

FOREIGN PATENT DOCUMENTS

| | | |
|---|---|---|
| CA | 2129172 A1 | 1/1996 |
| CN | 1506461 A | 6/2004 |
| DE | 19531944 A1 | 2/1997 |
| EP | 1586652 A1 | 10/2005 |
| FR | 2786784 A1 | 6/2000 |
| JP | 11-313683 A | 11/1999 |
| JP | 2003-30331 A | 1/2003 |
| JP | 2003-61663 A | 3/2003 |
| JP | 2005-245303 A | 9/2005 |
| JP | 2007-259803 A | 10/2007 |
| JP | 2008-131168 A | 6/2008 |
| JP | 2008-167712 A | 7/2008 |
| JP | 2008-169119 A | 7/2008 |
| JP | 2008-199977 A | 9/2008 |
| KR | 20030015943 A | 2/2003 |
| KR | 20030046570 A | 6/2003 |
| KR | 20040033143 A | 4/2004 |
| RU | 2197526 C1 | 1/2003 |
| WO | 91/17244 A1 | 11/1991 |
| WO | 94/21785 A1 | 9/1994 |
| WO | 95/18219 A1 | 7/1995 |
| WO | 95/30009 A2 | 11/1995 |
| WO | 95/34662 A1 | 12/1995 |
| WO | 97/00962 A1 | 1/1997 |
| WO | 97/12991 A1 | 4/1997 |
| WO | 97/13853 A2 | 4/1997 |

(Continued)

OTHER PUBLICATIONS

Accession B3C594. Jul. 22, 2008.*
Chica et al. Curr Opin Biotechnol. Aug. 2005;16(4):378-84.*
Sen et al. Appl Biochem Biotechnol. Dec. 2007;143(3):212-23.*
Invitation to Pay Additional Fees and Partial Search Report received for PCT Patent Application No. PCT/US2010/032589, mailed on Jan. 20, 2011, 7 pages.
International Search Report and Written Opinion received for PCT Patent Application No. PCT/US2010/032589, mailed on Mar. 1, 2011, 13 pages.

(Continued)

*Primary Examiner* — Christian Fronda
(74) *Attorney, Agent, or Firm* — Morrison & Foerster LLP

(57) ABSTRACT

The present disclosure provides methods for the conversion of hemicellulose into fermentable sugars using enzymes isolated from *Prevotella bryantii*. Hemicellulose-degrading enzymes include an endoxylanase, a β-xylosidase, a bifunctional β-xylosidase and β-glucosidase, a bifunctional arabinofuranosidase and β-xylosidase, a glucuronidase, and an acetyl xylan esterase. The enzymes can be used to release sugars present in hemicellulose for subsequent fermentation to produce value-added products such as ethanol.

13 Claims, 23 Drawing Sheets

(56) References Cited

FOREIGN PATENT DOCUMENTS

| | | |
|---|---|---|
| WO | 97/27290 A1 | 7/1997 |
| WO | 97/27292 A1 | 7/1997 |
| WO | 97/27306 A1 | 7/1997 |
| WO | 97/43423 A2 | 11/1997 |
| WO | 97/44361 A1 | 11/1997 |
| WO | 00/14243 A1 | 3/2000 |
| WO | 00/68396 A2 | 11/2000 |
| WO | 01/42433 A2 | 6/2001 |
| WO | 01/79507 A2 | 10/2001 |
| WO | 02/24926 A1 | 3/2002 |
| WO | 02/38746 A2 | 5/2002 |
| WO | 02/083905 A1 | 10/2002 |
| WO | 02/095014 A2 | 11/2002 |
| WO | 03/052118 A2 | 6/2003 |
| WO | 03/106654 A2 | 12/2003 |
| WO | 2004/099228 A2 | 11/2004 |
| WO | 2004/113521 A1 | 12/2004 |
| WO | 2005/047499 A1 | 5/2005 |
| WO | 2005/059084 A1 | 6/2005 |
| WO | 2005/096804 A2 | 10/2005 |
| WO | 2005/100557 A1 | 10/2005 |
| WO | 2005/118769 A1 | 12/2005 |
| WO | 2006/012904 A1 | 2/2006 |
| WO | 2006/066582 A1 | 6/2006 |
| WO | 2006/067198 A2 | 6/2006 |
| WO | 2006/101584 A2 | 9/2006 |
| WO | 2006/104448 A1 | 10/2006 |
| WO | 2006/114095 A1 | 11/2006 |
| WO | 2006/117247 A1 | 11/2006 |
| WO | 2007/019859 A2 | 2/2007 |
| WO | 2007/067525 A2 | 6/2007 |
| WO | 2007/094852 A2 | 8/2007 |
| WO | 2007/095335 A2 | 8/2007 |
| WO | 2007/146944 A2 | 12/2007 |
| WO | 2008/045977 A2 | 4/2008 |
| WO | 2008/057637 A2 | 5/2008 |
| WO | 2008/068498 A2 | 6/2008 |
| WO | 2008/074884 A2 | 6/2008 |
| WO | 2008/080017 A1 | 7/2008 |
| WO | 2008/095033 A2 | 8/2008 |
| WO | 2008/140749 A2 | 11/2008 |
| WO | 2008/148131 A1 | 12/2008 |
| WO | 2008/151043 A1 | 12/2008 |
| WO | 2008/151079 A2 | 12/2008 |

OTHER PUBLICATIONS

International Preliminary Report on Patentability received for PCT Patent Application No. PCT/US2010/032589, mailed on Nov. 10, 2011, 7 pages.

Altschul et al., "Basic Local Alignment Search Tool", Journal of Molecular Biology, vol. 215, 1990, pp. 403-410.

Altschul et al., "Gapped BLAST and PSI-BLAST: A New Generation of Protein Database Search Programs", Nucleic Acids Research, vol. 25 No. 17, 1997, pp. 3389-3402.

Cann et al., "Molecular Cloning, Sequencing, and Expression of a Novel Multidomain Mannanase Gene from Thermoanaerobacterium polysaccharolyticum", Journal of Bacteriology, vol. 181, No. 5, 1999, pp. 1643-1651.

Corpet, Florence, "Multiple Sequence Alignment with Hierarchical Clustering", Nucleic Acids Research, vol. 16 No. 22, 1988, pp. 10881-10890.

Dodd et al., "Functional Diversity of Four Glycoside Hydrolase Family 3 Enzymes from the Rumen Bacterium *Prevotella bryantii* B14", Journal of Bacteriology, vol. 192, No. 9, 2010, pp. 2335-2345.

Dodd et al., "Transcriptomic Analyses of Xylan Degradation by Prevotella Ryantii and Insights into Energy Acquisition by Xylanolytic Bacteroidetes", Journal of Biological Chemistry, vol. 285, No. 39, 2010, pp. 30261-30273.

Fields et al., "Transcriptional Regulation of Beta-Glucanase Activity in the Ruminal Bacterium, *Prevotella bryantii* B14", Current Microbiology, vol. 50, No. 3, 2005, pp. 155-159.

Griswold et al., "Degradation of Protein and Utilization of the Hydrolytic Products by a Predominant Ruminal Bacterium, *Prevotella Ruminicola* B14", Journal of Dairy Science, vol. 80, 1997, pp. 167-175.

Karlin et al., "Applications and Statistics for Multiple High-Scoring Segments in Molecular Sequences", Proceedings of the National Academy of Sciences USA, vol. 90, Jun. 1993, pp. 5873-5877.

Karlin et al., "Methods for Assessing the Statistical Significance of Molecular Sequence Features by Using General Scoring Schemes", Proceedings of the National Academy of Sciences USA, vol. 87, Mar. 1990, pp. 2264-2268.

Miyazaki et al., "Degradation and Utilization Xylans by the Rumen Anaerobe *Prevotella bryantii*", Anaerobe, vol. 3, No. 6, Dec. 1997, pp. 373-381.

Morag et al., "Relationship of Cellulosomal and Noncellulosomal Xylanases of *Clostridium thermocellum* to Cellulose-Degrading Enzymes", Journal of Bacteriology, vol. 172, No. 10, Oct. 1990, pp. 6098-6105.

Myers et al., "Optimal Alignments in Linear Space", CABIOS, vol. 4, 1988, 13 pages.

Needleman et al., "A General Method Applicable to the Search for Similarities in the Amino Acid Sequence of Two Proteins", J. Mol. Biol., vol. 48, 1970, pp. 443-453.

Pearson et al., "Improved Tools for Biological Sequence Comparison", Proceedings of the National Academy of Sciences U.S.A., vol. 85, Apr. 1988, pp. 2444-2448.

Rigden et al., "The PA14 Domain, a Conserved All-β Domain in Bacterial Toxins, Enzymes, Adhesins and Signaling Molecules", TRENDS in Biochemical Sciences, vol. 29, No. 7, Jul. 2004, pp. 335-339.

Smith et al., "Comparison of Biosequences", Advances in Applied Mathematics, vol. 2, 1981, pp. 482-489.

* cited by examiner

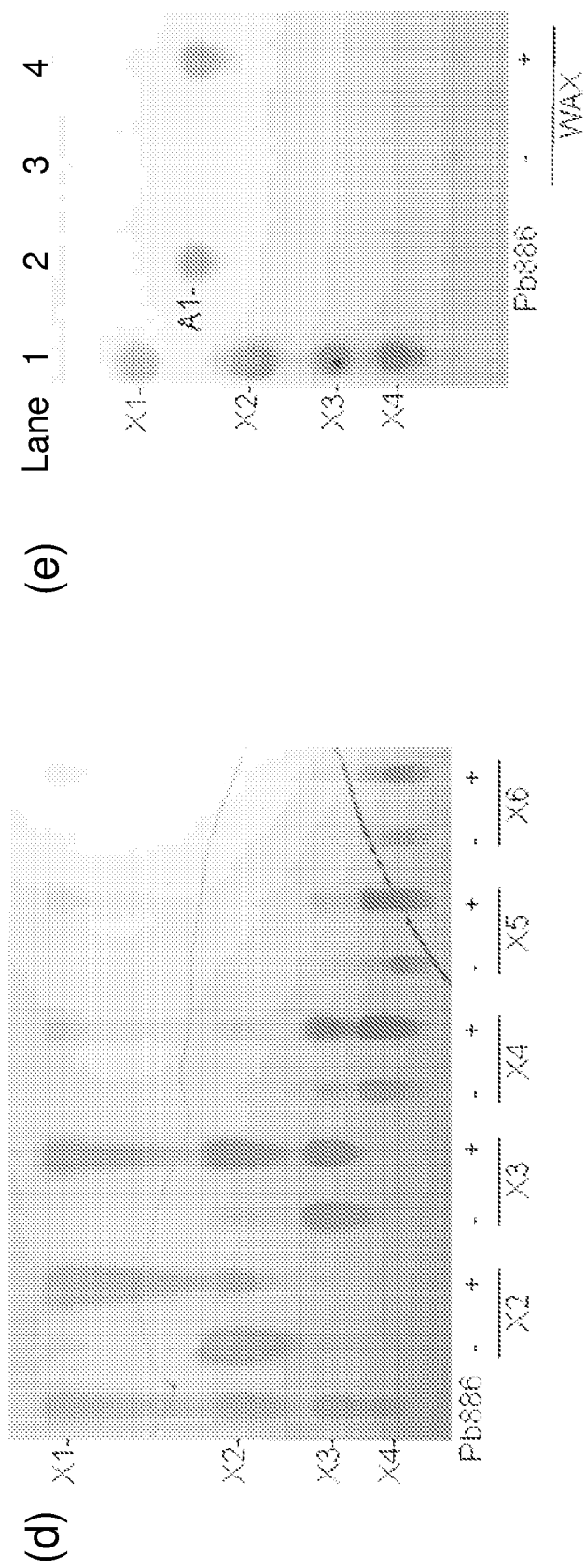
Figure 4, continued

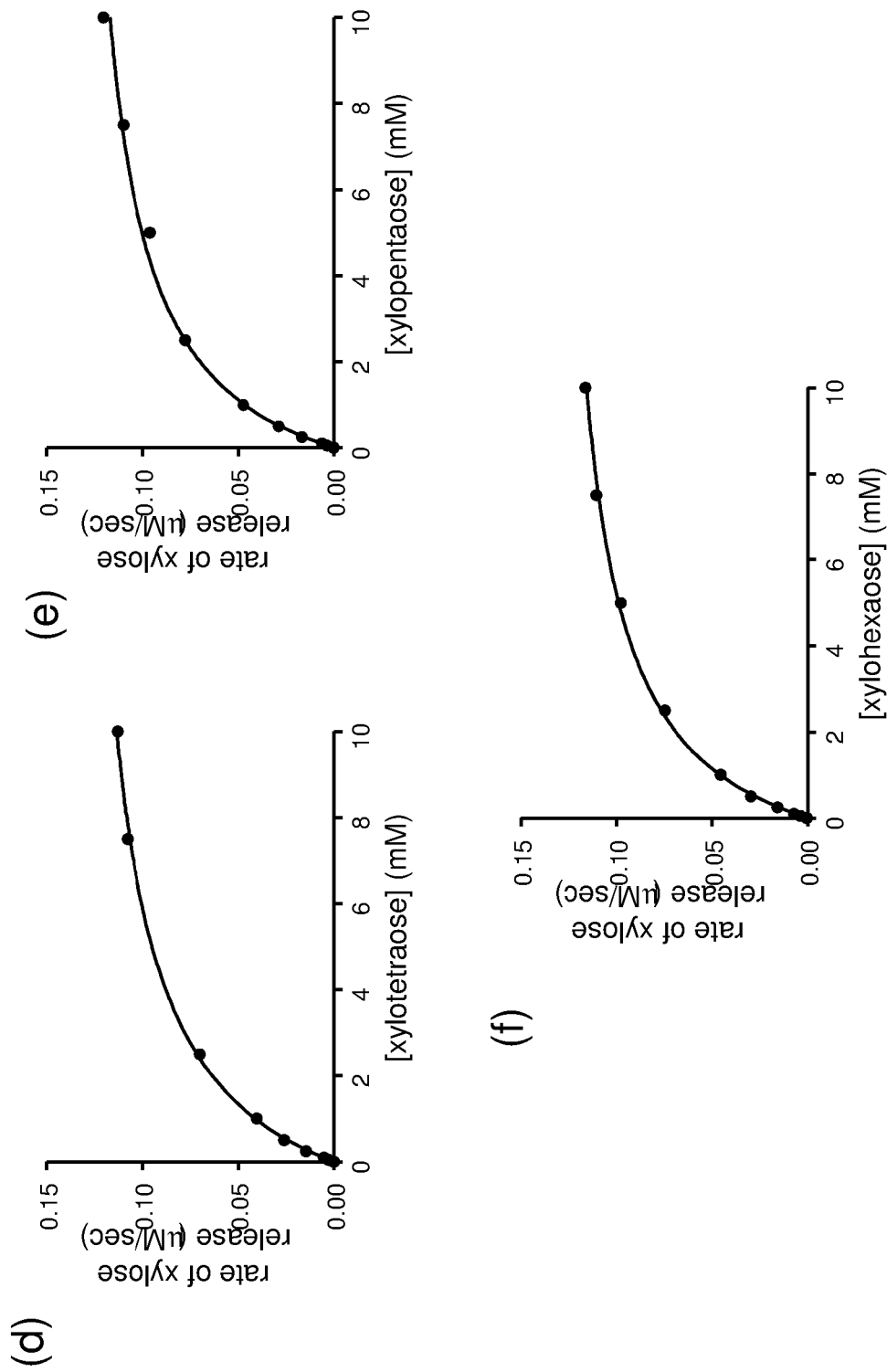

Figure 6, continued

Kinetic values for Pb911 hydrolysis of xylo-oligosaccharides

| | Pb911 WT | | |
|---|---|---|---|
| | $k_{cat}$ (s$^{-1}$) | $K_M$ (mM) | $k_{cat}/K_M$ (s$^{-1} \cdot$mM$^{-1}$) |
| Xylobiose | 16 ± 0.3 | 3.5 ± 0.1 | 4.6 ± 0.2 |
| Xylotriose | 17 ± 0.5 | 2.5 ± 0.2 | 6.8 ± 0.6 |
| Xylotetraose | 16 ± 0.2 | 2.4 ± 0.1 | 6.7 ± 0.3 |
| Xylopentaose | 16 ± 0.3 | 2.0 ± 0.1 | 8.0 ± 0.4 |
| Xylohexaose | 15 ± 0.2 | 2.0 ± 0.09 | 7.5 ± 0.4 |

(g)

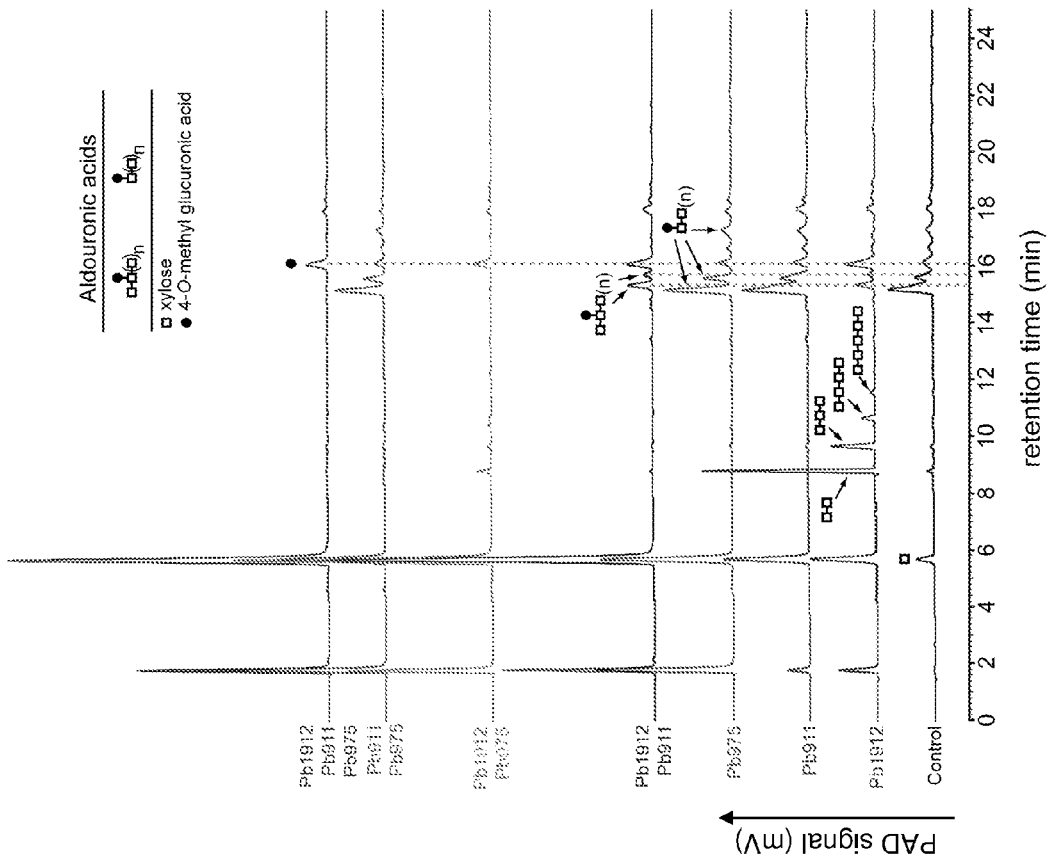
Figure 8, continued
(e)

(a)

| Substrate | $K_M$ ($\mu M$) | $k_{cat}$ ($s^{-1}$) |
|---|---|---|
| 1-Naphtyl acetate | 183.40 | 19.40 |
| 1-Naphtyl phosphate | 32.18 | 5.95 |
| 1-Naphtyl propionate | 25.48 | 2.32 |
| 1,2,3,4-tetra-acetyl-xylopyranose | 13.87 | 0.36 |

(b)

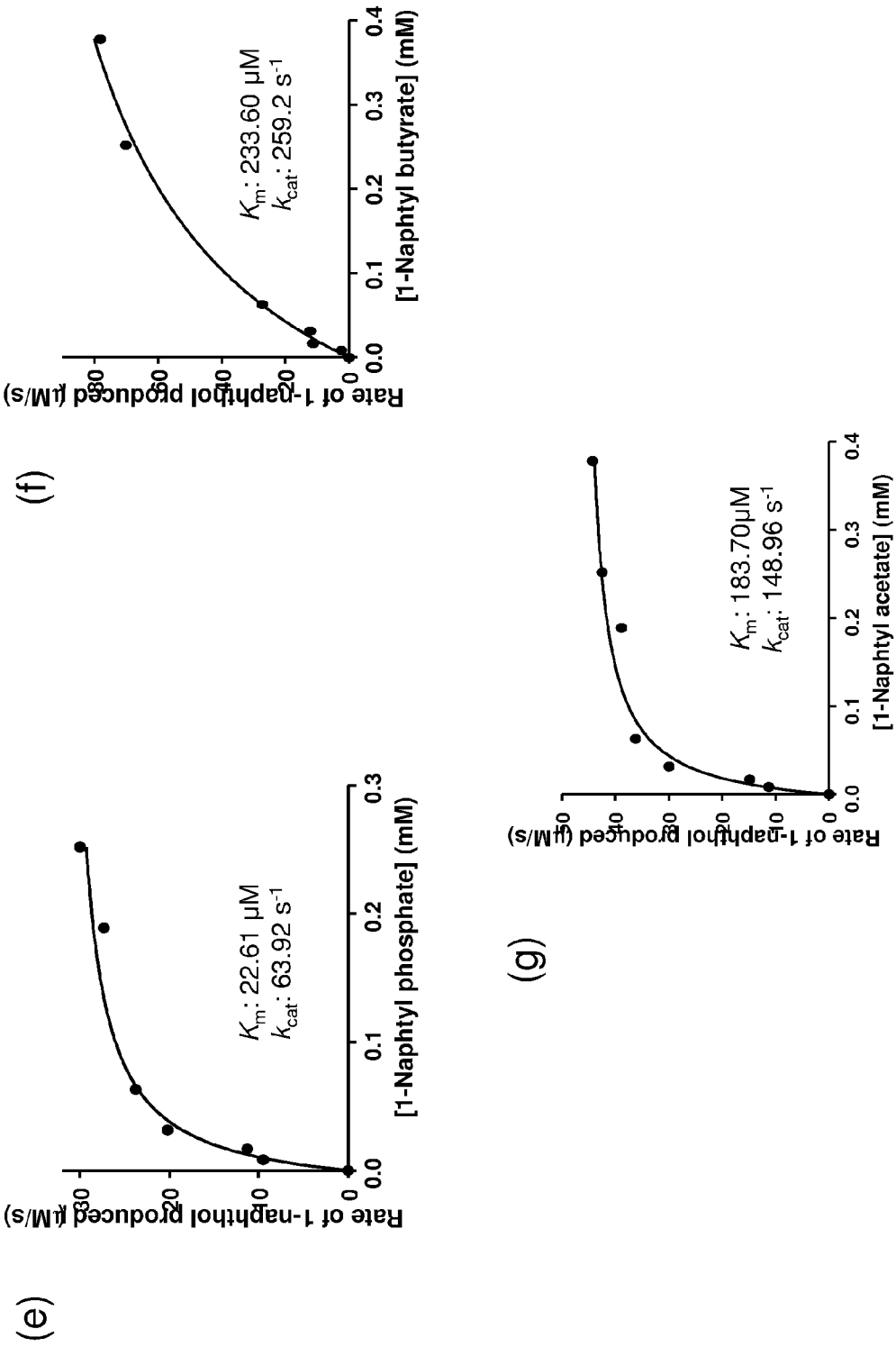
Figure 10, continued

HEMICELLULOSE-DEGRADING ENZYMES

CROSS-REFERENCE TO RELATED APPLICATIONS

This is a U.S. National Phase patent application of International Application No. PCT/US2010/032589, filed Apr. 27, 2010, which claims priority to U.S. Provisional Patent Application No. 61/173,174, filed Apr. 27, 2009, and U.S. Provisional Patent Application No. 61/245,619, filed Sep. 24, 2009, each of which is hereby incorporated by reference in the present disclosure in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 658012000300SEQLIST.txt, date recorded: Oct. 26, 2011, size: 313 KB).

FIELD

The present disclosure relates to methods for the degradation of hemicellulose using enzymes including an endoxylanase, a β-xylosidase, a bifunctional β-xylosidase and β-glucosidase, a bifunctional arabinofuranosidase and β-xylosidase, a glucuronidase, and an acetyl xylan esterase. Treatment of hemicellulose with one or more of the enzymes can lead to complete or near-complete degradation of the hemicellulose into its component sugars.

BACKGROUND

Microorganisms that are currently being used to ferment sugars to biofuels such as ethanol usually cannot utilize complex polysaccharides such as cellulose and hemicellulose. As a result, a significant bottleneck occurs in the conversion of lignocellulosic materials to biofuels. The cellulose component of plant matter may be hydrolyzed to glucose (a 6-carbon sugar) by a cellulase system, which usually comprises three important enzymes: an endoglucanase, an exoglucanase, and a beta-glucosidase. These enzymes, however, do not target the hemicellulose component of the plant material.

Hemicellulose is a complex polysaccharide that has a xylose-linked backbone, with side chains of arabinose, glucuronyl, and acetyl groups. A structural model of a hemicellulose illustrates the xylose backbone residues joined together in beta-1,4-linkages (FIG. 1a). Several functional groups decorate the backbone, including esters of acetyl (Ac) groups, arabinose, glucuronic acids, and esters of feroryl group. The feroryl groups link the entire structure to lignin.

Hemicellulose constitutes the second largest component of polysaccharides in perennial grasses, such as switchgrass and *Miscanthus*. Enzyme cocktails that hydrolyze hemicellulose into its major component sugars such as xylose (a 5-carbon sugar) and arabinose (a 5-carbon sugar) will significantly increase the fermentable sugars for biofuel production from lignocellulose-based feedstock. Enzymatic removal of hemicellulose by hemicellulases will also increase accessibility of cellulases to the cellulose component of plant cell walls or lignocellulosic feedstocks. Thus, the degradation of hemicellulose is a critical step in the utilization of lignocellulose feedstock for biofuel production.

Acid pretreatment is the current standard method for degrading hemicellulose prior to fermentation of its component sugars. This method, however, results in the production of toxic compounds that inhibit future fermentation. Thus, a significant need exists for improved pretreatment methods that can degrade hemicellulose without the production of toxic compounds.

BRIEF SUMMARY

Preferred embodiments of the invention meet this need by providing hemicellulose-degrading enzymes identified in *Prevotella bryantii*. Use of these enzymes provides a means by which the hemicellulose fraction of biomass can be degraded into fermentable sugars without the production of toxic compounds resulting from acid pretreatment. These enzymes can be utilized alone, in combination, or with other mixtures of enzymes. Methods for the degradation of hemicellulose are also provided herein.

Thus one aspect includes isolated nucleic acids including the nucleotide sequences of any of SEQ ID NOs: 1, 3, 5, 7, 9, 11, 13, 15, 17, 19, 21, 23, 25, 27, 29, 31, 33, 35, or 37. Another aspect includes vectors containing any of the preceding isolated nucleic acids. Yet another aspect includes isolated polypeptides including the amino acid sequences of any of SEQ ID NOs: 2, 4, 6, 8, 10, 12, 14, 16, 18, 20, 22, 24, 26, 28, 30, 32, 34, 36, or 38.

One aspect includes compositions containing the nucleotide sequence of SEQ ID NO: 1, and one or more nucleotide sequences selected from the group including SEQ ID NOs: 3, 5, 7, 9, 11, 13, and 15. Another aspect includes compositions containing the amino acid sequence of SEQ ID NO: 2, and one or more amino acid sequences selected from the group including SEQ ID NOs: 4, 6, 8, 10, 12, 14, and 16.

Another aspect includes methods for degrading hemicellulose including the steps of providing plant material containing hemicellulose, where the hemicellulose contains a xylose backbone containing β-1,4-linkages and one or more functional groups, and treating the hemicellulose with an enzyme selected from the group including enzymes corresponding to SEQ ID NOs: 4, 6, 8, 10, 12, 14, 16, 18, 20, 22, 24, 26, 28, 30, 32, 34, 36, and 38, where the treating cleaves the one or more functional groups from the xylose backbone to form cleaved hemicellulose. In certain embodiments, the method also includes the step of treating the cleaved hemicellulose with a second enzyme corresponding to SEQ ID NO: 2, where the second enzyme cleaves the β-1,4-linkages in the xylose backbone to produce xylose subunits, where the treating results in the degradation of at least 70% of the hemicellulose into functional groups and xylose subunits. In certain embodiments, degradation of the hemicellulose is at least 75%, 80%, 85%, 90%, 91%, 92%, 93%, 94%, 95%, 96%, 97%, 98%, 99%, or 100% complete. Completeness of degradation of hemicellulose refers to the conversion of a hemicellulose substrate to fermentable sugars. In preferred embodiments, the fermentable sugars are 5-carbon sugars. The 5-carbon sugars may be, for example, xylose or arabinose. In certain embodiments that may be combined with the preceding embodiments, the one or more functional groups are arabinose, glucuronyl, or acetyl. In certain embodiments that may be combined with the preceding embodiments, the plant material is *Miscanthus*, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, or energy cane. In certain embodiments that may be combined with the preceding embodiments, the treating is conducted at a pH between about 5 and about 6. In certain embodiments that may be combined with the preceding embodiments, the treating is conducted at a temperature between about 25 and about 40° C.

Another aspect includes methods for degrading hemicellulose, including the steps of providing plant material containing hemicellulose, where the hemicellulose contains a xylose backbone containing β-1,4-linkages and one or more functional groups, and contacting the hemicellulose with a transgenic *E. coli* or yeast that secretes an enzyme selected from the group including SEQ ID NOs: 2, 4, 6, 8, 10, 12, 14, and 16, where the contacting cleaves the one or more functional groups from the xylose backbone to form cleaved hemicellulose. In certain embodiments, the method also includes the step of contacting the cleaved hemicellulose with a second transgenic *E. coli* or yeast that secretes an enzyme corresponding to SEQ ID NO: 2, where the contacting cleaves the β-1,4-linkages in the xylose backbone to produce xylose subunits, where the contacting results in the degradation of at least 90% of the hemicellulose into functional groups and xylose subunits. In certain embodiments, degradation of the hemicellulose is at least 91%, 92%, 93%, 94%, 95%, 96%, 97%, 98%, 99%, or 100% complete.

DETAILED DESCRIPTION OF PREFERRED EMBODIMENTS

The present disclosure relates to hemicellulose-degrading enzymes and to methods of using these enzymes for the degradation of hemicellulose into sugars.

The hemicellulose-degrading enzymes of the present disclosure can be used alone, or in combination to degrade hemicellulose, i.e., convert hemicellulose into its structural components by cleavage of bonds, or linkages, between the component subunits present in hemicellulose. Bonds or linkages may include bonds between xylose subunits, or bonds between xylose and functional groups, or bonds between functional groups.

Hemicellulose treated with the methods of the present disclosure may be at least 70%, 75%, 80%, 85%, 90%, 91%, 92%, 93%, 94%, 95%, 96%, 97%, 98%, 99%, or 100% degraded. Degradation products may include xylose, arabinose, glucuronyl groups, and acetyl groups, in addition to other functional groups and hydrocarbons. The degradation products may find use as biofuels or other value-added compounds. For example, sugars released from the hemicellulose may be fermented for the production of ethanol.

Combinations of enzymes, i.e., an enzyme cocktail, can be tailored to the hemicellulose structure of a specific feedstock to increase the level of degradation. Initial analysis of the enzyme cocktails described herein suggests that the components have a long shelf life, an important characteristic in an industrial enzyme mix.

Figure 1:
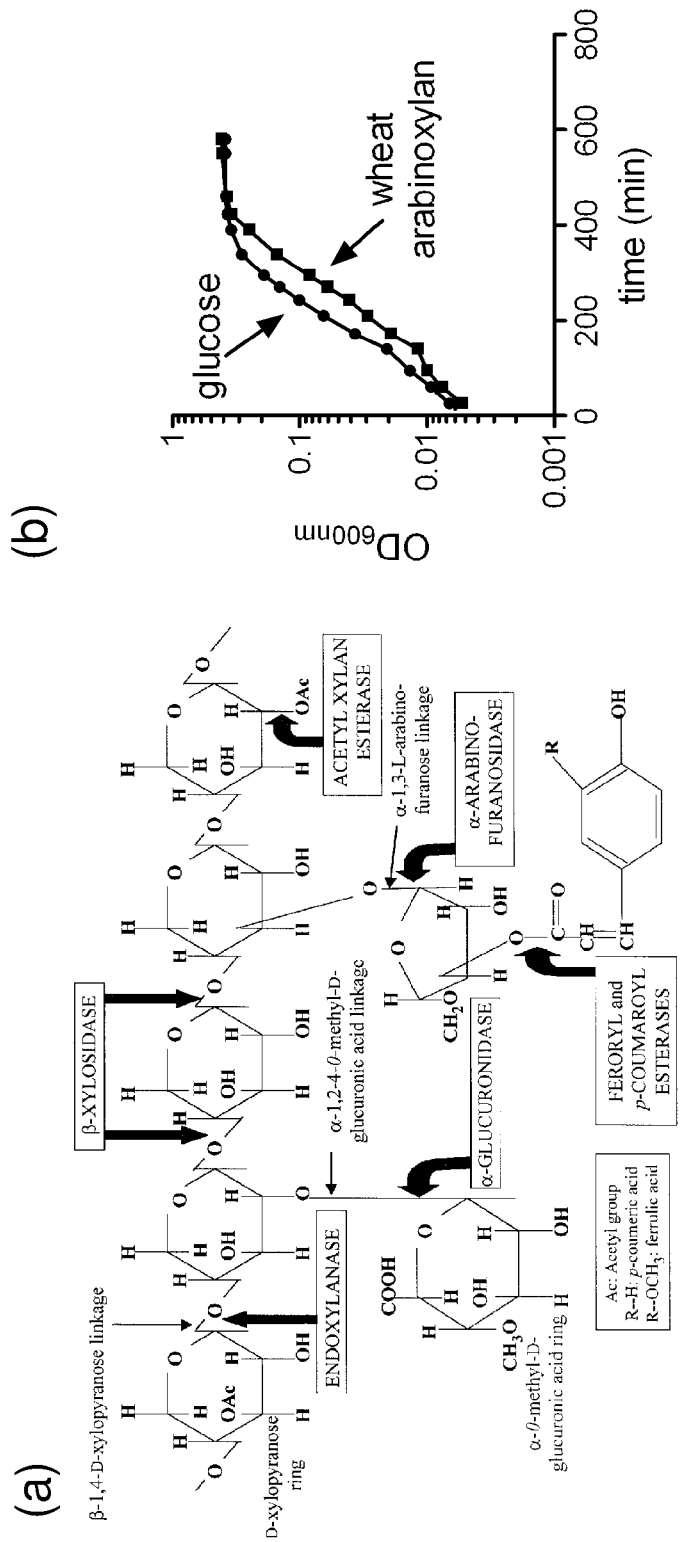
FIG. 1, part (a), shows a structural model of a hemicellulose. Part (b) shows that the rate of growth (gradient of curves) of *Prevotella bryantii* on wheat arabinoxylan is as rapid as its growth rate on glucose.

Without wishing to be bound by theory, another important feature of the enzyme cocktails described herein are that they are derived from the same organism, ensuring that the enzymes will function together to degrade hemicellulose. *Prevotella bryantii* contains a complete set of enzymes for degrading hemicellulose such as xylan. Xylan is the main hemicellulose in perennial grasses, such as switchgrass, and is most likely the main hemicellulose in the giant grass *Miscanthus. Prevotella bryantii* grows as rapidly on wheat arabinoxylan (hemicellulose) as on glucose (FIG. 1b).

The experiments described herein suggest that the bacterium has a set of enzymes that function synergistically to release components of the hemicellulose for fermentation and growth. Thus, this set of enzymes represents a group of enzymes that have evolved naturally in this organism to degrade hemicellulose and as such will be a better enzyme system than one that may be put together with components from different organisms.

The present disclosure provides nucleotide and amino acid sequences for enzymes that degrade hemicellulose, including Pb1893, Pb886 (alternatively named Pb2351), Pb911 (alternatively named Pb2369), Pb975 (alternatively named Pb2425), Pb1912, Pb1221, Pb0390 (alternatively named Pb1909), BACINT 0076, Pb398 (alternatively named Pb1917), Pb150, Pb1894, Pb1906, Pb1908, Pb1911, Pb2001, Pb2002, Pb2003, Pb2004, and Pb2350. Pb1893 functions as an endoxylanase. Pb886 is a bifunctional enzyme that functions as both an arabinofuranosidase and β-xylosidase. Pb911 functions as a β-xylosidase. Pb975 is a bifunctional enzyme that functions as both a β-xylosidase and β-glucosidase. Pb1912 functions as a glucuronidase. Pb1221 functions as an esterase. Pb0390 functions as an endoxylanase and can be used as a substitute for Pb1893. BACINT 0076 functions as an esterase and can be used as a substitute for Pb1221. Pb398 functions as a β-xylosidase. Pb150 functions as an endoxylanase. Pb1906 is predicted to function as an esterase and/or a β-xylosidase. Pb1908 is predicted to function as a β-xylosidase. Pb1911 is predicted to function as an esterase. Pb2001 is predicted to function as an α-glucosidase. Pb2002 is predicted to function as an endo-arabinase. Pb2003 is predicted to function as an α-L-arabinofuranosidase. Pb2004 is predicted to function as an α-xylosidase. Pb2350 is predicted to function as an α-L-arabinofuranosidase. Variants of the enzymes that retain partial or complete functional activity are also encompassed by the present disclosure. The enzymes disclosed herein can be used in various combinations.

Variants, Sequence Identity, and Sequence Similarity

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller (1988) CABIOS 4:11 17; the local homology algorithm of Smith et al. (1981) Adv. Appl. Math. 2:482; the homology alignment algorithm of Needleman and Wunsch (1970) J. Mol. Biol. 48:443 453; the search-for-similarity-method of Pearson and Lipman (1988) Proc. Natl. Acad. Sci. 85:2444 2448; the algorithm of Karlin and Altschul (1990) Proc. Natl. Acad. Sci. USA 872264, modified as in Karlin and Altschul (1993) Proc. Natl. Acad. Sci. USA 90:5873 5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237 244 (1988); Higgins et al. (1989) CABIOS 5:151 153; Corpet et al. (1988) Nucleic Acids Res. 16:10881 90; Huang et al. (1992) CABIOS 8:155 65; and Pearson et al. (1994) Meth. Mol. Biol. 24:307 331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

As used herein, sequence identity or identity in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical and often differ by conservative amino acid substitutions, where amino acid residues are substituted for other amino acid residues with similar chemical properties (e.g., charge or hydrophobicity), do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The functional activity of enzyme variants can be evaluated using standard molecular biology techniques including thin layer chromatography or a reducing sugar assay. Enzymatic activity can be determined using hemicellulose or an artificial substrate such a pNP.

Nucleotide Sequences Encoding Hemicellulose-Degrading Enzymes

The present disclosure provides nucleotide sequences encoding the hemicellulose-degrading enzymes Pb1893 (SEQ ID NO: 1), Pb886 (SEQ ID NO: 3), Pb911 (SEQ ID NO: 5), Pb975 (SEQ ID NO: 7), Pb1912 (SEQ ID NO: 9), Pb1221 (SEQ ID NO: 11), Pb0390 (SEQ ID NO: 13), and BACINT 0076 (SEQ ID NO: 15), Pb398 (SEQ ID NO: 17), Pb150 (SEQ ID NO: 19), Pb1894 (SEQ ID NO: 21), Pb1906 (SEQ ID NO: 23), Pb1908 (SEQ ID NO: 25), Pb1911 (SEQ ID NO: 27), PB2001 (SEQ ID NO: 29), PB2002 (SEQ ID NO: 31), Pb2003 (SEQ ID NO: 33), Pb2004 (SEQ ID NO: 35), Pb2350 (SEQ ID NO: 37), or subsequences thereof. The disclosure also provides for nucleotide sequences having at least about 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the nucleic acid sequences encoding Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350.

Nucleotide sequences of the present disclosure may encode one or more glycosyl hydrolase (GH) domains. Nucleotide sequence may also encode a carbohydrate binding module (CBM). The CBM module may interrupt a GH domain or be located in between two GH domains. In certain embodiments, the GH domain sequence is conserved in nucleotide variants.

The nucleic acids may be synthesized, isolated, or manipulated using standard molecular biology techniques such as those described in Sambrook, J. et al. 2000. Molecular Cloning: A Laboratory Manual (Third Edition). Techniques may include cloning, expression of cDNA libraries, and amplification of mRNA or genomic DNA.

The nucleic acids of the present disclosure, or subsequences thereof, may be incorporated into a cloning vehicle comprising an expression cassette or vector. The cloning vehicle can be a viral vector, a plasmid, a phage, a phagemid, a cosmid, a fosmid, a bacteriophage, or an artificial chromosome. The viral vector can comprise an adenovirus vector, a retroviral vector, or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The nucleic acids may be operably linked to a promoter. The promoter can be a viral, bacterial, mammalian or plant promoter. The promoter can be a constitutive promoter, an inducible promoter, a tissue-specific promoter, or an environmentally regulated or a developmentally regulated promoter.

The present disclosure further provides compositions including the isolated nucleotide sequence encoding Pb1893 alone or in combination with one or more of the isolated nucleotide sequences encoding Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. One composition includes the isolated nucleotide sequences encoding Pb1893 and Pb886. Another composition includes the isolated nucleotide sequences encoding Pb1893 and Pb911. Another composition includes the isolated nucleotide sequences encoding Pb1893 and Pb975. Another composition includes Pb1893 and Pb1912. Another composition includes Pb1893 and Pb1221. Another composition includes Pb1893 and Pb1912. Another composition includes Pb1893 and Pb0390. Another composition includes Pb1893 and BACINT 0076. Another composition includes Pb1893 and Pb398. Another composition includes Pb1893 and Pb150. Another composition includes Pb1893 and Pb1894. Another composition includes Pb1893 and Pb1906. Another composition includes Pb1893 and Pb1908. Another composition includes Pb1893 and Pb1911. Another composition includes Pb1893 and Pb2001. Another composition includes Pb1893 and Pb2002. Another composition includes Pb1893 and Pb2003. Another composition includes Pb1893 and Pb2004. Another composition includes Pb1893 and Pb2350.

Compositions may include vectors or transgenic host cells comprising the nucleotide sequence encoding Pb1893 alone or in combination with one or more of the isolated nucleotide sequences encoding Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350.

The present disclosure further provides for compositions including the isolated nucleotide sequence encoding Pb0390 alone or in combination with one or more of the isolated nucleotide sequences encoding Pb886, Pb911, Pb975, Pb1912, Pb1221, and BACINT 0076. One composition includes the isolated nucleotide sequences encoding Pb0390 and Pb886. Another composition includes the isolated nucleotide sequences encoding Pb0390 and Pb911. Another composition includes the isolated nucleotide sequences encoding Pb0390 and Pb975. Another composition includes Pb0390 and Pb1912. Another composition includes Pb0390 and Pb1221. Another composition includes Pb0390 and Pb1912. Another composition includes Pb0390 and BACINT 0076. Another composition includes Pb0390 and Pb398. Another composition includes Pb0390 and Pb150. Another composition includes Pb0390 and Pb1894. Another composition includes Pb0390 and Pb1906. Another composition includes Pb0390 and Pb1908. Another composition includes Pb0390 and Pb1911. Another composition includes Pb0390 and Pb2001. Another composition includes Pb0390 and Pb2002. Another composition includes Pb0390 and Pb2003. Another composition includes Pb0390 and Pb2004. Another composition includes Pb0390 and Pb2350.

The disclosure further provides for a transformed transgenic host cell comprising one or more of the nucleic acids encoding Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. The transformed cell can be, without limitation, a bacterial cell, a mammalian cell, a fungal cell, a yeast cell, an insect cell, or a plant cell. In certain embodiments, the transformed cell is E. coli.

Amino Acid Sequences Encoding Hemicellulose-Degrading Enzymes

The disclosure also provides for the amino acid sequences encoding the hemicellulose-degrading enzymes Pb1893 (SEQ ID NO: 2), Pb886 (SEQ ID NO: 4), Pb911 (SEQ ID NO: 6), Pb975 (SEQ ID NO: 8), Pb1912 (SEQ ID NO: 10), Pb1221 (SEQ ID NO: 12), Pb0390 (SEQ ID NO: 14), BACINT 0076 (SEQ ID NO: 16), Pb1917 (SEQ ID NO: 18), Pb150 (SEQ ID NO: 20), Pb1894 (SEQ ID NO: 22), Pb1906 (SEQ ID NO: 24), Pb1908 (SEQ ID NO: 26), Pb1911 (SEQ ID NO: 28), Pb2001 (SEQ ID NO: 30), Pb2002 (SEQ ID NO: 32), Pb2003 (SEQ ID NO: 34), Pb2004 (SEQ ID NO: 36), and Pb2350 (SEQ ID NO: 38), or subsequences thereof. The disclosure further provides for an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity/sequence similarity to Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350.

Amino acid sequences of the present disclosure may contain one or more glycosyl hydrolase (GH) domains. Amino acid sequences may also contain a carbohydrate binding module (CBM). The CBM module may interrupt a GH domain or be located in between two GH domains. In certain embodiments, the GH domain is conserved in polypeptide variants.

The polypeptides can be expressed in and purified from their native host, Prevotella bryantii. Polypeptides may also be expressed in and purified from transgenic expression systems. Transgenic expression systems can be prokaryotic or eukaryotic. Transgenic host cells may include yeast and E. coli. Transgenic host cells may secrete the polypeptide out of the host cell.

In certain embodiments, the isolated or recombinant polypeptide lacks a signal sequence. In other embodiments, the isolated or recombinant polypeptide is thermostable. In certain embodiments, the isolated or recombinant polypeptide is stable at about 25 to 40° C.

The present disclosure provides for compositions including the amino acid sequence encoding Pb1893 alone or in combination with one or more of the amino acid sequences encoding Pb886, Pb911, Pb975, Pb1912, Pb1221, Pb0390, and BACINT 0076. One composition includes the amino acid sequences encoding Pb1893 and Pb886. Another composition includes the amino acid sequences encoding Pb1893 and Pb911. Another composition includes the amino acid sequences encoding Pb1893 and Pb975. Another composition includes the amino acid sequences encoding Pb1893 and Pb1912. Another composition includes the amino acid sequences encoding Pb1893 and Pb1221. Another composition includes the amino acid sequences encoding Pb1893 and Pb0390. Another composition includes the amino acid sequences encoding Pb1893 and BACINT 0076. Another composition includes the amino acid sequences encoding Pb1893 and Pb398. Another composition includes the amino acid sequences encoding Pb1893 and Pb150. Another composition includes the amino acid sequences encoding Pb1893 and Pb1894. Another composition includes the amino acid sequences encoding Pb1893 and Pb1906. Another composition includes the amino acid sequences encoding Pb1893 and Pb1908. Another composition includes the amino acid sequences encoding Pb1893 and Pb1911. Another composition includes the amino acid sequences encoding Pb1893 and Pb2001. Another composition includes the amino acid sequences encoding Pb1893 and Pb2002. Another composition includes the amino acid sequences encoding Pb1893 and Pb2003. Another composition includes the amino acid sequences encoding Pb1893 and Pb2004. Another composition includes the amino acid sequences encoding Pb1893 and Pb2350.

The present disclosure also provides compositions including the amino acid sequence encoding Pb0390 alone or in combination with one or more of the amino acid sequences encoding Pb886, Pb911, Pb975, Pb1912, Pb1221, and BACINT 0076. One composition includes the amino acid sequences encoding Pb0390 and Pb886. Another composition includes the amino acid sequences encoding Pb0390 and Pb911. Another composition includes the amino acid sequences encoding Pb0390 and Pb975. Another composition includes the amino acid sequences encoding Pb0390 and Pb1912. Another composition includes the amino acid sequences encoding Pb0390 and Pb1221. Another composition includes the amino acid sequences encoding Pb0390 and BACINT 0076. Another composition includes the amino acid sequences encoding Pb0390 and Pb398. Another composition includes the amino acid sequences encoding Pb0390 and Pb150. Another composition includes the amino acid sequences encoding Pb0390 and Pb1894. Another composition includes the amino acid sequences encoding Pb0390 and Pb1906. Another composition includes the amino acid sequences encoding Pb0390 and Pb1908. Another composition includes the amino acid sequences encoding Pb0390 and Pb1911. Another composition includes the amino acid sequences encoding Pb0390 and Pb2001. Another composition includes the amino acid sequences encoding Pb0390 and Pb2002. Another composition includes the amino acid sequences encoding Pb0390 and Pb2003. Another composition includes the amino acid sequences encoding Pb0390 and Pb2004. Another composition includes the amino acid sequences encoding Pb0390 and Pb2350.

Compositions may include a transgenic host cell comprising one or more of the amino acid sequences encoding Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. The one or more polypeptides may be secreted from the transgenic host cell.

Compositions comprising a solution of polypeptides are also provided. Compositions comprising lyophilized polypeptides are provided. Compositions may be stable and suitable for storage over long periods of time. In certain embodiments, the compositions are stable for six months to one year. In other embodiments, the compositions are stable for longer than one year.

Treatment Methods

The above-described enzymes and variants can be used alone or in combination to degrade hemicellulose by cleaving one or more functional groups from the xylose backbone to form cleaved hemicellulose.

Hemicellulose treated with the methods of the present disclosure may be at least 91%, 92%, 93%, 94%, 95%, 96%, 97%, 98%, 99%, or 100% degraded. The hemicellulose substrate is degraded when the enzymes cleave the bonds or linkages present between the subunits present in the hemicellulose. Degradation products may comprise xylose, arabinose, glucuronyl groups, acetyl groups, in addition to other functional groups and hydrocarbons.

In one aspect, plant material containing hemicellulose, or isolated hemicellulose, is treated with one or more of the above-described enzymes, such as Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. Pb0390 may be used as a substitute for Pb1893. In one embodiment, hemicellulose is treated with Pb1893 in combination with one or more enzymes including Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. BACINT 0076 may be used as a substitute for Pb1221.

Without wishing to be bound by theory, Applicants believe that the methods of the present disclosure degrade hemicellulose via the following mechanisms. Treatment of hemicellulose with Pb1893 or a variant cleaves β-1,4-xylose linkages in the xylose backbone. Treatment of hemicellulose with Pb886 or a variant cleaves arabinofuranose linkages and β-1,4-xylose linkages. Treatment of hemicellulose with Pb911 or a variant cleaves β-1,4-xylose linkages. Treatment of hemicellulose with Pb975 or a variant cleaves β-1,4-xylose linkages. Treatment of hemicellulose with Pb1912 or a variant cleaves glucuronic acid linkages. Treatment of hemicellulose with Pb1221 or a variant cleaves ester linkages. Treatment of hemicellulose with Pb0390 or a variant cleaves β-1,4-xylose linkages in the xylose backbone. Treatment of hemicellulose with BACINT 0076 or a variant cleaves ester linkages. Treatment of hemicellulose with Pb398 cleaves β-1,4-xylose linkages. Using a combination or two or more enzymes is believed to provide synergistic hemicellulose degradation activity.

In certain embodiments, plant material containing hemicellulose, or isolated hemicellulose, may be treated with one or more isolated or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity/sequence similarity to Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350.

The polypeptides may be administered directly, either alone, or as a composition.

In other methods of the present disclosure, hemicellulose is degraded by contact with a transgenic host cell secreting one or more polypeptides including Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350. The transgenic host cell may be *E. coli* or yeast. The transgenic host cell may contain a vector encoding Pb1893, Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, Pb2350, or variants thereof. In some embodiments, the hemicellulose is degraded by treating with Pb1893 or a variant alone, or in combination with one or more of Pb886, Pb911, Pb975, Pb1912, Pb1221, Pb0390, BACINT 0076, Pb398, Pb150, Pb1894, Pb1906, Pb1908, Pb1911, Pb2001, Pb2002, Pb2003, Pb2004, and Pb2350, and variants thereof.

The methods of the present disclosure can be practiced with any plant material that contains hemicellulose. Plant material suitable for use with the currently disclosed methods include *Miscanthus*, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, and energy cane. The methods may also be practiced on isolated hemicellulose.

In certain embodiments, enzymes are provided at a concentration of at least 0.5 μM per enzyme for every 15 mg of substrate. In certain embodiments, the substrate consists of 15 mg of hemicellulose.

The methods of the present disclosure can be practiced at any pH and temperature at which hemicellulose can be degraded; however, in certain embodiments, the methods of the present disclosure are practiced in a pH range of about 5 to about 6 and at or between a temperature between about 25 and about 40° C.

Applications

The methods described herein can be practiced in combination with other methods useful for converting lignocellulosic materials into biofuels.

For example, plant material may be subjected to pretreatment including ammonia fiber expansion (AFEX), steam explosion, treatment with alkaline aqueous solutions, acidic solutions, organic solvents, ionic liquids (IL), electrolyzed water, phosphoric acid, and combinations thereof. Pretreatments that remove lignin from the plant material may increase the overall amount of sugar released from the hemicellulose.

In certain embodiments, where a cellulase mixture is being used to release glucose from plant cell walls, the enzyme cocktail may be used to hydrolyze the hemicellulosic component of the plant material and increase accessibility of the cellulase cocktail to the cellulose fraction of the plant material.

Typically, the compositions and methods of the invention are used to generate biofuels or specialty chemicals. The compositions and methods of the invention are used to degrade hemicellulose into fermentable sugars. The fermentable sugars are then converted into biofuel components, such as ethanol, propanol, and butanol, or specialty chemicals, such as ketones and aldehydes. The fermentable sugars may be converted by a microorganism, such as yeast, or by isolated enzymes.

The methods described herein can be practiced in combination with cellulases. Additional methods are provided for the use of the polypeptides and compositions as feed additives for monogastric animal agriculture, including pigs and poultry production.

EXAMPLES

The following Examples are merely illustrative and are not meant to limit any aspects of the present disclosure in any way. Hemicellulose-degrading enzymes from the rumen bacteria *Prevotella bryantii* were purified and characterized for hemicellulose degradation activity. The amino acid and nucleotide sequences for the identified enzymes are provided. Enzyme activity for each enzyme was determined by thin layer chromatography (TLC) or reducing sugar assays.

SUMMARY OF EXAMPLES

Example 1: Endoxylanases Pb1893 and Pb0390/Pb1909
Example 2: Arabinofuranosidase/β-xylosidase Pb886/Pb2351
Example 3: β-xylosidase/β-glucosidase Pb911
Example 4: Glucuronidase Pb1912
Example 5: β-xylosidase/β-glucosidase Pb975
Example 6: Acetyl Xylan Esterases Pb1221 and BACINT 0076
Example 7: Synergistic Activity of Hemicellulase Enzyme Cocktail
Example 8: β-xylosidase Pb398/Pb1917
Example 9: Sequence Alignments Example 10: Transcriptional Analysis of *P. bryantii* Grown on Polysaccharide and Monosaccharide Substrates Example 11: Improvement of Hemicellulase Enzyme Cocktail Example 1

Endoxylanase Pb1893 (SEQ ID NOs: 1 & 2)

Figure 2:
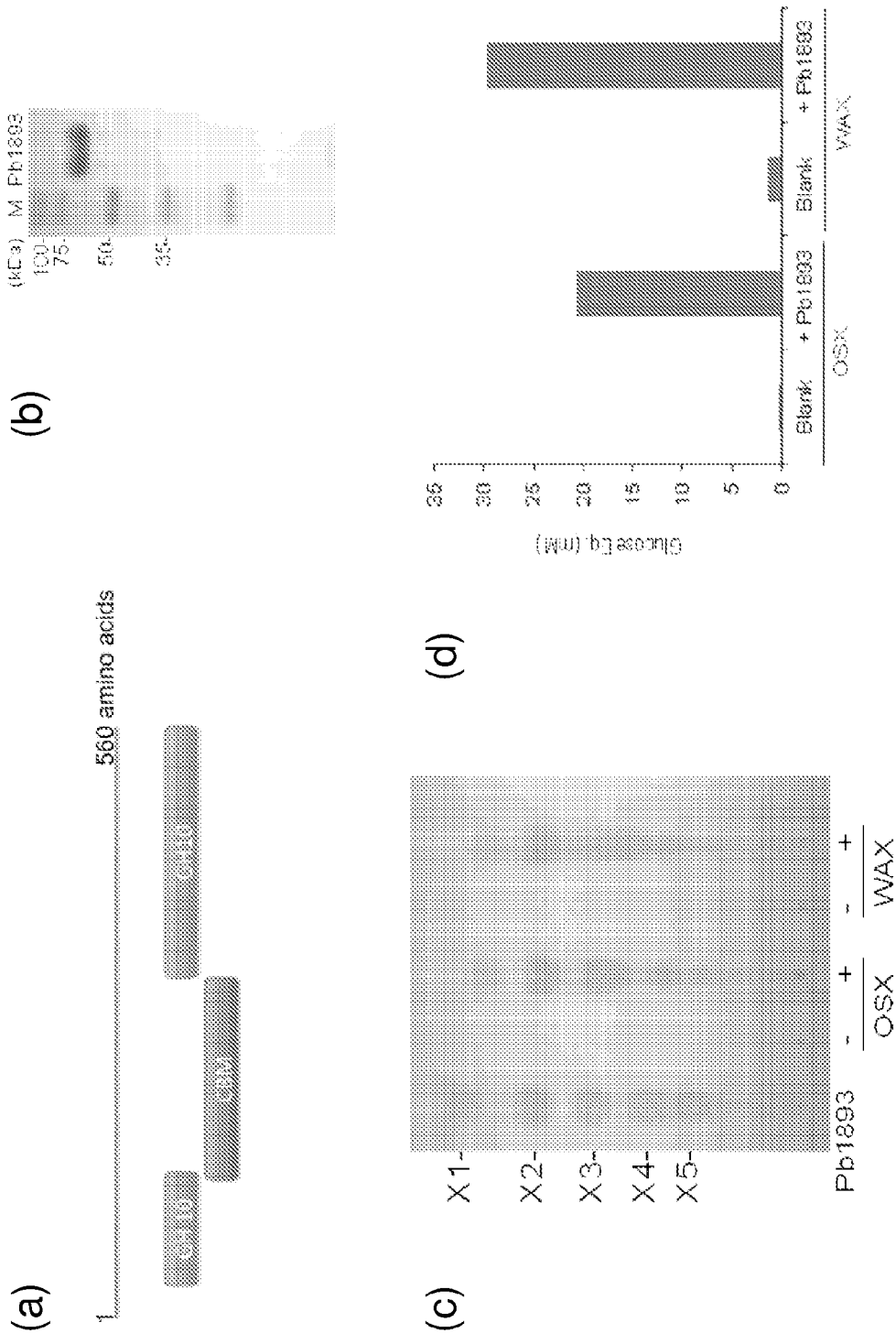
FIG. 2 shows the protein expression and activity of Pb1893. Part (a) shows the domain architecture of Pb1893, part (b) shows SDS-PAGE of purified Pb1893 from *Prevotella bryantii*, part (c) shows thin layer chromatography (TLC) analysis of Pb1893 activity, and part (d) shows reducing sugar assays of Pb1893.

An endoxylanase, Pb1893, was identified in *Prevotella bryantii*. The enzyme is the gene product of Pb1893, where Pb stands for *P. bryantii*. The endoxylanase cleaves the xylose backbone of hemicellulose at random to generate shorter chains of xylose in β-1,4-linkages. These xylo-oligosaccharides can range from containing two or more sugar subunits. The Pb1893 protein is 561 amino acids long and has a molecular weight of 62.3 kDa (His-tag+truncated Pb1893 protein). The protein has a unique architecture due to a putative carbohydrate binding module (CBM) inserted within the Glycoside Hydrolase (GH) family 10 catalytic domain (FIG. 2a).

Cloning of Pb1893

The gene for Pb1893 was amplified from *Prevotella bryantii* B14 genomic DNA by PCR using PrimeSTAR HS DNA polymerase (TaKaRa). The Pb1893 gene was amplified using the following primer set:

```
Pb1893ForNdeI
                                        (SEQ ID NO: 39)
5'-CATATGGACCAGGATATTCCTGGTTTCACAACGGATGAGC-3'

Pb1893RevXhoI
                                        (SEQ ID NO: 40)
5'-CTCGAGTTACTCCTGTTTCAAACCTTCACAGAAGCCTAC-3'
```

The polymerase chain reaction mixture contained the following:

| PCR reaction | |
|---|---|
| 2.5 U/mL PrimeSTAR DNA polymerase | 0.5 |
| 19 ng/mL *P. bryantii* gDNA | 1 |
| 10 mM Fw Primer | 1 |
| 10 mM Rv Primer | 1 |
| 2.5 mM dNTP Mixture | 4 |
| 5× PrimeSTAR Buffer | 10 |
| dH$_2$O | 32.5 |
| Total | 50 mL |

To amplify the gene from the genomic DNA, the following PCR cycling was used:

| PCR protocol | | | |
|---|---|---|---|
| Denaturing | 98° C. | 10 sec | 30 cycles |
| Annealing | 55° C. | 5 sec | |
| Elongation | 72° C. | 90 sec | |
| Last | 4° C. | ∞ | |

After the PCR reaction described above, the amplification of Pb1893 gene was confirmed by 1% agarose gel electrophoresis. GoTaq DNA polymerase (Promega) was then added to the reaction mixture to add adenine bases to the 3' terminus of the amplified gene product to facilitate cloning into a TA cloning vector. The reaction for addition of the nucleotide was as follows:

| Reaction | | Incubation | |
|---|---|---|---|
| 5 U/mL GoTaq DNA polymerase | 1 | 72° C. | 15 min |
| Reaction Mixture | 49 | | |
| Total | 50 mL | | |

After the reaction, the following ligation reaction was carried out to clone the amplified Pb1893 gene into the pGEM-T Easy vector (Promega):

| Ligation | | Incubation | |
|---|---|---|---|
| 3 U/mL T4 DNA ligase | 1 | 4° C. | O/N |
| Reaction Mixture | 3 | | |
| 2× Rapid Ligation Buffer | 5 | | |
| pGEM-T Easy vector | 1 | | |
| Total | 10 mL | | |

The ligation mixtures for Pb1893-pGEM-T Easy were introduced into *E. coli* JM109 by heat shock method, and the cells were plated on LB-ampicillin-X-gal-IPTG. After overnight incubation at 37° C., two white colonies were selected and used to inoculate 3 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene had been inserted into the plasmid, the genes were sequenced to confirm their identity. In order to abolish the NdeI site in the wild-type Pb1893 gene, one nucleotide substitution was introduced (CATATG->CATACG) into the gene in the pGEM-T Easy plasmid by PCR-mediated mutagenesis using the following primer set and the reaction mixture below:

```
Pb1893mtFor
                                        (SEQ ID NO: 41)
5'-GACGAAATCAATTCATACGGTACGTTGAAG-3'

Pb1893mtRev
                                        (SEQ ID NO: 42)
5'-CTTCAACGTACCGTATGAATTGATTTCGTC-3'
```

| PCR Reaction | |
|---|---|
| 2.5 U/mL PrimeSTAR DNA polymerase | 0.5 |
| 10 ng/mL Pb1893-pGEM-T Easy | 3 |
| 10 mM Fw Primer | 1 |
| 10 mM Rv Primer | 1 |
| 2.5 mM dNTP Mixture | 4 |
| 5× PrimeSTAR Buffer | 10 |
| dH$_2$O | 30.5 |
| Total | 50 mL |

The PCR cycling that introduced the mutation into the gene for Pb1893 was as follows. The mutation was designed to abolish a restriction site, but maintain the amino acid at that position in the polypeptide.

| PCR Protocol | | | |
|---|---|---|---|
| Denature | 98° C. | 10 sec | 16 Cycles |
| Anneal | 53° C. | 5 sec | |

-continued

| PCR Protocol | | |
|---|---|---|
| Elongate | 72° C. | 4 min 35 sec |
| Last | 4° C. | ∞ |

After the PCR reaction described above, the amplification of Pb1893-pGEM-T Easy was confirmed by 1% agarose gel electrophoresis. The restriction enzyme DpnI (NEB) was then added to the reaction mixture to degrade the parental plasmid DNA, which harbored the original gene containing the targeted restriction site (NdeI). The reaction was as follows:

| Reaction | | Incubation | |
|---|---|---|---|
| 20 U/mL DpnI | 1 | 37° C. | 3 hour |
| Reaction Mixture | 49 | | |
| Total | 50 mL | | |

The DpnI-treated Pb1893-pGEM-T Easy was introduced into *E. coli* JM109 by the heat shock method, and the cells were plated on LB-ampicillin. After overnight incubation at 37° C., six colonies were selected and used to inoculate 3 mL cultures of LB-ampicillin. The cultures were grown at 37° C. with vigorous aeration for 16 hours, and minipreps were made of the cell cultures to extract plasmids. The plasmids were then electrophoresed on a 1% agarose gel to check the size of plasmid DNA. Next, the gene was sequenced to ensure that the mutagenesis was successful and that the NdeI site was abolished. The cloned gene was excised by NdeI-XhoI and separated by 1% agarose gel. The reaction to cleave the gene out of the plasmid (pGEMT vector) was as follows:

| Digestion | | Incubation | |
|---|---|---|---|
| pDNA (total 2300 ng) | 16 | 37° C. | 3 hour |
| 10× NEBuffer 4 | 2 | | |
| 20 U/mL NdeI | 1 | | |
| 20 U/mL XhoI | 1 | | |
| Total | 20 mL | | |

After the digestion to remove the gene out of the PGEM-T vector, the gene was purified from an agarose gel by a gel extraction kit (QIAGEN) and inserted by DNA ligation into the corresponding sites of pET28a harboring an ampicillin resistance gene (Novagen). The ligation reaction was as follows:

| Ligation | | Incubation | |
|---|---|---|---|
| 2000 U/mL T4 DNA ligase (NEB) | 1 | 16° C. | O/N |
| 17 ng/mL digested gene fragment | 1.6 | | |
| 23 ng/mL digested pET28a vector | 1.3 | | |
| 10× T4 DNA Ligase Buffer (NEB) | 2 | | |
| dH$_2$O | 14.1 | | |
| Total | 20 mL | | |

The ligation mixtures for Pb1893-pET28a were introduced into *E. coli* JM109 by heat shock method and the cells were plated on LB-ampicillin. After overnight incubation at 37° C., four colonies were selected and used to inoculate, individually, 10 mL of LB-ampicillin. The cultures were grown at 37° C. with vigorous aeration for 16 hours, and minipreps were made of the cell cultures. The plasmids were then electrophoresed on a 1% agarose gel to check the size of the plasmid DNA. For gene expression, one of the plasmids was transformed into *E. coli* BL21 codon plus DE3 RIL by the heat shock method and plated on LB plates supplemented with chloramphenicol and ampicillin at 100 μg/ml and 50 μg/ml and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.5 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed several times to remove the unbound proteins. The bound protein (6-Histidine-tagged Pb1893) was then eluted from the resin with an elution buffer composed of the lysis buffer supplemented with 150 mM imidazole.

The gene product of Pb1893 was expressed in a truncated form. The first 20 amino acids, which represent a signal peptide, were removed. In the native organism, *P. bryantii*, the signal peptide facilitates transport of the PB1893 out of the cell so that it can act on its target substrate (xylan or plant cell wall) in the medium. Usually after transportation outside the cell, the signal peptide is processed (cleaved) off the protein. Signal peptides can often become a problem during production of recombinant proteins. To circumvent this potential problem, i.e., to prevent secretion of the protein, the PCR primers were designed to remove the signal peptide. The signal peptide does not influence catalytic activity. The design of the PCR primers also ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

The Pb1893 (ENDO-1,4-BETA-XYLANASE A PRECURSOR (EC 3.2.1.8)) amino acid sequence is found in SEQ ID NO: 43. The first 20 amino acids comprise the signal peptide, which was removed. The corresponding nucleotide sequence is found in SEQ ID NO: 44. Thus, the sequence encoding the signal peptide was not present in the gene cloned to make Pb1893.

The procedure of cloning the gene for Pb1893 into the plasmid pET28a led to fusion of the gene to a short nucleotide sequence encoding a peptide that contains six histidines. The short peptide comprises the first 21 amino acids of SEQ ID NO: 46 (pET28a-Pb1893). The corresponding nucleotide sequence of pET28a-Pb1893 is SEQ ID NO: 45.

In the protein sequence SEQ ID NO: 48, the sequence before DQD at residues 22-24 originates from the plasmid. The histidines (6-H) facilitated protein purification as described above.

The PB1893 gene was expressed in *E. coli* cells, and the protein was purified in a single step, making use of the 6-histidines encoded by the plasmid. FIG. 2b shows an SDS-PAGE of purified Pb1893. The molecular markers are in the lane marked M.

Enzyme Activity

The enzymatic activity of Pb1893 was measured according to the methods of Morag, E., Bayer, E. A., and Lamed, R. (Relationship of cellulosomal and non-cellulosomal xylanases of *Clostridium thermocellum* to cellulose degrading enzymes. J. Bacteriol. 1990: 172; 6098-6105). 50 μL of sample supernatant (substrate reacted with enzyme) was transferred to a clean 1.5 mL centrifuge tube and 100 μL of ethyl alcohol were added. The tube was centrifuged at 10,000 rpm for 5 min at 4° C. 100 μL of sample supernatant was transferred to a clean 1.5 mL centrifuge tube. A marker mixture was made by combining 0.8 μL of 12.5 mg/mL xylose, 1 μL of 12.5 mg/mL xylobiose, 1 μL of 12.5 mg/mL xylotriose, 1.5 μL of 12.5 mg/mL xylotetraose, and 8.6 μL of ethyl alcohol. All sugars were purchased from Megazyme. The samples and maker mixture were evaporated with a concentrator. 2.5 mL of dH$_2$O were added to the tubes. 0.5 to 1 μL of the sample solution was spotted on a TLC plate. The spots were dried and the TLC plate was developed in a developing tank for 3 to 4 hours. The plate was dried in a chamber for 30 min. The plate was sprayed with visualizing reagent and incubated for 5 to 10 min at 75° C. to visualize the results.

FIG. 2c shows the enzymatic activity of Pb1893 on natural substrates using TLC analysis. Two different hemicellulosic substrates were tested: oat-spelt xylan (OSX) and wheat arabinoxylan (WAX). In each case, in the presence of Pb1893 (+), short xylose chains were released. In the minus (−) lanes, no enzyme was added and therefore no products of hydrolysis were released. X1 (xylose monomer), X2 (xylose dimer or a disaccharide), X3 (trisaccharide), X4 (tetrasaccharide), and pentasaccharide (X5) were loaded in the first lane (M) as markers. The results showed that this enzyme releases shorter chains or oligosaccharides from more the complex substrates (OSX and WAX).

The concentration of glucose equivalents was determined following enzymatic hydrolysis of wheat arabinoxylan (WAX) and oat-spelt xylan (OSX) according to the methods of Lever, M. (A new reaction for colorimetric determination carbohydrates. Anal. Biochem. 1972: 47; 273-279). 1.5 mL microcentrifuge tubes were "zeroed" in an analytical balance. Next, 5±0.1 mg WAX or OSX were added to each tube, and the mass measured and recorded. The volumes needed to be added to each tube were calculated based on the mass. Sodium citrate reaction buffer and enzymes were added to each tube beginning with the reaction buffer. The tubes were incubated with constant mixing in a Rotisserie-style tube mixer at 37° C. for 18 h. The tubes were centrifuged at 10,000 rpm for 5 min at 4° C. 100 μL of sample supernatant was transferred to a clean 1.5 mL centrifuge tube for the pHBAH assay, and 150 μL of sodium citrate reaction buffer was added for a final volume of 250 μL. 1 mL of a stock solution of glucose was made at a concentration of 20 mM in sodium citrate buffer, and then serial dilutions were made in sodium citrate buffer to the following concentrations (20 mM, 10 mM, 5 mM, 2.5 mM, 1.25 mM, 0.625 mM, 0.3125 mM). 50 mg of pHBAH was dissolved in 50 mL of ice-cold citrate/NaOH solution for a final concentration of 0.1% (w/v), and the solution kept on ice. 750 μL of pHBAH solution was added to 250 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbances.

FIG. 2d shows the enzymatic activity of Pb1893 on natural substrates from a reducing sugar assay. In this experiment, a different assay for reducing sugars was used to determine the release of products from the two substrates. A standard was made based on known glucose concentrations and their absorbance (color development) in the presence of para-hydroxybenzoic acid hydrazide (Cann et al. 1999. J. Bacterial. 181: 1643-1651 and other reference above-Layer, M. 1972.). Incubation of enzymes with the substrates led to release of products that were quantified as a concentration of glucose equivalents. Hydrolysis of WAX (wheat arabinoxylan) was higher than hydrolysis of oat-spelt xylan (OSX).

Pb0390(Pb1909)

Figure 3:
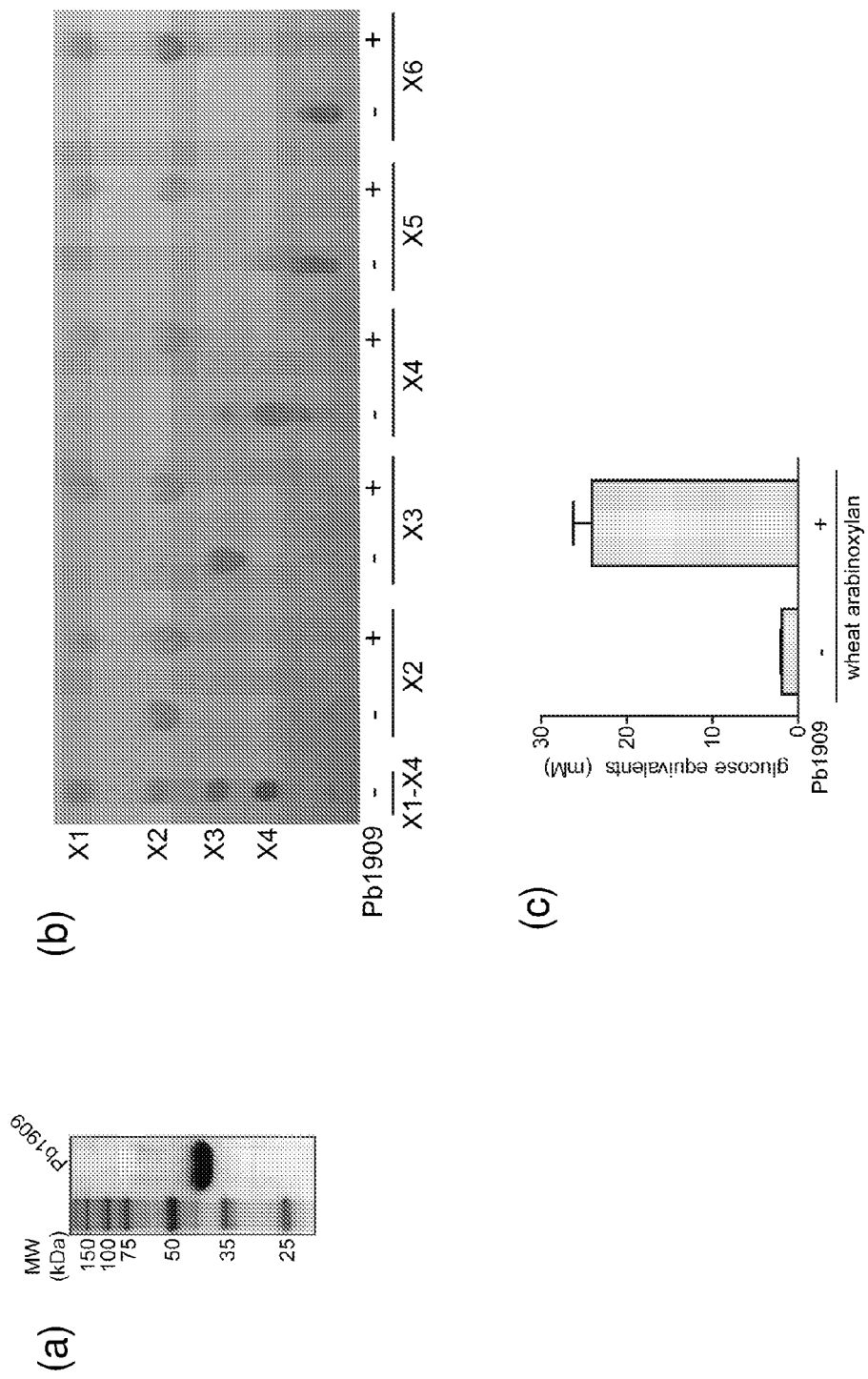
FIG. 3 shows the protein expression and activity of Pb1909. Part (a) shows SDS-PAGE of purified Pb1909 from *Prevotella bryantii*, part (b) shows TLC analysis of Pb1909 activity, and part (c) shows a reducing sugar assay of Pb1909.

An additional endoxylanase from *Prevotella bryantii*, Pb0390 (alternatively named Pb1909), was identified that may be used as a substitute for Pb1893 in any enzyme mixture. The protein was expressed and purified as described above. Purified Pb1909 is shown in FIG. 3a. Activity was determined by TLC and reducing sugar assays performed as described above for Pb1893 (FIGS. 3b and 3c). The protein sequence is provided as SEQ ID NO: 14. The nucleic acid sequence including sequence encoding a predicted signal peptide for Pb0390 glycosyl hydrolase family 10 (PEG1909) is SEQ ID NO: 49. The corresponding amino acid sequence is SEQ ID NO: 50.

Example 2

Arabinofuranosidase/Beta-Xylosidase Pb886 (Alternatively Named Pb2351) (SEQ ID NOs: 3 & 4)

An arabinofuranosidase, Pb886, was identified in *Prevotella bryantii*. This enzyme was also found to have β-xylosidase activity and thus is a bifunctional enzyme. As shown below, the first enzymatic activity (arabinofuranosidase) was higher than the second activity. Arabinofuranosidases cleave the arabinose side chains that decorate the β-1,4 xylose main chain. Since it was also shown to have beta-xylosidase activity, Pb886 must also attack the short chain xylo-oligosaccharides generated by endoxylanases (e.g., Pb1893) to generate xylose monomers. The protein is 560 amino acids in length and has a molecular weight of 62.9 kDa (His-tag+truncated Pb886 protein). It is a GH 43 arabinoxylan arabinofuranohydrolase.

Cloning of Pb886

The gene for Pb886 was amplified from *Prevotella bryantii* B14 genomic DNA by PCR using PrimeSTAR HS DNA polymerase (TaKaRa). The Pb886 gene was amplified using the following primer set:

```
Pb886ForNdeI
                                           (SEQ ID NO: 51)
5'-CATATGCAGGATGCTGTTTTCCAGAATTTTAAGTATACTGG-3'

Pb886RevXhoI
                                           (SEQ ID NO: 52)
5'-CTCGAGTTATTTCACAGCATAAAGTCCGATTACCGC-3'
```

The PCR amplification method used to amplify the gene from the *P. bryantii* genome was as follows:

| PCR mixture | |
| --- | --- |
| 2.5 U/mL PrimeSTAR DNA polymerase | 0.5 |
| 19 ng/mL *P. bryantii* gDNA | 1 |
| 10 mM Fw Primer | 1 |
| 10 mM Rv Primer | 1 |
| 2.5 mM dNTP Mixture | 4 |
| 5× PrimeSTAR Buffer | 10 |
| dH$_2$O | 32.5 |
| Total | 50 mL |

| PCR Protocol | | | |
| --- | --- | --- | --- |
| Denature | 98° C. | 10 sec | 30 Cycles |
| Anneal | 55° C. | 5 sec | |
| Elongate | 72° C. | 90 sec | |
| Last | 4° C. | ∞ | |

After the PCR amplification described above, the product (Pb886 gene) was confirmed by 1% agarose gel electrophoresis. GoTaq DNA polymerase (Promega) was then added to the reaction mixture to add adenine bases to the 3' terminus of the amplified gene product. The reaction was as follows:

| Reaction | | Incubation | |
| --- | --- | --- | --- |
| 5 U/mL GoTaq DNA polymerase | 1 | 72° C. | 15 min |
| Reaction Mixture | 49 | | |
| Total | 50 mL | | |

After the reaction, the PCR product was ligated into the TA-cloning vector pGEM-T Easy (Promega) through the following reaction:

| Ligation | | Incubation | |
| --- | --- | --- | --- |
| 3 U/mL T4 DNA ligase | 1 | 4° C. | O/N |
| Reaction Mixture (PCR product) | 3 | | |
| 2× Rapid Ligation Buffer | 5 | | |
| pGEM-T Easy vector | 1 | | |
| Total | 10 mL | | |

The ligation mixture for Pb886-pGEM-T Easy was introduced into *E. coli* JM109 by heat shock method, and the cells were plated on LB-ampicillin-X-gal-IPTG. After overnight incubation at 37° C., two white colonies were selected and used to inoculate 3 mL cultures of LB-ampicillin. The cultures were grown at 37° C. with vigorous aeration for 16 hours, and minipreps were made of the cell cultures. The plasmids from the miniprep were then electrophoresed on a 1% agarose gel to check the size of the plasmid DNA. The plasmids with inserts were sequenced to confirm the integrity of the coding sequence. The cloned gene was excised by NdeI-XhoI using the reaction below and separated by 1% agarose gel.

| Digestion | | Incubation | |
| --- | --- | --- | --- |
| Plasmid DNA (1900 ng) with insert | 16 | 37° C. | 3 hour |
| 10× NEBuffer 4 | 2 | | |
| 20 U/mL NdeI | 1 | | |
| 20 U/mL XhoI | 1 | | |
| Total | 20 mL | | |

The gene, released from the pGEM-T vector, was purified by a gel extraction kit (QIAGEN) and inserted into the corresponding sites of pET28a (Novagen) through the following reaction.

| Ligation | | Incubation | |
| --- | --- | --- | --- |
| 2000 U/mL T4 DNA ligase (NEB) | 1 | 16° C. | O/N |
| 17 ng/mL digested gene fragment | 1.6 | | |
| 22 ng/mL digested pET28a vector | 1.5 | | |
| 10× T4 DNA Ligase Buffer (NEB) | 2 | | |
| dH$_2$O | 13.9 | | |
| Total | 20 mL | | |

The ligation mixture for Pb886-pET28a was introduced into *E. coli* JM109 by heat shock method, and the cells were plated on LB-ampicillin. After overnight incubation at 37° C., one colony was selected and used to inoculate 10 mL cultures of LB-ampicillin. The cultures were grown at 37° C. with vigorous aeration for 16 hours, and minipreps were made of the cell cultures. The plasmid was then electrophoresed on a 1% agarose gel to confirm the size of plasmid/insert DNA.

SEQ ID NO: 53 contains the amino acid sequence of XYLOSIDASE-ARABINOSIDASE (EC 3.2.1.37(xyl), EC 3.2.1.55(ara)) including a predicted signal peptide in the first 19 residues. The signal peptide sequence was excluded in the cloning. The corresponding nucleotide sequence is SEQ ID NO: 54.

Pb886 was expressed in pET2a with an amino terminal six histidine tag to facilitate protein purification. The amino acid sequence of pET28a-Pb886 is SEQ ID NO: 55. The corresponding nucleotide sequence is SEQ ID NO: 56.

The nucleotide and amino acid sequences of Pb886 together with the N-terminal six histidines to facilitate protein purification are found in SEQ ID NO: 57 (DNA) and SEQ ID NO: 58 (protein).

Purification and Enzyme Activity

Figure 4:
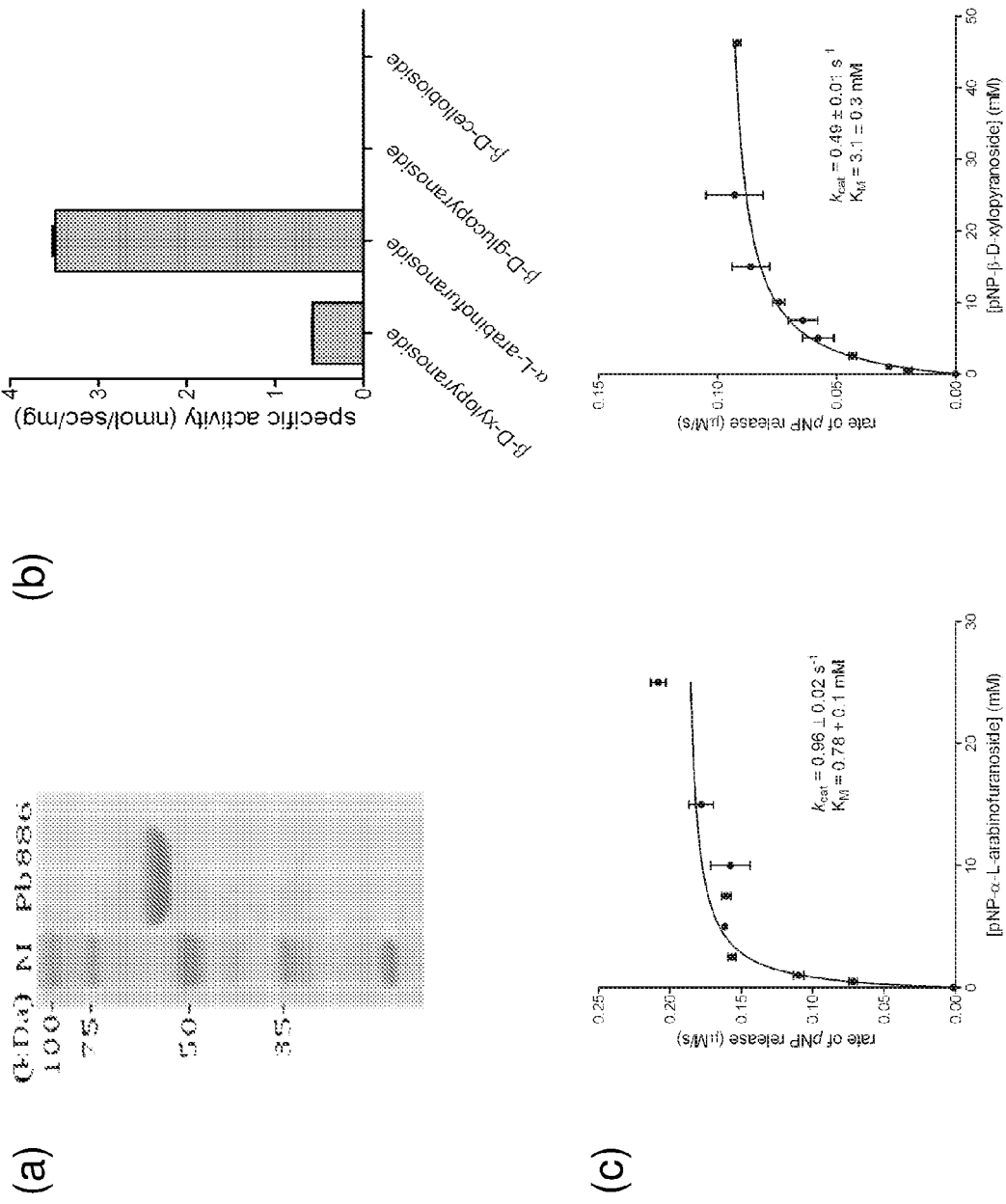
FIG. 4 shows protein expression and activity of Pb886 (alternatively named Pb 2351). Part (a) shows SDS-PAGE of purified Pb886 from *Prevotella bryantii*, part (b) shows screening of Pb886 activity on para-nitrophenyl (pNP) derivatives, part (c) shows the kinetics of pNP substrate hydrolysis, part (d) shows TLC analysis of Pb886 activity on xylo-oligosaccharide substrates, and part (e) shows TLC analysis of Pb886 arabinofuranosidase activity on wheat arabinoxylan (WAX).

Pb886 protein was expressed and purified as described in Example 1. FIG. 4a shows an SDS-PAGE of purified *P. bryantii* Pb886 protein. FIG. 4b shows the results of a screening assay of Pb886 activity on para-nitrophenyl (pNP) substrates. Higher arabinofuranosidase activity was detected with pNP substrates. There was also a significant activity on xylose linked by β-1,4-linkages.

Enzyme-catalyzed hydrolysis of para-nitrophenyl (pNP)-linked monosaccharide substrates was assayed using a thermostated Synergy II multi-mode microplate reader from BioTek Instruments Inc. (Winooski, Vt.). A library of pNP substrates were screened for activity including: pNP-α-L-arabinopyranoside, pNP-α-L-arabinofuranoside, pNP-β-D-fucopyranoside, pNP-α-L-fucopyranoside, pNP-α-D-galactopyranoside, pNP-β-D-galactopyranoside, pNP-α-D-glucopyranoside, pNP-β-D-glucopyranoside, pNP-β-D-maltopyranoside, pNP-α-D-maltopyranoside, pNP-α-D-mannopyranoside, pNP-β-D-mannopyranoside, pNP-α-L-rhamnopyranoside, pNP-β-D-xylopyranoside, pNP-β-D-cellobioside. The substrates (1 mM) in citrate buffer (100 μL; 50 mM sodium citrate, 150 mM NaCl, pH 5.5) were incubated at 37° C. in the presence or absence of Pb886 (0.2 µM) for 30 min, and the level of pNP release was determined by continuously monitoring the absorbance at 400 nm. The pathlength correction feature of the instrument was employed to convert the absorbance values recorded to correspond to a 1 cm pathlength. The extinction coefficient for pNP at pH 5.5 and a wavelength of 400 nm was measured as 0.673 mM$^{-1}$cm$^{-1}$.

FIG. 4c illustrates the kinetics of pNP substrate hydrolysis. The activity of Pb886 was verified with para-nitrophenyl derivatives of xylose and arabinose as indicated in the x-axes. These substrates are artificial substrates for the enzyme. Kinetic studies of Pb886 were performed using a thermostated Synergy II multi-mode microplate reader from BioTek Instruments Inc. (Winooski, Vt.). pNP-β-D-Xylopyranoside (0-46.25 mM) or pNP-α-L-arabinofuranoside (0-25 mM) were incubated in a citrate reaction buffer (100 µL; 50 mM sodium citrate, 150 mM NaCl, pH 5.5) at 37° C. in a 96-well flat bottom microtiter plate, and reactions were initiated by the addition of Pb886 (0.2 µM). Hydrolysis of pNP-β-D-xylopyranoside and pNP-α-L-arabinofuranoside were continuously monitored by recording the UV signal at 400 nm. Initial rate data were then plotted against the substrate concentration, and kinetic values were estimated by applying a nonlinear curve fit using GraphPad Prism v5.02 from GraphPad Software (San Diego, Calif.). The extinction coefficient for para-nitrophenol at pH 5.5 and a wavelength of 400 nm was measured as 0.673 mM$^{-1}$cm$^{-1}$.

The activity of Pb886 on β-1,4-linked xylose chains, which mimic more of the natural substrate (xylan), were further demonstrated with thin layer chromatography (TLC) as described in Example 1. Xylose (monomer) was released from short-chain xylo-oligomers (X2 and X3) more effectively than from longer chains (X4, X5, X6). FIG. 4d shows the activity of Pb886 on xylo-oligosaccharide substrates (β-xylosidase activity). FIG. 4e shows arabinofuranosidase activity of Pb886 on wheat arabinoxylan, a natural substrate. To clearly demonstrate that Pb886 released arabinose from a natural substrate such as wheat arabinoxylan (WAX), arabinose alone (A1 in lane 2) was compared to standards based on different xylose chains (lane 1). As shown in FIG. 4e, without enzyme (−), no product was generated (lane 3). In lane 4, which contains the Pb886 enzyme (+), a product with a migration pattern similar to arabinose was released from WAX. These results demonstrate that the enzyme released arabinose from a hemicellulose substrate.

Example 3

Beta-Xylosidase/Beta-Glucosidase Pb911 (SEQ ID NOs: 5 & 6)

A β-xylosidase, Pb911, was identified in *P. bryantii*. During the degradation of hemicellulose, β-xylosidases convert xylo-oligosaccharides produced by an endoxylanase to their monomeric sugars (xylose). *P. bryantii* has four genes encoding β-xylosidase-like enzymes. All four genes were cloned and expressed as soluble proteins. As shown below, one of these enzymes, Pb911, was initially screened on pNP substrates. The results suggested that Pb911 releases mostly xylose from a β-1,4-linked pNP and to a lesser extent arabinose from arabinose linked to pNP. The protein is 776 amino acids in length and has a molecular weight of 86.3 kDa (His-tag+truncated Pb911 protein). This protein is a GH 3 protein.

Cloning of Pb911

The gene for Pb911 was amplified and cloned into the Novagen pET-15b vector using the following primer sets Takara PrimeSTAR HS DNA Polymerase:

```
Pb911ForNdeI
                                      (SEQ ID NO: 59)
5'-GCGCCATATGCAAACTATACTTATTAATCAGCAGG-3'

Pb911RevXhoI
                                      (SEQ ID NO: 60)
5'-CGCGCTCGAGTCACTTGATGACTTCAG-3'
```

Pb911 (Amino Acid Sequence)

SEQ ID NO: 61 contains the protein sequence of ORF00911 xylosidase-arabinosidase (*Prevotella bryantii*) in the first 19 amino acids that were predicted to constitute a signal peptide. The corresponding nucleotide sequence is SEQ ID NO: 62.

The thymine at base 669 in SEQ ID NO: 63 (*Prevotella bryantii* B14 ORF0911) was a potential point mutation in the gene, but since it did not change the codon, the gene was expressed without any attempt to correct it. There was a silent mutation introduced at position 221 of the corresponding amino acid sequence (SEQ ID NO: 64). This mutation did not result in a change in the amino acid sequence.

The pET15b expressing Pb911 contained the nucleotide sequence SEQ ID NO: 65 and encoded the amino acid sequence SEQ ID NO: 66. The six histidines at the N-terminus were used to facilitate protein purification.

Purification and Enzyme Activity

Figure 5:
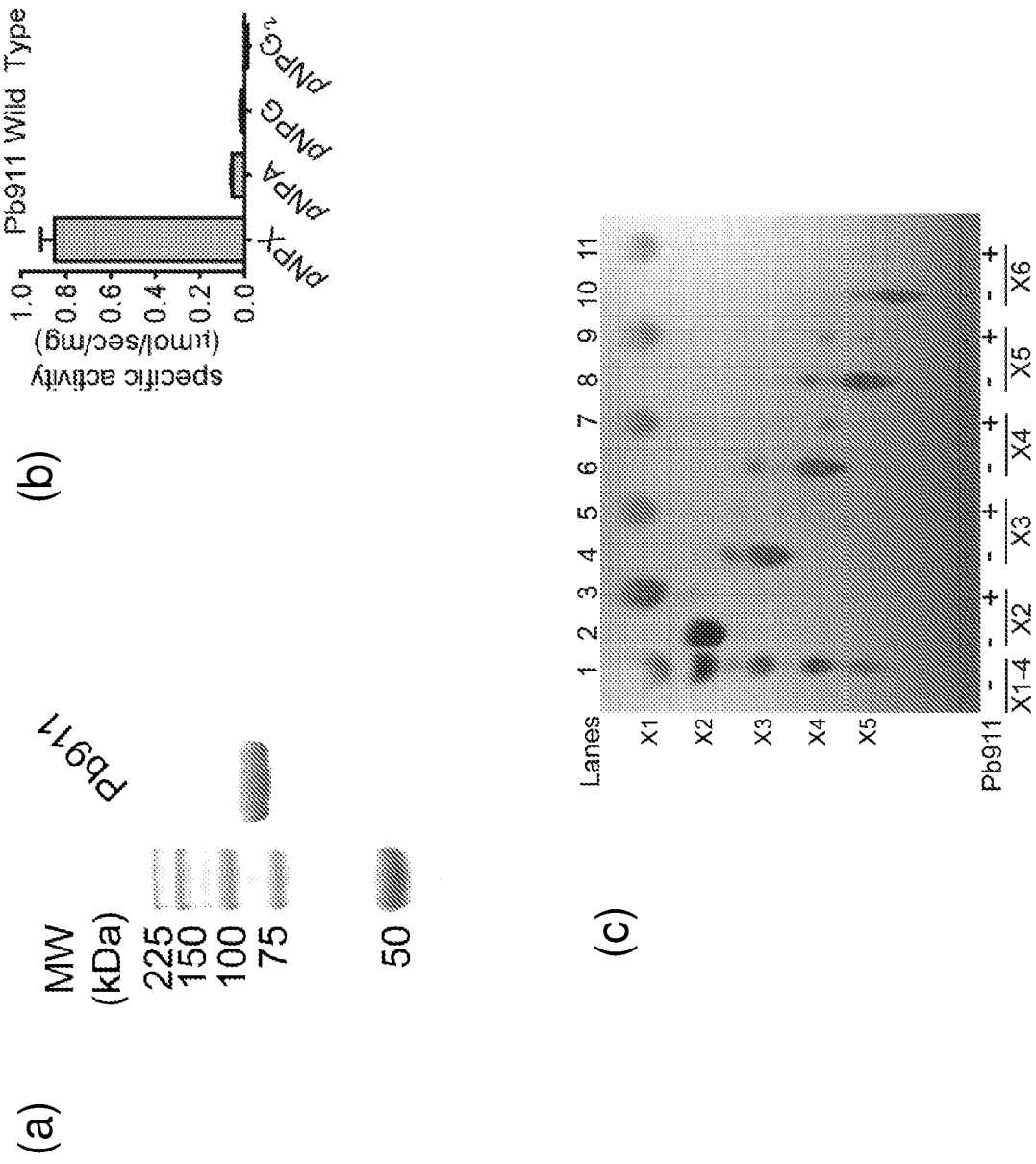
FIG. 5 shows the protein expression and activity of Pb911 (alternatively named Pb 2369). Part (a) shows SDS-PAGE of purified Pb911 from *Prevotella bryantii*, part (b) shows Pb911 activity on pNP substrates, and part (c) shows TLC analysis of Pb911 activity.

Pb911 protein was expressed and purified according to the methods described in Example 1. FIG. 5a shows an SDS-PAGE of purified Pb911. FIG. 5b shows that *P. bryantii* Pb911 hydrolyzed xylose linked to pNP in beta-1,4 linkages. The activity of Pb911 on pNP substrates was measured according to the methods described in Example 2.

TLC performed as described in Example 1 showed that xylo-oligosaccharides, from disaccharides (two xylose sugars) to hexaose (six xylose monomers in a chain) chains, were converted to the monosaccharide xylose by Pb911 (FIG. 5c). The data suggested that Pb911 can convert xylo-oligosaccharides released by an endoxylanase into xylose.

Figure 6:
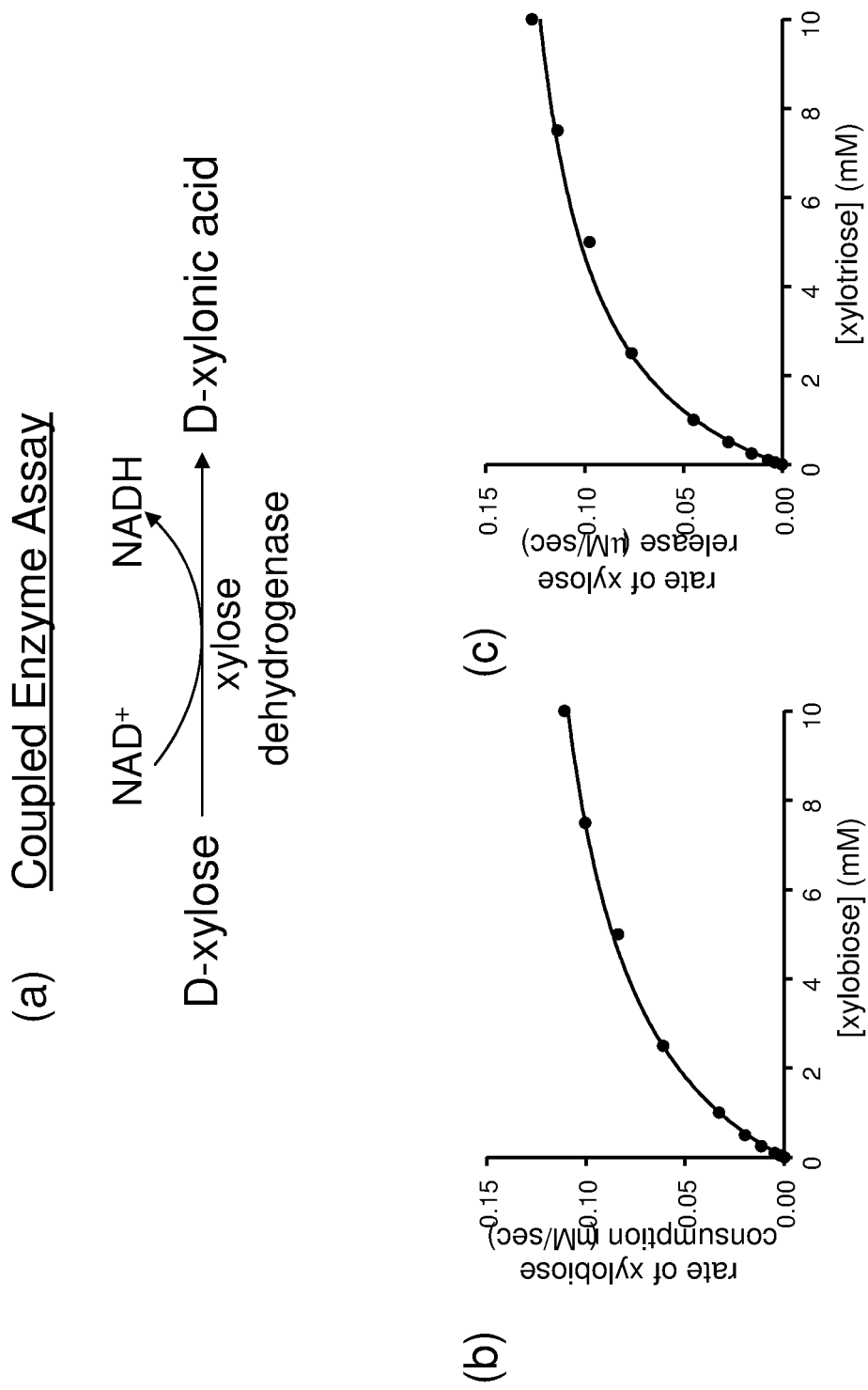
FIG. 6 shows the kinetics of xylo-oligosaccharide hydrolysis by Pb911. Part (a) describes the coupled enzyme assay, part (b) shows consumption of xylobiose, part (c) shows rate of release of xylotriose, part (d) shows rate of release of xylotetraose, part (e) shows release of xylopentaose, part (f) shows release of xylohexaose, and part (g) shows the kinetic values for hydrolysis of all five substrates.

A coupled enzyme assay was used to measure the kinetics of xylo-oligosaccharide hydrolysis by Pb911 (FIG. 6). To continuously monitor the hydrolysis of xylo-oligosaccharides by Pb911 for subsequent determination of kinetic parameters with these natural substrates, a coupled enzyme assay was employed based upon the xylose assay kit from Megazyme (Bray, Ireland). This assay system includes a xylose mutarotase (XMR) enzyme, which catalyzes the interconversion of the α- and β-anomers of D-xylose, and a β-D-xylose dehydrogenase (β-XDH) enzyme, which couples xylose oxidation to the reduction of β-nicotinamide adenine dinucleotide (NAD$^+$). The NADH production can be monitored continuously using a spectrophotometer tuned to a wavelength of 340 nm. The reactions were prepared in 100 µL final volumes in independent wells of a 96-well microtiter plate. The reaction components included XMR (41 µg/mL, final concentration), β-XDH (1.2 U/mL, final concentration), NAD (2 mM, final concentration), adenosine 5'-triphosphate (24 µM, final concentration), xylo-oligosaccharides ($X_2$-$X_6$) (50 µM-10 mM, final concentrations), and all of these components were diluted in a sodium citrate reaction buffer (50 mM sodium citrate, 150 mM NaCl, pH 5.5). The plates were equilibrated to 37° C., and the reactions were initiated by the addition of Xyl3A (9 nM, final concentration). The level of NADH production was measured by continuously monitoring the absorbance at 340 nm using a Synergy II multimode plate reader from BioTek Instruments Inc. (Winooski, Vt.). The pathlength correction feature of the instrument was employed to convert the absorbance values recorded to correspond to a 1 cm pathlength.

Table 1 shows the kinetic values for the activity of wild type and mutant Pb911 enzymes. Pb911 showed improved steady-state kinetic parameters with pNP-β-D-xylopyranoside as compared to pNP-β-D-glucopyranoside, suggesting that xylose-linked chains may be better substrates for this enzyme. Analysis of mutant Pb911 proteins demonstrated that the glutamate 115 residue of the protein is important for determining substrate specificity.

TABLE 1

Steady state kinetic parameters for wild type and mutant enzymes.

| | pNP-β-D-xylopyranoside | | | pNP-β-D-glucopyranoside | | |
|---|---|---|---|---|---|---|
| | $k_{cat}$ ($s^{-1}$) | $K_M$ (mM) | $k_{cat}/K_M$ ($s^{-1} \cdot mM^{-1}$) | $k_{cat}$ ($s^{-1}$) | $K_M$ (mM) | $k_{cat}/K_M$ ($s^{-1} \cdot mM^{-1}$) |
| Pb911 WT | 250 ± 10 | 8.4 ± 1 | 30 ± 4 | 19 ± 0.6 | 22 ± 1 | 0.86 ± 0.05 |
| Pb911 E115A | 0.35 ± 0.02 | 28 ± 3 | 0.013 ± 0.002 | 0.087 ± 0.005 | 39 ± 4 | 0.0022 ± 0.0003 |
| Pb911 E115D | 87 ± 5 | 39 ± 4 | 2.2 ± 0.2 | 16 ± 0.4 | 17 ± 1 | 0.94 ± 0.06 |

Example 4

Glucuronidase Pb1912 (SEQ ID NOs: 9 & 10)

Figure 7:
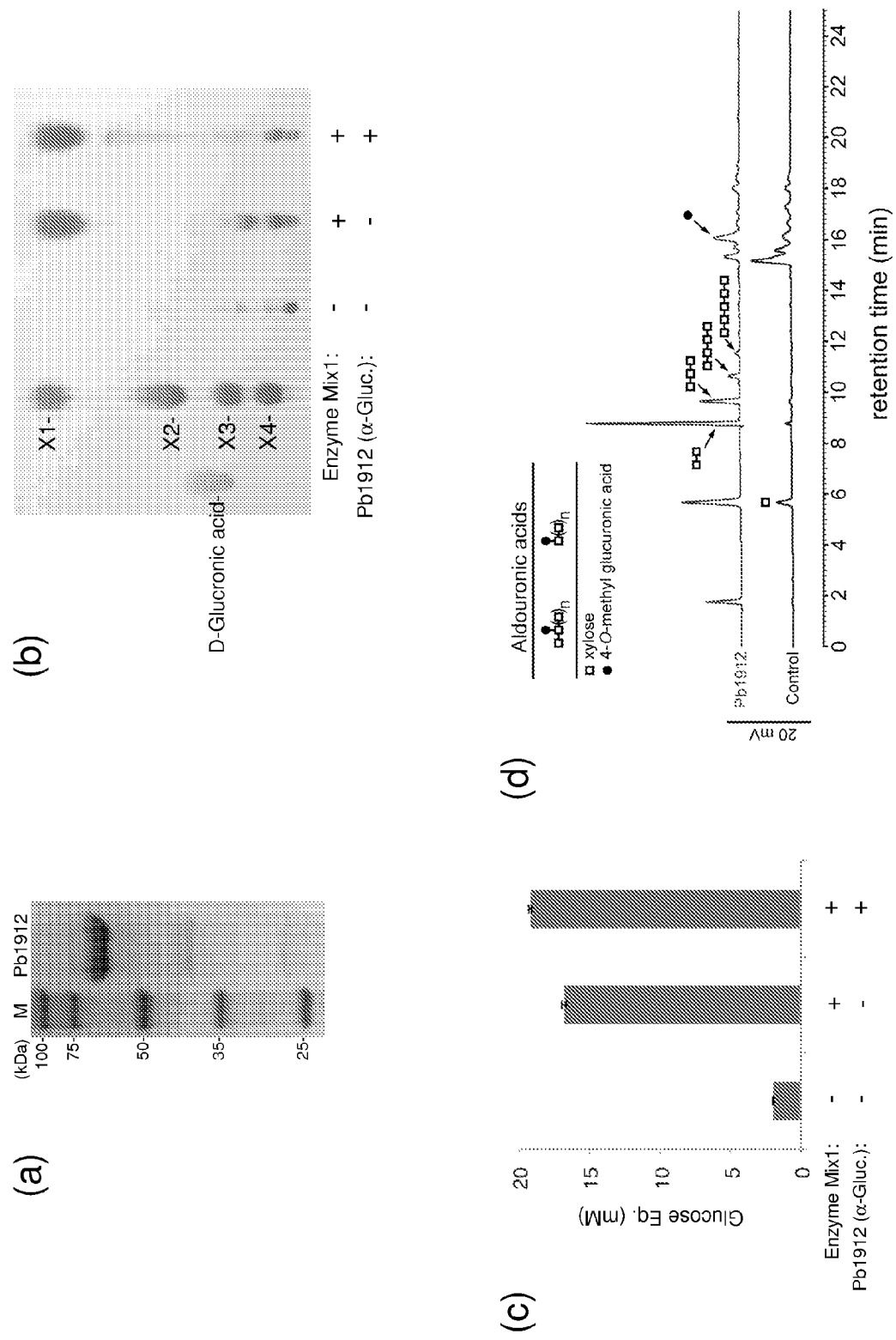
FIG. 7 shows the protein expression and activity of Pb1912 (alternatively named Pb 2425). Part (a) shows SDS-PAGE of purified Pb1912 from *Prevotella bryantii*, part (b) shows TLC analysis of Pb1912 activity, part (c) shows reducing sugar assays of Pb1912, and part (d) shows HPLC analysis of Pb1912 activity with aldouronic acids.

Alpha-glucuronidase removes side chains of glucuronic acids which, if present in hemicellulose or lignocellulose, will limit release of sugars for fermentation. Attempts to express the *P. bryantii* gene coding for this protein in *E. coli* were unsuccessful. The entire gene was synthesized based on the codons commonly used by *E. coli* while ensuring that the polypeptide encoded by the "synthesized gene" was the same as the *P. bryantii* α-glucuronidase. The production of Pb1912, the *P. bryantii* glucuronidase, is shown in FIG. 7a. The protein is 625 amino acids in length and has a molecular weight of 71.5 kDa (His-tag+truncated Pb1912 protein).

Cloning of Pb1912

The gene for Pb1912 was artificially synthesized by Gen-Script Corporation (Piscataway, N.J.) to optimize codon usage. The synthesized gene was cloned into pUC57 vector (hereafter, designated as Pb1912-pUC57). The Pb1912 gene was amplified by PCR using PrimeSTAR HS DNA polymerase (TaKaRa) and subcloned into pET46 Ek/LIC vector using Ek/LIC Cloning Kits (Novagen). The primer sequences are below:

```
Pb1912For
                                       (SEQ ID NO: 67)
5'-GACGACGACAAGATGGAAGATGGCCATCAGCTG-3'

Pb1912Rev
                                       (SEQ ID NO: 68)
5'-GAGGAGAAGCCCGGTTTATTCAATCGGCATTTT-3'
```

| PCR mixture | |
|---|---|
| 2.5 U/mL PrimeSTAR DNA polymerase | 0.5 |
| 0.2 ng/mL Pb1912-pUC57 | 1 |
| 10 mM Fw Primer | 1 |
| 10 mM Rv Primer | 1 |
| 2.5 mM dNTP Mixture | 4 |
| 5x PrimeSTAR Buffer | 10 |
| dH$_2$O | 32.5 |
| Total | 50 mL |

| PCR Protocol | | | |
|---|---|---|---|
| Denature | 98° C. | 10 sec | |
| Anneal | 55° C. | 5 sec | 30 Cycles |
| Elongate | 72° C. | 105 sec | |
| Last | 4° C. | ∞ | |

After the PCR amplification described above, the amplification of Pb1912 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/mL T4 DNA Polymerase | 0.2 | 22° C. | 30 min |
| Purified PCR Product | 2.1 | 75° C. | 20 min |
| 25 mM dATP | 1 | 4° C. | ∞ |
| 100 mM DTT | 0.5 | | |
| 10x T4 DNA Polymerase Buffer | 1 | | |
| dH$_2$O | 5.2 | | |
| Total | 10 mL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 mL | | |

After the incubation, EDTA was added to the reaction.

| Annealing | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 mL | | |

The annealing mixtures for Pb1912-pET46 Ek/LIC were introduced into *E. coli* JM109 by electroporation, and the cells were plated on LB-ampicillin. After overnight incubation at 37° C., three colonies were selected and used to inoculate 10 mL cultures of LB-ampicillin. The cultures were grown at 37° C. with vigorous aeration for 16 hours, and minipreps were made of the cell cultures. The plasmids were then electrophoresed on a 1% agarose gel to confirm the size of plasmid/insert DNA. Next, the integrity of the gene was confirming by nucleotide sequencing.

The first 28 residues of the Pb1912 (ALPHA-GLUCU-RONIDASE (EC 3.2.1.139) amino acid sequence comprise a predicted signal peptide (SEQ ID NO: 69).

Expression of engineered Pb1912 in pET46EK/LIC led to a protein with an N-terminal six histidine tag to facilitate protein purification. The amino acid sequence of pET46Ek/LIC-Pb1912 is found in SEQ ID NO: 70. The corresponding engineered nucleotide sequence optimized for *E. coli* is found in SEQ ID NO: 71.

The pET15b expressing the engineered Pb1912 contains following nucleotide sequence in SEQ ID NO: 72 that codes for the corresponding amino acid sequence SEQ ID NO: 73. The six histidines at the N-terminus facilitated protein purification.

Purification and Enzyme Activity

Pb1912 protein was expressed and purified according to the methods described in Example 1. FIG. 7a shows the SDS-PAGE of purified Pb1912. TLC analysis performed as described in Example 1 demonstrated the synergistic activity of Pb1912 and Enzyme Mix 1 (endoxylanase (Pb1893), arabinofuranosidase (Pb886), and beta-xylosidase (Pb911) on the hydrolysis of glucuronic acid (4-O-methyl-D-glucurono-D-xylan) (FIG. 7b). The addition of Pb1912 to the mixture increased the release of glucose equivalents by about 14% (FIG. 7c). In the presence of Enzyme Mix 1, a large amount of xylose (X1) was released, but two products remained near the bottom of the TLC plate. The addition of glucuronidase (Pb1912) resulted in the disappearance of the top product with the concomitant appearance of other products (streak) (FIG. 7b). The data, therefore, suggested that the glucuronidase enhanced hydrolysis of xylo-oligosaccharides into smaller or shorter products. However, another larger product (seen as a spot) was still remaining after the addition of Pb1912. HPLC analysis of products released following the incubation of Pb1912 with aldouronic acid mixtures demonstrated that another *P. bryantii* protein helped to remove this product. After incubating Pb1912 with aldouronic acids, xylo-oligosaccharides and glucuronic acid were liberated, although there were still some peaks that Pb1912 was not able to degrade (FIG. 7d). The results clearly showed the synergistic action of the glucuronidase with the enzyme mix to improve the release of sugars from a glucuronic acid substrate.

For analysis of aldouronic acid hydrolysis, the enzymes (0.5 μM, final concentration) were incubated with the aldouronic acid mixture from Megazyme (60 μg/mL, final concentration) in citrate buffer (50 mM sodium citrate, 150 mM NaCl, pH 5.5) at 37° C. After 16 hours, 100 μL aliquots were removed, and the reactions were terminated by the addition of 300 μL 0.1 M NaOH. The oligosaccharide composition of these neutral and acidic oligosaccharide mixtures following enzymatic hydrolysis were then assessed by high performance anion exchange chromatography (HPAEC-PAD) with a System Gold® HPLC instrument from Beckman Coulter (Fullerton, Calif.) equipped with a CarboPac™ PA1 guard column (4×50 mm) and a CarboPac™ PA1 analytical column (4×250 mm) from Dionex Corporation (Sunnyvale, Calif.) and a Coulochem® III electrochemical detector from ESA Biosciences (Chelmsford, Mass.). Monomeric xylose ($X_1$) and xylo-oligosaccharides ($X_2$-$X_6$) were used as standards. Oligosaccharides were resolved using a mobile phase of 100 mM NaOH with a linear gradient ending with 125 mM NaOAc over 25 min.

Example 5

β-Xylosidase/β-Glucosidase Pb975 (SEQ ID NOs: 7 & 8)

Figure 8:
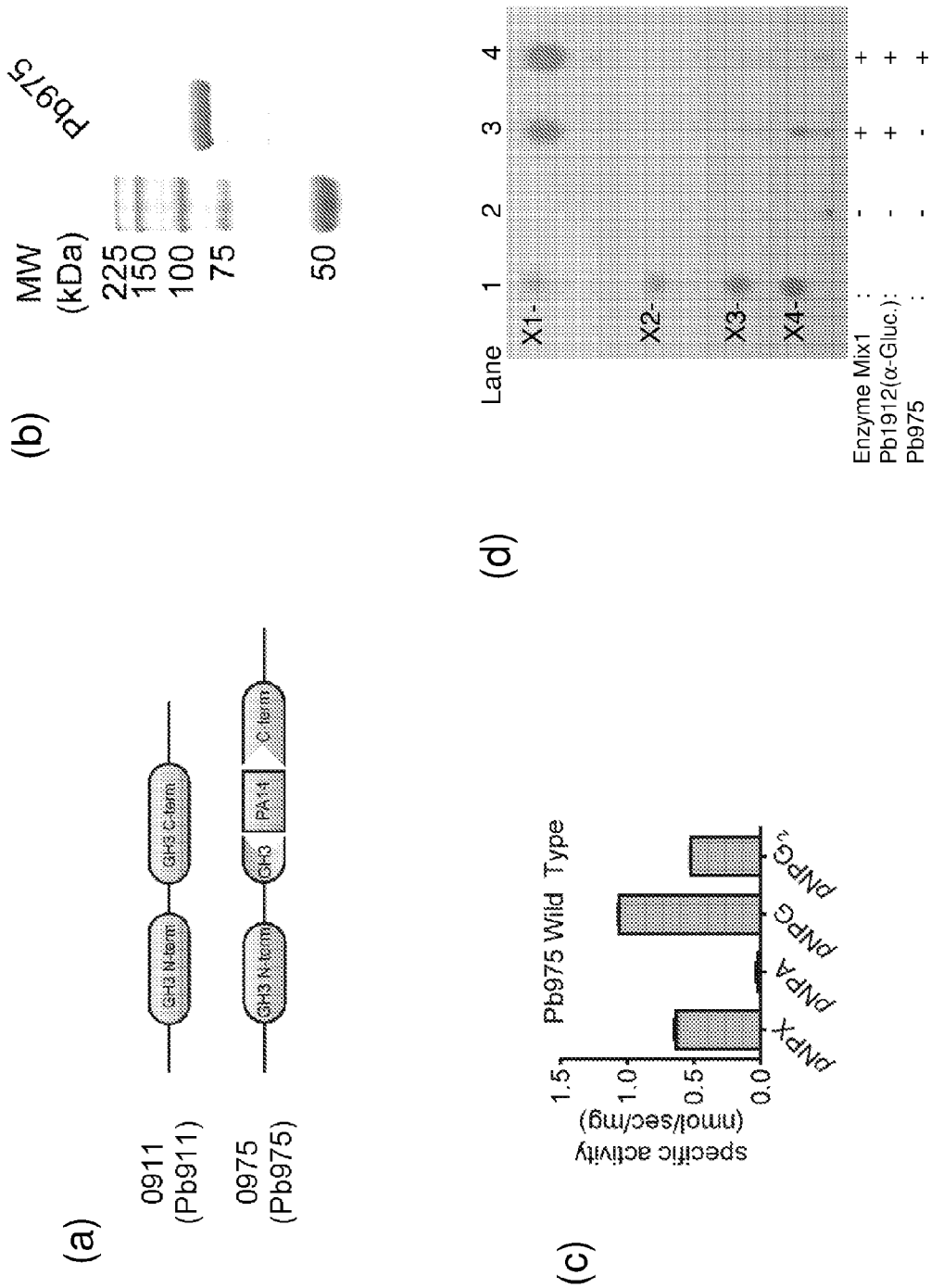
FIG. 8 shows the protein expression and activity of Pb975. Part (a) shows the protein domain architecture of Pb911 and Pb975, part (b) shows SDS-PAGE of purified Pb975 from *Prevotella bryantii*, part (c) shows Pb975 activity on pNP substrates, part (d) shows TLC analysis of Pb975 activity, and part (e) shows HPLC analysis of Pb975 activity.

Another β-xylosidase-like enzyme, Pb975, was identified in *P. bryantii*. In this example, it is shown that Pb975 has both the capacity to release xylose from β-1,4-linked xylose (β-xylosidase activity) and glucose from β-1,4-linked glucose (β-glucosidase activity) units. The gene product of Pb975 is different from Pb911 because Pb975 was found to contain an insertion sequence commonly referred to as the protective antigen, or PA14. The domain architectures of Pb911 and Pb975 are shown in FIG. 8a. It has been predicted that these insertion sequences, which assume a β-barrel shape, engage in binding rather than in a catalytic role (Ridgen et al. 2004. Trends in Biochemical Sciences 29:335-339). Enzymatic activities were demonstrated for Pb975 using pNP (artificial) substrates. Furthermore, adding Pb975 to the enzyme mix, together with glucuronidase, resulted in the removal of the final large product that remained, even upon addition of glucuronidase.

Cloning of Pb975

The gene for Pb975 was amplified and cloned into the Novagen pET-15b vector using the following primer sets with Takara PrimeSTAR HS DNA Polymerase:

```
Pb975For#2
                                       (SEQ ID NO: 74)
5'-GCGCCATATGATGAAAAGTAAACAACTAATAAC-3'

Pb975PADnRev
                                       (SEQ ID NO: 75)
5'-CGCGCTCGAGTTATTTTAGGTAAATAATTAATTTTTTC-3'
```

The gene product contained an N-terminal predicted signal peptide as underlined in the sequence below. The signal peptide was eliminated from the protein during expression. The protein is 857 amino acids in length with a molecular weight of 95.7 kDa.

The following conditions were used for amplification of the preceding genes by polymerase chain reaction using PrimeSTAR HS DNA Polymerase from Takara:

| PrimeSTAR | | | | | |
|---|---|---|---|---|---|
| # of rxns | 1 | | PCR Protocol | | |
| Buffer | 10 | | Denature | 98° C. | 10 sec |
| PrimeSTAR | 0.5 | 30 Cycles | Anneal | 55° C. | 15 sec |
| 2.5 mM dNTPs | 4 | | Elongate | 72° C. | 3 min |
| Genomic DNA | 1 | | Last | 4° C. | ∞ |
| Primers (5 μM Mix) | 2.5 | | | | |
| H₂O | 32 | | | | |
| Total | 50 | | | | |

Five microliters of the PCR product was then electrophoresed on a 1% agarose gel, and the bands were stained with ethidium bromide and visualized with a UV transilluminator. Next, the PCR products were purified using a PCR purification kit from QIAGEN and restriction enzyme digestions were prepared for the two PCR products as follows:

| Digestion | | | |
|---|---|---|---|
| # of rxns | 1 | | Incubation |
| 10X Buffer 4 | 2 | 3 h | 37° C. |
| ORF0975 PCR Product | 10 | | |
| NdeI | 1 | | |
| XhoI | 1 | | |
| H₂O | 6 | | |
| Total | 20 | | |

The following day, the two enzyme digestions were purified using a PCR purification kit from QIAGEN, and the digested product was eluted in 20 uL of water. The following ligation was prepared with previously digested pET-15b vector:

| Ligation | | | |
|---|---|---|---|
| # of rxns | 1 | | Incubation |
| 10X Buffer | 1 | 16 h | 4° C. |
| pET-15b | 2 | | |
| T4 Ligase | 1 | | |
| PCR Product | 6 | | |
| Total | 10 | | |

The ligation mixtures for ORF0975-pET15b were introduced into *E. coli* DH5 alpha by electroporation, and the cells were plated on LB-ampicillin. After overnight incubation at 37° C., approximately 50 colonies were identified on each plate. Five colonies were selected and used to inoculate 3 mL cultures of LB-amp, and the cultures were grown at 37° C. with vigorous aeration for 8 hours. Minipreps were made of the cell cultures. The plasmids were then electrophoresed on a 1% agarose gel and stained with ethidium bromide. Three plasmids were sequenced to confirm the integrity of inserts (Pb975). The correct plasmid was used for gene expression.

The amino acid sequence of ORF00975 xylosidase-arabinosidase (*Prevotella bryantii*) including the predicted signal peptide is SEQ ID NO: 76. The corresponding nucleotide sequence is SEQ ID NO: 77.

Pb975 (Amino Acid Sequence)

The sequence of the expressed Pb975 protein is found in SEQ ID NO: 78 (*Prevotella bryantii* B14 ORF0975). The N-terminal tag contains a 6-histidine tag to facilitate protein purification. The corresponding nucleotide sequence is SEQ ID NO: 79.

The pET15b expressing Pb975 contained the nucleotide sequence in SEQ ID NO: 80 that encodes for the corresponding and amino acid sequence SEQ ID NO: 81. The six histidines to facilitate protein purification are underlined.

Purification and Enzyme Activity

Pb975 protein was expressed and purified as described in Example 1. FIG. 8*b* shows an SDS-PAGE of purified Pb975. FIG. 8*c* shows hydrolysis of pNP-substrates by Pb975. FIG. 8*d* shows the synergistic effect of Pb975 when combined with Enzyme Mix 1 and Pb1912. Pb975 helped to hydrolyze the remaining product shown in lane 3. Addition of Pb975 to the enzyme mix (lane 4) led to hydrolysis of the large product, close to the bottom of the plate, in lane 3. A concomitant increase in the amount of xylose (X1) released was observed in lane 4. FIG. 8*e* shows the synergistic effect of Pb975 in the hydrolysis of aldouronic acids. Pb975 helped to hydrolyze several peaks that were not hydrolyzed by Pb911 and Pb1912. The addition of Pb975 to the mixture increased the release of glucose equivalents by about 10% (FIG. 8*d*). Experiments were carried out as described in previous examples.

Example 6

Acetyl Xylan Esterase Pb1221 (SEQ ID NOs: 11 & 12)

An acetyl xylan esterase, Pb1221, was identified in *P. bryantii*. Hemicellulose usually contains acetyl groups as side chains. The linkage of the acetyl groups to the main chain is through ester bonds. The side-chain acetyl groups may inhibit hydrolysis of the main chain in hemicellulose by influencing the enzyme/substrate interaction at the active site. The side-chain acetyl groups can be cleaved by use of an enzyme called acetyl xylan esterase. As described below, Pb1221, which is one of several esterases in *P. bryantii*, was demonstrated to exhibit acetyl xylan esterase activity.

Cloning of Pb1221

The gene for the acetyl xylan esterase was amplified using the two primers shown below (PEG1221F and PEG1221R).

```
PEG1221F (Forward PCR primer)
                                        (SEQ ID NO: 82)
5'-CATATGAAGACGACTATTGATGAACATTGGGTAGG-3'

PEG1221R (Reverse PCR primer)
                                        (SEQ ID NO: 83)
5'-CTCGAGCTATCGCAGAATTTCAGCAGCATACTGTC-3'
```

The forward primer PEG1221F was designed to remove the signal peptide from the protein. The PCR product was initially cloned into the TA-cloning vector, pGEM-T, and sequenced to confirm the integrity of the coding sequence. Since the primers incorporated NdeI and XhoI sites, the gene was released from the TA-cloning plasmid and sub-cloned into a pET28a plasmid that had been digested with the same restriction enzymes (NdeI/XhoI). The product was transformed into *E. coli* JM109, and the cells were plated onto LB plates supplemented with ampicillin at 100 μg/mL and incubated at 37° C. overnight. The next day, colonies were picked and grown in LB broth supplemented with ampicillin (100 μg/mL) and cultured to saturation. Plasmids were then extracted (QIAGEN), and the inserts were sequenced to confirm the integrity of the esterase coding sequence. The NdeI site placed the gene in frame with the 6-Histidine tag encoded by the plasmid. Therefore, when the gene was expressed, the product was a N-terminally His-tagged protein.

For expression of the gene, the pET2a plasmid containing the gene was transformed into *E. coli* BL21 codon plus DE3 RIL, and the cells were plated onto LB plates supplemented with ampicillin and chloramphenicol at 100 μg/mL and 50 μg/mL, respectively, and incubated at 37° C. overnight. A single colony was picked and cultured (37° C.) in LB broth supplemented with the two antibiotics at the concentrations stated above until the O.D. at 600 nm reached 0.3. Gene expression was induced by adding 0.1 mM IPTG to the cell culture. The temperature was dropped to 16° C. and culturing was continued overnight. The cell pellet was collected through centrifugation, and proteins were released from the cells through lysis with a French press. The protein was purified through the one-step protein purification method described in Example 1 using a cobalt-charged affinity resin (TALON affinity resin, CLONTECH).

The first 20 residues of SEQ ID NO: 85 (fig|666666.450.peg.1221 [*Prevotella bryantii* B14] [putative esterase]) code for a putative signal peptide. This sequence was deleted during expression. The corresponding nucleotide sequence is SEQ ID NO: 84.

The nucleotide sequence of Pb1221 in PET-28a is found in SEQ ID NO: 86. An N-terminal tag containing six histidines was used to facilitate protein purification. The corresponding amino acid sequence is SEQ ID NO: 87.

The pET28a plasmid expressing Pb1221 contains the nucleotide sequence SEQ ID NO: 88 that encodes for the corresponding amino acid sequence SEQ ID NO: 89. Six histidines at the N-terminus were used to facilitate protein purification.

Purification and Enzyme Activity

Figure 9:
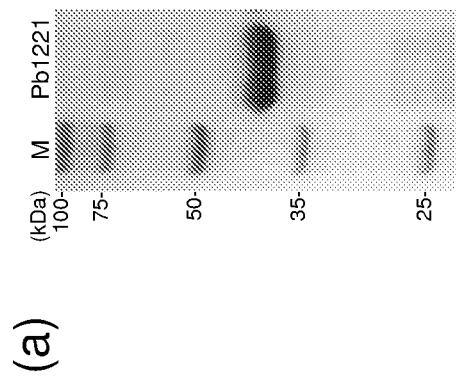
FIG. 9 shows the protein expression and activity of Pb1221. Part (a) shows SDS-PAGE of purified Pb1221 from *Prevotella bryantii*, and part (b) shows steady-state kinetic data for Pb1221.

Pb1221 was expressed and purified according to the methods described in Example 1. FIG. 9a shows an SDS-PAGE of purified Pb1221. Steady-state kinetic data for Pb1221 was determined at pH 7.0 and 40° C. (FIG. 9b). Kinetic properties of Pb1221 with 1-naphtyl acetate, 1-naphtyl phosphate and 1-naphtyl propionate as substrates were determined at 40° C. and pH 7.0 (NaH$_2$PO$_4$—Na$_2$HPO$_4$, 50 mM). The substrate concentrations ranged from 10 to 300 μM. The reactions were initiated by the addition of Pb1221 (0.5 μM, final concentration) and performed for 10 minutes at a final volume of 200 μL. The reaction was stopped by addition of 150 μL of Fast Garnet GBC (7 mM) and lauryl sulfate (10%, w/v) and incubated for 15 min at room temperature. The products were then determined by absorbance at 560 nm with 1-naphthol as a standard.

BACINT 0076 (Alternatively Named Bi4505)

A putative xylanase-esterase from *Bacteroides* intestinalis that can substitute for Pb1221 in hemicellulose enzyme-degrading mixtures was identified. The following primers were used to clone the gene (the nucleotide sequence in bold was necessary to allow cloning into pET46 as the expression vector)]:

```
BACINT 0076For
                                         (SEQ ID NO: 90)
5'-GACGACGACAAGATGCAAAGCGGCGAAACAG-3'

BACINT 0076Rev
                                         (SEQ ID NO: 91)
5'-GAGGAGAAGCCCGGTTATTTGAAAAGCAACTGTG-3'
```

SEQ ID NO: 92 contains amino acid sequence of BACINT 0076 [*Bacteroides intestinalis* DSM 17393] [xylanase-esterase]. The first 32 residues represent the predicted signal peptide that was removed during cloning. SEQ ID NO: 93 contains the corresponding nucleotide sequence.

Purification and Enzyme Activity

Figure 10:
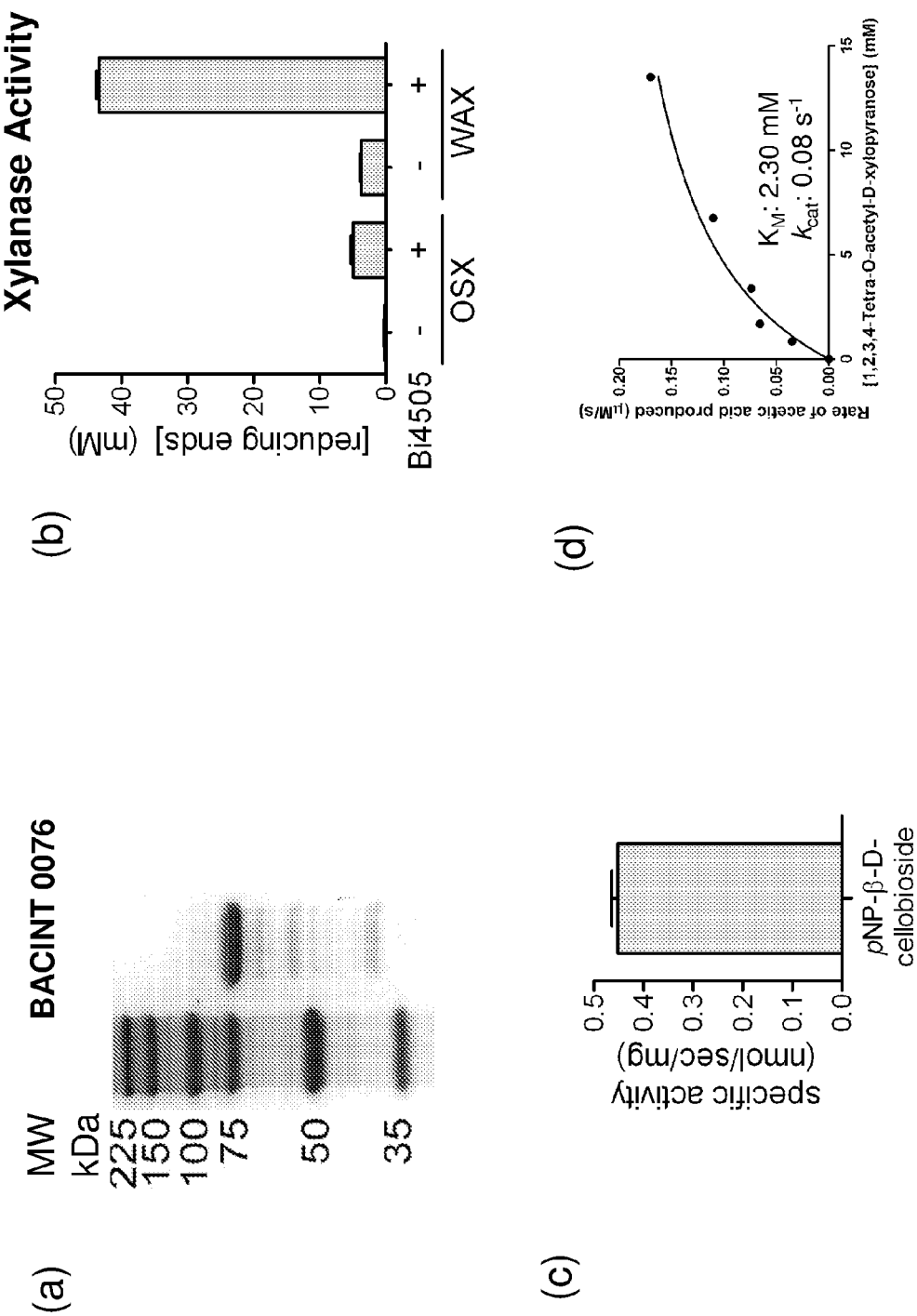
FIG. 10 shows the protein expression and activity of BACINT 0076. Part (a) shows SDS-PAGE of purified BACINT 0076, part (b) shows xylanase activity of BACINT 0076 on oat-spelt xylan (OSX) and WAX substrates, part (c) shows the specific hydrolysis activity of BACINT 0076 on pNP-β-D-cellobioside, and parts (d) through (g) show the hydrolysis kinetics of other esterase substrates.

BACINT 0076 was expressed and purified according to the methods described in Example 1 (FIG. 10a). Xylanase activity of BACINT 0076 was determined to be greater with WAX substrate compared to OSX (FIG. 10b). The specific hydrolysis activity of the enzyme on pNP-β-D-cellobioside as well as the hydrolysis kinetics of other pNP substrates were also determined (FIG. 10c-g). Experiments were performed as described in Examples 1 and 2.

Example 7

Synergistic Activity of Hemicellulase Enzyme Cocktail

Figure 11:
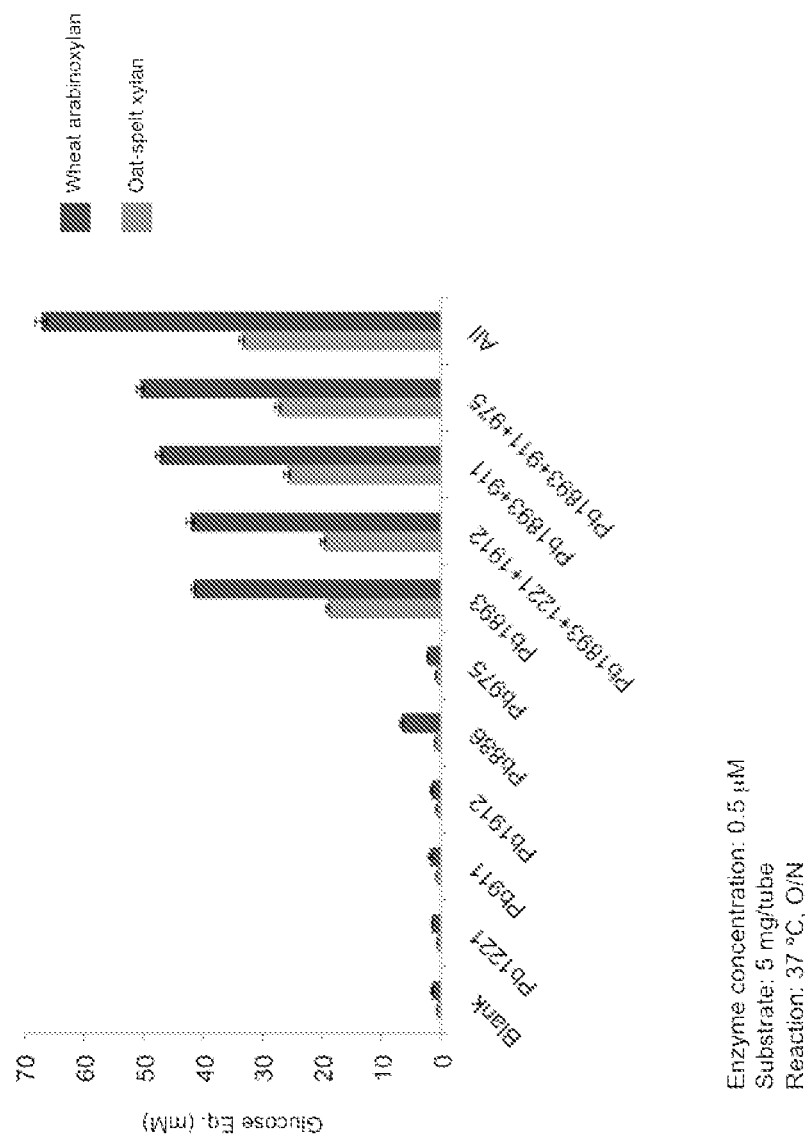
FIG. 11 shows the glucose equivalents released from WAX and OSX after treatment with hemicellulase enzyme cocktail.

The enzymes described in Examples 1-6 were combined into a hemicellulase enzyme cocktail. The synergistic activities of the enzymes in the hemicellulase cocktail are illustrated in FIG. 11. The individual enzymes and their mixtures were reacted with either wheat arabinoxylan (WAX) or oat-spelt xylan (OSX) in 50 mM sodium citrate buffer pH 5.5. "All" includes each of the enzymes in the mixture at 0.5 μM concentration: Pb1893 (endoxylanase), Pb911 (β-xylosidase), Pb975 (β-xylosidase/β-glucosidase), Pb886 (arabinofuranosidase/β-xylosidase), Pb1912 (glucuronidase), and Pb1221 (acetyl xylan esterase).

Figure 12:
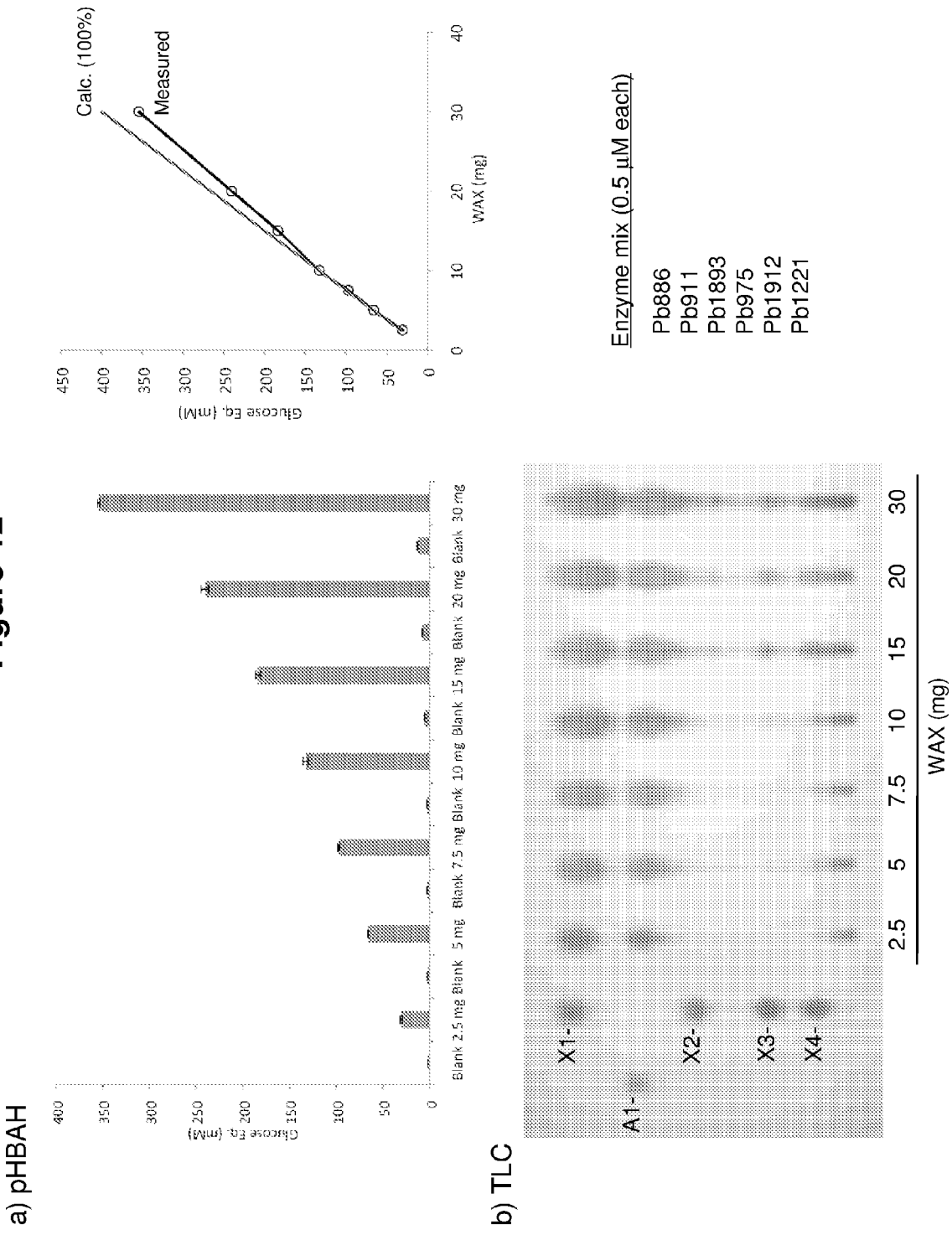
FIG. 12 shows that increasing the amount of substrate in a reaction leads to an increase in the amount of sugar released. Part (a) shows glucose equivalents released as a function of the amount of substrate, and part (b) shows TLC analysis of the enzyme mix.

The addition of higher amounts of wheat arabinoxylan substrate led to an increased release of sugar. The enzyme mixture (ALL, with each enzyme at 0.5 μM) was tested to determine if adding more substrate to the reaction mixture would lead to more or less products released (FIG. 12). Wheat arabinoxylan (WAX) was added to the reaction in amounts ranging from 2.5 milligrams to 40 milligrams. The amount of product released was determined as glucose equivalents according to the methods described in Example 1 and is presented as a histogram and line graph (FIG. 12a). TLC was used to visualize the contents of the released products (FIG. 12b). As more substrate was added, more products were released. In each case, most of the products were the five carbon sugars xylose and arabinose. Table 2 contains the calculated amount of xylose and arabinose released. Under these conditions, a substrate concentration of about 30 mg/reaction was optimal since at that concentration almost 90% of substrate was converted to fermentable sugars. The amount of enzyme mixture can be increased to increase product yield.

TABLE 2

Xylose and arabinose released with increasing amount of substrate

| | WAX (mg) | | | | | | | |
|---|---|---|---|---|---|---|---|---|
| | 2.5 | 5 | 7.5 | 10 | 15 | 20 | 30 | 40 |
| % degradation | 91.7 | 98.9 | 97.4 | 99.7 | 91.7 | 90.4 | 88.5 | 80.1 |
| total sugar (mg) | 2.3 | 4.9 | 7.3 | 10.0 | 13.8 | 18.1 | 26.6 | 32.0 |
| Xylose* (mg) | 1.4 | 2.9 | 4.3 | 5.9 | 8.1 | 10.7 | 15.7 | 18.9 |
| Arabinose* (mg) | 0.9 | 2.0 | 3.0 | 4.1 | 5.6 | 7.4 | 10.9 | 13.1 |

*Ara:Xyl = 41:59

Figure 13:
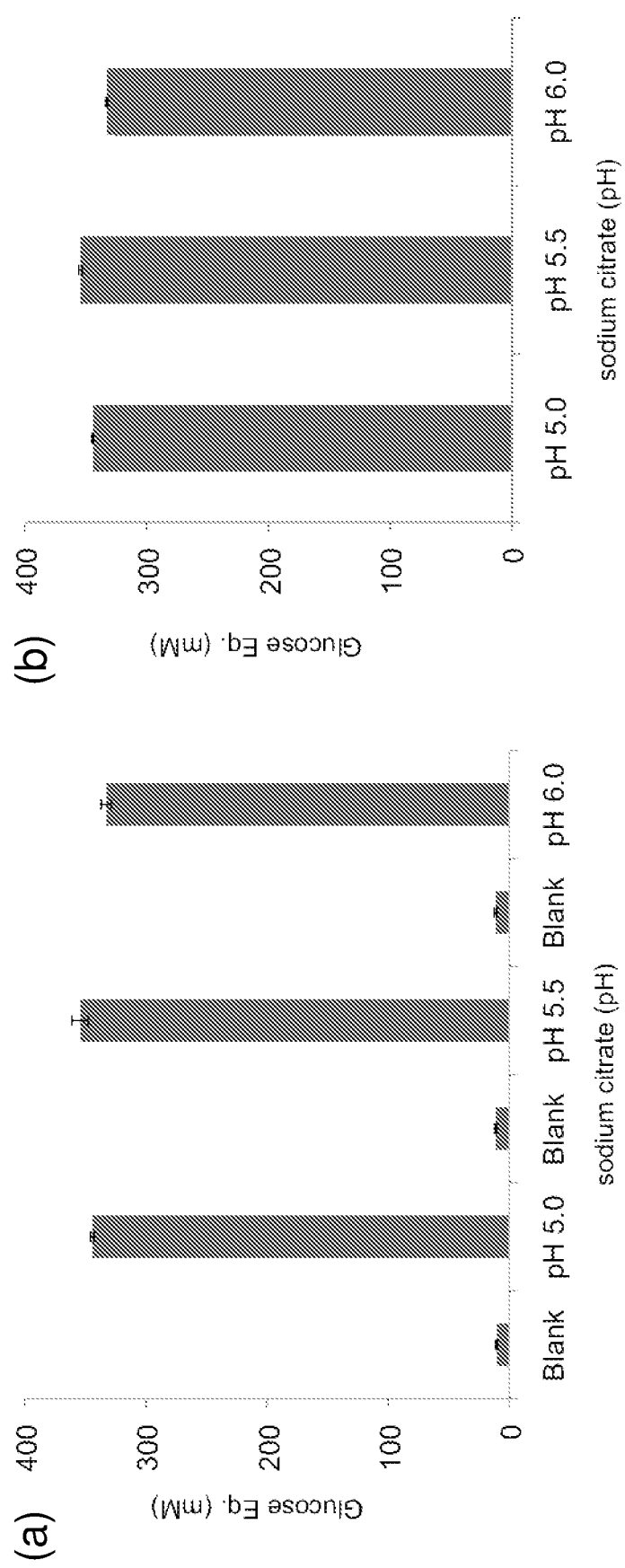
FIG. 13 shows hemicellulase activity of the enzyme mix at a pH range of 5 to 6.
Figure 14:
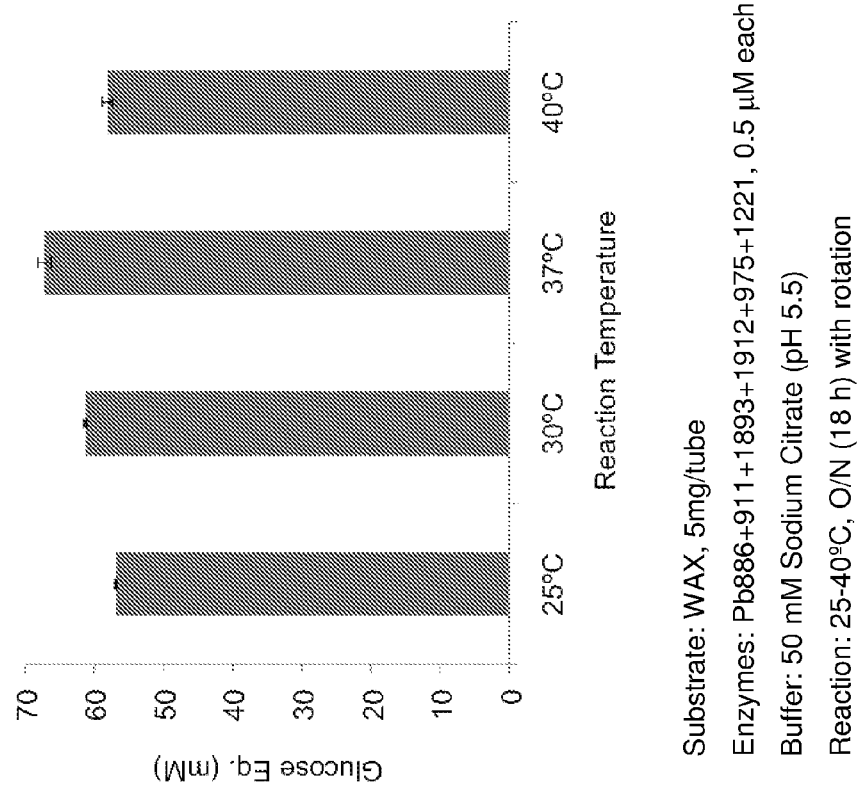
FIG. 14 shows the optimum temperature range of the hemicellulose enzyme mix.

The optimal pH and reaction temperature were also investigated. The enzyme mixture (All, with each enzyme at 0.5 μM) was reacted with WAX at 37° C. overnight in 50 mM sodium citrate at various pHs (FIG. 13). To determine optimum temperature, the enzyme mixture was reacted overnight with WAX (5 mg per tube) in 50 mM sodium citrate (pH 5.5) at various temperatures (FIG. 13).

Example 8

Beta-Xylosidase Pb398 (SEQ ID NOs: 17 & 18)

Figure 15:
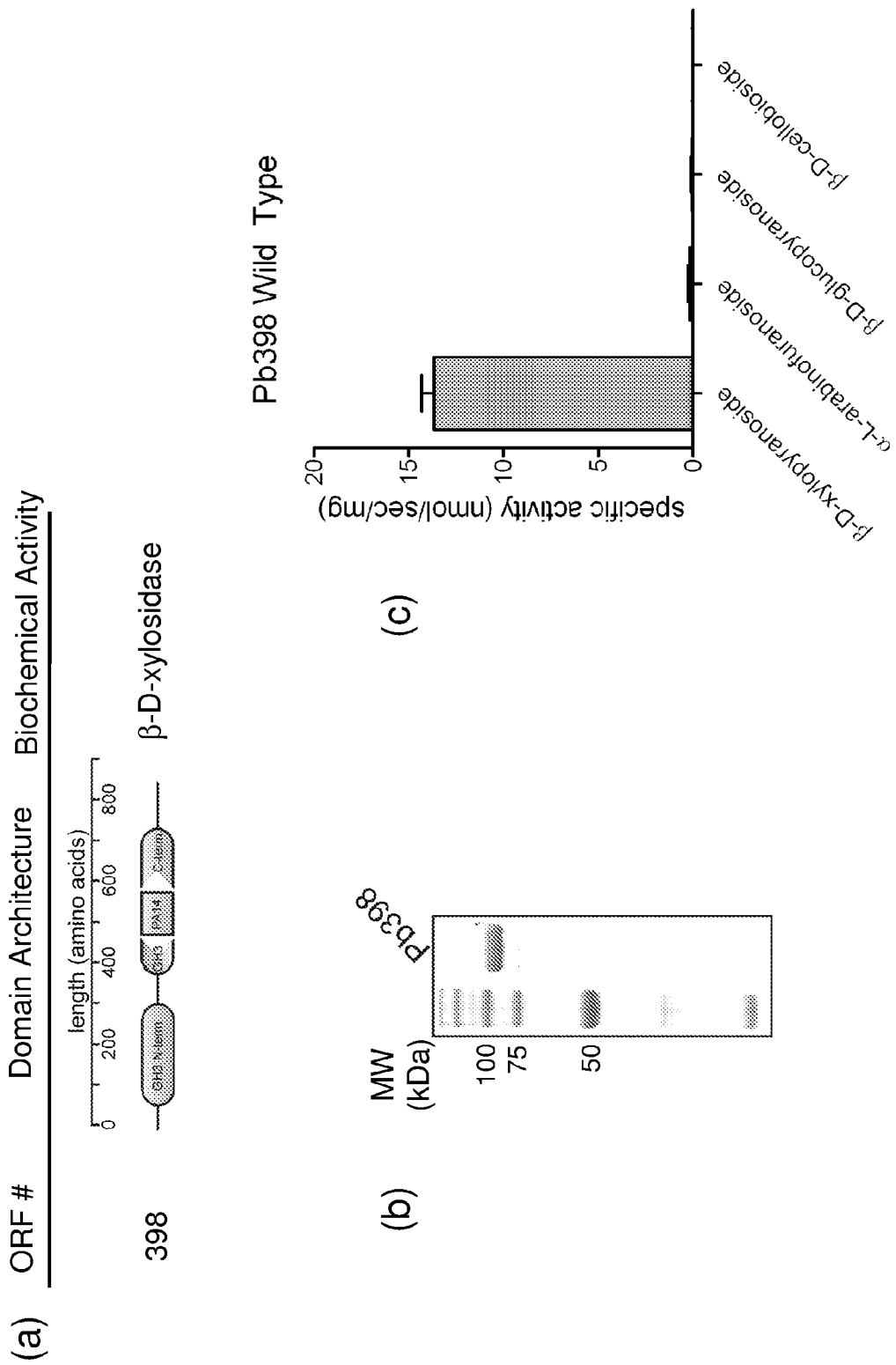
FIG. 15 shows the protein expression and activity of Pb398. Part (a) shows the domain architecture of Pb398, part (b) shows SDS-PAGE of purified Pb398 from *Prevotella bryantii*, and part (c) shows the specific activity of the hydrolysis of pNP substrates.

An additional enzyme that may be used in the enzyme cocktail is a β-xylosidase. The xylo-oligosaccharides that are produced by an endoxylanase (e.g., Pb1893) must be converted to the monomeric sugar, xylose. This process can be achieved with a β-xylosidase. *Prevotella bryantii* has four genes encoding β-xylosidase-like enzymes. All four genes were cloned and expressed as soluble proteins. As described below, the enzyme Pb398 (alternatively named Pb1917) was initially screened on pNP substrates. The results suggested that Pb398 releases mostly xylose from a β-linked pNP. The protein is 878 amino acids in length and has a molecular weight of 98.6 kDa (His-tag+truncated Pb398 protein). This protein is a GH 3 protein. Its domain architecture is shown in FIG. 15a.

Cloning of Pb398

The Pb398 gene was amplified by PCR using PrimeSTAR HS DNA polymerase (TaKaRa) and sub-cloned into pET46 Ek/LIC vector using Ek/LIC Cloning Kits (Novagen). The primer sequences and PCR protocol are below:

```
Pb398For
                                                (SEQ ID NO: 94)
5'-GACGACGACAAGATGCTCATCTGCGCTGCTGAAAAG-3'

Pb398Rev
                                                (SEQ ID NO: 95)
5'-GAGGAGAAGCCCGGTTAATTTAACGTATAATGTATCTG-3'
```

| PCR mixture | |
|---|---|
| 2.5 U/mL PrimeSTAR DNA polymerase | 0.5 |
| Genomic DNA | 1 |
| 10 mM Fw Primer | 1 |
| 10 mM Rv Primer | 1 |
| 2.5 mM dNTP Mixture | 4 |
| 5x PrimeSTAR Buffer | 10 |
| dH$_2$O | 32.5 |
| Total | 50 mL |

| PCR Protocol | | | |
|---|---|---|---|
| Denature | 98° C. | 10 sec | |
| Anneal | 55° C. | 5 sec | 30 Cycles |
| Elongate | 72° C. | 105 sec | |
| Last | 4° C. | ∞ | |

After the PCR amplification described above, the amplification of Pb398 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/mL T4 DNA Polymerase | 0.2 | 22° C. | 30 min |
| Purified PCR Product | 2.1 | 75° C. | 20 min |
| 25 mM dATP | 1 | 4° C. | ∞ |
| 100 mM DTT | 0.5 | | |
| 10x T4 DNA Polymerase Buffer | 1 | | |
| dH$_2$O | 5.2 | | |
| Total | 10 mL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 mL | | |

After the incubation, EDTA was added to the reaction.

| Annealing | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 mL | | |

The annealing mixtures for Pb398-pET46 Ek/LIC were introduced into *E. coli* JM109 by electroporation, and the cells were plated on LB-ampicillin. After overnight incubation at 37° C., three colonies were selected and used to inoculate 10 mL cultures of LB-ampicillin. The cultures were grown at 37° C. with vigorous aeration for 16 hours, and minipreps were made of the cell cultures. The plasmids were then electrophoresed on a 1% agarose gel to confirm the size of plasmid/insert DNA. Next, the integrity of the gene was confirmed by nucleotide sequencing.

Pb398 (Amino Acid Sequence)

The first 22 amino acids of SEQ ID NO: 96 (*Prevotella bryantii* ORF00398 xylosidase) were predicted to constitute a signal peptide. SEQ ID NO: 97 contains the corresponding nucleotide sequence.

The cytosine at bases 2232 and 2436 of SEQ ID NO: 98 was a potential point mutation in the gene, but since it did not change the codon, the gene was expressed without any attempt to correct it. A silent mutation was introduced at codon positions 744 and 812 of SEQ ID NO: 99. This mutation did not result in a change in the amino acid sequence.

The pET46b vector expressing Pb398 contained the nucleotide sequence SEQ ID NO: 100 and encodes the amino acid sequence SEQ ID NO: 101. The N-terminal six histidines were used to facilitate protein purification.

Purification and Enzyme Activity

Pb398 was expressed and purified according to the methods described in Example 1. FIG. 15*b* shows an SDS-PAGE of purified Pb398. FIG. 15*c* shows the results of enzymatic activity assays performed with Pb398 on pNP substrates according to the methods described in Example 2. Pb398 hydrolyzed xylose linked to pNP in a beta linkage.

Example 9

Sequence Alignments

Sequence alignments were performed with proteins from the Genbank database. Alignments were carried out with the GenBank default settings.

Pb1893 and *Prevotella bryantii* XynC (GenBank accession No. CAB01855) were found to share 99% identity.

Pb0390 and *Prevotella bryantii* endo-1,4-beta xylanase (GenBank accession No. P48789) were found to share 99% identity.

Pb886 and a *Prevotella copri* hypothetical protein (GenBank accession No. EEF20542) were found to share 66% identity.

Pb911 and a *Prevotella copri* hypothetical protein (GenBank accession No. ED052403) were found to share 76% identity.

Pb1912 and a *Prevotella copri* DSM 18205 hypothetical protein (GenBank accession No. ZP03458538) were found to share 60% identity.

Pb975 and a *Bacteroides cellulosilyticus* hypothetical protein (GenBank accession No. ZP03677923) were found to share 53% identity.

Pb1221 and a *Prevotella copri* DSM18205 hypothetical protein (EEF18747) were found to share 67% identity.

*Bacteroides intestinalis* hypothetical protein was found to share 100% identity with itself (GenBank accession No. EDV07678), 97% identity with *Bacteroides cellulosilyticus* DSM 14838 hypothetical protein (GenBank accession No. EEF91240), and 92% identity with *Bacteroides eggerthii* DSM 20697 hypothetical protein (EEC53451).

Example 10

Transcriptional Analysis of *Prevotella bryantii* B₁4 Grown on Polysaccharide and Monosaccharide Substrates

*Prevotella bryantii* B₁4 was grown anaerobically in a defined medium previously described by Griswold and Mackie (Griswold, K. E. and Mackie, R. I. 1997. Journal of Dairy Science. 80(1): 167-175.). Media preparations with two different carbohydrate sources at 0.15% w/v final concentrations were used for comparison of gene expression profiles. For one media preparation, medium viscosity wheat arabinoxylan was used from Megazyme (Bray, Ireland). This polymeric xylan substrate contains only xylose and arabinose sugars in a proportion of Ara:Xyl=41:59. In the second medium, the soluble sugars, xylose, and arabinose were used in the same proportion as that found in the polymeric wheat arabinoxylan substrate. Thus, comparison of growth patterns and gene expression profiles between the two media preparations is directly related to depolymerization of the xylan growth substrate as the energetic potential in both media preparations is equal.

Triplicate 30 mL cultures of *Prevotella bryantii* B₁4 were grown in each of the aforementioned media preparations to an optical density of 0.2, and then the cells were mixed with two volumes of Bacteria RNAprotect from QIAGEN (Valencia, Calif.). The bacteria were harvested by centrifugation. Total bacterial RNA was purified using an RNeasy Mini kit from QIAGEN with an optional on column DNase digestion and stored at −80° C. until used for microarray or cDNA sequencing analysis.

Custom 4×72 k microarray gene chips were designed and printed by Roche NimbleGen (Madison, Wis.) including 9 oligonucleotide probes in triplicate for each of the 2589 putative coding sequences within the *Prevotella bryantii* B₁4 genome. Total bacterial RNA was converted to double stranded cDNA using a superscript double stranded cDNA synthesis kit from Invitrogen (Carlsbad, Calif.). The cDNA was labeled with Cy3 dye by using a one-color labeling kit from Roche NimbleGen. The labeled oligonucleotides were hybridized with the microarray slides for 16 hours at 42° C. The slides were then washed and then scanned with a microarray scanner from Agilent (Santa Clara, Calif.). The high resolution .tiff images were then analyzed with NimbleScan software, and data analysis was performed using CLC Genomics Workbench version 3 from CLC bio (Cambridge, Mass.).

For cDNA sequencing, 1 μg of total bacterial RNA was depleted of bacterial ribosomal RNA using a RiboMinus kit from Invitrogen. Library preparation was then performed using reagents and protocols from Illumina (San Diego, Calif.), and the cDNA was sequenced using an Illumina genome analyzer. Two RNA samples were used from each growth medium, and each sample was run in an independent lane on the genome analyzer instrument. The cDNA sequencing data was then assembled onto the *P. bryantii* B₁4 reference genome using CLC Genomics Workbench version 3.

Figure 16:
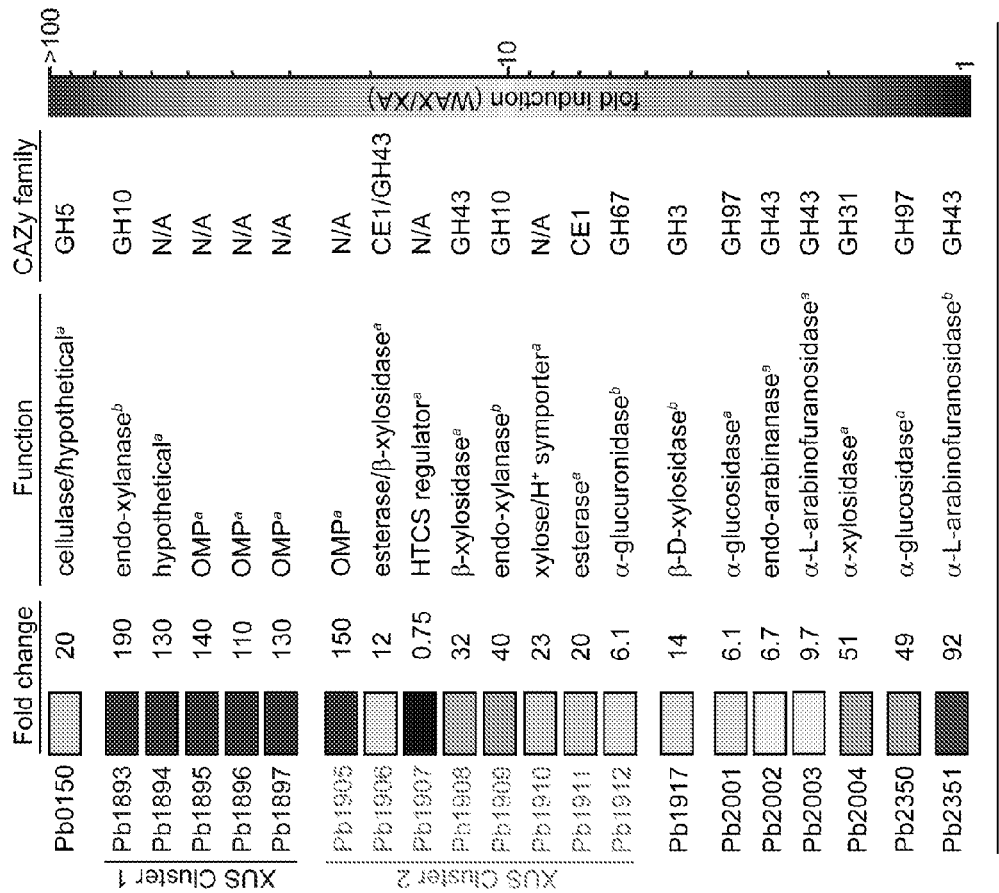
FIG. 16 shows the subset of genes found to be overexpressed by *Prevotella bryantii* when grown on WAX as determined by microarray analysis.

The microarray gene expression data is shown in FIG. 16. This data shows that a subset of genes was overexpressed by *Prevotella bryantii* B₁4 when grown on polymeric wheat arabinoxylan relative to the soluble monosaccharides, xylose and arabinose. Among the genes that were upregulated on wheat arabinoxylan compared to xylose/arabinose are Pb1893, Pb1909 (Pb0390), Pb1912, Pb1917 (Pb398), and Pb2351 (Pb886). Our biochemical data suggested that these enzymes are involved in deconstruction of polymeric xylan substrates to their constituent monosaccharides (FIGS. 2, 3, 4, 7, and 15), and these results provide validation that the microarray experiment identified genes that are involved in depolymerization of hemicellulosic polysaccharides.

Additional genes that were overexpressed in the experiment were not biochemically characterized in our studies (Pb150, Pb1894, Pb1906, Pb1908, Pb1911, Pb2001, Pb2002, Pb2003, Pb2004, and Pb2350). Although the biochemical function of these genes is currently unknown, the fact that they were overexpressed under these experimental conditions indicated that these genes and their corresponding gene products are important for the depolymerization of hemicellulose. Such genes can be cloned, and the proteins expressed for use in enzyme mixtures.

Figure 17:
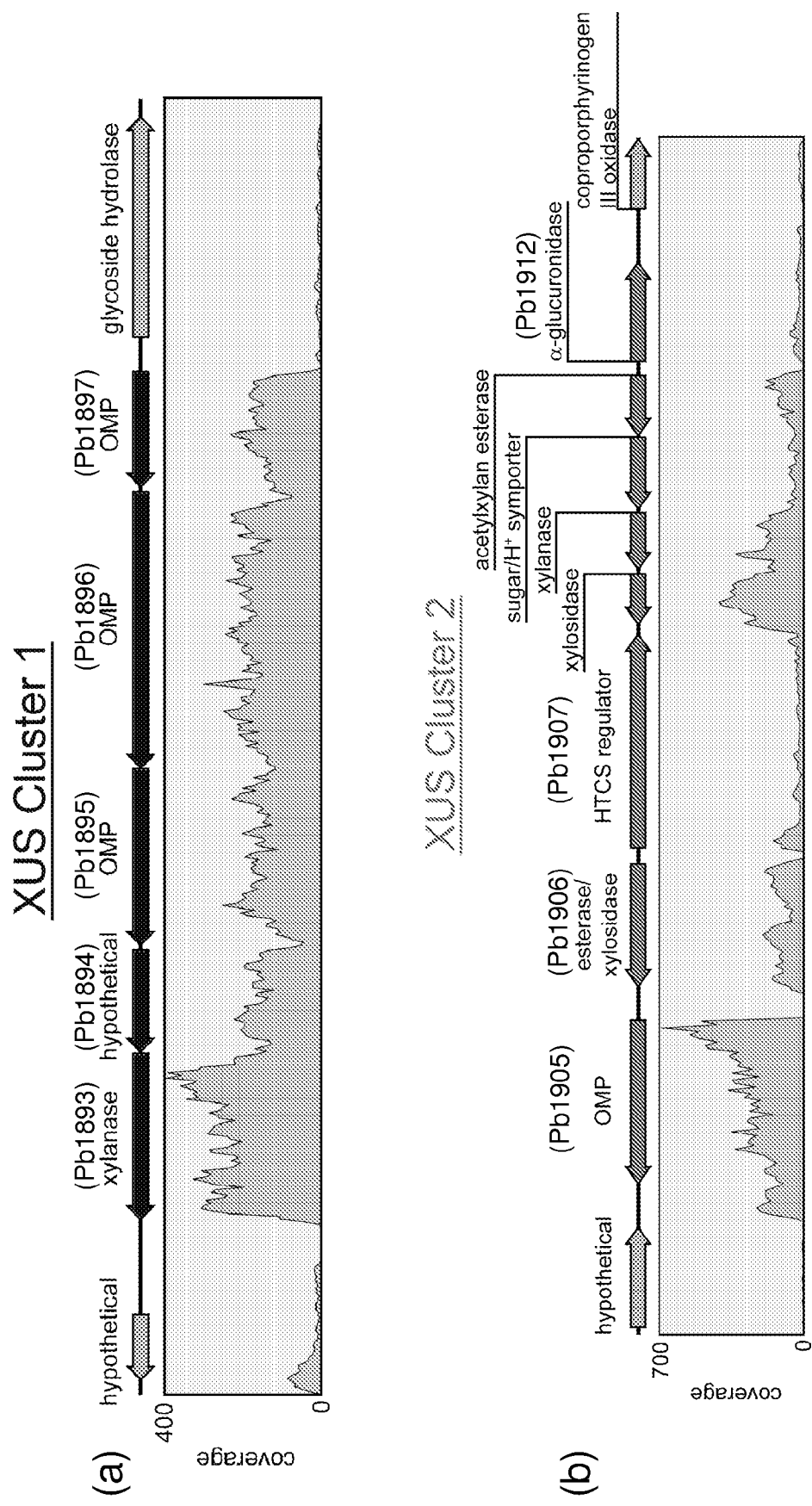
FIG. 17 shows the Xylan Utilization System (XUS) gene clusters.

The RNAseq analysis of transcript structure is shown in FIG. 17. Many bacteria coordinate the expression of genes that have related functions by expressing multiple genes from a polycistronic mRNA molecule (i.e., an operon). The RNAseq analysis showed that many of the genes that are overexpressed by *Prevotella bryantii* B₁4 during growth on polymeric wheat arabinoxylan relative to the constituent monosaccharides arabinose and xylose are arranged in operons. Specifically, Pb1893, Pb1894, Pb1895, Pb1896, and Pb1897 were found to be co-transcribed on a single messenger RNA (FIG. 17). In addition, Pb1911, Pb1910, Pb1909, and Pb1908 were also found to be co-transcribed on a single messenger RNA molecule (FIG. 17). These observations indicated that the aforementioned genes are very likely involved in the depolymerization of hemicellulose by *Prevotella bryantii* B₁4. These two regions of the chromosome for *P. bryantii* thus represent two xylan utilization systems (XUS) as indicated in FIG. 17.

The transcriptomic studies described herein indicated that the following additional genes find use in depolymerizing hemicellulose: Pb150 (SEQ ID NOs: 19 and 20), Pb1894 (SEQ ID NOs: 21 and 22), Pb1906 (SEQ ID NOs: 23 and 24), Pb1908 (SEQ ID NOs: 25 and 26), Pb1911 (SEQ ID NOs: 27 and 28), Pb2001 (SEQ ID NOs: 29 and 30), Pb2002 (SEQ ID NOs: 31 and 32), Pb2003 (SEQ ID NOs: 33 and 34), Pb2004 (SEQ ID NOs: 35 and 36), and Pb2350 (SEQ ID NOs: 37 and 38). These proteins can be used alone or in combination with the other proteins described herein.

Example 11

Improvement of Hemicellulase Enzyme Cocktail

Figure 18:
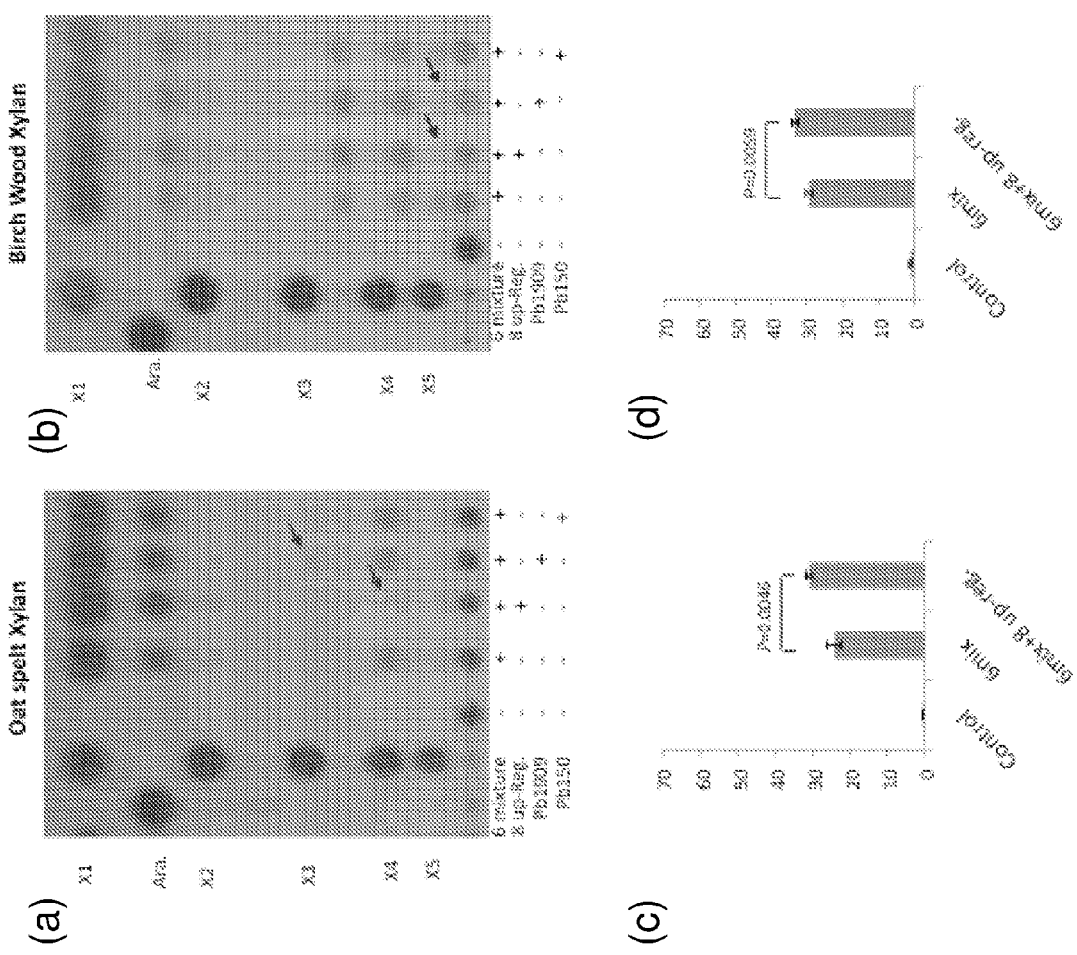
FIG. 18*a* shows TLC analysis of sugars released from oat-spelt xylan by combinations of the six-enzyme hemicellulase mix with proteins found to be upregulated in the microarray and RNAseq experiments.
FIG. 18*b* shows TLC analysis of sugars released from birch wood xylan.
FIG. 18*c* shows reducing sugar assays for the hydrolysis of oat-spelt xylan by different enzyme mixture combinations.
FIG. 18*d* shows reducing sugar assays for the hydrolysis of birch wood xylan by different enzyme mixture combinations.

Eight genes that were upregulated in the microarray and RNAseq experiments when *P. bryantii* cells were grown on arabinoxylan (Pb1909/Pb390, Pb2350, Pb1908, Pb150, Pb1917/Pb398, Pb2003, Pb2002, and Pb2001) were expressed and tested together with the six proteins (Pb1893, Pb911, Pb975, Pb886, Pb1912, Pb1221) originally constituting the mesophilic hemicellulase enzyme mix. Supplementation of the hemicellulase mix with the eight new proteins led to a significant release of reducing sugars on oat-spelt xylan and birch wood xylan (FIG. 18).

Each enzyme from the group of eight enzymes was tested individually with the original mixture of six hemicellulases. These experiments demonstrated that Pb1909 and Pb150 were responsible for the significant effects observed from the addition of the group of eight new enzymes (FIG. 18a and b). Therefore, adding Pb1909 and Pb150 to the original mix of six enzymes will improve release of sugars from hemicellulose.

What is claimed:

1. An isolated cDNA comprising a nucleotide sequence, wherein the nucleotide sequence is selected from the group consisting of SEQ ID NOs: 3, 5, 7, 9, 11, and 13.

2. A vector comprising the isolated cDNA of claim 1.

3. A composition comprising the isolated cDNA of claim 1.

4. The composition of claim 3, wherein the composition further comprises the nucleotide sequence of SEQ ID NO: 1.

5. A method for degrading hemicellulose, said method comprising the steps of:
   a) providing plant material comprising hemicellulose, wherein said hemicellulose comprises a xylose backbone comprising β-1,4-linkages and one or more functional groups; and
   b) treating said hemicellulose with an enzyme selected from of the group consisting of the enzyme comprising the amino acid sequence of SEQ ID NO: 4, the enzyme comprising the amino acid sequence of SEQ ID NO: 6, the enzyme comprising the amino acid sequence of SEQ ID NO: 8, the enzyme comprising the amino acid sequence of SEQ ID NO: 10, the enzyme comprising the amino acid sequence of SEQ ID NO: 12, and the enzyme comprising the amino acid sequence of SEQ ID NO: 14,
   wherein said treating cleaves said one or more functional groups from said xylose backbone to form cleaved hemicellulose.

6. The method of claim 5, wherein the enzyme is secreted by a transgenic *E. coli* or yeast.

7. The method of claim 5, comprising the further step of:
   c) treating said cleaved hemicellulose with a second enzyme, wherein said second enzyme comprises the amino acid sequence of SEQ ID NO: 2 and cleaves said β-1,4-linkages in said xylose backbone to produce xylose subunits,
   wherein said treating results in the degradation of at least 90% of said hemicellulose into said functional groups and said xylose subunits.

8. The method of claim 7, wherein said degradation of said hemicellulose is at least 91%, 92%, 93%, 94%, 95%, 96%, 97%, 98%, 99%, or 100% complete.

9. The method of claim 7, wherein the second enzyme is secreted by a transgenic *E. coli* or yeast.

10. The method of claim 5, wherein said one or more functional groups are selected from the group consisting of arabinose, glucuronyl, and acetyl.

11. The method of claim 5, wherein said plant material is selected from the group consisting of *Miscanthus*, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, and energy cane.

12. The method of claim 5, wherein said treating is conducted at a pH between 5 and 6.

13. The method of claim 5, wherein said treating is conducted at a temperature between 25 and 40° C.

* * * * *

SEQUENCE LISTING

<160> NUMBER OF SEQ ID NOS: 101

<210> SEQ ID NO 1
<211> LENGTH: 1623
<212> TYPE: DNA
<213> ORGANISM: Prevotella bryantii

<400> SEQUENCE: 1

| | |
|---|---|
| gaccaggata ttcctggttt cacaacggat gagcctgctg aggttatcgc tcaagacgaa | 60 |
| atcaattcat atggtacgtt gaagagctat gttaaccgtg ataaatatcc tcagtttgta | 120 |
| atggccggtg ccgttaatgc agaacagttt aaccaagtag gtcagcttta ttcgctggct | 180 |
| aaagctaact atgatgaagt ggtaacaggt aatgcgttta gtatgcttc tgttgttggt | 240 |
| tcagatggta ccttgaatac tgctacggta gagtctttg tgaataatgc tacaaatgca | 300 |
| ggtcttactg ttttcggtca tactctctgt tggcactctc agcagcaagt agcttatctg | 360 |
| aatagcctta taacagaccc taatgctact aagcatgtgc tttatatcca catgggcgaa | 420 |
| cctaaaacca caactgggga tcgtgagtta tatgttaatc ctactactga attacagagc | 480 |
| ggcaaaactt acaccttaaa gttgcgtgta aaaacttctg ctgcttgtga tgtaacggta | 540 |
| tggcctcagg gtgatgcaac tcagtattgg ccaactcctt cattcaagtc tactacagag | 600 |
| tggactactg ttgcgcaggc tttcgaggct aagagtgctt tgaagcaact tcgtttcgag | 660 |
| ttgggtactc ttggtggtga tatttggatg gatgatgtac agctactcga tccagatgga | 720 |
| ataacttga tagccaatgg tacttttgag gaaaatgcag acggttggac caagccttct | 780 |
| tggcatgaat acgaaatcaa gacggtagcc gacccagacc aagaaggtgg tggcggtggt | 840 |
| atgaccgaag aagtaaagaa agataccctt acttgggcac tcaataactt tatctctggc | 900 |
| atgatgaagg cttgtaatgg taaagttaag gcttgggatg tcgtaaatga gcctatgagt | 960 |
| gacgccgctc ctgcagaact taagaccgct ggtcgtgatg tgatcctaa gaagtgtttc | 1020 |
| ttctggcaag atcatcttgg taaagattat gcccgtttag ctgtgaagtt ggctcgtaag | 1080 |
| gctgccagcg attcggtaca gttgaaactg tttatcaacg attataatct tgaagctgct | 1140 |
| tataataaga atgctaaact tcagggtctt atcgatatga taaaatattg ggaaagcgat | 1200 |
| ggtgttacca aaattgatgg tataggtagt cagatgcacg ttacttatag catgaatcct | 1260 |
| aaaactcagg ctgctaacga ggaagcttat gtaaaccatc tgaagatgat ggcagcaaca | 1320 |
| ggtaagttgg tgcgtatctc tgagctcgat atgggtatcg cagatgcaga aggcaatacc | 1380 |
| attaatactg ctgacgttac tgaagaacag cagcagttga tggctcaata ctataagttt | 1440 |
| attgtatcga agtactttga aatcattcct gctaaccagc agtatggtat ttgtaactgg | 1500 |
| ggtcttcagg atagtcctaa aggtagtggc tggagagctg atgaacctat cggtctttgg | 1560 |
| gatgcaaatt gggtacgtaa acctgcttat gtaggcttct gtgaaggttt gaaacaggag | 1620 |
| taa | 1623 |

<210> SEQ ID NO 2
<211> LENGTH: 540
<212> TYPE: PRT
<213> ORGANISM: Prevotella bryantii

<400> SEQUENCE: 2

Asp Gln Asp Ile Pro Gly Phe Thr Thr Asp Glu Pro Ala Glu Val Ile
1               5                   10                  15

Ala Gln Asp Glu Ile Asn Ser Tyr Gly Thr Leu Lys Ser Tyr Val Asn
            20                  25                  30

```
Arg Asp Lys Tyr Pro Gln Phe Val Met Ala Gly Ala Val Asn Ala Glu
         35                  40                  45

Gln Phe Asn Gln Val Gly Gln Leu Tyr Ser Leu Ala Lys Ala Asn Tyr
 50                  55                  60

Asp Glu Val Val Thr Gly Asn Ala Phe Lys Tyr Ala Ser Val Val Gly
 65                  70                  75                  80

Ser Asp Gly Thr Leu Asn Thr Ala Thr Val Glu Ser Phe Val Asn Asn
                 85                  90                  95

Ala Thr Asn Ala Gly Leu Thr Val Phe Gly His Thr Leu Cys Trp His
                100                 105                 110

Ser Gln Gln Val Ala Tyr Leu Asn Ser Leu Ile Thr Asp Pro Asn
        115                 120                 125

Ala Thr Lys His Val Leu Tyr Ile His Met Gly Glu Pro Lys Thr Asn
        130                 135                 140

Asn Trp Asp Arg Glu Leu Tyr Val Asn Pro Thr Thr Glu Leu Gln Ser
145                 150                 155                 160

Gly Lys Thr Tyr Thr Leu Lys Leu Arg Val Lys Thr Ser Ala Ala Cys
                165                 170                 175

Asp Val Thr Val Trp Pro Gln Gly Asp Ala Thr Gln Tyr Trp Pro Thr
                180                 185                 190

Pro Ser Phe Lys Ser Thr Thr Glu Trp Thr Thr Val Ala Gln Ala Phe
        195                 200                 205

Glu Ala Lys Ser Ala Leu Lys Gln Leu Arg Phe Glu Leu Gly Thr Leu
        210                 215                 220

Gly Gly Asp Ile Trp Met Asp Asp Val Gln Leu Leu Asp Pro Asp Gly
225                 230                 235                 240

Asn Asn Leu Ile Ala Asn Gly Thr Phe Glu Glu Asn Ala Asp Gly Trp
                245                 250                 255

Thr Lys Pro Ser Trp His Glu Tyr Glu Ile Lys Thr Val Ala Asp Pro
                260                 265                 270

Asp Gln Glu Gly Gly Gly Gly Met Thr Glu Glu Val Lys Lys Asp
        275                 280                 285

Thr Leu Thr Trp Ala Leu Asn Asn Phe Ile Ser Gly Met Met Lys Ala
        290                 295                 300

Cys Asn Gly Lys Val Lys Ala Trp Asp Val Val Asn Glu Pro Met Ser
305                 310                 315                 320

Asp Ala Ala Pro Ala Glu Leu Lys Thr Ala Gly Arg Asp Gly Asp Pro
                325                 330                 335

Lys Lys Cys Phe Phe Trp Gln Asp His Leu Gly Lys Asp Tyr Ala Arg
                340                 345                 350

Leu Ala Val Lys Leu Ala Arg Lys Ala Ala Ser Asp Ser Val Gln Leu
                355                 360                 365

Lys Leu Phe Ile Asn Asp Tyr Asn Leu Glu Ala Ala Tyr Asn Lys Asn
        370                 375                 380

Ala Lys Leu Gln Gly Leu Ile Asp Met Ile Lys Tyr Trp Glu Ser Asp
385                 390                 395                 400

Gly Val Thr Lys Ile Asp Gly Ile Gly Ser Gln Met His Val Thr Tyr
                405                 410                 415

Ser Met Asn Pro Lys Thr Gln Ala Ala Asn Glu Glu Ala Tyr Val Asn
                420                 425                 430

His Leu Lys Met Met Ala Ala Thr Gly Lys Leu Val Arg Ile Ser Glu
        435                 440                 445
```

```
Leu Asp Met Gly Ile Ala Asp Ala Glu Gly Asn Thr Ile Asn Thr Ala
    450                 455                 460

Asp Val Thr Glu Glu Gln Gln Gln Leu Met Ala Gln Tyr Tyr Lys Phe
465                 470                 475                 480

Ile Val Ser Lys Tyr Phe Glu Ile Ile Pro Ala Asn Gln Gln Tyr Gly
                485                 490                 495

Ile Cys Asn Trp Gly Leu Gln Asp Ser Pro Lys Gly Ser Gly Trp Arg
                500                 505                 510

Ala Asp Glu Pro Ile Gly Leu Trp Asp Ala Asn Trp Val Arg Lys Pro
            515                 520                 525

Ala Tyr Val Gly Phe Cys Glu Gly Leu Lys Gln Glu
    530                 535                 540

<210> SEQ ID NO 3
<211> LENGTH: 1620
<212> TYPE: DNA
<213> ORGANISM: Prevotella bryantii

<400> SEQUENCE: 3
caggatgctg ttttccagaa ttttaagtat actggtaacg aaagtcgttt tgctaaaaat      60
atcgacacca gtaaagaata ttataatccg gtattggctg ttttttatcc agatccatct     120
ttatgccgta agggtgatac ctattatttg gtaaactctt cttttagttt ttatcctggt     180
gtaccattga gtacgagtaa ggatttgatt cattggaaac cggctggata tgttctcaat     240
cgtgaatctc agttgccttt gactcgccaa atatttcag gcggtatttt gctccagcg      300 atttcttata atgagaagaa taaaactttt tatatgatta ccacaaatgt gggcgcaggt     360
aacttcttcg taaagagtaa ggatcctgag aagggatgga gtgacccgat ttatcttcct     420
aaggtaaatg gtattgaccc aagtttcttc tttgataagg atggtaaagg ctatattgtt     480
cataatggtc ctgtaacagg taaacaggaa tatgagggtc agcgtgctat tcgtctttc     540 gagtttgatg tgaagggtga tagcattaag ggcgatttta cagagattgt tcgtggtggt     600
acccatgttc agaaaaatcc gatttggata gagggtccac atcttttccg tgttggcaaa     660
tattattatc tgatgtgtgc tgaaggtggt acctgtgatt ggcattctga agtaatcttc     720
cgtgccaaga gtccaaaggg tccttgggag gaatgtcctg ataaccctat attgactcag     780
cgtactggtc ttgatcctaa tcgtcctgat atcgtaacca gtgccggtca tgcagatatt     840
gtgcagagta aggaaggtga ttggtgggct gtattcctcg gctgtcgccc atatcaggat     900
gacttctata atacaggtcg tgatacttat cttttgcctg taacctggaa aaatggttgg     960
cctattattc agcctaagaa tactgcaatt cctgctgtta gcaagatgac gaagtggcag    1020
gaaaaactga gtgcaggact gaagaatcag ggtgaattct ctggtaattt cagctatgaa    1080
gataagtttg atggtgaaag cttaaatcag cgttggatgt tccttcgtaa tccttctgct    1140
ttctggaaga cctcttccga gggattggtg atttctccaa acatgctaa gattaatgaa    1200 aaggagagtc cttctgttat ctttactcgt cagcagcata ctaactttac tgctgagact    1260
actgttcgtt tcgctcctac aagtgaaaaa acacaggctg gtttggtttt gatgcagaaa    1320
gaggatcata acttcgtgtt tgtcaaaact cttcgtgctg gtaaaccggt acttgttctt    1380
gaaagagctg aacgtggtaa tgcggttata gcttctacgg aattgacagg tgtacatgct    1440
gctggtaacg aacctcttcg tctcaaggtg gtaggtaacg gtcgttacta tgatttctat    1500
tatgcagagt gtgatgctga ttaccagctc ttagctaagg gtgtcgatgc tgttaatttg    1560
agtacacacc agagtggtgg tttcattggt gcggtaatcg gactttatgc tgtgaaataa    1620
```

```
<210> SEQ ID NO 4
<211> LENGTH: 539
<212> TYPE: PRT
<213> ORGANISM: Prevotella bryantii

<400> SEQUENCE: 4

Gln Asp Ala Val Phe Gln Asn Phe Lys Tyr Thr Gly Asn Glu Ser Arg
 1               5                  10                  15

Phe Ala Lys Asn Ile Asp Thr Ser Lys Glu Tyr Tyr Asn Pro Val Leu
            20                  25                  30

Ala Gly Phe Tyr Pro Asp Pro Ser Leu Cys Arg Lys Gly Asp Thr Tyr
        35                  40                  45

Tyr Leu Val Asn Ser Ser Phe Ser Phe Tyr Pro Gly Val Pro Leu Ser
    50                  55                  60

Thr Ser Lys Asp Leu Ile His Trp Lys Pro Ala Gly Tyr Val Leu Asn
65                  70                  75                  80

Arg Glu Ser Gln Leu Pro Leu Thr Arg Gln Asn Ile Ser Gly Gly Ile
                85                  90                  95

Phe Ala Pro Ala Ile Ser Tyr Asn Glu Lys Asn Lys Thr Phe Tyr Met
            100                 105                 110

Ile Thr Thr Asn Val Gly Ala Gly Asn Phe Phe Val Lys Ser Lys Asp
        115                 120                 125

Pro Glu Lys Gly Trp Ser Asp Pro Ile Tyr Leu Pro Lys Val Asn Gly
    130                 135                 140

Ile Asp Pro Ser Phe Phe Phe Asp Lys Asp Gly Lys Gly Tyr Ile Val
145                 150                 155                 160

His Asn Gly Pro Val Thr Gly Lys Gln Glu Tyr Glu Gly Gln Arg Ala
                165                 170                 175

Ile Arg Leu Phe Glu Phe Asp Val Lys Gly Asp Ser Ile Lys Gly Asp
            180                 185                 190

Phe Thr Glu Ile Val Arg Gly Gly Thr His Val Gln Lys Asn Pro Ile
        195                 200                 205

Trp Ile Glu Gly Pro His Leu Phe Arg Val Gly Lys Tyr Tyr Tyr Leu
    210                 215                 220

Met Cys Ala Glu Gly Gly Thr Cys Asp Trp His Ser Glu Val Ile Phe
225                 230                 235                 240

Arg Ala Lys Ser Pro Lys Gly Pro Trp Glu Glu Cys Pro Asp Asn Pro
                245                 250                 255

Ile Leu Thr Gln Arg Thr Gly Leu Asp Pro Asn Arg Pro Asp Ile Val
            260                 265                 270

Thr Ser Ala Gly His Ala Asp Ile Val Gln Ser Lys Glu Gly Asp Trp
        275                 280                 285

Trp Ala Val Phe Leu Gly Cys Arg Pro Tyr Gln Asp Asp Phe Tyr Asn
    290                 295                 300

Thr Gly Arg Asp Thr Tyr Leu Leu Pro Val Thr Trp Lys Asn Gly Trp
305                 310                 315                 320

Pro Ile Ile Gln Pro Lys Asn Thr Ala Ile Pro Ala Val Ser Lys Met
                325                 330                 335

Thr Lys Trp Gln Glu Lys Leu Ser Ala Gly Leu Lys Asn Gln Gly Glu
            340                 345                 350

Phe Ser Gly Asn Phe Ser Tyr Glu Asp Lys Phe Asp Gly Glu Ser Leu
        355                 360                 365

Asn Gln Arg Trp Met Phe Leu Arg Asn Pro Ser Ala Phe Trp Lys Thr
```

```
                370                 375                 380
Ser Ser Glu Gly Leu Val Ile Ser Pro Lys His Ala Lys Ile Asn Glu
385                 390                 395                 400

Lys Glu Ser Pro Ser Val Ile Phe Thr Arg Gln Gln His Thr Asn Phe
            405                 410                 415

Thr Ala Glu Thr Thr Val Arg Phe Ala Pro Thr Ser Glu Lys Thr Gln
                420                 425                 430

Ala Gly Leu Val Leu Met Gln Lys Glu Asp His Asn Phe Val Phe Val
            435                 440                 445

Lys Thr Leu Arg Ala Gly Lys Pro Val Leu Val Leu Glu Arg Ala Glu
            450                 455                 460

Arg Gly Asn Ala Val Ile Ala Ser Thr Glu Leu Thr Gly Val His Ala
465                 470                 475                 480

Ala Gly Asn Glu Pro Leu Arg Leu Lys Val Val Gly Asn Gly Arg Tyr
                485                 490                 495

Tyr Asp Phe Tyr Tyr Ala Glu Gly Asp Ala Asp Tyr Gln Leu Leu Ala
            500                 505                 510

Lys Gly Val Asp Ala Val Asn Leu Ser Thr His Gln Ser Gly Gly Phe
            515                 520                 525

Ile Gly Ala Val Ile Gly Leu Tyr Ala Val Lys
            530                 535

<210> SEQ ID NO 5
<211> LENGTH: 2274
<212> TYPE: DNA
<213> ORGANISM: Prevotella bryantii

<400> SEQUENCE: 5
caaactatac ttattaatca gcaggttgac gctctttacg atagaatgtc gcaggaagaa      60
cgcattaacc aattacgtag tggatatatg gatgacttgt ttgatgaaca gggtaatctg    120
gataccgtaa aatgtaaaga gttgattccg tttggtatcg gtcacttctc tcaatatgcc    180
agccaaaaac cgctcgatgc aaatattctt cgagaccgcg ttgctgctgt acaagactgg    240
ctcatacatc atactcctaa cggaattcct gctctattcc acgaagaagt gctctcgggt    300
gttaacacga aagatgctac gatctatcca caacaaatag acaagcatg ctcttttaat    360
cccgaactag ctgagcgaaa gaccttacaa acgggtatcg atatgcgcaa aatgggaggc    420
gtactctcct tatcgcctat ggtagacgta tgccgaaatc caagtttcaa ccggctcgaa    480
gagtcgtatg gcgaagatgg gtatctgtca gctgtaatgg gtactgcctt tgtcaaggga    540
ttgcaacagg gcgacttaac caagggtgtg ggggcttgca gcaagcacta tctcggatat    600
ggtggcggag gcgatgctaa ggaaaaggag atgatggaag aaattctact tcctcacgaa    660
acaatgattc gactggctgg aagcaaagcg ctgatgcctg ttatcacgc tgtacatggt    720
actaactgtg tagctaatca tgagatactg accgatattc ttcgtggcta tctcggcttc    780
gatggtatgg tggttagtga ctatacagcc atagaccaaa ttcctggtct tgatactcct    840
cttcagaagg ctactgcagc gatcaacgct ggcaacgatg tggattttcc gcatggggcc    900
aactataagt tcctgcagga aggtctcgat aaaggtatgg ttaagtccga ggcttttgag    960
cgtgctgtaa agatgttct tcgccataaa tatcgccaag ggctcttcga caagaacgct   1020
tatctctaca gcaaagatcc tattcagctc gatagtaagg aggagcgaca gactgcctac   1080
gatatcgcta cacaaagtgt cgttttactt gaaaataaag ggatattacc gcttcgaggc   1140
aaacagaata tcttcgtcac aggtccgaat gcgaatacaa tgtgggccat gtgtggtgac   1200
```

```
tattcgttcc cggcaatgac ttatttctgg aagaaggtaa ctgaagatct tgaccatcct    1260
catatcgtga aactcctcga aggtatgaaa gaccgaaagc ctgcggggat aaatatttct    1320
tattcccgcg gatgtgactg gactgatact atcgaaacca gtatgctgt atctggtgat    1380 gaacgtgctt gggaatacga ggtattacat cgtaaggtcg attctggtga aaaggctgat    1440
gaaactgaag ctctggccat ggcaaaggag gcggatgtta tcatcgcagc tgttggtgag    1500
aatgtaatgc tatgtggcga aaatcgtgat cgacaggggc tttgcctccc gggacatcag    1560
gaacaatatg tagaacgact tctggctaca ggaaaacctg ttgtgctggt gttttttggt    1620
ggaagagcgc aagtcatctc taacattgcc aaccgttgtg ctgctgttat ccaggcttgg    1680
tatcctggtg aggaaggtgg tcatgctgtt gcagatattc tctacggtaa cgtgtctcca    1740
tcagctaaac tttctgtaag ttatccgaat gtagaactga cgagcctat ctgctataac    1800 tattctgcca acaggattc acgtgtggct tggccttcg gctatggtct gagctatacc    1860
actttcgact atagtaatct tgaagttcct acagaagtga agacttctga tgaaagcttg    1920
catatcgcat tcgaagtagc aaatacggga aaaatggatg ctgatgaaat cgctcaggtt    1980
tacttgtctc ctactcaaga gaatcagaat atccgcccta tccaactgca gggctttgcc    2040
cgcatatcac tcaaggctgg tgagcgtaag aaagtaaagg taaaactcta cactgaacag    2100
tttggctatt attctaacaa cggtaaacga caatggaata tcgcccctgg cacatttacg    2160
gtcaagatag gagcctcatc acaggatatc aaattgcaaa aaaatataac cgtcaaggga    2220
gatatcgtag tgaaaccttt gcgtgatttt tacttctctg aagtcatcaa gtga           2274
```

<210> SEQ ID NO 6
<211> LENGTH: 757
<212> TYPE: PRT
<213> ORGANISM: Prevotella bryantii

<400> SEQUENCE: 6

```
Gln Thr Ile Leu Ile Asn Gln Gln Val Asp Ala Leu Tyr Asp Arg Met
 1               5                  10                  15

Ser Gln Glu Glu Arg Ile Asn Gln Leu Arg Ser Gly Tyr Met Asp Asp
            20                  25                  30

Leu Phe Asp Glu Gln Gly Asn Leu Asp Thr Val Lys Cys Lys Glu Leu
        35                  40                  45

Ile Pro Phe Gly Ile Gly His Phe Ser Gln Tyr Ala Ser Gln Lys Pro
    50                  55                  60

Leu Asp Ala Asn Ile Leu Arg Asp Arg Val Ala Ala Val Gln Asp Trp
65                  70                  75                  80

Leu Ile His His Thr Pro Asn Gly Ile Pro Ala Leu Phe His Glu Glu
                85                  90                  95

Val Leu Ser Gly Val Asn Thr Lys Asp Ala Thr Ile Tyr Pro Gln Gln
           100                 105                 110

Ile Gly Gln Ala Cys Ser Phe Asn Pro Glu Leu Ala Glu Arg Lys Thr
       115                 120                 125

Leu Gln Thr Gly Ile Asp Met Arg Lys Met Gly Gly Val Leu Ser Leu
   130                 135                 140

Ser Pro Met Val Asp Val Cys Arg Asn Pro Phe Asn Arg Leu Glu
145                 150                 155                 160

Glu Ser Tyr Gly Glu Asp Gly Tyr Leu Ser Ala Val Met Gly Thr Ala
                165                 170                 175

Phe Val Lys Gly Leu Gln Gln Gly Asp Leu Thr Lys Gly Val Gly Ala
```

-continued

```
            180                 185                 190
Cys Ser Lys His Tyr Leu Gly Tyr Gly Gly Gly Asp Ala Lys Glu
        195                 200                 205
Lys Glu Met Met Glu Glu Ile Leu Leu Pro His Glu Thr Met Ile Arg
210                 215                 220
Leu Ala Gly Ser Lys Ala Leu Met Pro Gly Tyr His Ala Val His Gly
225                 230                 235                 240
Thr Asn Cys Val Ala Asn His Glu Ile Leu Thr Asp Ile Leu Arg Gly
            245                 250                 255
Tyr Leu Gly Phe Asp Gly Met Val Val Ser Asp Tyr Thr Ala Ile Asp
            260                 265                 270
Gln Ile Pro Gly Leu Asp Thr Pro Leu Gln Lys Ala Thr Ala Ala Ile
            275                 280                 285
Asn Ala Gly Asn Asp Val Asp Phe Pro His Gly Ala Asn Tyr Lys Phe
            290                 295                 300
Leu Gln Glu Gly Leu Asp Lys Gly Met Val Lys Ser Glu Ala Phe Glu
305                 310                 315                 320
Arg Ala Val Lys Asp Val Leu Arg His Lys Tyr Arg Gln Gly Leu Phe
            325                 330                 335
Asp Lys Asn Ala Tyr Leu Tyr Ser Lys Asp Pro Ile Gln Leu Asp Ser
            340                 345                 350
Lys Glu Glu Arg Gln Thr Ala Tyr Asp Ile Ala Thr Gln Ser Val Val
            355                 360                 365
Leu Leu Glu Asn Lys Gly Ile Leu Pro Leu Arg Gly Lys Gln Asn Ile
            370                 375                 380
Phe Val Thr Gly Pro Asn Ala Asn Thr Met Trp Ala Met Cys Gly Asp
385                 390                 395                 400
Tyr Ser Phe Pro Ala Met Thr Tyr Phe Trp Lys Lys Val Thr Glu Asp
            405                 410                 415
Leu Asp His Pro His Ile Val Lys Leu Leu Glu Gly Met Lys Asp Arg
            420                 425                 430
Lys Pro Ala Gly Ile Asn Ile Ser Tyr Ser Arg Gly Cys Asp Trp Thr
            435                 440                 445
Asp Thr Ile Glu Thr Lys Tyr Ala Val Ser Gly Asp Glu Arg Ala Trp
            450                 455                 460
Glu Tyr Glu Val Leu His Arg Lys Val Asp Ser Gly Lys Ala Asp
465                 470                 475                 480
Glu Thr Glu Ala Leu Ala Met Ala Lys Glu Ala Asp Val Ile Ala
            485                 490                 495
Ala Val Gly Glu Asn Val Met Leu Cys Gly Glu Asn Arg Asp Arg Gln
            500                 505                 510
Gly Leu Cys Leu Pro Gly His Gln Glu Gln Tyr Val Glu Arg Leu Leu
            515                 520                 525
Ala Thr Gly Lys Pro Val Val Leu Val Val Phe Gly Gly Arg Ala Gln
            530                 535                 540
Val Ile Ser Asn Ile Ala Asn Arg Cys Ala Ala Val Ile Gln Ala Trp
545                 550                 555                 560
Tyr Pro Gly Glu Glu Gly Gly His Ala Val Ala Asp Ile Leu Tyr Gly
            565                 570                 575
Asn Val Ser Pro Ser Ala Lys Leu Ser Val Ser Tyr Pro Asn Val Glu
            580                 585                 590
Leu Asn Glu Pro Ile Cys Tyr Asn Tyr Ser Ala Lys Gln Asp Ser Arg
            595                 600                 605
```

```
Val Ala Trp Pro Phe Gly Tyr Gly Leu Ser Tyr Thr Thr Phe Asp Tyr
        610                 615                 620

Ser Asn Leu Glu Val Pro Thr Glu Val Lys Thr Ser Asp Glu Ser Leu
625                 630                 635                 640

His Ile Ala Phe Glu Val Ala Asn Thr Gly Lys Met Asp Ala Asp Glu
                645                 650                 655

Ile Ala Gln Val Tyr Leu Ser Pro Thr Gln Glu Asn Gln Asn Ile Arg
            660                 665                 670

Pro Ile Gln Leu Gln Gly Phe Ala Arg Ile Ser Leu Lys Ala Gly Glu
        675                 680                 685

Arg Lys Lys Val Lys Val Lys Leu Tyr Thr Glu Gln Phe Gly Tyr Tyr
    690                 695                 700

Ser Asn Asn Gly Lys Arg Gln Trp Asn Ile Ala Pro Gly Thr Phe Thr
705                 710                 715                 720

Val Lys Ile Gly Ala Ser Ser Gln Asp Ile Lys Leu Gln Lys Asn Ile
                725                 730                 735

Thr Val Lys Gly Asp Ile Val Val Lys Pro Leu Arg Asp Phe Tyr Phe
            740                 745                 750

Ser Glu Val Ile Lys
        755

<210> SEQ ID NO 7
<211> LENGTH: 2511
<212> TYPE: DNA
<213> ORGANISM: Prevotella bryantii

<400> SEQUENCE: 7
caacatttac cttatcaaaa tccttcttta tcggcagaac aaagagcaga agatctctgt      60
agtcgattaa cattagaaga aaaatgtaaa ctcatgcaaa atggttctcc agccatcaaa     120
agactcaaca taccagcatt cgaatggtgg agcgaagccc tgcatggcac agcccgcaac     180
ggatttgcta ctgtatttcc taatacaaca ggcatggcgg cttcatggaa tgatcagtta     240
cttctgcaga ttttttcagc tataggtaat gaatcacgta ttaaaaatac actggctcgc     300
aaatcaggaa acataaaaag atatcaaggc ctttctatct ggacaccaaa tatcaatatt     360
ttcagagatc cacgttgggg aagaggtcaa gaaacttatg gtgaagatcc gtatctgaca     420
ggtaagatgg gactagctgt tgtagaaggt ttacaaggac taaaaatag caaatattat      480 aaactacttg cttgtgccaa acattttgcc gtacatagtg gtcccgaata tctccgacat     540
tcatttaaca tcgaaaatct gcccgcaaga gatctttggg aaacctatct accagcattc     600
aagacattaa acaagaagg caatgtagcc gaagttatgt gtgcatatca tagtatggat      660
ggtctacctt gctgtggtag taacaagtat cttcaacaaa tattacgtca agacttagga     720
ttcaaaggaa tggttgttag tgattgtggt gctattggtg atttctggat acaaggcaga     780
catgaagttg ctcaagacgc agcacaagca tcagctcaag cagtactggc aggaacagac     840
gtagaatgtg gagcaaacta tgataaatta ccagaagctg taaaaagagg agaaatatca     900
gaagaaaaaa ttaatgtaag cgtaatgcgt ctgcttaaag ctagatttaa actcggtgac     960
tttgattctg ataacatggt ggaatggaca caactaccag aaagcctcat tgcttgctct    1020
aaacataaac agcttgccta ccaaatggct caagaatcaa tgacacttct taaaaataat    1080
ggtatacttc ccctccaaaa gaatgcaaga attgcagtta tgggagcaaa tgccaacgat    1140
tcaatcatgc tttggggcaa ctataacggc tatcctacaa aaactatcag tatactagaa    1200
```

-continued

```
ggcttgcaaa ataaaagcaa acatatatca tatattccag gatgtggtct gaccaaaaac    1260
gaattcattg acagtagatt cagccaattc aaaactcctg atggcaaagt tggtatgcgc    1320
gcaacttact ggaacaatac taaaatgaat ggtacaccag ccactactat ggatattact    1380
gagcctatca atctcagtaa cggtggagca accgttttcg cccctggtgt aaatttagaa    1440 cactttctg ctaaatatga aggaaccttc catgcaaata atcagaaga tattcaccta     1500 aaactttcaa gtgatgattt ggctcgcata attatagacg gtgacaccat aatcaatagt    1560
tggaaagcac gcgaaagagt caatgtaagt gataaaattg tacatgtaga agccaacaaa    1620
gattataaga tacaaataga ttatgtacag aatgacgcag ctgctatcat acaattcgac    1680
cttgggccat tagtaaagat gaccgaaaaa gagctcttac aaaaagtagg ggatgcccag    1740
gttgtcatct atgttggtgg tatatcacca agattagaag gtgaagaaat gaaagtaaac    1800
gaacttggat ttaaaggagg cgatcgaacc actatagaac ttccacaatc tcagcgtgat    1860
atgatagctt tacttcacaa ctctggtaaa aaagtaatat ttgtaaactg ttcgggtggc    1920
gcaatagctc ttgaaccgga aagcagaaat gcagatgcca ttttacaagc ttggtatgga    1980
ggagagatgg gtggacaagc agtcgctgat gttctctttg gtgattataa tccaaatgga    2040
aaattacctg taaccttcta caagaatgat agtcagctac ctgactataa tgattataca    2100
atgaaaggta aacgtatcg ttatctgcac caagctcctc tttatccttt cggatatgga    2160
ttaagctata ccacatttgc atacgataat gccaaatatg accgtcgaaa gggcaacctc    2220
tctctagaag ttaccaatac tggtaaatgc gaaggcacta caacgataca agtatacata    2280
cgacggactg cagatataaa tggacctata aaaacattaa aagctttcca aaaagtttca    2340
ttgcaagcta atgaaaagaa aagagttaca ataaatctac ctcgcgaacg ttttgaagga    2400
tgggatgaaa cgactaacac gatgcgaata gtccctggaa aatacgaaat catggttggc    2460
caacatagtg acgatcctga tatgaaaaaa ttaattattt acctaaaata a            2511
```

```
<210> SEQ ID NO 8
<211> LENGTH: 836
<212> TYPE: PRT
<213> ORGANISM: Prevotella bryantii

<400> SEQUENCE: 8
```

```
Gln His Leu Pro Tyr Gln Asn Pro Ser Leu Ser Ala Glu Gln Arg Ala
 1               5                  10                  15

Glu Asp Leu Cys Ser Arg Leu Thr Leu Glu Glu Lys Cys Lys Leu Met
            20                  25                  30

Gln Asn Gly Ser Pro Ala Ile Lys Arg Leu Asn Ile Pro Ala Phe Glu
        35                  40                  45

Trp Trp Ser Glu Ala Leu His Gly Thr Ala Arg Asn Gly Phe Ala Thr
    50                  55                  60

Val Phe Pro Asn Thr Thr Gly Met Ala Ala Ser Trp Asn Asp Gln Leu
65                  70                  75                  80

Leu Leu Gln Ile Phe Ser Ala Ile Gly Asn Glu Ser Arg Ile Lys Asn
                85                  90                  95

Thr Leu Ala Arg Lys Ser Gly Asn Ile Lys Arg Tyr Gln Gly Leu Ser
            100                 105                 110

Ile Trp Thr Pro Asn Ile Asn Ile Phe Arg Asp Pro Arg Trp Gly Arg
        115                 120                 125

Gly Gln Glu Thr Tyr Gly Glu Asp Pro Tyr Leu Thr Gly Lys Met Gly
    130                 135                 140
```

```
Leu Ala Val Val Glu Gly Leu Gln Gly Pro Lys Asn Ser Lys Tyr Tyr
145                 150                 155                 160

Lys Leu Leu Ala Cys Ala Lys His Phe Ala Val His Ser Gly Pro Glu
            165                 170                 175

Tyr Leu Arg His Ser Phe Asn Ile Glu Asn Leu Pro Ala Arg Asp Leu
        180                 185                 190

Trp Glu Thr Tyr Leu Pro Ala Phe Lys Thr Leu Ile Gln Glu Gly Asn
        195                 200                 205

Val Ala Glu Val Met Cys Ala Tyr His Ser Met Asp Gly Leu Pro Cys
210                 215                 220

Cys Gly Ser Asn Lys Tyr Leu Gln Gln Ile Leu Arg Gln Asp Leu Gly
225                 230                 235                 240

Phe Lys Gly Met Val Val Ser Asp Cys Gly Ala Ile Gly Asp Phe Trp
            245                 250                 255

Ile Gln Gly Arg His Glu Val Ala Gln Asp Ala Ala Gln Ala Ser Ala
        260                 265                 270

Gln Ala Val Leu Ala Gly Thr Asp Val Glu Cys Gly Ala Asn Tyr Asp
        275                 280                 285

Lys Leu Pro Glu Ala Val Lys Arg Gly Glu Ile Ser Glu Glu Lys Ile
    290                 295                 300

Asn Val Ser Val Met Arg Leu Leu Lys Ala Arg Phe Lys Leu Gly Asp
305                 310                 315                 320

Phe Asp Ser Asp Asn Met Val Glu Trp Thr Gln Leu Pro Glu Ser Leu
            325                 330                 335

Ile Ala Cys Ser Lys His Lys Gln Leu Ala Tyr Gln Met Ala Gln Glu
            340                 345                 350

Ser Met Thr Leu Leu Lys Asn Asn Gly Ile Leu Pro Leu Gln Lys Asn
        355                 360                 365

Ala Arg Ile Ala Val Met Gly Ala Asn Ala Asn Asp Ser Ile Met Leu
    370                 375                 380

Trp Gly Asn Tyr Asn Gly Tyr Pro Thr Lys Thr Ile Ser Ile Leu Glu
385                 390                 395                 400

Gly Leu Gln Asn Lys Ser Lys His Ile Ser Tyr Ile Pro Gly Cys Gly
            405                 410                 415

Leu Thr Lys Asn Glu Phe Ile Asp Ser Arg Phe Ser Gln Phe Lys Thr
        420                 425                 430

Pro Asp Gly Lys Val Gly Met Arg Ala Thr Tyr Trp Asn Asn Thr Lys
        435                 440                 445

Met Asn Gly Thr Pro Ala Thr Thr Met Asp Ile Thr Glu Pro Ile Asn
450                 455                 460

Leu Ser Asn Gly Gly Ala Thr Val Phe Ala Pro Gly Val Asn Leu Glu
465                 470                 475                 480

His Phe Ser Ala Lys Tyr Glu Gly Thr Phe His Ala Asn Lys Ser Glu
            485                 490                 495

Asp Ile His Leu Lys Leu Ser Ser Asp Leu Ala Arg Ile Ile Ile
        500                 505                 510

Asp Gly Asp Thr Ile Ile Asn Ser Trp Lys Ala Arg Glu Arg Val Asn
        515                 520                 525

Val Ser Asp Lys Ile Val His Val Glu Ala Asn Lys Asp Tyr Lys Ile
    530                 535                 540

Gln Ile Asp Tyr Val Gln Asn Asp Ala Ala Ile Ile Gln Phe Asp
545                 550                 555                 560

Leu Gly Pro Leu Val Lys Met Thr Glu Lys Glu Leu Leu Gln Lys Val
```

Gly Asp Ala Gln Val Val Ile Tyr Val Gly Gly Ile Ser Pro Arg Leu
             580                 585                 590

Glu Gly Glu Glu Met Lys Val Asn Glu Leu Gly Phe Lys Gly Gly Asp
         595                 600                 605

Arg Thr Thr Ile Glu Leu Pro Gln Ser Gln Arg Asp Met Ile Ala Leu
         610                 615                 620

Leu His Asn Ser Gly Lys Lys Val Ile Phe Val Asn Cys Ser Gly Gly
625                 630                 635                 640

Ala Ile Ala Leu Glu Pro Glu Ser Arg Asn Ala Asp Ala Ile Leu Gln
             645                 650                 655

Ala Trp Tyr Gly Gly Glu Met Gly Gly Gln Ala Val Ala Asp Val Leu
             660                 665                 670

Phe Gly Asp Tyr Asn Pro Asn Gly Lys Leu Pro Val Thr Phe Tyr Lys
             675                 680                 685

Asn Asp Ser Gln Leu Pro Asp Tyr Asn Asp Tyr Thr Met Lys Gly Arg
690                 695                 700

Thr Tyr Arg Tyr Leu His Gln Ala Pro Leu Tyr Pro Phe Gly Tyr Gly
705                 710                 715                 720

Leu Ser Tyr Thr Thr Phe Ala Tyr Asp Asn Ala Lys Tyr Asp Arg Arg
                 725                 730                 735

Lys Gly Asn Leu Ser Leu Glu Val Thr Asn Thr Gly Lys Cys Glu Gly
             740                 745                 750

Thr Thr Thr Ile Gln Val Tyr Ile Arg Arg Thr Ala Asp Ile Asn Gly
             755                 760                 765

Pro Ile Lys Thr Leu Lys Ala Phe Gln Lys Val Ser Leu Gln Ala Asn
770                 775                 780

Glu Lys Lys Arg Val Thr Ile Asn Leu Pro Arg Glu Arg Phe Glu Gly
785                 790                 795                 800

Trp Asp Glu Thr Thr Asn Thr Met Arg Ile Val Pro Gly Lys Tyr Glu
                 805                 810                 815

Ile Met Val Gly Gln His Ser Asp Asp Pro Asp Met Lys Lys Leu Ile
             820                 825                 830

Ile Tyr Leu Lys
         835

<210> SEQ ID NO 9
<211> LENGTH: 1833
<212> TYPE: DNA
<213> ORGANISM: Prevotella bryantii

<400> SEQUENCE: 9
gaagatggcc atcagctgtg gctgcgctat cagcagaccc atgcgcaggt gaacgcgccg      60
cagggcggcg aaattctgaa caccgcgtgc cgcgaactgc gcaactattg ctgggccag      120 gcgattaacc tgcagctggt gagccagaac attgtggcgc ggaaggcta taccttttgat     180 ggcaaaaccc tgaaagcgag caccgaaagc ggcctgctgt atggcgcgta tgcgctgctg     240
cgcgaacaga ccgtgcgcgg caccgcgaaa ggcattattc tgaaaagcac cccgaaaagc     300
aaatatcgca ttctgaacca ttgggataac ctggatggca gcattgaacg cggctatgcg     360
ggcaaaagca ttttttggaa cagcccgatt aaaggcgaag cgtatgatac ccgcctgaaa     420
gaatatgcgc gcgcgaacgc gagcgtgggc attaacggca ccgtgctgga taacgtgaac     480
gcgagcccga aatgctgac ccataccat ctggatagcg tggcgcatat tgcgaacatt     540

```
ctgcgcccgt atggcctgcg cgtgtatctg agcgtgaact ttggcacccc gaaagcgctg      600
ggcgcgacca acaccgcgga tccgctgaac aaacgcgtga ttagctggtg aacaaaaaa      660
gcgaaagaaa tttataaact gattccggat tttggcggct tttgcgtgaa agcgaacagc      720
gaaggccagc cgggcccgtt tgattatggc cgcacccatg cgcagggcgc gaacatgctg      780
gcggatgcgc tgaaaccgta tggcggcctg gtgttttggc gcagctttgt gtatggcagc      840
aaacataaag gcgaagatcg cgtgaaacag gcggtgagcg aatttgcgga tctggatggc      900
acctttcgcg aaaacgtgat tctgcagagc aaaaacggcc cgctggattt tcagccgcgc      960
gaaccgtatg cgccgatttt tgatcagatg catcgcacca cccaggcggt ggaactgcag     1020
attacccagg aatatctggg ccatgataaa catctggtgt atctggcgcc gatgtggcag     1080
gaatttttta gctttgtgag cgtgaaccgc ctgaaaggcg tggtgggcgt ggcgaacatt     1140
ggcgatcata ttaactggtg cggccatccg tttgcgcaga gcaactggta tgcgtttggc     1200
cgcctggcgt gggatgcgag cctgaacagc aaaaccattg cgaagaatg gctgattcag     1260
acctataccg ataaatatca gtttgtggcg ccggtgctgg atatgatgct gagcagccgc     1320
gaagcgtgcg tggattatat ggaaccgctg ggcctgcatc atattatggc gtttgatcat     1380
cattatggcc cggaaccgga tggctttatt gcgagctatc cgattgaatg gtgcccggtg     1440
tattatcata agcggatgc gcatggcctg gctttgaac gcagcagcaa aggcaccaac     1500
gcgaccgcgc agtatccgga accgtatcgc agcctgtatg ataacctggc gacctgcccg     1560
ccggaatatc tgctgtggtt tcatcatgtg gcgtggaact atcgcatgcc gagcggccgc     1620
accatgtggc aggaactgaa cgcgcattat aacaaaggcg tgaaaaccgt gcagaactat     1680
gaaaacctgt ggcagcagat gaaaccgtat attgatgaag cgcgctggca gcataccgcg     1740
aacctgctgc atctgcagga acagaacgcg gaactgtggc gcaacaccctg cctgaaatat     1800
tttgcgaccct ttagcaaaat gccgattgaa taa                                  1833
```

<210> SEQ ID NO 10
<211> LENGTH: 610
<212> TYPE: PRT
<213> ORGANISM: Prevotella bryantii

<400> SEQUENCE: 10

Glu Asp Gly His Gln Leu Trp Leu Arg Tyr Gln Gln Thr His Ala Gln
 1               5                  10                  15

Val Asn Ala Pro Gln Gly Gly Glu Ile Leu Asn Thr Ala Cys Arg Glu
            20                  25                  30

Leu Arg Asn Tyr Trp Leu Gly Gln Ala Ile Asn Leu Gln Leu Val Ser
        35                  40                  45

Gln Asn Ile Val Ala Pro Glu Gly Tyr Thr Phe Asp Gly Lys Thr Leu
    50                  55                  60

Lys Ala Ser Thr Glu Ser Gly Leu Leu Tyr Gly Ala Tyr Ala Leu Leu
65                  70                  75                  80

Arg Glu Gln Thr Val Arg Gly Thr Ala Lys Gly Ile Ile Leu Lys Ser
                85                  90                  95

Thr Pro Lys Ser Lys Tyr Arg Ile Leu Asn His Trp Asp Asn Leu Asp
            100                 105                 110

Gly Ser Ile Glu Arg Gly Tyr Ala Gly Lys Ser Ile Phe Trp Asn Ser
        115                 120                 125

Pro Ile Lys Gly Glu Ala Tyr Asp Thr Arg Leu Lys Glu Tyr Ala Arg
    130                 135                 140

```
Ala Asn Ala Ser Val Gly Ile Asn Gly Thr Val Leu Asp Asn Val Asn
145                 150                 155                 160

Ala Ser Pro Lys Met Leu Thr His Thr Tyr Leu Asp Ser Val Ala His
            165                 170                 175

Ile Ala Asn Ile Leu Arg Pro Tyr Gly Leu Arg Val Tyr Leu Ser Val
                180                 185                 190

Asn Phe Gly Thr Pro Lys Ala Leu Gly Ala Thr Asn Thr Ala Asp Pro
        195                 200                 205

Leu Asn Lys Arg Val Ile Ser Trp Trp Asn Lys Ala Lys Glu Ile
210                 215                 220

Tyr Lys Leu Ile Pro Asp Phe Gly Phe Cys Val Lys Ala Asn Ser
225                 230                 235                 240

Glu Gly Gln Pro Gly Pro Phe Asp Tyr Gly Arg Thr His Ala Gln Gly
            245                 250                 255

Ala Asn Met Leu Ala Asp Ala Leu Lys Pro Tyr Gly Gly Leu Val Phe
            260                 265                 270

Trp Arg Ser Phe Val Tyr Gly Ser Lys His Lys Gly Glu Asp Arg Val
        275                 280                 285

Lys Gln Ala Val Ser Glu Phe Ala Asp Leu Asp Gly Thr Phe Arg Glu
290                 295                 300

Asn Val Ile Leu Gln Ser Lys Asn Gly Pro Leu Asp Phe Gln Pro Arg
305                 310                 315                 320

Glu Pro Tyr Ala Pro Ile Phe Asp Gln Met His Arg Thr Thr Gln Ala
                325                 330                 335

Val Glu Leu Gln Ile Thr Gln Glu Tyr Leu Gly His Asp Lys His Leu
            340                 345                 350

Val Tyr Leu Ala Pro Met Trp Gln Glu Phe Phe Ser Phe Val Ser Val
        355                 360                 365

Asn Arg Leu Lys Gly Val Val Gly Val Ala Asn Ile Gly Asp His Ile
370                 375                 380

Asn Trp Cys Gly His Pro Phe Ala Gln Ser Asn Trp Tyr Ala Phe Gly
385                 390                 395                 400

Arg Leu Ala Trp Asp Ala Ser Leu Asn Ser Lys Thr Ile Gly Glu Glu
                405                 410                 415

Trp Leu Ile Gln Thr Tyr Thr Asp Lys Tyr Gln Phe Val Ala Pro Val
            420                 425                 430

Leu Asp Met Met Leu Ser Ser Arg Glu Ala Cys Val Asp Tyr Met Glu
        435                 440                 445

Pro Leu Gly Leu His His Ile Met Ala Phe Asp His His Tyr Gly Pro
    450                 455                 460

Glu Pro Asp Gly Phe Ile Ala Ser Tyr Pro Ile Glu Trp Cys Pro Val
465                 470                 475                 480

Tyr Tyr His Lys Ala Asp Ala His Gly Leu Gly Phe Glu Arg Ser Ser
            485                 490                 495

Lys Gly Thr Asn Ala Thr Ala Gln Tyr Pro Glu Pro Tyr Arg Ser Leu
        500                 505                 510

Tyr Asp Asn Leu Ala Thr Cys Pro Pro Glu Tyr Leu Leu Trp Phe His
        515                 520                 525

His Val Ala Trp Asn Tyr Arg Met Pro Ser Gly Arg Thr Met Trp Gln
        530                 535                 540

Glu Leu Asn Ala His Tyr Asn Lys Gly Val Lys Thr Val Gln Asn Tyr
545                 550                 555                 560

Glu Asn Leu Trp Gln Gln Met Lys Pro Tyr Ile Asp Glu Ala Arg Trp
```

```
                   565                 570                 575
Gln His Thr Ala Asn Leu Leu His Leu Gln Glu Gln Asn Ala Glu Leu
                580                 585                 590

Trp Arg Asn Thr Cys Leu Lys Tyr Phe Ala Thr Phe Ser Lys Met Pro
        595                 600                 605

Ile Glu
    610

<210> SEQ ID NO 11
<211> LENGTH: 1137
<212> TYPE: DNA
<213> ORGANISM: Prevotella bryantii

<400> SEQUENCE: 11
aagacgacta ttgatgaaca ttgggtaggt acttgggcaa cggctcagca gatacctgta    60
aaatcgtata tgccatacaa taatgacatg tctaatcgtt cggttcgtca gatcgttaaa   120
gtctcaatag gtggtgatat gattcgcctt caattgtcaa atgaattaag ttctgaaccg   180
gtatatatac gttccgtata tgtcgctact tctgtagatt cttttacgat tctgccaaag   240
acggcaaaat atctaaagtt tggtaatcag tataaggctg ttattcctgc aggtaagact   300
ttaacaagtg atgctttgct cttaaactg gccccactgc aaaaacttgc tattaccatc    360
aattacacga agctccttc taaacctacg gtacacatgg ggtctcgcac tacttcttat   420
atcatgaagg gtgtaaccaa tgcgcacagc aattttgcac catcttttcg cgaaaatcac   480
tggtttaata tctcggccat agatgtctat tctaccaaag ctcatgctat cggtattatt   540
ggcaattcga ttacagacgg aaagggtagt accgataatg cgcaaaatcg ctggccggat   600 atgcttctg aatatctaca gttaaaacat aaagtagata cgtgggtat tctgaatatg     660 ggcattggta ataatcgtgt agctactacc ggtggcttcg gaacaatggc caagttgcgc   720
ttcaatcgtg atattttaga gcagcagggc ttagagagcg tggtaatctt tgagggtgtg   780
aatgatatcg gcaatagcaa aggtaatagt gaggctgtag cggcgttgct tattgctacc   840
tacgaagaaa tgataaaaaa atgcaaagcc cgtaaactga agtgtatct aggtaccata    900 actccgttta agggagctgg ctactattct ccattccacg aggccgcccg acttacggtg   960
aacgaatgga taagaagtca gagaggtaag gtggatggta tactcgattt cgacgaactg  1020
ctacgcgatc cggtagagac cgacagaatg atgaaaaact atcagagtga ctggctacat  1080
ccgaatgcag aaggctataa actgatggga cagtatgctg ctgaaattct gcgatag      1137

<210> SEQ ID NO 12
<211> LENGTH: 378
<212> TYPE: PRT
<213> ORGANISM: Prevotella bryantii

<400> SEQUENCE: 12

Lys Thr Thr Ile Asp Glu His Trp Val Gly Thr Trp Ala Thr Ala Gln
  1               5                  10                  15

Gln Ile Pro Val Lys Ser Tyr Met Pro Tyr Asn Asn Asp Met Ser Asn
             20                  25                  30

Arg Ser Val Arg Gln Ile Val Lys Val Ser Ile Gly Gly Asp Met Ile
         35                  40                  45

Arg Leu Gln Leu Ser Asn Glu Leu Ser Ser Glu Pro Val Tyr Ile Arg
     50                  55                  60

Ser Val Tyr Val Ala Thr Ser Val Asp Ser Phe Thr Ile Leu Pro Lys
 65                  70                  75                  80
```

```
Thr Ala Lys Tyr Leu Lys Phe Gly Asn Gln Tyr Lys Ala Val Ile Pro
                85                  90                  95
Ala Gly Lys Thr Leu Thr Ser Asp Ala Leu Leu Phe Lys Leu Ala Pro
            100                 105                 110
Leu Gln Lys Leu Ala Ile Thr Ile Asn Tyr Thr Lys Ala Pro Ser Lys
        115                 120                 125
Pro Thr Val His Met Gly Ser Arg Thr Thr Ser Tyr Ile Met Lys Gly
    130                 135                 140
Val Thr Asn Ala His Ser Asn Phe Ala Pro Ser Phe Arg Glu Asn His
145                 150                 155                 160
Trp Phe Asn Ile Ser Ala Ile Asp Val Tyr Ser Thr Lys Ala His Ala
                165                 170                 175
Ile Gly Ile Ile Gly Asn Ser Ile Thr Asp Gly Lys Gly Ser Thr Asp
            180                 185                 190
Asn Ala Gln Asn Arg Trp Pro Asp Met Leu Ser Glu Tyr Leu Gln Leu
        195                 200                 205
Lys His Lys Val Asp Asn Val Gly Ile Leu Asn Met Gly Ile Gly Asn
    210                 215                 220
Asn Arg Val Ala Thr Thr Gly Gly Phe Gly Thr Met Ala Lys Leu Arg
225                 230                 235                 240
Phe Asn Arg Asp Ile Leu Glu Gln Gln Gly Leu Glu Ser Val Val Ile
                245                 250                 255
Phe Glu Gly Val Asn Asp Ile Gly Asn Ser Lys Gly Asn Ser Glu Ala
            260                 265                 270
Val Ala Ala Leu Leu Ile Ala Thr Tyr Glu Met Ile Lys Lys Cys
        275                 280                 285
Lys Ala Arg Lys Leu Lys Val Tyr Leu Gly Thr Ile Thr Pro Phe Lys
    290                 295                 300
Gly Ala Gly Tyr Tyr Ser Pro Phe His Glu Ala Ala Arg Leu Thr Val
305                 310                 315                 320
Asn Glu Trp Ile Arg Ser Gln Arg Gly Lys Val Asp Gly Ile Leu Asp
                325                 330                 335
Phe Asp Glu Leu Leu Arg Asp Pro Val Glu Thr Asp Arg Met Met Lys
            340                 345                 350
Asn Tyr Gln Ser Asp Trp Leu His Pro Asn Ala Glu Gly Tyr Lys Leu
        355                 360                 365
Met Gly Gln Tyr Ala Ala Glu Ile Leu Arg
    370                 375

<210> SEQ ID NO 13
<211> LENGTH: 1050
<212> TYPE: DNA
<213> ORGANISM: Prevotella bryantii

<400> SEQUENCE: 13
caaaatcagc ctacgatgaa ggatgtctta ggtaaatact tcttggtcgg aacagcactt      60
aatagtcatc agatttggac gcatgatccc aaaatcgttc atgctataac tgataatttt     120
aattcggttg tcgctgaaaa ttgtatgaaa ggtgagatta ttcatccaga agaggattat     180
tatgattggc atgatgctga ccagttggtt aaatttgcgg aacagcataa gatgacagtt     240
catggccact gtttggtttg cactcacag gctccaaaat ggatgtttac cgataaggaa     300
ggtaaagaag ttcccgtga ggtgctcatc gaccgtatgt atcatcacat tactaatgtc      360
gttaagcgat ataaaggtaa aatcaagggt tgggatgtcg ttaacgaggc tatccttgat     420
```

```
aatggtgaat atcgtcagtc tccttattat aagatcattg gtcctgattt tatcaagctt    480
gcatttattt ttgctcatca ggcagatcct gatgcagaat tgtattataa tgactattcg    540
atgtctattc ctgctaagcg taatgctgta gtcaaactgg ttaaggagtt gaaagctgca    600
ggatgtcgta ttgatgctgt aggtatgcag agccataacg ttttaactat cctaatctt    660 gaggattatg aaaattctat caaggctttc attgctgcag gtgtagatgt tcagtttaca    720
gaactcgatg tcaatatgct acctaatcct aagagctttg gtggtgcaga gattagccag    780
aactataagt ataataagga acttaatcca tatgtaaatg ggttgactaa agctgctcag    840
aagactttcg atcagcagta tctgtcattc tttaagattt atcgtaagta tgtagatcat    900
attaagcgtg taacgctttg gggtgtggac gacggaagca gctggctgaa tggttggcct    960
gtgcctggtc gtaccaacta tggtctgctt atcgaccgca actacaaggt aaaacctgtg   1020
gttaaagaaa ttatcaaact ttatgagtaa                                    1050
```

<210> SEQ ID NO 14
<211> LENGTH: 349
<212> TYPE: PRT
<213> ORGANISM: Prevotella bryantii

<400> SEQUENCE: 14

```
Gln Asn Gln Pro Thr Met Lys Asp Val Leu Gly Lys Tyr Phe Leu Val
1               5                   10                  15

Gly Thr Ala Leu Asn Ser His Gln Ile Trp Thr His Asp Pro Lys Ile
            20                  25                  30

Val His Ala Ile Thr Asp Asn Phe Asn Ser Val Val Ala Glu Asn Cys
        35                  40                  45

Met Lys Gly Glu Ile Ile His Pro Glu Glu Asp Tyr Tyr Asp Trp His
    50                  55                  60

Asp Ala Asp Gln Leu Val Lys Phe Ala Glu Gln His Lys Met Thr Val
65                  70                  75                  80

His Gly His Cys Leu Val Trp His Ser Gln Ala Pro Lys Trp Met Phe
                85                  90                  95

Thr Asp Lys Glu Gly Lys Glu Val Thr Arg Glu Val Leu Ile Asp Arg
            100                 105                 110

Met Tyr His His Ile Thr Asn Val Val Lys Arg Tyr Lys Gly Lys Ile
        115                 120                 125

Lys Gly Trp Asp Val Val Asn Glu Ala Ile Leu Asp Asn Gly Glu Tyr
    130                 135                 140

Arg Gln Ser Pro Tyr Tyr Lys Ile Ile Gly Pro Asp Phe Ile Lys Leu
145                 150                 155                 160

Ala Phe Ile Phe Ala His Gln Ala Asp Pro Asp Ala Glu Leu Tyr Tyr
                165                 170                 175

Asn Asp Tyr Ser Met Ser Ile Pro Ala Lys Arg Asn Ala Val Val Lys
            180                 185                 190

Leu Val Lys Glu Leu Lys Ala Ala Gly Cys Arg Ile Asp Ala Val Gly
        195                 200                 205

Met Gln Ser His Asn Gly Phe Asn Tyr Pro Asn Leu Glu Asp Tyr Glu
    210                 215                 220

Asn Ser Ile Lys Ala Phe Ile Ala Ala Gly Val Asp Val Gln Phe Thr
225                 230                 235                 240

Glu Leu Asp Val Asn Met Leu Pro Asn Pro Lys Ser Phe Gly Gly Ala
                245                 250                 255
```

```
Glu Ile Ser Gln Asn Tyr Lys Tyr Asn Lys Glu Leu Asn Pro Tyr Val
                260                 265                 270

Asn Gly Leu Thr Lys Ala Ala Gln Lys Thr Phe Asp Gln Gln Tyr Leu
            275                 280                 285

Ser Phe Phe Lys Ile Tyr Arg Lys Tyr Val Asp His Ile Lys Arg Val
        290                 295                 300

Thr Leu Trp Gly Val Asp Asp Gly Ser Ser Trp Leu Asn Gly Trp Pro
305                 310                 315                 320

Val Pro Gly Arg Thr Asn Tyr Gly Leu Leu Ile Asp Arg Asn Tyr Lys
                325                 330                 335

Val Lys Pro Val Val Lys Glu Ile Ile Lys Leu Tyr Glu
            340                 345

<210> SEQ ID NO 15
<211> LENGTH: 2082
<212> TYPE: DNA
<213> ORGANISM: Bacteroides intestinalis

<400> SEQUENCE: 15
```

| | | | | | |
|---|---|---|---|---|---|
| caaagcggcg | aaacaggact | gaaggatgct | tataaagatt | acttctctat | tggcgtggct | 60 |
| gttaatatgc | gtaatatcgc | aaatcccgaa | cagattgcca | tcatcaaaaa | agactttaac | 120 |
| agtattacgg | cggaaaacga | catgaagccg | caacccaccg | agcctgccta | cggacagttc | 180 |
| aactgggaga | atgccgacaa | gatcgccaac | ttttgccgta | gcaacggtat | caacttcgc | 240 |
| gggcattgct | tgatgtggca | tgcccagata | ggagaatgga | tgtataagga | tgaaaaaggc | 300 |
| gattttgtgt | cgaaagagaa | attattccag | aatatgaagc | atcatatcac | agccatcgtg | 360 |
| gaacgttata | agacgtgat | atatgcgtgg | gacgtggtga | acgaagctat | ctccgatggt | 420 |
| ggctggcagg | gtgccggcg | aggcatggga | gagcaaccaa | gtccatatcg | caattccccc | 480 |
| ctttatcaga | ttgccggtga | cgagttcatt | aagaaagcct | tatttatgc | ccgtgaggcc | 540 |
| gacctaatg | tactcctttt | ctataatgac | tataatgctg | ccgatcccgg | aaagcgcgac | 600 |
| cgcatctata | atatggtgaa | atccatgaag | gaagaaggtg | tgcccattga | tggtatcggc | 660 |
| atgcagggac | attacaatgt | ctacggtccg | agtatggaag | atgtagatgc | tgccttgaca | 720 |
| aaatactcta | cgatagtgaa | acatattcat | attaccgagt | tggatattcg | tgccaatcag | 780 |
| gagatgggag | acagctcaa | cttcagccgt | gacggcggca | atatcagtca | ggtggtgaaa | 840 |
| acgcttcagg | aagatcagta | tgctcgcctg | tttaaagtgc | ttcgcaagca | taaggatgtg | 900 |
| gtagacaatg | ttactttctg | gaatctttcc | gaccgcgact | catggctcgg | cgcacgcaat | 960 |
| tatccgttgc | cttacgatga | gaattataag | ccgaaacgtg | tctatagcat | cattaaggat | 1020 |
| tttgatccgg | cacacgataa | tgctgtggtg | aaagaagatt | tccgtccttc | tgtgcttaat | 1080 |
| cagcccggac | ggcagtatcc | tatggttaat | tcgcagggat | atgcccgctt | ccgtgtagtt | 1140 |
| gctcctgatg | ccaaatcagt | cattgtcagc | cttggactgg | gaggtcgtgg | cggcacagtt | 1200 |
| ctccgtaagg | ataaagaagg | tgtatggtg | ggtactacag | atggcccat | ggacgaggga | 1260 |
| ttccattatt | accacctcac | tatcgacggt | ggcgtgttta | atgacccggg | cgccaagaat | 1320 |
| tattacggtt | cttgccgatg | ggaaagcggc | attgagattc | cggctcatga | cgaagatttc | 1380 |
| tatgccatga | acaagtgcc | tcacggcaat | gttcagcagg | tttatttcta | ttccaagagt | 1440 |
| acggacactc | accgtcgtgc | atttgtttat | acaccgccca | cttatggcaa | ggataagaag | 1500 |
| aagtatccgg | ttctttattt | acagcacgga | tgggagaag | atgaaacggc | atggtccaac | 1560 |
| cagggcatg | cgaatctgat | tatggacaac | ctgattgccg | aaggcaagat | tgaaccgttc | 1620 |

```
atcattgtaa tgacgtatgg catgacgaat gatgtgaaat ttgggcatat caaagagttc  1680
acggctaagg agtttgaaac ggtgctggtg gacgaactaa taccttatat tgatagtaac  1740
ttccgtacac aggccgacaa gaagcaccgt gctatggcag gactttctat gggtggcttt  1800
gagacgaaac tgattactct gcgacgtccg gaagtattca attactatgg actgttgagc  1860
ggtggcactt atgcaccgga cgacatcaag gataaaaagc aggtggaatc catcttcatc  1920
agttgcggaa gcaaggagaa tccggatggt gtgactaagg ctgtgaacga cctcaaggct  1980
gccggtttca aggctacgtc gttcgtttct cccgatacgg cgcatgaatt cctgacttgg  2040
cgtagaagtt tgtatcacat ggcacagttg cttttcaaat aa                      2082
```

<210> SEQ ID NO 16
<211> LENGTH: 693
<212> TYPE: PRT
<213> ORGANISM: Bacteroides intestinalis

<400> SEQUENCE: 16

```
Gln Ser Gly Glu Thr Gly Leu Lys Asp Ala Tyr Lys Asp Tyr Phe Ser
  1               5                  10                  15

Ile Gly Val Ala Val Asn Met Arg Asn Ile Ala Asn Pro Glu Gln Ile
             20                  25                  30

Ala Ile Ile Lys Lys Asp Phe Asn Ser Ile Thr Ala Glu Asn Asp Met
         35                  40                  45

Lys Pro Gln Pro Thr Glu Pro Ala Tyr Gly Gln Phe Asn Trp Glu Asn
     50                  55                  60

Ala Asp Lys Ile Ala Asn Phe Cys Arg Ser Asn Gly Ile Lys Leu Arg
 65                  70                  75                  80

Gly His Cys Leu Met Trp His Ala Gln Ile Gly Glu Trp Met Tyr Lys
                 85                  90                  95

Asp Glu Lys Gly Asp Phe Val Ser Lys Glu Lys Leu Phe Gln Asn Met
            100                 105                 110

Lys His His Ile Thr Ala Ile Val Glu Arg Tyr Lys Asp Val Ile Tyr
        115                 120                 125

Ala Trp Asp Val Val Asn Glu Ala Ile Ser Asp Gly Gly Trp Gln Gly
    130                 135                 140

Gly Arg Arg Gly Met Gly Glu Gln Pro Ser Pro Tyr Arg Asn Ser Pro
145                 150                 155                 160

Leu Tyr Gln Ile Ala Gly Asp Glu Phe Ile Lys Lys Ala Phe Ile Tyr
                165                 170                 175

Ala Arg Glu Ala Asp Pro Asn Val Leu Leu Phe Tyr Asn Asp Tyr Asn
            180                 185                 190

Ala Ala Asp Pro Gly Lys Arg Asp Arg Ile Tyr Asn Met Val Lys Ser
        195                 200                 205

Met Lys Glu Glu Gly Val Pro Ile Asp Gly Ile Gly Met Gln Gly His
    210                 215                 220

Tyr Asn Val Tyr Gly Pro Ser Met Glu Asp Val Asp Ala Ala Leu Thr
225                 230                 235                 240

Lys Tyr Ser Thr Ile Val Lys His Ile His Ile Thr Glu Leu Asp Ile
                245                 250                 255

Arg Ala Asn Gln Glu Met Gly Gly Gln Leu Asn Phe Ser Arg Asp Gly
            260                 265                 270

Gly Asn Ile Ser Gln Val Val Lys Thr Leu Gln Glu Asp Gln Tyr Ala
        275                 280                 285
```

-continued

```
Arg Leu Phe Lys Val Leu Arg Lys His Lys Asp Val Asp Asn Val
    290                 295                 300
Thr Phe Trp Asn Leu Ser Asp Arg Asp Ser Trp Leu Gly Ala Arg Asn
305                 310                 315                 320
Tyr Pro Leu Pro Tyr Asp Glu Asn Tyr Lys Pro Lys Arg Val Tyr Ser
                325                 330                 335
Ile Ile Lys Asp Phe Asp Pro Ala His Asp Asn Ala Val Val Lys Glu
            340                 345                 350
Asp Phe Arg Pro Ser Val Leu Asn Gln Pro Gly Arg Gln Tyr Pro Met
        355                 360                 365
Val Asn Ser Gln Gly Tyr Ala Arg Phe Arg Val Ala Pro Asp Ala
    370                 375                 380
Lys Ser Val Ile Val Ser Leu Gly Leu Gly Gly Arg Gly Gly Thr Val
385                 390                 395                 400
Leu Arg Lys Asp Lys Glu Gly Val Trp Val Gly Thr Thr Asp Gly Pro
                405                 410                 415
Met Asp Glu Gly Phe His Tyr Tyr His Leu Thr Ile Asp Gly Gly Val
            420                 425                 430
Phe Asn Asp Pro Gly Ala Lys Asn Tyr Tyr Gly Ser Cys Arg Trp Glu
        435                 440                 445
Ser Gly Ile Glu Ile Pro Ala His Asp Glu Asp Phe Tyr Ala Met Lys
    450                 455                 460
Gln Val Pro His Gly Asn Val Gln Gln Val Tyr Phe Tyr Ser Lys Ser
465                 470                 475                 480
Thr Asp Thr His Arg Arg Ala Phe Val Tyr Thr Pro Pro Thr Tyr Gly
                485                 490                 495
Lys Asp Lys Lys Lys Tyr Pro Val Leu Tyr Leu Gln His Gly Trp Gly
            500                 505                 510
Glu Asp Glu Thr Ala Trp Ser Asn Gln Gly His Ala Asn Leu Ile Met
        515                 520                 525
Asp Asn Leu Ile Ala Glu Gly Lys Ile Glu Pro Phe Ile Ile Val Met
    530                 535                 540
Thr Tyr Gly Met Thr Asn Asp Val Lys Phe Gly His Ile Lys Glu Phe
545                 550                 555                 560
Thr Ala Lys Glu Phe Glu Thr Val Leu Val Asp Glu Leu Ile Pro Tyr
                565                 570                 575
Ile Asp Ser Asn Phe Arg Thr Gln Ala Asp Lys Lys His Arg Ala Met
            580                 585                 590
Ala Gly Leu Ser Met Gly Gly Phe Glu Thr Lys Leu Ile Thr Leu Arg
        595                 600                 605
Arg Pro Glu Val Phe Asn Tyr Tyr Gly Leu Leu Ser Gly Gly Thr Tyr
    610                 615                 620
Ala Pro Asp Asp Ile Lys Asp Lys Lys Gln Val Glu Ser Ile Phe Ile
625                 630                 635                 640
Ser Cys Gly Ser Lys Glu Asn Pro Asp Gly Val Thr Lys Ala Val Asn
                645                 650                 655
Asp Leu Lys Ala Ala Gly Phe Lys Ala Thr Ser Phe Val Ser Pro Asp
            660                 665                 670
Thr Ala His Glu Phe Leu Thr Trp Arg Arg Ser Leu Tyr His Met Ala
        675                 680                 685
Gln Leu Leu Phe Lys
    690
```

<210> SEQ ID NO 17
<211> LENGTH: 2592
<212> TYPE: DNA
<213> ORGANISM: Prevotella bryantii

<400> SEQUENCE: 17

| | | | | | | |
|---|---|---|---|---|---|---|
| ctcatctgcg | ctgctgaaaa | gtctgctcaa | aatacccata | ctacaagcag | aacatcggac | 60 |
| aagacttcaa | ctctattacc | ttatcagaat | ccaaatcttt | cagcctacga | aagagccata | 120 |
| gatctctgcc | atagacttac | cttagaagaa | aaggctttac | ttatgcagga | tgaatcacct | 180 |
| gcaataccaa | gacttggcat | taaaaaattt | ttctggtgga | gcgaagcatt | acatggtgct | 240 |
| gccaatatgg | gcaatgtaac | caattttcca | gaacccatag | ctatggcctc | atcctttaat | 300 |
| cccactttgc | tcaaatctgt | ttttctgct | gcaagcgatg | agatgcgtgc | acaatatcat | 360 |
| catcgtatgg | ataatggtgg | agaagatgaa | aaatttcata | gcctctctgt | ttggacacca | 420 |
| aacgtaaata | tctttagaga | cccgagatgg | ggacgtggac | aagagacata | cggtgaggac | 480 |
| ccttatctca | cttcggttat | gggatgtgcc | gtagtcgaag | ggttgcaggg | acctgaaagc | 540 |
| agtaaatatc | gaaaactgtg | ggcctgtgcc | aagcactttg | ccgtacatag | tggcccagaa | 600 |
| tctactcgcc | atacagccaa | cctaaataac | atctcgccac | gcgatctcta | tgaaacctat | 660 |
| ctacctgctt | tccagtccac | agtacaggat | ggtcatgtgc | gtgaggtaat | gtgtgcctat | 720 |
| cagcgtctcg | atgacgaacc | atgctgtagt | aataatcgtt | tgctacaaca | aattctccgc | 780 |
| gaagaatggg | gtttcaaata | tctcgtcgta | agcgactgcg | gtgctgtaag | tgatatttgg | 840 |
| cagagtcata | agacatcaag | tgatgctgta | catgcttcac | gacaagctac | acttgcaggt | 900 |
| acagatgtgg | aatgtggcta | tggctatacc | tatgcaaaaa | tacctgaagc | ggtaaaacga | 960 |
| ggccttctca | cagaagaaga | aatcgacaaa | catgtcataa | gactacttga | aggacgtttc | 1020 |
| gatttaggcg | aaatggatga | ttctaaactt | gtggaatgga | gtaagatacc | ttattccatc | 1080 |
| atgtcatgca | aagctcatgc | acaactggct | ctcgacatgg | cacgacagag | tattgtatta | 1140 |
| cttcagaaca | agggaaatat | cttgccatta | caactcaaaa | aaaatgaacg | tatcgccgtt | 1200 |
| attggtccaa | atgcagataa | taaaccgatg | atgtggggca | actataatgg | tacacctaac | 1260 |
| catacagtat | cgattctcga | aggtattcgc | aagcaatata | aaaatgtagt | atatcttcct | 1320 |
| gcctgcgact | aacagataa | aatggtcgtt | aaaccactgt | tcaatcaatg | taaagtagca | 1380 |
| aataagaccg | gtttgaaggg | tacttttttgg | aataatacta | agatgagtgg | caaacctgta | 1440 |
| accactcagt | attataatgc | cccttttggct | gtaacgacag | caggtatgca | caattttgcc | 1500 |
| ccaggtgtaa | aagtagaaga | cttttctgca | aaatacgaaa | ctactttcac | tcctcaaaaa | 1560 |
| aatggtgaag | tcgtcatcaa | cgtagaaggt | tgcggagatt | tcgctctcta | tgtaaatggc | 1620 |
| aaagaaatgc | aaaaattcca | tacttggcgt | actacaccta | cccgcacacc | gctacaggta | 1680 |
| aaaagtggcg | aacagtattt | gatagaggta | cgttttacct | acgtaaaaac | ctgggggggct | 1740 |
| aatcttaaga | ttaatatcgg | tgaagaacat | cctgtcgatt | atgctgctaa | tatcgctcaa | 1800 |
| ctcaagggta | tagataaggt | catctttgtg | ggtggtattg | ctccttcact | ggaaggtgaa | 1860 |
| gagatgccgg | tgaatattcc | tggatttaaa | ggtggagatc | gcactgatat | tgaaatgcca | 1920 |
| caagtacaga | gagactttat | caaagcttta | gctgaagcag | gtaaacagat | tattttagta | 1980 |
| aactgctctg | gttctgctat | cgctctaaca | cctgaagcac | agcgttgtca | ggctattatt | 2040 |
| caggcgtggt | atcctgggca | agaaggaggt | acggctgttg | ccgatatact | tatgggtaag | 2100 |
| gtaaatccta | tgggaaaact | accggtaacc | ttctataaga | gtacccaaca | gttacctgat | 2160 |

-continued

```
tttgaggatt attctatgaa gaaccgcaca tatcggtatt ttgaagatgc tctctatccc    2220
ttcggatatg gtttgagcta tacttcgttc gaaataggaa cagctaaaact gcaaacactt    2280 acgaacaata gcataactct tcagattccg gtaaccaata cggggaaacg ggagggcaca    2340
gaactagttc aagtatatct ccgcagagat gatgacgtag aaggaccatc caaaacactg    2400
aggtcttttg ctcatatcac actgaaagct ggggaaacaa aaaggctat tctcaaacta    2460 aaccgaaatc agtttgaatg ctgggacgcg tctaccaata ctatgcgggt aatacccggt    2520
aaatatacca tctttatgg taacagttcg aaaaagaag atttaaaaca gatacattat    2580
acgttaaatt aa                                                         2592
```

```
<210> SEQ ID NO 18
<211> LENGTH: 863
<212> TYPE: PRT
<213> ORGANISM: Prevotella bryantii

<400> SEQUENCE: 18

Leu Ile Cys Ala Ala Glu Lys Ser Ala Gln Asn Thr His Thr Thr Ser
 1               5                  10                  15

Arg Thr Ser Asp Lys Thr Ser Thr Leu Leu Pro Tyr Gln Asn Pro Asn
             20                  25                  30

Leu Ser Ala Tyr Glu Arg Ala Ile Asp Leu Cys His Arg Leu Thr Leu
         35                  40                  45

Glu Glu Lys Ala Leu Leu Met Gln Asp Glu Ser Pro Ala Ile Pro Arg
     50                  55                  60

Leu Gly Ile Lys Lys Phe Phe Trp Trp Ser Glu Ala Leu His Gly Ala
 65                  70                  75                  80

Ala Asn Met Gly Asn Val Thr Asn Phe Pro Glu Pro Ile Ala Met Ala
                 85                  90                  95

Ser Ser Phe Asn Pro Thr Leu Leu Lys Ser Val Phe Ser Ala Ala Ser
            100                 105                 110

Asp Glu Met Arg Ala Gln Tyr His His Arg Met Asp Asn Gly Gly Glu
        115                 120                 125

Asp Glu Lys Phe His Ser Leu Ser Val Trp Thr Pro Asn Val Asn Ile
    130                 135                 140

Phe Arg Asp Pro Arg Trp Gly Arg Gly Gln Glu Thr Tyr Gly Glu Asp
145                 150                 155                 160

Pro Tyr Leu Thr Ser Val Met Gly Cys Ala Val Val Glu Gly Leu Gln
                165                 170                 175

Gly Pro Glu Ser Ser Lys Tyr Arg Lys Leu Trp Ala Cys Ala Lys His
            180                 185                 190

Phe Ala Val His Ser Gly Pro Glu Ser Thr Arg His Thr Ala Asn Leu
        195                 200                 205

Asn Asn Ile Ser Pro Arg Asp Leu Tyr Glu Thr Tyr Leu Pro Ala Phe
    210                 215                 220

Gln Ser Thr Val Gln Asp Gly His Val Arg Glu Val Met Cys Ala Tyr
225                 230                 235                 240

Gln Arg Leu Asp Asp Glu Pro Cys Cys Ser Asn Asn Arg Leu Leu Gln
                245                 250                 255

Gln Ile Leu Arg Glu Glu Trp Gly Phe Lys Tyr Leu Val Val Ser Asp
            260                 265                 270

Cys Gly Ala Val Ser Asp Ile Trp Gln Ser His Lys Thr Ser Ser Asp
        275                 280                 285

Ala Val His Ala Ser Arg Gln Ala Thr Leu Ala Gly Thr Asp Val Glu
```

```
                290                 295                 300
Cys Gly Tyr Gly Tyr Thr Tyr Ala Lys Ile Pro Glu Ala Val Lys Arg
305                 310                 315                 320

Gly Leu Leu Thr Glu Glu Ile Asp Lys His Val Ile Arg Leu Leu
                325                 330                 335

Glu Gly Arg Phe Asp Leu Gly Glu Met Asp Asp Ser Lys Leu Val Glu
                340                 345                 350

Trp Ser Lys Ile Pro Tyr Ser Ile Met Ser Cys Lys Ala His Ala Gln
                355                 360                 365

Leu Ala Leu Asp Met Ala Arg Gln Ser Ile Val Leu Leu Gln Asn Lys
                370                 375                 380

Gly Asn Ile Leu Pro Leu Gln Leu Lys Lys Asn Glu Arg Ile Ala Val
385                 390                 395                 400

Ile Gly Pro Asn Ala Asp Asn Lys Pro Met Met Trp Gly Asn Tyr Asn
                405                 410                 415

Gly Thr Pro Asn His Thr Val Ser Ile Leu Glu Gly Ile Arg Lys Gln
                420                 425                 430

Tyr Lys Asn Val Val Tyr Leu Pro Ala Cys Asp Leu Thr Asp Lys Met
                435                 440                 445

Val Val Lys Pro Leu Phe Asn Gln Cys Lys Val Ala Asn Lys Thr Gly
450                 455                 460

Leu Lys Gly Thr Phe Trp Asn Asn Thr Lys Met Ser Gly Lys Pro Val
465                 470                 475                 480

Thr Thr Gln Tyr Tyr Asn Ala Pro Leu Ala Val Thr Thr Ala Gly Met
                485                 490                 495

His Asn Phe Ala Pro Gly Val Lys Val Glu Asp Phe Ser Ala Lys Tyr
                500                 505                 510

Glu Thr Thr Phe Thr Pro Gln Lys Asn Gly Glu Val Val Ile Asn Val
                515                 520                 525

Glu Gly Cys Gly Asp Phe Ala Leu Tyr Val Asn Gly Lys Glu Met Gln
                530                 535                 540

Lys Phe His Thr Trp Arg Thr Thr Pro Thr Arg Thr Pro Leu Gln Val
545                 550                 555                 560

Lys Ser Gly Glu Gln Tyr Leu Ile Glu Val Arg Phe Thr Tyr Val Lys
                565                 570                 575

Thr Trp Gly Ala Asn Leu Lys Ile Asn Ile Gly Glu Glu His Pro Val
                580                 585                 590

Asp Tyr Ala Ala Asn Ile Ala Gln Leu Lys Gly Ile Asp Lys Val Ile
                595                 600                 605

Phe Val Gly Gly Ile Ala Pro Ser Leu Glu Gly Glu Met Pro Val
610                 615                 620

Asn Ile Pro Gly Phe Lys Gly Gly Asp Arg Thr Asp Ile Glu Met Pro
625                 630                 635                 640

Gln Val Gln Arg Asp Phe Ile Lys Ala Leu Ala Glu Ala Gly Lys Gln
                645                 650                 655

Ile Ile Leu Val Asn Cys Ser Gly Ser Ala Ile Ala Leu Thr Pro Glu
                660                 665                 670

Ala Gln Arg Cys Gln Ala Ile Ile Gln Ala Trp Tyr Pro Gly Gln Glu
                675                 680                 685

Gly Gly Thr Ala Val Ala Asp Ile Leu Met Gly Lys Val Asn Pro Met
                690                 695                 700

Gly Lys Leu Pro Val Thr Phe Tyr Lys Ser Thr Gln Gln Leu Pro Asp
705                 710                 715                 720
```

```
Phe Glu Asp Tyr Ser Met Lys Asn Arg Thr Tyr Arg Tyr Phe Glu Asp
                725                 730                 735

Ala Leu Tyr Pro Phe Gly Tyr Gly Leu Ser Tyr Thr Ser Phe Glu Ile
            740                 745                 750

Gly Thr Ala Lys Leu Gln Thr Leu Thr Asn Asn Ser Ile Thr Leu Gln
            755                 760                 765

Ile Pro Val Thr Asn Thr Gly Lys Arg Glu Gly Thr Glu Leu Val Gln
        770                 775                 780

Val Tyr Leu Arg Arg Asp Asp Asp Val Glu Gly Pro Ser Lys Thr Leu
785                 790                 795                 800

Arg Ser Phe Ala His Ile Thr Leu Lys Ala Gly Glu Thr Lys Lys Ala
                805                 810                 815

Ile Leu Lys Leu Asn Arg Asn Gln Phe Glu Cys Trp Asp Ala Ser Thr
            820                 825                 830

Asn Thr Met Arg Val Ile Pro Gly Lys Tyr Thr Ile Phe Tyr Gly Asn
        835                 840                 845

Ser Ser Lys Lys Glu Asp Leu Lys Gln Ile His Tyr Thr Leu Asn
    850                 855                 860

<210> SEQ ID NO 19
<211> LENGTH: 2136
<212> TYPE: DNA
<213> ORGANISM: Prevotella bryantii

<400> SEQUENCE: 19
atgaataaga aaattattat tgtctgccta gcttgcgcca tatcattatc gtccatggct    60
caatatcgaa ctctaaacaa tttacacgta gagggcagaa atctgaaaga ttctcaagga   120
catacaattg tgcttcatgg cgttatggat atgccgagtc cctactttaa tgattatcgt   180
tggaccaagt gggtacctga attaacatcg aataatatac ctgcttgtct aacctatttt   240
gataaattat tctccgctat taccgacacc agccaaggag cttattgtga cgctttccgc   300
ctacatatgg atccctgctg acgaatgat cctaacaaaa cggccactaa tggtggaggt   360
gaaaacgata tcacgcttt tagtgaaagt aggtacgaat attatctaca gaatctctat   420
gtgcctcttg ctaaaagtgc caatgaacat gggctctatg tcgtagttcg tccacctgga   480
gtatgtccta ccaacattta cgtagatggt gattatcaac aatatcttct ctatgtttgg   540
gatcaattca gcaagaatac atacatacaa gaacacgctg tgtcatcgg aatcgaactg   600 gctaatgaac ctgtcaatgt acttaatgcc gatggaagta atacagctaa taccttgcac   660
gatttcttcc aacctattgt tgataaaatc agagcaaatg gttttaaagg tatcatctgg   720
gtaccgggat cttcatggca agctaattat accggatatg caacatatcc tataaccgat   780
gaactgaaaa atattggcta tgcggtacac gattatgtag atggtatgg aagtgatgaa   840 aacaatccga atgtagatgg cgctatctct caatttaaaa gccaggtacc tgtcgtagaa   900
actaatccta ttatgataac ggaggtagac tggagtccac aggttgccaa cttcgatgag   960
aacgatgctt ctacctatca tgtcaatgaa catggtgaaa aaatacctaa taatctggga  1020
acatgggcta caggtaccac aagcaactgg ggcaatgcat ataaaaaact catggaacac  1080
tatggtaata tctccatgac actgtccggt acaggatgct atattgatat cgattcatac  1140
atcaataata taaggttat tcctgctttc tcaaacaaaa ctggaggaga cgaagcatgt  1200
ggtgtagctt gttttaactg gtacaagacg tatgccgaag aaaacatgga acgtatcaac  1260
tatgtgccta caacagaaga tctcgatata gaaagtatca cagctagctc gaacaatttt  1320
```

```
accatttcag taggaagcaa tgctgtcgta acgatcatta gtcatgctaa aagcggtaaa   1380
gaggaagaaa taacaggaaa atgcacagta acaagtagtg atgaaaatgt ggcatactac   1440
aatggaagtc gaatcatcgc caaagaacaa ggtgcatgca cggttacctt caagtataca   1500
gacacaaatg gtaagacact aaccacaacg gtagatattc atgttccgga gtatttccca   1560
ctcactaatg taggtttaaa cccaagcatc tatggtaatg gattttcga tgaaactaca   1620 ggaaaacttc agacaggcca atatggtttt ggtggatgga aatttgcatc aggtcttgac   1680
ctttcggctt acgactatct cactgtagaa cttcaagagg ctaatacaag ttgggggttg   1740
tcgttccgcc tattcgacag tgataattac tggagtaatc catatagtaa gactttcgac   1800
ggaaaaactt ctattaccat aaatttgaac catcttgata tagaatacga agatgccaac   1860
aaagtaaaac attatcgcac tgtagatcct tctcatatct atattgctgg tttctggaca   1920
atgggagact ctcctattta tatcaagagt attacgctta caaaaaaagc aacatctgga   1980
atcagtcagc ttgacaataa tgaaaaagat gaaattgcat ctgtgaaata ctacacagtg   2040
gatggccatg aggttaatga tggatacaac aaaggcatga aaatcaaaaa aataacttat   2100
aagaacggta atgttaagat caataaatgc ttataa                             2136
```

<210> SEQ ID NO 20
<211> LENGTH: 711
<212> TYPE: PRT
<213> ORGANISM: Prevotella bryantii

<400> SEQUENCE: 20

```
Met Asn Lys Lys Ile Ile Val Cys Leu Ala Cys Ala Ile Ser Leu
  1               5                  10                  15

Ser Ser Met Ala Gln Tyr Arg Thr Leu Asn Asn Leu His Val Glu Gly
             20                  25                  30

Arg Asn Leu Lys Asp Ser Gln Gly His Thr Ile Val Leu His Gly Val
         35                  40                  45

Met Asp Met Pro Ser Pro Tyr Phe Asn Asp Tyr Arg Trp Thr Lys Trp
     50                  55                  60

Val Pro Glu Leu Thr Ser Asn Asn Ile Pro Ala Cys Leu Thr Tyr Phe
 65                  70                  75                  80

Asp Lys Leu Phe Ser Ala Ile Thr Asp Thr Ser Gln Gly Ala Tyr Cys
                 85                  90                  95

Asp Ala Phe Arg Leu His Met Asp Pro Cys Trp Thr Asn Asp Pro Asn
            100                 105                 110

Lys Thr Ala Thr Asn Gly Gly Gly Glu Asn Asp Ile Ser Arg Phe Ser
        115                 120                 125

Glu Ser Arg Tyr Glu Tyr Tyr Leu Gln Asn Leu Tyr Val Pro Leu Ala
    130                 135                 140

Lys Ser Ala Asn Glu His Gly Leu Tyr Val Val Arg Pro Gly
145                 150                 155                 160

Val Cys Pro Thr Asn Ile Tyr Val Asp Gly Asp Tyr Gln Gln Tyr Leu
                165                 170                 175

Leu Tyr Val Trp Asp Gln Phe Ser Lys Asn Thr Tyr Ile Gln Glu His
            180                 185                 190

Ala Gly Val Ile Gly Ile Glu Leu Ala Asn Glu Pro Val Asn Val Leu
        195                 200                 205

Asn Ala Asp Gly Ser Asn Thr Ala Asn Thr Leu His Asp Phe Phe Gln
    210                 215                 220
```

-continued

Pro Ile Val Asp Lys Ile Arg Ala Asn Gly Phe Lys Gly Ile Ile Trp
225                 230                 235                 240

Val Pro Gly Ser Ser Trp Gln Ala Asn Tyr Thr Gly Tyr Ala Thr Tyr
            245                 250                 255

Pro Ile Thr Asp Glu Leu Lys Asn Ile Gly Tyr Ala Val His Asp Tyr
        260                 265                 270

Val Gly Trp Tyr Gly Ser Asp Glu Asn Asn Pro Asn Val Asp Gly Ala
    275                 280                 285

Ile Ser Gln Phe Lys Ser Gln Val Pro Val Val Glu Thr Asn Pro Ile
290                 295                 300

Met Ile Thr Glu Val Asp Trp Ser Pro Gln Val Ala Asn Phe Asp Glu
305                 310                 315                 320

Asn Asp Ala Ser Thr Tyr His Val Asn Glu His Gly Glu Lys Ile Pro
            325                 330                 335

Asn Asn Leu Gly Thr Trp Ala Thr Gly Thr Thr Ser Asn Trp Gly Asn
        340                 345                 350

Ala Tyr Lys Lys Leu Met Glu His Tyr Gly Asn Ile Ser Met Thr Leu
    355                 360                 365

Ser Gly Thr Gly Cys Tyr Ile Asp Ile Asp Ser Tyr Ile Asn Asn Asn
370                 375                 380

Lys Val Ile Pro Ala Phe Ser Asn Lys Thr Gly Gly Asp Glu Ala Cys
385                 390                 395                 400

Gly Val Ala Cys Phe Asn Trp Tyr Lys Leu Thr Tyr Ala Glu Glu Asn Met
            405                 410                 415

Glu Arg Ile Asn Tyr Val Pro Thr Thr Glu Asp Leu Asp Ile Glu Ser
        420                 425                 430

Ile Thr Ala Ser Ser Asn Asn Phe Thr Ile Ser Val Gly Ser Asn Ala
    435                 440                 445

Val Val Thr Ile Ile Ser His Ala Lys Ser Gly Lys Glu Glu Ile
450                 455                 460

Thr Gly Lys Cys Thr Val Thr Ser Ser Asp Glu Asn Val Ala Tyr Tyr
465                 470                 475                 480

Asn Gly Ser Arg Ile Ile Ala Lys Glu Gln Gly Ala Cys Thr Val Thr
            485                 490                 495

Phe Lys Tyr Thr Asp Thr Asn Gly Lys Thr Leu Thr Thr Thr Val Asp
        500                 505                 510

Ile His Val Pro Glu Tyr Phe Pro Leu Thr Asn Val Gly Leu Asn Pro
    515                 520                 525

Ser Ile Tyr Gly Asn Gly Phe Phe Asp Glu Thr Thr Gly Lys Leu Gln
530                 535                 540

Thr Gly Gln Tyr Gly Phe Gly Gly Trp Lys Phe Ala Ser Gly Leu Asp
545                 550                 555                 560

Leu Ser Ala Tyr Asp Tyr Leu Thr Val Glu Leu Gln Glu Ala Asn Thr
            565                 570                 575

Ser Trp Gly Leu Ser Phe Arg Leu Phe Asp Ser Asp Asn Tyr Trp Ser
        580                 585                 590

Asn Pro Tyr Ser Lys Thr Phe Asp Gly Lys Thr Ser Ile Thr Ile Asn
    595                 600                 605

Leu Asn His Leu Asp Ile Glu Tyr Glu Asp Ala Asn Lys Val Lys His
610                 615                 620

Tyr Arg Thr Val Asp Pro Ser His Ile Tyr Ile Ala Gly Phe Trp Thr
625                 630                 635                 640

Met Gly Asp Ser Pro Ile Tyr Ile Lys Ser Ile Thr Leu Thr Lys Lys

```
              645                 650                 655
Ala Thr Ser Gly Ile Ser Gln Leu Asp Asn Asn Glu Lys Asp Glu Ile
              660                 665                 670

Ala Ser Val Lys Tyr Tyr Thr Val Asp Gly His Glu Val Asn Asp Gly
          675                 680                 685

Tyr Asn Lys Gly Met Lys Ile Lys Lys Ile Thr Tyr Lys Asn Gly Asn
          690                 695                 700

Val Lys Ile Asn Lys Cys Leu
705                 710
```

<210> SEQ ID NO 21
<211> LENGTH: 1038
<212> TYPE: DNA
<213> ORGANISM: Prevotella bryantii

<400> SEQUENCE: 21

```
atgaaaaaga tcttttttgc aatattatct ctctgttcac tcgttcttgc ttcttcttgc      60
aagaacggtg atgtagagtt cgccgatttt gattaccagt ctgtgtattt tgctaagcag     120
acaccaattc gtaccattac tctaggcgag gatgatgcat tccctaatga acttgataat     180
gcacacatgt gccagcttca agtggtgctc ggtggtgttt ggtctaacaa agtcgatcgt     240
catgtgaaaa tagctgttga taacagtttg gtagataatc tcaaatttaa tcagattgaa     300
ggtgaaaaat ttgtgaatac aggtaaacct gttgtagcaa tgccttctga ttactattct     360
ctagagacaa cagatgtcgt tattcctgca ggtaaggttc gtggtgttgt taatgtaaaa     420
ctgaacgaag ctttcttcaa cgatttgaag tctgcttatg ttacttacgt tattccagtt     480
cgtattcttg aggcaggtaa tgataccatt ttagaaaata gaactatac cctttatgca     540
gtagaatata gaatccgta ttctggcatt tggctcaata ccgctgacaa tacatctaag     600
agcatgctta cctgttatga tatgaattca gtaaactatg cacatagcga acggttaca     660
gctgcagagt ttaatgctaa tggtgaacct gtttacaaag atggtaaact tcagactgta     720
tctaagacac ttgatggcaa tgctattctg acgattggtg ctgatggtaa cataaccttc     780
tctactaata gtgctgactg caaaatcaag ggaaccggta gtttgtcaa aaacggttca     840
aaagttgacc atagcgtggc ttggggtgac agagaacgtg atcttatcga agtaaatttt     900
gatgttattt acagctatga agattatgat gaagccactc agaagaaagt aactcgtgaa     960
gtaactaaga actacaacga gaaactagtt ctgatttctc gtggcaatca cttgcgtgaa    1020
ttcacaacaa ccaaataa                                                  1038
```

<210> SEQ ID NO 22
<211> LENGTH: 345
<212> TYPE: PRT
<213> ORGANISM: Prevotella bryantii

<400> SEQUENCE: 22

```
Met Lys Lys Ile Phe Phe Ala Ile Leu Ser Leu Cys Ser Leu Val Leu
  1               5                  10                  15

Ala Ser Ser Cys Lys Asn Gly Asp Val Glu Phe Ala Asp Phe Asp Tyr
             20                  25                  30

Gln Ser Val Tyr Phe Ala Lys Gln Thr Pro Ile Arg Thr Ile Thr Leu
         35                  40                  45

Gly Glu Asp Asp Ala Phe Pro Asn Glu Leu Asp Asn Ala His Met Cys
     50                  55                  60

Gln Leu Gln Val Val Leu Gly Gly Val Trp Ser Asn Lys Val Asp Arg
```

```
                65                  70                  75                  80
His Val Lys Ile Ala Val Asp Asn Ser Leu Val Asp Asn Leu Lys Phe
                    85                  90                  95

Asn Gln Ile Glu Gly Glu Lys Phe Val Asn Thr Gly Lys Pro Val Val
            100                 105                 110

Ala Met Pro Ser Asp Tyr Tyr Ser Leu Glu Thr Thr Asp Val Val Ile
        115                 120                 125

Pro Ala Gly Lys Val Arg Gly Val Val Asn Val Lys Leu Asn Glu Ala
    130                 135                 140

Phe Phe Asn Asp Leu Lys Ser Ala Tyr Val Thr Tyr Val Ile Pro Val
145                 150                 155                 160

Arg Ile Leu Glu Ala Gly Asn Asp Thr Ile Leu Glu Asn Lys Asn Tyr
                165                 170                 175

Thr Leu Tyr Ala Val Glu Tyr Lys Asn Pro Tyr Ser Gly Ile Trp Leu
            180                 185                 190

Asn Thr Ala Asp Asn Thr Ser Lys Ser Met Leu Thr Cys Tyr Asp Met
        195                 200                 205

Asn Ser Val Asn Tyr Ala His Ser Glu Thr Val Thr Ala Ala Glu Phe
    210                 215                 220

Asn Ala Asn Gly Glu Pro Val Tyr Lys Asp Gly Lys Leu Gln Thr Val
225                 230                 235                 240

Ser Lys Thr Leu Asp Gly Asn Ala Ile Leu Thr Ile Gly Ala Asp Gly
                245                 250                 255

Asn Ile Thr Phe Ser Thr Asn Ser Ala Asp Cys Lys Ile Lys Gly Thr
            260                 265                 270

Gly Lys Phe Val Lys Asn Gly Ser Lys Val Asp His Ser Val Ala Trp
        275                 280                 285

Gly Asp Arg Glu Arg Asp Leu Ile Glu Val Asn Phe Asp Val Ile Tyr
    290                 295                 300

Ser Tyr Glu Asp Tyr Asp Glu Ala Thr Gln Lys Lys Val Thr Arg Glu
305                 310                 315                 320

Val Thr Lys Asn Tyr Asn Glu Lys Leu Val Leu Ile Ser Arg Gly Asn
                325                 330                 335

His Leu Arg Glu Phe Thr Thr Thr Lys
            340                 345

<210> SEQ ID NO 23
<211> LENGTH: 2358
<212> TYPE: DNA
<213> ORGANISM: Prevotella bryantii

<400> SEQUENCE: 23
atgaaaaata aaaccgtat tctgaagtat cttatgttag ccttgggct attaccttca      60 tcggctatgg cacaagctga tcctaatttt tatatttacc tctgttttgg ccagtcgaat    120
atggagggta tgccaaaat tcagcctcaa gatttgctat ctatagattc tgcttttcag    180
atgatggcag ctgtagacaa tcctgcgatg aatcgcaaga tggggaatg gtcggtagca    240 gtccctccgt tgtgtcgtcc gaatacgggt ttgactcctg ttgattattt tggtcgtact    300
cttgtaaaat atcttcctaa taatattaag gtaggtgtta ttcatgttgc atcggaggt    360 tgtaagatag aagcatacat gactgattct attgggaatt atgtcaagac ggctcccgac    420
tggatggtac caatgcttgc tgcttatgat aataatcctt atcagcgtat cgttacgctg    480
gctcgtaaag cgcaaaagca gggtgtaatt aaaggtatcc ttctgcatca aggagaaagt    540
```

```
aattgtggac aggaggattg gccggttaag gtaaaatctg tatatgatca tcttttgaag      600
gacttgtctc taaaagcaga agatgtgcct ttgttagcag gtgaggtggt acgagctaat      660
ggaggggac gatgtatctc gatgaatccg attatcaatc gtctgcctga ggttattccg       720
acagcccatg tcatttcttc cgaaggatgt tctaatgcaa gtgattctct cactttgat       780
gcagccggtt atcgtatgtt aggtaaacgg tacgcatatg agatgcttca cctgatgggt      840
caagatgtgg ttgtcaagaa tccgatgcta tgggcagatg ttcctgatcc tgatgtaatt      900
cgtgtcggtg aatactatta tttagtaagc acaacgatgc atcttatgcc aggtgcacct      960
gtgatgcgtt ctaaagattt tcaaaactgg gaaccgtaa gctatatctt tgataagttg      1020
actgattctc caaatataa tatggagaaa ggtacggtgt atggtcgagg tcaatgggct      1080
acttctctga aatatcataa aggtaaattc tatgcactct ttgctcctaa tgataatcct      1140
ggtggtgata cctatatata tagtgcagat aaagccgaag gagaatggaa actggtgagt      1200
cgtatgaagc atttccatga tgcatcgctt tttttcgatg atgatgatcg tgtatatgtg      1260
gtttatggta ccggtcaaat ctgtgaattg aagagtgatt taagtggtgt tattccaggt      1320
acagatcgta ttctcttta gcgtgaagct gatgaaacgg gacttcttga aggaagtcga      1380
atggtaaagc atgacggcaa gtattatctt accatgatat cttggcctgc tggtaaggct      1440
cgccatcagg tatgctatcg tatgacagt ctgaatggac ttttggagaa aaaacaata      1500
ctacttagtt cttttggcgg attcccatac gtagggcagg gtactatcgt agatggtgct      1560
gatggtaact ggtatggtat tatatttcag gatcgtggtg gagtaggacg tgtacttaca      1620
tgtatgccat gtcgatggat agatggttgg ccaatgcttg gcgatgagaa tggtcatgta      1680
cctacttata tggtaaagcc tgtgcttggt gaagctgtta aaaccattta tgcttcagat      1740
gaatttgaag gttctgagct gaacaaagcg tggcagtgga atcataaccc tattgatcat      1800
gcctggaagg ttggtaatgg taaacttacg ctcaaagtgg ctcgcatagc tcattctatt      1860
tatgatgcac caaataccat aagtcagcgt actatgggtc ctaagagtag tgtatctgtg      1920
caagttgatg tgaagcattt gaagagaggt gattatgccg gtctggctgt cttcaatgat      1980
gatggtgctt tacttcagat agaaaagacg gctttgggtt atcgcttgag tcagaaaact      2040
acttctgtac agttgggcca gaaagataag gagattcagg attataaga agaaagtcat      2100
ggtcaacttg aatttgttaa ggataacata tggttgaaga ttaatgcaga tttccgacct      2160
ggtaaggata ttgcgacatt tgagtatagt ttggatggta gacgtggaa gacaattggt      2220
ctaccttca agatgggtta tgattatcgt cgcttcttta tgggtgcccg ttttgcctta      2280
ttcaactatg gcacaaaggt caagggcggt aaagctgaat tcaagcattt ctgttataac      2340
gtaaatgata tgcgataa                                                    2358
```

<210> SEQ ID NO 24
<211> LENGTH: 785
<212> TYPE: PRT
<213> ORGANISM: Prevotella bryantii

<400> SEQUENCE: 24

Met Lys Asn Lys Asn Arg Ile Leu Lys Tyr Leu Met Leu Ala Leu Gly
 1               5                  10                  15

Leu Leu Pro Ser Ser Ala Met Ala Gln Ala Asp Pro Asn Phe Tyr Ile
            20                  25                  30

Tyr Leu Cys Phe Gly Gln Ser Asn Met Glu Gly Asn Ala Lys Ile Gln
        35                  40                  45

-continued

Pro Gln Asp Leu Leu Ser Ile Asp Ser Arg Phe Gln Met Met Ala Ala
    50                      55                      60

Val Asp Asn Pro Ala Met Asn Arg Lys Met Gly Glu Trp Ser Val Ala
65              70                      75                      80

Val Pro Pro Leu Cys Arg Pro Asn Thr Gly Leu Thr Pro Val Asp Tyr
                85                      90                      95

Phe Gly Arg Thr Leu Val Lys Tyr Leu Pro Asn Asn Ile Lys Val Gly
            100                 105                 110

Val Ile His Val Ala Ile Gly Gly Cys Lys Ile Glu Ala Tyr Met Thr
        115                 120                 125

Asp Ser Ile Gly Asn Tyr Val Lys Thr Ala Pro Asp Trp Met Val Pro
    130                 135                 140

Met Leu Ala Ala Tyr Asp Asn Asn Pro Tyr Gln Arg Ile Val Thr Leu
145             150                 155                     160

Ala Arg Lys Ala Gln Lys Gly Val Ile Lys Gly Ile Leu Leu His
                165                 170                 175

Gln Gly Glu Ser Asn Cys Gly Gln Glu Asp Trp Pro Val Lys Val Lys
            180                 185                 190

Ser Val Tyr Asp His Leu Leu Lys Asp Leu Ser Leu Lys Ala Glu Asp
        195                 200                 205

Val Pro Leu Leu Ala Gly Glu Val Arg Ala Asn Gly Gly Gly Arg
    210                 215                 220

Cys Ile Ser Met Asn Pro Ile Ile Asn Arg Leu Pro Glu Val Ile Pro
225                 230                 235                 240

Thr Ala His Val Ile Ser Ser Glu Gly Cys Ser Asn Ala Ser Asp Ser
                245                 250                 255

Leu His Phe Asp Ala Ala Gly Tyr Arg Met Leu Gly Lys Arg Tyr Ala
            260                 265                 270

Tyr Glu Met Leu His Leu Met Gly Gln Asp Val Val Lys Asn Pro
        275                 280                 285

Met Leu Trp Ala Asp Val Pro Asp Pro Asp Val Ile Arg Val Gly Glu
290                 295                 300

Tyr Tyr Tyr Leu Val Ser Thr Thr Met His Leu Met Pro Gly Ala Pro
305                 310                 315                 320

Val Met Arg Ser Lys Asp Phe Gln Asn Trp Glu Thr Val Ser Tyr Ile
                325                 330                 335

Phe Asp Lys Leu Thr Asp Ser Pro Lys Tyr Asn Met Glu Lys Gly Thr
            340                 345                 350

Val Tyr Gly Arg Gly Gln Trp Ala Thr Ser Leu Lys Tyr His Lys Gly
        355                 360                 365

Lys Phe Tyr Ala Leu Phe Ala Pro Asn Asp Asn Pro Gly Gly Asp Thr
370                 375                 380

Tyr Ile Tyr Ser Ala Asp Lys Ala Glu Gly Glu Trp Lys Leu Val Ser
385                 390                 395                 400

Arg Met Lys His Phe His Asp Ala Ser Leu Phe Phe Asp Asp Asp
                405                 410                 415

Arg Val Tyr Val Val Tyr Gly Thr Gly Gln Ile Cys Glu Leu Lys Ser
            420                 425                 430

Asp Leu Ser Gly Val Ile Pro Gly Thr Asp Arg Ile Leu Phe Lys Arg
        435                 440                 445

Glu Ala Asp Glu Thr Gly Leu Leu Glu Gly Ser Arg Met Val Lys His
450                 455                 460

Asp Gly Lys Tyr Tyr Leu Thr Met Ile Ser Trp Pro Ala Gly Lys Ala

```
                465                 470                 475                 480
Arg His Gln Val Cys Tyr Arg Met Asp Ser Leu Asn Gly Pro Leu Glu
                            485                 490                 495
Lys Lys Thr Ile Leu Ser Ser Phe Gly Gly Phe Pro Tyr Val Gly
                500                 505                 510
Gln Gly Thr Ile Val Asp Gly Ala Asp Gly Asn Trp Tyr Gly Ile Ile
                515                 520                 525
Phe Gln Asp Arg Gly Val Gly Arg Val Leu Thr Cys Met Pro Cys
        530                 535                 540
Arg Trp Ile Asp Gly Trp Pro Met Leu Gly Asp Glu Asn Gly His Val
545                 550                 555                 560
Pro Thr Tyr Met Val Lys Pro Val Leu Gly Glu Ala Val Lys Thr Ile
                    565                 570                 575
Tyr Ala Ser Asp Glu Phe Glu Gly Ser Glu Leu Asn Lys Ala Trp Gln
                580                 585                 590
Trp Asn His Asn Pro Ile Asp His Ala Trp Lys Val Gly Asn Gly Lys
            595                 600                 605
Leu Thr Leu Lys Val Ala Arg Ile Ala His Ser Ile Tyr Asp Ala Pro
        610                 615                 620
Asn Thr Ile Ser Gln Arg Thr Met Gly Pro Lys Ser Ser Val Ser Val
625                 630                 635                 640
Gln Val Asp Val Lys His Leu Lys Arg Gly Asp Tyr Ala Gly Leu Ala
                    645                 650                 655
Val Phe Asn Asp Asp Gly Ala Leu Leu Gln Ile Glu Lys Thr Ala Leu
                660                 665                 670
Gly Tyr Arg Leu Ser Gln Lys Thr Thr Ser Val Gln Leu Gly Gln Lys
            675                 680                 685
Asp Lys Glu Ile Gln Asp Tyr Lys Glu Glu Ser His Gly Gln Leu Glu
        690                 695                 700
Phe Val Lys Asp Asn Ile Trp Leu Lys Ile Asn Ala Asp Phe Arg Pro
705                 710                 715                 720
Gly Lys Asp Ile Ala Thr Phe Glu Tyr Ser Leu Asp Gly Lys Thr Trp
                    725                 730                 735
Lys Thr Ile Gly Leu Pro Phe Lys Met Gly Tyr Asp Tyr Arg Arg Phe
                740                 745                 750
Phe Met Gly Ala Arg Phe Ala Leu Phe Asn Tyr Gly Thr Lys Val Lys
            755                 760                 765
Gly Gly Lys Ala Glu Phe Lys His Phe Cys Tyr Asn Val Asn Asp Met
    770                 775                 780
Arg
785

<210> SEQ ID NO 25
<211> LENGTH: 960
<212> TYPE: DNA
<213> ORGANISM: Prevotella bryantii

<400> SEQUENCE: 25
atgaaggcaa aatacgtgtt tccaagtgat tatatggcag accctgctgc caacgtgttt      60
gatggtaaac tctatatcta tcctagtcac gactatgata gtggtgagtg ttttgatgat     120
gatggtggtc atttccagat gaaagactat catgtactct gtattgatgg tgatccaatg     180
gaacaggatg ccaaggactg tggtaaacag tttggtatcg aggatatccc atgggtagag     240
aagcagttgt gggataacga ctgtgtagag aaggatggta atactatct tatctatagt     300
```

```
gccaaggatt ataccggtgt gtttcatctt ggtgtagcag tagccgataa acctgaggga    360
ccatttgtgc cagaagcaga tcctattcgt ggttcgtata gtatcgaccc atgcgttttc    420
aaggatgatg atggtgaaat ttatgtgtat tttggtggta tctggggtgg tcagctccaa    480
tggtacaagg ataataagat gctaaaggct gaacacttgc ctgagggtaa ggaagatcca    540
cttccttcta gagttgctcg tatgaccggt gatgttaagc agtttgctga ggctccacgt    600
gctgtcatta tcgtagacga gacaggtaaa cctttaccag cagacgatcc tcaccgtttc    660
ttcgaggctt catggatgca caatataat ggaaagtatt attttagtta tagtactgga    720
gatacacatt tactctgcta cgctgtaggc gataatcctt atggtccatt tacttaccag    780
ggtgttattc ttgaaccagt tgtaggttgg actactcatc attctattgt agaatataaa    840
ggcaagtggt atcttttcca tcacgactgt gtaccttcta atgacactac ttggttacgt    900
tctttgaagg tagctgagtt ggaatatgac gctgaaggtc atatcaagac agtaaaataa    960
```

<210> SEQ ID NO 26
<211> LENGTH: 319
<212> TYPE: PRT
<213> ORGANISM: Prevotella bryantii

<400> SEQUENCE: 26

```
Met Lys Ala Lys Tyr Val Phe Pro Ser Asp Tyr Met Ala Asp Pro Ala
1               5                   10                  15

Ala Asn Val Phe Asp Gly Lys Leu Tyr Ile Tyr Pro Ser His Asp Tyr
            20                  25                  30

Asp Ser Gly Glu Cys Phe Asp Asp Gly Gly His Phe Gln Met Lys
        35                  40                  45

Asp Tyr His Val Leu Cys Ile Asp Gly Asp Pro Met Glu Gln Asp Ala
    50                  55                  60

Lys Asp Cys Gly Lys Gln Phe Gly Ile Glu Asp Ile Pro Trp Val Glu
65                  70                  75                  80

Lys Gln Leu Trp Asp Asn Asp Cys Val Glu Lys Asp Gly Lys Tyr Tyr
                85                  90                  95

Leu Ile Tyr Ser Ala Lys Asp Tyr Thr Gly Val Phe His Leu Gly Val
            100                 105                 110

Ala Val Ala Asp Lys Pro Glu Gly Pro Phe Val Pro Glu Ala Asp Pro
        115                 120                 125

Ile Arg Gly Ser Tyr Ser Ile Asp Pro Cys Val Phe Lys Asp Asp Asp
    130                 135                 140

Gly Glu Ile Tyr Val Tyr Phe Gly Gly Ile Trp Gly Gly Gln Leu Gln
145                 150                 155                 160

Trp Tyr Lys Asp Asn Lys Met Leu Lys Ala Glu His Leu Pro Glu Gly
                165                 170                 175

Lys Glu Asp Pro Leu Pro Ser Arg Val Ala Arg Met Thr Gly Asp Val
            180                 185                 190

Lys Gln Phe Ala Glu Ala Pro Arg Ala Val Ile Val Asp Glu Thr
        195                 200                 205

Gly Lys Pro Leu Pro Ala Asp Asp Pro His Arg Phe Phe Glu Ala Ser
    210                 215                 220

Trp Met His Lys Tyr Asn Gly Lys Tyr Tyr Phe Ser Tyr Ser Thr Gly
225                 230                 235                 240

Asp Thr His Leu Leu Cys Tyr Ala Val Gly Asp Asn Pro Tyr Gly Pro
                245                 250                 255
```

```
Phe Thr Tyr Gln Gly Val Ile Leu Glu Pro Val Gly Trp Thr Thr
            260                 265                 270

His His Ser Ile Val Glu Tyr Lys Gly Lys Trp Tyr Leu Phe His His
        275                 280                 285

Asp Cys Val Pro Ser Asn Asp Thr Thr Trp Leu Arg Ser Leu Lys Val
    290                 295                 300

Ala Glu Leu Glu Tyr Asp Ala Glu Gly His Ile Lys Thr Val Lys
305                 310                 315

<210> SEQ ID NO 27
<211> LENGTH: 1185
<212> TYPE: DNA
<213> ORGANISM: Prevotella bryantii

<400> SEQUENCE: 27
atgaatacac gtagattatt agttaagttg ttattcttag cctgtgcctg tccagctata      60
gcgcaaaaca caagttgggt gggcacgtgg gcttctgcca gcgaatgggc tgggggaaat    120
gacctgccaa aaacatcttt ggccaatcgt accattcgac aggttatccg tacttcgata    180
gcaggtaata catttcgtat gaaactctct aacgagttta gtgaagttcc tgtcgaaatt    240
cgccaaattt atctgtccct ggttgatgac tcctcggcta ttcagaaaaa cacgagtgtt    300
gtgcttcgag tgaaaggaaa acacagcttt actattgaaa agggtaaagc cctttatact    360
gatgccttta gatgaatat tcctaaactc tctagagttg cggtaaccat atgttacggc    420
aatcaggtgc ctgaacatat gacttcacat cgtgggtctc gaacaacttc ttatatcgct    480
cagggtatgg tttctccaaa acagacttt aagacagagg agaaacttga ccattggtat    540
accatggcaa cacttgaaac aaagagtgat aagcaggatg ctattgctat cttgggtaat    600
agtattactg atggacgtgg tacaacaact aatgcccaaa accgttggcc cgatagaatg    660
gccgaggcat tgaatggtga acaggtgta ctcaatctcg gtattggcgg taactgtgtc    720
gtagaatatg gtataagtga acctgcattg aaacgattcg accgagatat tctttctcag    780
cagggtatca gtagcgtggt tatctttgaa ggtactaatg atataggtat aagtaacaaa    840
aattacgaac atgttgctga tacgcttatt gcttcttatc gagtgcttgc ctcgcgtgct    900
aaggcaaagg gacttaaggt tatggagca acgattactc ctactaaagg taacggctgg    960
tattcactgt ggcatgaggc tatccgccaa acagtaaatg aatggattcg tcagacggat   1020
gtctttgatg gtgttatcga tttcgataag gctgtacgtg atccgaagga tgaacagcag   1080
ttgctgcctg cttattctga agacggactt catttgaatc ctgaaggata tcgtgttatg   1140
ggagaatttg cagcatcttt ttttaaaaat cttaaaaaca aataa                   1185

<210> SEQ ID NO 28
<211> LENGTH: 394
<212> TYPE: PRT
<213> ORGANISM: Prevotella bryantii

<400> SEQUENCE: 28

Met Asn Thr Arg Arg Leu Leu Val Lys Leu Leu Phe Leu Ala Cys Ala
1               5                   10                  15

Cys Pro Ala Ile Ala Gln Asn Thr Ser Trp Val Gly Thr Trp Ala Ser
            20                  25                  30

Ala Ser Glu Trp Ala Gly Gly Asn Asp Leu Pro Lys Thr Ser Leu Ala
        35                  40                  45

Asn Arg Thr Ile Arg Gln Val Ile Arg Thr Ser Ile Ala Gly Asn Thr
    50                  55                  60
```

```
Phe Arg Met Lys Leu Ser Asn Glu Phe Ser Glu Val Pro Val Glu Ile
 65                  70                  75                  80

Arg Gln Ile Tyr Leu Ser Leu Val Asp Asp Ser Ser Ala Ile Gln Lys
             85                  90                  95

Asn Thr Ser Val Val Leu Arg Val Lys Gly Lys His Ser Phe Thr Ile
            100                 105                 110

Glu Lys Gly Lys Ala Leu Tyr Thr Asp Ala Phe Lys Met Asn Ile Pro
        115                 120                 125

Lys Leu Ser Arg Val Ala Val Thr Ile Cys Tyr Gly Asn Gln Val Pro
130                 135                 140

Glu His Met Thr Ser His Arg Gly Ser Arg Thr Thr Ser Tyr Ile Ala
145                 150                 155                 160

Gln Gly Met Val Ser Pro Lys Gln Thr Phe Lys Thr Glu Glu Lys Leu
                165                 170                 175

Asp His Trp Tyr Thr Met Ala Thr Leu Glu Thr Lys Ser Asp Lys Gln
            180                 185                 190

Asp Ala Ile Ala Ile Leu Gly Asn Ser Ile Thr Asp Gly Arg Gly Thr
        195                 200                 205

Thr Thr Asn Ala Gln Asn Arg Trp Pro Asp Arg Met Ala Glu Ala Leu
210                 215                 220

Asn Gly Glu Thr Gly Val Leu Asn Leu Gly Ile Gly Gly Asn Cys Val
225                 230                 235                 240

Val Glu Tyr Gly Ile Ser Glu Pro Ala Leu Lys Arg Phe Asp Arg Asp
                245                 250                 255

Ile Leu Ser Gln Gln Gly Ile Ser Ser Val Val Ile Phe Glu Gly Thr
            260                 265                 270

Asn Asp Ile Gly Ile Ser Asn Lys Asn Tyr Glu His Val Ala Asp Thr
        275                 280                 285

Leu Ile Ala Ser Tyr Arg Val Leu Ala Ser Arg Ala Lys Ala Lys Gly
290                 295                 300

Leu Lys Val Tyr Gly Ala Thr Ile Thr Pro Thr Lys Gly Asn Gly Trp
305                 310                 315                 320

Tyr Ser Leu Trp His Glu Ala Ile Arg Gln Thr Val Asn Glu Trp Ile
                325                 330                 335

Arg Gln Thr Asp Val Phe Asp Gly Val Ile Asp Phe Asp Lys Ala Val
            340                 345                 350

Arg Asp Pro Lys Asp Glu Gln Gln Leu Leu Pro Ala Tyr Ser Glu Asp
        355                 360                 365

Gly Leu His Leu Asn Pro Glu Gly Tyr Arg Val Met Gly Glu Phe Ala
370                 375                 380

Ala Ser Phe Phe Lys Asn Leu Lys Asn Lys
385                 390

<210> SEQ ID NO 29
<211> LENGTH: 1890
<212> TYPE: DNA
<213> ORGANISM: Prevotella bryantii

<400> SEQUENCE: 29
atggaattta agacaacaat gattaaatat ttaggtatcg ctttaatgtc cgttctttcg      60
ttcggtataa atgcaaagac aaaccataca aatcatgtca cgcaggtttc tcaaatcacg     120
aatcaggcga tatcaccaga tggtaaaatc aaggtctcgg tagaaggtca ttctctgaaa     180
gtaagctact gcaaacgaca catgatggat atccaaatag gtatggataa agctgaattt     240
```

```
acccccgtcat tgttgcaac aaaaccaatt gtagaggatt ataagatgct taccggcaaa      300
aagagtcatt gcaccaatca gggtacggaa tatcagttgg gcaatctgca actacgactc      360
tttaacgatg gtcttgcatt cagatatgtc atcaatggct tgcaaaatga gaaagtacca      420
aaagaatata ccagttatcg tataacctgaa ggaatgaaac gctggatgat ggagtggact     480
gacgcttatg aaagtctata cccagaaatg acttcgcata aaatgaaacc gaaacgtttg      540
tttcagggta tcgaactcac tactgatggt aatgtaaaac gatggggcta tccagctttg      600
ctcgaaccac aaaaagattg ctatgttctt atatctgagg caaatatcga acgtaaccag      660
agtgcttctt gcctttacaa cgagggagaa cagtttaaag ttactcctgc tgaaaacgat      720
gtaaaaatac atgggaactg gcatactcca tggcgagtgc tgatgatagg taaaaaagaa      780
aaactcgttg aatctacctt aattactgat ttatctgaac cttctaaaat aaaggatacg      840
agttggatta atccaggtgt cgtatcatgg atatactggg catataacca tggcagtaat      900
gattatgcca ttatccaaaa gtacgtagac atggcaaaag cactacaact acccctatgta  960
ctcatcgatg cagaatggga tcagatgaaa aatggaaaaa ccatagaaga tgctatacgc     1020
tatgcccacg aaaaaggcgt taaaccgatg atttggtaca attctagtgt cggttggact     1080
aatggtgctc ctactccact atttcgactc aacaaacctg aagatagaga aaaggaattt     1140
gcatggtgcg aaaagctggg tattgcaggt gtcaaaatcg atttctttttc gggtgacaac    1200
caaatgaata tggaatactg catcgacttg cttgaatgtg cggccagaca tcatctcctg     1260
gttaactttc atggagcaac gattccgcgc gggtggcaac gcacctaccc taacttgatg     1320
agcacagagg cggtatatgg agcggaatgg tataataacg tacctacctt tactcacgaa     1380
gctgcctgcc acaacgcaac cctaccattt acccgaaata tcattggatc tatggattac     1440
actccgtgtg ccttcagcaa ttcacagcat cctcacatta ctactaatgc acatgagttg     1500
gcactcacag tactctttga gagtggttta cagcatttgg cagataaacc agaaagttac     1560
ctgactcaac cacaagaagt acaaagtttc ttatcccaac ttccttcaac ctgggatgaa     1620
acgaaattga taaagggtga tattgggaaa aatgttatca tcgcacgaag aaaaggcaaa    1680
acttggtttg tcgcaggtat aaatggaacc gaccaaaact gtatcgtaaa atgttgtctc     1740
aatcaaaaga taaagctctc atctatccaa gaagtaaccg tattcgaaga taacagcaaa    1800
gagtggaaaa tcagtaaata taagaagata ccaagcactt tccatgaatg gcccaatggt    1860
ggattcgtga tggtaattca gcagggataa                                      1890
```

<210> SEQ ID NO 30
<211> LENGTH: 629
<212> TYPE: PRT
<213> ORGANISM: Prevotella bryantii

<400> SEQUENCE: 30

```
Met Glu Phe Lys Thr Thr Met Ile Lys Tyr Leu Gly Ile Ala Leu Met
  1               5                  10                  15

Ser Val Leu Ser Phe Gly Ile Asn Ala Lys Thr Asn His Thr Asn His
                 20                  25                  30

Val Thr Gln Val Ser Gln Ile Thr Asn Gln Ala Ile Ser Pro Asp Gly
             35                  40                  45

Lys Ile Lys Val Ser Val Glu Gly His Ser Leu Lys Val Ser Tyr Cys
         50                  55                  60

Lys Arg His Met Met Asp Ile Gln Ile Gly Met Asp Lys Ala Glu Phe
 65                  70                  75                  80
```

```
Thr Pro Ser Phe Val Ala Thr Lys Pro Ile Val Glu Asp Tyr Lys Met
                85                  90                  95

Leu Thr Gly Lys Lys Ser His Cys Thr Asn Gln Gly Thr Glu Tyr Gln
            100                 105                 110

Leu Gly Asn Leu Gln Leu Arg Leu Phe Asn Asp Gly Leu Ala Phe Arg
        115                 120                 125

Tyr Val Ile Asn Gly Leu Gln Asn Glu Lys Val Pro Lys Glu Tyr Thr
    130                 135                 140

Ser Tyr Arg Ile Pro Glu Gly Met Lys Arg Trp Met Met Glu Trp Thr
145                 150                 155                 160

Asp Ala Tyr Glu Ser Leu Tyr Pro Glu Met Thr Ser His Lys Met Lys
                165                 170                 175

Pro Lys Arg Leu Phe Gln Gly Ile Glu Leu Thr Thr Asp Gly Asn Val
            180                 185                 190

Lys Arg Trp Gly Tyr Pro Ala Leu Leu Glu Pro Gln Lys Asp Cys Tyr
        195                 200                 205

Val Leu Ile Ser Glu Ala Asn Ile Glu Arg Asn Gln Ser Ala Ser Cys
    210                 215                 220

Leu Tyr Asn Glu Gly Glu Gln Phe Lys Val Thr Pro Ala Glu Asn Asp
225                 230                 235                 240

Val Lys Ile His Gly Asn Trp His Thr Pro Trp Arg Val Leu Met Ile
                245                 250                 255

Gly Lys Lys Glu Lys Leu Val Glu Ser Thr Leu Ile Thr Asp Leu Ser
            260                 265                 270

Glu Pro Ser Lys Ile Lys Asp Thr Ser Trp Ile Asn Pro Gly Val Val
        275                 280                 285

Ser Trp Ile Tyr Trp Ala Tyr Asn His Gly Ser Asn Asp Tyr Ala Ile
    290                 295                 300

Ile Gln Lys Tyr Val Asp Met Ala Lys Ala Leu Gln Leu Pro Tyr Val
305                 310                 315                 320

Leu Ile Asp Ala Glu Trp Asp Gln Met Lys Asn Gly Lys Thr Ile Glu
                325                 330                 335

Asp Ala Ile Arg Tyr Ala His Glu Lys Gly Val Lys Pro Met Ile Trp
            340                 345                 350

Tyr Asn Ser Ser Val Gly Trp Thr Asn Gly Ala Pro Thr Pro Leu Phe
        355                 360                 365

Arg Leu Asn Lys Pro Glu Asp Arg Glu Lys Glu Phe Ala Trp Cys Glu
    370                 375                 380

Lys Leu Gly Ile Ala Gly Val Lys Ile Asp Phe Phe Ser Gly Asp Asn
385                 390                 395                 400

Gln Met Asn Met Glu Tyr Cys Ile Asp Leu Leu Glu Cys Ala Ala Arg
                405                 410                 415

His His Leu Leu Val Asn Phe His Gly Ala Thr Ile Pro Arg Gly Trp
            420                 425                 430

Gln Arg Thr Tyr Pro Asn Leu Met Ser Thr Glu Ala Val Tyr Gly Ala
        435                 440                 445

Glu Trp Tyr Asn Asn Val Pro Thr Phe Thr His Glu Ala Ala Cys His
    450                 455                 460

Asn Ala Thr Leu Pro Phe Thr Arg Asn Ile Ile Gly Ser Met Asp Tyr
465                 470                 475                 480

Thr Pro Cys Ala Phe Ser Asn Ser Gln His Pro His Ile Thr Thr Asn
                485                 490                 495
```

Ala His Glu Leu Ala Leu Thr Val Leu Phe Glu Ser Gly Leu Gln His
            500                 505                 510

Leu Ala Asp Lys Pro Glu Ser Tyr Leu Thr Gln Pro Gln Glu Val Gln
        515                 520                 525

Ser Phe Leu Ser Gln Leu Pro Ser Thr Trp Asp Glu Thr Lys Leu Ile
    530                 535                 540

Lys Gly Asp Ile Gly Lys Asn Val Ile Ile Ala Arg Arg Lys Gly Lys
545                 550                 555                 560

Thr Trp Phe Val Ala Gly Ile Asn Gly Thr Asp Gln Asn Cys Ile Val
                565                 570                 575

Lys Cys Cys Leu Asn Gln Lys Ile Lys Leu Ser Ser Ile Gln Glu Val
            580                 585                 590

Thr Val Phe Glu Asp Asn Ser Lys Glu Trp Lys Ile Ser Lys Tyr Lys
        595                 600                 605

Lys Ile Pro Ser Thr Phe His Glu Trp Pro Asn Gly Gly Phe Val Met
    610                 615                 620

Val Ile Gln Gln Gly
625

<210> SEQ ID NO 31
<211> LENGTH: 1449
<212> TYPE: DNA
<213> ORGANISM: Prevotella bryantii

<400> SEQUENCE: 31
atgaactggc gtaaaatatc ctatatatat atgttggcac ttacacaaca agtgtctgct      60
caaatcggtg aaccctatat tcacgacccc tcgacaatcg tggcctgtga tggaaaatac     120
tacacctttg gcacgggtga aggtggactc atctctgaag atggctggac atggcacgat     180
ggagctgtca gacccggaag aggtgccgct cccgatgtga tgaaaatcgg agaccgatac     240
ttagttatat atggtgccac gggtggcgga ctgatgggtg acataatggg cgtattctg     300 accatgtgga ataagacgct cgatcctcta tcacctgatt tcaaatacac agcacccgta     360
gaggtagcta attctgatgg cctcgaagac tgtgatgcca tagacccaag cctgttattt     420
gatcccaaga ccggaaaact atgggtaact tatggtacct attggggcaa tatccgacaa     480
atagaattag accctaaaac gggtagacgc gttgagggta atattgaaaa agatatcgct     540
atcgactgtg aggctacaga tatgatagag catgatggct ggtattatct tctgggtacg     600
cacggtacct gttgcgatgg ggtcaattct acttataata atatgtggg tcgctctaaa     660 agtccaaatg gccccttgt ggataacgtc ggcagagata tgctagccgg tggaggaaaa     720
atggttgttg ctggcggcga cagagtagtg ggtacaggac atttcggacg agtatgcatc     780
gatgaagggg ttgagattat ttcactccac tacgaggcag acttcgatca gggtggaaga     840
agtgtactgg gtatcagacc attactctgg aaaaatggat ggcctaaagc tggcaatcgc     900
tttaaggctg gcatctacga aatagaatct gaacgccgtg gatatgcact agagcttgct     960
actgatttcg tcagaatacc tcaggagata catttctggg ggcagaagga tacgactgaa    1020
gccaaaccga tagacagcca gcgtctcgaa gaggtggaaa agacatggcc taaaggagaa    1080
atcgggattc gctgtaatga ttatatgttc agacctaatc aacgctggga aattaaaccg    1140
gcagagggaa aagtggcta tctcggtgga ccatattata cgataggaat gctggaaca    1200 tctcgtatgc tcagctac tgctcatggc gaactcatcg ctagcacagt ttatactgga    1260
gctgatgaac agttgtggcg tatagagcag ctcactgatg gcactttcag aattatgccg    1320

```
aaagccatac ctggaatcga aggcgaaaat aaaaaatatt gcttgtattc tgcaggcgat   1380
agtacaccaa ctttggcaga atataatttt aaatcagata actcaaaatg gaatttaaga   1440
caacaatga                                                           1449
```

<210> SEQ ID NO 32
<211> LENGTH: 482
<212> TYPE: PRT
<213> ORGANISM: Prevotella bryantii

<400> SEQUENCE: 32

```
Met Asn Trp Arg Lys Ile Ser Tyr Ile Tyr Met Leu Ala Leu Thr Gln
  1               5                  10                  15

Gln Val Ser Ala Gln Ile Gly Glu Pro Tyr Ile His Asp Pro Ser Thr
             20                  25                  30

Ile Val Ala Cys Asp Gly Lys Tyr Tyr Thr Phe Gly Thr Gly Glu Gly
         35                  40                  45

Gly Leu Ile Ser Glu Asp Gly Trp Thr Trp His Asp Gly Ala Val Arg
     50                  55                  60

Pro Gly Arg Gly Ala Ala Pro Asp Val Met Lys Ile Gly Asp Arg Tyr
 65                  70                  75                  80

Leu Val Ile Tyr Gly Ala Thr Gly Gly Gly Leu Met Gly His Gly Asn
                 85                  90                  95

Gly Arg Ile Leu Thr Met Trp Asn Lys Thr Leu Asp Pro Leu Ser Pro
            100                 105                 110

Asp Phe Lys Tyr Thr Ala Pro Val Glu Val Ala Asn Ser Asp Gly Leu
        115                 120                 125

Glu Asp Cys Asp Ala Ile Asp Pro Ser Leu Phe Ile Asp Pro Lys Thr
    130                 135                 140

Gly Lys Leu Trp Val Thr Tyr Gly Thr Tyr Trp Gly Asn Ile Arg Gln
145                 150                 155                 160

Ile Glu Leu Asp Pro Lys Thr Gly Arg Arg Val Glu Gly Asn Ile Glu
                165                 170                 175

Lys Asp Ile Ala Ile Asp Cys Glu Ala Thr Asp Met Ile Glu His Asp
            180                 185                 190

Gly Trp Tyr Tyr Leu Leu Gly Thr His Gly Thr Cys Cys Asp Gly Val
        195                 200                 205

Asn Ser Thr Tyr Asn Ile Ile Cys Gly Arg Ser Lys Ser Pro Asn Gly
    210                 215                 220

Pro Phe Val Asp Asn Val Gly Arg Asp Met Leu Ala Gly Gly Gly Lys
225                 230                 235                 240

Met Val Val Ala Gly Gly Asp Arg Val Val Gly Thr Gly His Phe Gly
                245                 250                 255

Arg Val Cys Ile Asp Glu Gly Val Glu Ile Ser Leu His Tyr Glu
            260                 265                 270

Ala Asp Phe Asp Gln Gly Gly Arg Ser Val Leu Gly Ile Arg Pro Leu
        275                 280                 285

Leu Trp Lys Asn Gly Trp Pro Lys Ala Gly Asn Arg Phe Lys Ala Gly
    290                 295                 300

Ile Tyr Glu Ile Glu Ser Glu Arg Arg Gly Tyr Ala Leu Glu Leu Ala
305                 310                 315                 320

Thr Asp Phe Val Arg Ile Pro Gln Glu Ile His Phe Trp Gly Gln Lys
                325                 330                 335

Asp Thr Thr Glu Ala Lys Pro Ile Asp Ser Gln Arg Leu Glu Glu Val
            340                 345                 350
```

```
Glu Lys Thr Trp Pro Lys Gly Glu Ile Gly Ile Arg Cys Asn Asp Tyr
            355                 360                 365

Met Phe Arg Pro Asn Gln Arg Trp Glu Ile Lys Pro Ala Glu Gly Lys
    370                 375                 380

Gly Gly Tyr Leu Gly Pro Tyr Tyr Thr Ile Gly Ile Ala Gly Thr
385                 390                 395                 400

Ser Arg Met Leu Thr Ala Thr Ala His Gly Glu Leu Ile Ala Ser Thr
                405                 410                 415

Val Tyr Thr Gly Ala Asp Glu Gln Leu Trp Arg Ile Glu Gln Leu Thr
                420                 425                 430

Asp Gly Thr Phe Arg Ile Met Pro Lys Ala Ile Pro Gly Ile Glu Gly
                435                 440                 445

Glu Asn Lys Lys Tyr Cys Leu Tyr Ser Ala Gly Asp Ser Thr Pro Thr
    450                 455                 460

Leu Ala Glu Tyr Asn Phe Lys Ser Asp Asn Ser Lys Trp Asn Leu Arg
465                 470                 475                 480

Gln Gln
```

<210> SEQ ID NO 33
<211> LENGTH: 2094
<212> TYPE: DNA
<213> ORGANISM: Prevotella bryantii

<400> SEQUENCE: 33

```
atgaaaaacc gtaataactg cacaaagca ggcattatcg tatccgcact ctgcttattg    60
ccccaactta gccgagcaca aaatccgatc atcagtgaac agtttactgc tgacccgaca   120
gctcgtgtat ttaataataa ggtgtatctt tatccttcgc atgatattgt agccccacaa   180
ggtcaacgac aagactggtt tgtatggca gactatcatg tatattctac tgataatctt   240
acagactgga cagatcatgg ggtaatctta tcacagcaag atgtgccttg ggtaagaaa    300
gatggctatt cgatgtgggc acccgactgt gtatataaga atggcaaata ttatttttat   360
tttcccgatg caccccaaga aggcaaaggc tttgcaatcg gtgtggcgac agcaaaccat   420
ccagaaggtc cgtttacctg tctgcctcaa cctatagctg gcgttatggg catagatccc   480
tgtgtacttc tcgatgacga tggcaaagca tatattact gggccggaat gggtatacgt   540
ggcgcccaat acaagataa catgacagaa attgtcggat catcctga gccaacatg     600
ccttccggaa atactccttc tccacaagac atggaacaaa taatggctcc gttgagatg    660
aaaggtttac cagaaggttt caagaaggt ccatttgcct ttaagcataa aggtaaatat   720
tacctcacct ttccatgggt aagaaggaa aaaggcaccg aaacacttgc ttatgcgatg   780
agcgataacc tctaggtcc atgggatttt aaaggtatca tcatgagcga acacgctaac   840
ggatgctgga ctaatcatca tagcatcgtt aattatcagg acaatggta tttgttttac   900
caccacaacg acttatcccc tcatttcgac aaaaaccgct cggtatgtat cgataaacta   960
actttaatg ctgacgggac catacaagag gtaaaaccga cgttcagagg tgtgggtatc  1020
agtaatgcta ctcaacccat acagatagcc cggtatagtt ctctgaaagg aaatgcaaaa  1080
atagattata tctttgagcg tatgccacaa atgggatgga tggtagatct gaaaaagggg  1140
gcttcggtaa gttatgagca tgtaaacttt gccctcgcca agcaaaatat ggtgatacgt  1200
gttatgggta aggaaaatgc ttctattctc gtcaacggta agaagattgc cacttttgat  1260
gtcgatgcac cacgatggac agaagaatat ctgaaaactg atcatttcat caaaggaata  1320
```

```
gaaaatctct caaatactac tgcacctaat aaatgcatcg gtaatatcga aatcgtctgc   1380
aatacgggta atgttcaaat cgactggctc cgattcctag ctcttgatga agaagtaccg   1440
caagcaccta agctggagga ctattttatg aaaatagatg gtaagagttc gtcatcacag   1500
actctacttc gagatccatt ttcgacaccc gatgaggaag gatttattca ccgatggtta   1560
ttacttgaac caatcaataa accgaatcgc agtaatttaa tcttctcgta tgctttcatg   1620
caacaagagt ttgcccgcaa ggactatcaa acgctcttta agaatatgcc taaagatgga   1680
caaactgtcc attggaaaga gactaatcaa aaactgaaat ggcatgcgct agacagcaaa   1740
caatttaata ccaaactatt ccgatttgcc tctggtctga ataagtctat gtatggtgtt   1800
ctcttctggg caactaccat tgtggaatgt caagaggata tcccaaatgt gcgattggct   1860
gccggttcta acggagcttc acaatggtgg gttaacaatg ctccagtact tacccctgga   1920
agtgaccgac gcatggtaaa ggatgatggc atgtctcaac gccttacatt acataaaggt   1980
aagaatatcg ttcgtgtggc tgtcatcaat ggtcccggaa tgagcgatat gtgtatgcga   2040
tttgtgcacg aatcgggcaa accggttacc aatattacta tcaaaaccaa ataa          2094
```

<210> SEQ ID NO 34
<211> LENGTH: 697
<212> TYPE: PRT
<213> ORGANISM: Prevotella bryantii

<400> SEQUENCE: 34

Met Lys Asn Arg Asn Asn Trp His Lys Ala Gly Ile Ile Val Ser Ala
1               5                   10                  15

Leu Cys Leu Leu Pro Gln Leu Ser Arg Ala Gln Asn Pro Ile Ile Ser
                20                  25                  30

Glu Gln Phe Thr Ala Asp Pro Thr Ala Arg Val Phe Asn Asn Lys Val
            35                  40                  45

Tyr Leu Tyr Pro Ser His Asp Ile Val Ala Pro Gln Gly Gln Arg Gln
        50                  55                  60

Asp Trp Phe Cys Met Ala Asp Tyr His Val Tyr Ser Thr Asp Asn Leu
65                  70                  75                  80

Thr Asp Trp Thr Asp His Gly Val Ile Leu Ser Gln Gln Asp Val Pro
                85                  90                  95

Trp Gly Lys Lys Asp Gly Tyr Ser Met Trp Ala Pro Asp Cys Val Tyr
            100                 105                 110

Lys Asn Gly Lys Tyr Tyr Phe Tyr Phe Pro Asp Ala Pro Gln Glu Gly
        115                 120                 125

Lys Gly Phe Ala Ile Gly Val Ala Thr Ala Asn His Pro Glu Gly Pro
    130                 135                 140

Phe Thr Cys Leu Pro Gln Pro Ile Ala Gly Val Met Gly Ile Asp Pro
145                 150                 155                 160

Cys Val Leu Leu Asp Asp Gly Lys Ala Tyr Ile Tyr Trp Ala Gly
                165                 170                 175

Met Gly Ile Arg Gly Ala Gln Leu Gln Asp Asn Met Thr Glu Ile Val
            180                 185                 190

Gly Tyr His Pro Glu Ala Asn Met Pro Ser Gly Asn Thr Pro Ser Pro
        195                 200                 205

Gln Asp Met Glu Gln Ile Met Ala Pro Phe Glu Met Lys Gly Leu Pro
    210                 215                 220

Glu Gly Phe Lys Glu Gly Pro Phe Ala Phe Lys His Lys Gly Lys Tyr
225                 230                 235                 240

-continued

```
Tyr Leu Thr Phe Pro Trp Val Arg Lys Glu Lys Gly Thr Glu Thr Leu
                245                 250                 255
Ala Tyr Ala Met Ser Asp Asn Pro Leu Gly Pro Trp Asp Phe Lys Gly
            260                 265                 270
Ile Ile Met Ser Glu His Ala Asn Gly Cys Trp Thr Asn His His Ser
        275                 280                 285
Ile Val Asn Tyr Gln Gly Gln Trp Tyr Leu Phe Tyr His His Asn Asp
    290                 295                 300
Leu Ser Pro His Phe Asp Lys Asn Arg Ser Val Cys Ile Asp Lys Leu
305                 310                 315                 320
Thr Phe Asn Ala Asp Gly Thr Ile Gln Glu Val Lys Pro Thr Phe Arg
                325                 330                 335
Gly Val Gly Ile Ser Asn Ala Thr Gln Pro Ile Gln Ile Asp Arg Tyr
            340                 345                 350
Ser Ser Leu Lys Gly Asn Ala Lys Ile Asp Tyr Ile Phe Glu Arg Met
        355                 360                 365
Pro Gln Met Gly Trp Met Val Asp Leu Lys Lys Gly Ala Ser Val Ser
    370                 375                 380
Tyr Glu His Val Asn Phe Ala Leu Ala Lys Gln Asn Met Val Ile Arg
385                 390                 395                 400
Val Met Gly Lys Gly Asn Ala Ser Ile Leu Val Asn Gly Lys Lys Ile
                405                 410                 415
Ala Thr Phe Asp Val Asp Ala Pro Arg Trp Thr Glu Glu Tyr Leu Lys
            420                 425                 430
Thr Asp His Phe Ile Lys Gly Ile Glu Asn Leu Ser Asn Thr Thr Ala
        435                 440                 445
Pro Asn Lys Cys Ile Gly Asn Ile Glu Ile Val Cys Asn Thr Gly Asn
    450                 455                 460
Val Gln Ile Asp Trp Leu Arg Phe Leu Ala Leu Asp Glu Glu Val Pro
465                 470                 475                 480
Gln Ala Pro Lys Leu Glu Asp Tyr Phe Met Lys Ile Asp Gly Lys Ser
                485                 490                 495
Ser Ser Ser Gln Thr Leu Leu Arg Asp Pro Phe Ser Thr Pro Asp Glu
            500                 505                 510
Glu Gly Phe Ile His Arg Trp Leu Leu Glu Pro Ile Asn Lys Pro
        515                 520                 525
Asn Arg Ser Asn Leu Ile Phe Ser Tyr Ala Phe Met Gln Gln Glu Phe
    530                 535                 540
Ala Arg Lys Asp Tyr Gln Thr Leu Phe Lys Asn Met Pro Lys Asp Gly
545                 550                 555                 560
Gln Thr Val His Trp Lys Glu Thr Asn Gln Lys Leu Lys Trp His Ala
                565                 570                 575
Leu Asp Ser Lys Gln Phe Asn Thr Lys Leu Phe Arg Phe Ala Ser Gly
            580                 585                 590
Leu Asn Lys Ser Met Tyr Gly Val Leu Phe Trp Ala Thr Thr Ile Val
        595                 600                 605
Glu Cys Gln Glu Asp Ile Pro Asn Val Arg Leu Ala Ala Gly Ser Asn
    610                 615                 620
Gly Ala Ser Gln Trp Trp Val Asn Asn Ala Pro Val Leu Thr Leu Glu
625                 630                 635                 640
Ser Asp Arg Arg Met Val Lys Asp Asp Gly Met Ser Gln Arg Leu Thr
                645                 650                 655
Leu His Lys Gly Lys Asn Ile Val Arg Val Ala Val Ile Asn Gly Pro
```

```
             660                 665                 670
Gly Met Ser Asp Met Cys Met Arg Phe Val His Glu Ser Gly Lys Pro
         675                 680                 685

Val Thr Asn Ile Thr Ile Lys Thr Lys
         690                 695

<210> SEQ ID NO 35
<211> LENGTH: 2217
<212> TYPE: DNA
<213> ORGANISM: Prevotella bryantii

<400> SEQUENCE: 35
atgcaacgtt taatttaac tattttatca ctattcatgg tactcacgtc tatggggcag      60
gaacgtttgc cgggatggca gcaagaactg acccaagtag accgtaatgc gattcgtgta     120
cgttattatc cgaaggttaa ctcttcagat agtaaaaaat acccactttt acccgattgg     180
ctttatgaag aagagccga taaaacctat caagctcagg gaaattcgcg taaaaatcgt     240
gacaaaggaa aagagaagat aaaggtatct ttcgatcagg ctaaaaatga gatacaattt     300
atgaacccaa aaggagaagt cgttttccgt gatatcaatc gccgcttgga aaatggaaga     360
gcttcgctca cctttgctac agattctgat gagtatcttt ttggactggg acaatttcag     420
gatggatata gtaatgtacg agggttgtcg agacgactta ctcaggtgaa tactcagata     480
tctattccga tgttgatctc aagtaagggc tatggtatcc tctggaataa ttatggtatg     540
acagaatata atccatgttc ataccatatt aatttagtaa agcgcggggg caaaggtata     600
caggatgttg tagaggtaac ttctacagaa ggaggaaaaa aggaagtgcg tgaaagacat     660
atctttgaag ccgatctgac cataacaaag gctggtgatt attctctact gcttgatgta     720
ggacagaaaa tggctcgcag acatcatctg ttaatcgatg aaaaactgt aattgatatg     780 caaaatatct ggctaccccc aaccgcttcg agtatcgtgc atctcgaagc gggtgtgcac     840
catttacagg cagagttgac gaaagacgat cgccctgtgc tttattatga tatggtgaag     900
aatagcacca cctttctctt acctgtggcc gatgctgtag attataccgt atttgttggc     960
actccggatg aaattatcgc ttcttatcgc agacttacag gtaatgccc tgttatgcca    1020 tcatgggctt tgggatatat acattgtcgt gaacgcttcc actcgtcaga cgaaataata    1080
cagacggcta tcgatttctc acaggaacaa atgccacttc gtatgattgt gcaagactgg    1140
cagtattggg gcagatatgg ttggaattcg atgaagtttg atgaacaata ttaccctaat    1200
ccgaaagcgt taaccgatag tttgcatcgt tgggtgtaa aactgatggt atctgtctgg    1260
tctaaaatcg accgaaattc tgaagtcggc aagcaaatgg cagctgacaa ctattatatc    1320
aaaaatacag actggataga tttctttaac cctaaagctg cagaagccta ttggaaaaat    1380
tttaatgagc gcttggttcc gctgggaata gatgcttggt ggcaggatgc taccgaaccc    1440
gaaaatgatg atttggcggg tcgtatggtc aaccaagaac aatggtcggg tgagcaagtg    1500
cgcaatgtct atccgcttct tgtcaacaag acggtatacg aaggattaat gaaggcagga    1560 aaacaccga tgatacttac tcgatgcggt ttccctggta ttcagcgata tggaagtgcc    1620
ctctggagtg gcgatgtcgg taacgattgg gagactttc gccgacagat aactgcaggg    1680
ttgggattgc aagctgcagg tataccttgg tggacttatg atgccggtgg attcttcaga    1740
ccaggaaatc agtatactga tccaaactat atcgaacgta tgttgcgatg gattcagacg    1800
agtgtttatc ttcctcttat gcgtgttcat gggtatatga gtaatacaga accatggaat    1860
tatggtgaaa aggctcaaca gatcatagct gcttgtatac atgagcgtga acaacttcgc    1920
```

-continued

```
ccatacatcg agcactgtgc taagcgtata tcttctgaag ggtatacgat tatgcgtcca    1980
cttgttttcg attttgccaa tgatcaagag gctcttcgac aaaaatatga atatatgttt    2040
ggtgataaat atcttgtaag tccgataaca gaacctaagg ttacgacttg gaccacttat    2100
ctgccgaaaa ataaaaaggg atggcgcgac catcgtacag gtaagtggta tgctggagga    2160
caatatgtta caactcgagt agacttaacc gcaataccta tatttgaacg tcaataa      2217
```

```
<210> SEQ ID NO 36
<211> LENGTH: 738
<212> TYPE: PRT
<213> ORGANISM: Prevotella bryantii

<400> SEQUENCE: 36

Met Gln Arg Phe Asn Leu Thr Ile Leu Ser Leu Phe Met Val Leu Thr
1               5                   10                  15

Ser Met Gly Gln Glu Arg Leu Pro Gly Trp Gln Gln Glu Leu Thr Gln
            20                  25                  30

Val Asp Arg Asn Ala Ile Arg Val Arg Tyr Tyr Pro Lys Val Asn Ser
        35                  40                  45

Ser Asp Ser Lys Lys Leu Pro Thr Leu Pro Asp Trp Leu Tyr Glu Gly
    50                  55                  60

Arg Ala Asp Lys Thr Tyr Gln Ala Gln Gly Asn Ser Arg Lys Asn Arg
65                  70                  75                  80

Asp Lys Gly Lys Glu Lys Ile Lys Val Ser Phe Asp Gln Ala Lys Asn
                85                  90                  95

Glu Ile Gln Phe Met Asn Pro Lys Gly Glu Val Val Phe Arg Asp Ile
            100                 105                 110

Asn Arg Arg Leu Glu Asn Gly Arg Ala Ser Leu Thr Phe Ala Thr Asp
        115                 120                 125

Ser Asp Glu Tyr Leu Phe Gly Leu Gly Gln Phe Gln Asp Gly Tyr Ser
    130                 135                 140

Asn Val Arg Gly Leu Ser Arg Arg Leu Thr Gln Val Asn Thr Gln Ile
145                 150                 155                 160

Ser Ile Pro Met Leu Ile Ser Ser Lys Gly Tyr Gly Ile Leu Trp Asn
                165                 170                 175

Asn Tyr Gly Met Thr Glu Tyr Asn Pro Cys Ser Tyr His Ile Asn Leu
            180                 185                 190

Val Lys Arg Gly Gly Lys Gly Ile Gln Asp Val Val Glu Val Thr Ser
        195                 200                 205

Thr Glu Gly Gly Lys Lys Glu Val Arg Glu Arg His Ile Phe Glu Ala
    210                 215                 220

Asp Leu Thr Ile Thr Lys Ala Gly Asp Tyr Ser Leu Leu Asp Val
225                 230                 235                 240

Gly Gln Lys Met Ala Arg Arg His His Leu Leu Ile Asp Gly Lys Thr
                245                 250                 255

Val Ile Asp Met Gln Asn Ile Trp Leu Pro Pro Thr Ala Ser Ser Ile
            260                 265                 270

Val His Leu Glu Ala Gly Val His His Leu Gln Ala Glu Leu Thr Lys
        275                 280                 285

Asp Asp Arg Pro Val Leu Tyr Tyr Asp Met Val Lys Asn Ser Thr Thr
    290                 295                 300

Phe Ser Ser Pro Val Ala Asp Ala Val Asp Tyr Thr Val Phe Val Gly
305                 310                 315                 320
```

```
Thr Pro Asp Glu Ile Ile Ala Ser Tyr Arg Arg Leu Thr Gly Glu Cys
            325                 330                 335

Pro Val Met Pro Ser Trp Ala Leu Gly Tyr Ile His Cys Arg Glu Arg
            340                 345                 350

Phe His Ser Ser Asp Glu Ile Ile Gln Thr Ala Asn Arg Phe Leu Gln
            355                 360                 365

Glu Gln Met Pro Leu Arg Met Ile Val Gln Asp Trp Gln Tyr Trp Gly
            370                 375                 380

Arg Tyr Gly Trp Asn Ser Met Lys Phe Asp Glu Gln Tyr Tyr Pro Asn
385                 390                 395                 400

Pro Lys Ala Leu Thr Asp Ser Leu His Arg Leu Gly Val Lys Leu Met
            405                 410                 415

Val Ser Val Trp Ser Lys Ile Asp Arg Asn Ser Glu Val Gly Lys Gln
            420                 425                 430

Met Ala Ala Asp Asn Tyr Tyr Ile Lys Asn Thr Asp Trp Ile Asp Phe
            435                 440                 445

Phe Asn Pro Lys Ala Ala Glu Ala Tyr Lys Asn Phe Asn Glu Arg
450                 455                 460

Leu Val Pro Leu Gly Ile Asp Ala Trp Trp Gln Asp Ala Thr Glu Pro
465                 470                 475                 480

Glu Asn Asp Asp Leu Ala Gly Arg Met Val Asn Gln Glu Gln Trp Ser
            485                 490                 495

Gly Glu Gln Val Arg Asn Val Tyr Pro Leu Leu Val Asn Lys Thr Val
            500                 505                 510

Tyr Glu Gly Leu Met Lys Ala Gly Lys Thr Pro Met Ile Leu Thr Arg
            515                 520                 525

Cys Gly Phe Pro Gly Ile Gln Arg Tyr Gly Ser Ala Leu Trp Ser Gly
            530                 535                 540

Asp Val Gly Asn Asp Trp Glu Thr Phe Arg Arg Gln Ile Thr Ala Gly
545                 550                 555                 560

Leu Gly Leu Gln Ala Ala Gly Ile Pro Trp Trp Thr Tyr Asp Ala Gly
                    565                 570                 575

Gly Phe Phe Arg Pro Gly Asn Gln Tyr Thr Asp Pro Asn Tyr Ile Glu
            580                 585                 590

Arg Met Leu Arg Trp Ile Gln Thr Ser Val Tyr Leu Pro Leu Met Arg
            595                 600                 605

Val His Gly Tyr Met Ser Asn Thr Glu Pro Trp Asn Tyr Gly Glu Lys
            610                 615                 620

Ala Gln Gln Ile Ile Ala Ala Cys Ile His Glu Arg Glu Gln Leu Arg
625                 630                 635                 640

Pro Tyr Ile Glu His Cys Ala Lys Arg Ile Ser Ser Glu Gly Tyr Thr
            645                 650                 655

Ile Met Arg Pro Leu Val Phe Asp Phe Ala Asn Asp Gln Glu Ala Leu
            660                 665                 670

Arg Gln Lys Tyr Glu Tyr Met Phe Gly Asp Lys Tyr Leu Val Ser Pro
            675                 680                 685

Ile Thr Glu Pro Lys Val Thr Thr Trp Thr Thr Tyr Leu Pro Lys Asn
            690                 695                 700

Lys Lys Gly Trp Arg Asp His Arg Thr Gly Lys Trp Tyr Ala Gly Gly
705                 710                 715                 720

Gln Tyr Val Thr Thr Arg Val Asp Leu Thr Ala Ile Pro Ile Phe Glu
            725                 730                 735

Arg Gln
```

<210> SEQ ID NO 37
<211> LENGTH: 1971
<212> TYPE: DNA
<213> ORGANISM: Prevotella bryantii

<400> SEQUENCE: 37

| | | | | | | |
|---|---|---|---|---|---|---|
| atgaaaatct | ttcaaaaatt | actgcttgcc | tcttcgtttt | ttgcgagtct | ccagatgcag | 60 |
| gctcgtgaaa | tccaagtgaa | gagtcctaat | ggacaaatcg | ccgttacatt | gagcgatgac | 120 |
| gctggtctat | aaactatca | agtcaatctt | gatcagtata | cttttatcct | tccttcgcgt | 180 |
| ctaggtctga | agatggattt | gggtgattat | actgatcagc | ttgctttgac | tgaagaatat | 240 |
| caagtgaaga | aggtgacgga | tcattatgaa | cttcaaacga | taaaatgcag | ccgtgtagac | 300 |
| tatgaagcca | atgaacttac | agcaacttgt | actcaacatg | gtaataaggt | ttttgatatt | 360 |
| gtgtttcgtg | tgagcaatcg | tgacgttgct | tattgttatc | gtgtatatcc | tcaggggaa | 420 |
| aaaaactcgg | gagtgataac | aagcgaggcg | agcagtttta | aatttccgtc | aaataccacg | 480 |
| actttccttt | gtccacaggc | tgagccgatg | catggttttg | ccggtacatc | gccaagttac | 540 |
| gaaacttcgt | atactatgga | tgatcagttg | ggtaaaaatg | gatgggggca | aggatatact | 600 |
| ttcccatgtc | ttttccgcga | gggtaatgcc | ggttgggtac | tggtttctga | gacgggtgta | 660 |
| gatgcaaatt | atgtaggaag | tcgactcatg | ggccataaag | atggtactta | tagtataggt | 720 |
| tttccacagg | cagctgagat | gaatggacag | ggaagtacct | ctgtagctat | tgcccttcct | 780 |
| ggtagtactc | cgtggcgcac | gcttactctt | ggcaaaacgc | ttgcacctat | cgtcgaaact | 840 |
| actgttcctt | atgatttggt | gcaaccgaaa | tatgaagcat | ctcaaccttta | tatttatggg | 900 |
| gcaggtactt | ggagctggat | tatccagatg | gatggttata | ctcgctatga | tgaacagaag | 960 |
| cgatatatag | attttgcagc | ggctatggga | tataaatcgg | ttcttatcga | tgctctttgg | 1020 |
| gatacacaga | taggaagaga | taaaattgca | gaacttgccc | gatatggtgc | tgccaaaggt | 1080 |
| gtgggtattt | atctttggta | taactctaat | ggagcgtgga | actatgctcc | tcaagggcct | 1140 |
| cgtggtatca | tgaataatac | gatagcccgt | aagaaggaga | tgaaatggat | gcatcagatt | 1200 |
| ggtatacgtg | gtattaaggt | agacttcttt | ggtggtgaca | acagccgat | gatgaaactt | 1260 |
| tatgaagata | ttttgagcga | tgccaatgat | tatggtctga | tggttatttt | ccatggatgt | 1320 |
| actctgccgc | gtggctggga | gcgtatgtat | cctaattatg | tagccagtga | ggctgttttg | 1380 |
| gctagtgaga | atcttcactt | tgggcagggc | gcctgcgatg | cagaagcctt | taatgcttgc | 1440 |
| atccatccgt | ttatccgtaa | cactgtaggt | agtatggatt | ttggcggaag | tactctcaat | 1500 |
| aagcattata | gtcgtgataa | ccagaagggt | actacccgta | gaacttcaga | tgtttatgct | 1560 |
| ttggctacag | ccgtactttt | ccaaagtagt | gttcagcatt | tgccatggc | gcctaacaat | 1620 |
| cttgaggatg | ctcctgcatg | ggctattgat | tttatgaaga | agtaccgac | tacttgggat | 1680 |
| gaggtgaggt | ttattgatgg | ttatcctggt | aagtatgtta | ttttagctcg | tcgtcatggt | 1740 |
| aatacttggt | atattgctgg | tgtaaatgcg | aataagactc | ctgttagatt | aactcttcat | 1800 |
| ttaccgatgc | ttcaagcagg | acaggcaact | ctgtatgctg | ataaatggac | caagaaggtg | 1860 |
| actgatattc | tgtcagaaaa | tttgggaaat | gtttctcagg | ttaaggttgg | taaaaaggga | 1920 |
| acattgacta | tcgaaatgaa | acaaaactgt | ggtttgttc | tcgtgcaata | a | 1971 |

<210> SEQ ID NO 38
<211> LENGTH: 656
<212> TYPE: PRT

<213> ORGANISM: Prevotella bryantii

<400> SEQUENCE: 38

```
Met Lys Ile Phe Gln Lys Leu Leu Leu Ala Ser Ser Phe Phe Ala Ser
1               5                   10                  15

Leu Gln Met Gln Ala Arg Glu Ile Gln Val Lys Ser Pro Asn Gly Gln
            20                  25                  30

Ile Ala Val Thr Leu Ser Asp Asp Ala Gly Leu Leu Asn Tyr Gln Val
        35                  40                  45

Asn Leu Asp Gln Tyr Thr Phe Ile Leu Pro Ser Arg Leu Gly Leu Lys
    50                  55                  60

Met Asp Leu Gly Asp Tyr Thr Asp Gln Leu Ala Leu Thr Glu Glu Tyr
65                  70                  75                  80

Gln Val Lys Lys Val Thr Asp His Tyr Glu Leu Gln Thr Ile Lys Cys
                85                  90                  95

Ser Arg Val Asp Tyr Glu Ala Asn Glu Leu Thr Ala Thr Cys Thr Gln
            100                 105                 110

His Gly Asn Lys Val Phe Asp Ile Val Phe Arg Val Ser Asn Arg Asp
        115                 120                 125

Val Ala Tyr Cys Tyr Arg Val Tyr Pro Gln Gly Glu Lys Asn Ser Gly
    130                 135                 140

Val Ile Thr Ser Glu Ala Ser Ser Phe Lys Phe Pro Ser Asn Thr Thr
145                 150                 155                 160

Thr Phe Leu Cys Pro Gln Ala Glu Pro Met His Gly Phe Ala Gly Thr
                165                 170                 175

Ser Pro Ser Tyr Glu Thr Ser Tyr Thr Met Asp Asp Gln Leu Gly Lys
            180                 185                 190

Asn Gly Trp Gly Gln Gly Tyr Thr Phe Pro Cys Leu Phe Arg Glu Gly
        195                 200                 205

Asn Ala Gly Trp Val Leu Val Ser Glu Thr Gly Val Asp Ala Asn Tyr
    210                 215                 220

Val Gly Ser Arg Leu Met Gly His Lys Asp Gly Thr Tyr Ser Ile Gly
225                 230                 235                 240

Phe Pro Gln Ala Ala Glu Met Asn Gly Gln Gly Ser Thr Ser Val Ala
                245                 250                 255

Ile Ala Leu Pro Gly Ser Thr Pro Trp Arg Thr Leu Thr Leu Gly Lys
            260                 265                 270

Thr Leu Ala Pro Ile Val Glu Thr Val Pro Tyr Asp Leu Val Gln
        275                 280                 285

Pro Lys Tyr Glu Ala Ser Gln Pro Tyr Ile Tyr Gly Ala Gly Thr Trp
    290                 295                 300

Ser Trp Ile Ile Gln Met Asp Gly Tyr Thr Arg Tyr Asp Glu Gln Lys
305                 310                 315                 320

Arg Tyr Ile Asp Phe Ala Ala Met Gly Tyr Lys Ser Val Leu Ile
                325                 330                 335

Asp Ala Leu Trp Asp Thr Gln Ile Gly Arg Asp Lys Ile Ala Glu Leu
            340                 345                 350

Ala Arg Tyr Gly Ala Ala Lys Gly Val Gly Ile Tyr Leu Trp Tyr Asn
        355                 360                 365

Ser Asn Gly Ala Trp Asn Tyr Ala Pro Gln Gly Pro Arg Gly Ile Met
    370                 375                 380

Asn Asn Thr Ile Ala Arg Lys Lys Glu Met Lys Trp Met His Gln Ile
385                 390                 395                 400
```

Gly Ile Arg Gly Ile Lys Val Asp Phe Phe Gly Gly Asp Lys Gln Pro
                405                 410                 415

Met Met Lys Leu Tyr Glu Asp Ile Leu Ser Asp Ala Asn Asp Tyr Gly
            420                 425                 430

Leu Met Val Ile Phe His Gly Cys Thr Leu Pro Arg Gly Trp Glu Arg
        435                 440                 445

Met Tyr Pro Asn Tyr Val Ala Ser Glu Ala Val Leu Ala Ser Glu Asn
    450                 455                 460

Leu His Phe Gly Gln Gly Ala Cys Asp Ala Glu Ala Phe Asn Ala Cys
465                 470                 475                 480

Ile His Pro Phe Ile Arg Asn Thr Val Gly Ser Met Asp Phe Gly Gly
                485                 490                 495

Ser Thr Leu Asn Lys His Tyr Ser Arg Asp Asn Gln Lys Gly Thr Thr
            500                 505                 510

Arg Arg Thr Ser Asp Val Tyr Ala Leu Ala Thr Ala Val Leu Phe Gln
        515                 520                 525

Ser Ser Val Gln His Phe Ala Met Ala Pro Asn Asn Leu Glu Asp Ala
    530                 535                 540

Pro Ala Trp Ala Ile Asp Phe Met Lys Lys Val Pro Thr Thr Trp Asp
545                 550                 555                 560

Glu Val Arg Phe Ile Asp Gly Tyr Pro Gly Lys Tyr Val Ile Leu Ala
                565                 570                 575

Arg Arg His Gly Asn Thr Trp Tyr Ile Ala Gly Val Asn Ala Asn Lys
            580                 585                 590

Thr Pro Val Arg Leu Thr Leu His Leu Pro Met Leu Gln Ala Gly Gln
        595                 600                 605

Ala Thr Leu Tyr Ala Asp Lys Trp Thr Lys Lys Val Thr Asp Ile Leu
    610                 615                 620

Ser Glu Asn Leu Gly Asn Val Ser Gln Val Lys Val Gly Lys Lys Gly
625                 630                 635                 640

Thr Leu Thr Ile Glu Met Lys Gln Asn Cys Gly Phe Val Leu Val Gln
                645                 650                 655

<210> SEQ ID NO 39
<211> LENGTH: 40
<212> TYPE: DNA
<213> ORGANISM: Artificial Sequence
<220> FEATURE:
<223> OTHER INFORMATION: Synthesized Construct

<400> SEQUENCE: 39
catatggacc aggatattcc tggtttcaca acggatgagc                    40

<210> SEQ ID NO 40
<211> LENGTH: 39
<212> TYPE: DNA
<213> ORGANISM: Artificial Sequence
<220> FEATURE:
<223> OTHER INFORMATION: Synthesized Construct

<400> SEQUENCE: 40
ctcgagttac tcctgtttca aaccttcaca gaagcctac                     39

<210> SEQ ID NO 41
<211> LENGTH: 30
<212> TYPE: DNA
<213> ORGANISM: Artificial Sequence
<220> FEATURE:
<223> OTHER INFORMATION: Synthesized Construct

<400> SEQUENCE: 41
gacgaaatca attcatacgg tacgttgaag                              30

<210> SEQ ID NO 42
<211> LENGTH: 30
<212> TYPE: DNA
<213> ORGANISM: Artificial Sequence
<220> FEATURE:
<223> OTHER INFORMATION: Synthesized Construct

<400> SEQUENCE: 42
cttcaacgta ccgtatgaat tgatttcgtc                              30

<210> SEQ ID NO 43
<211> LENGTH: 560
<212> TYPE: PRT
<213> ORGANISM: Prevotella bryantii

<400> SEQUENCE: 43

Met Lys Val Leu Asn Ser Leu Leu Tyr Val Ala Ala Gly Leu Ser Leu
1               5                   10                  15

Thr Ala Cys Ala Asp Gln Asp Ile Pro Gly Phe Thr Thr Asp Glu Pro
            20                  25                  30

Ala Glu Val Ile Ala Gln Asp Glu Ile Asn Ser Tyr Gly Thr Leu Lys
        35                  40                  45

Ser Tyr Val Asn Arg Asp Lys Tyr Pro Gln Phe Val Met Ala Gly Ala
    50                  55                  60

Val Asn Ala Glu Gln Phe Asn Gln Val Gly Gln Leu Tyr Ser Leu Ala
65                  70                  75                  80

Lys Ala Asn Tyr Asp Glu Val Val Thr Gly Asn Ala Phe Lys Tyr Ala
                85                  90                  95

Ser Val Val Gly Ser Asp Gly Thr Leu Asn Thr Ala Thr Val Glu Ser
            100                 105                 110

Phe Val Asn Asn Ala Thr Asn Ala Gly Leu Thr Val Phe Gly His Thr
        115                 120                 125

Leu Cys Trp His Ser Gln Gln Val Ala Tyr Leu Asn Ser Leu Ile
    130                 135                 140

Thr Asp Pro Asn Ala Thr Lys His Val Leu Tyr Ile His Met Gly Glu
145                 150                 155                 160

Pro Lys Thr Asn Asn Trp Asp Arg Glu Leu Tyr Val Asn Pro Thr Thr
                165                 170                 175

Glu Leu Gln Ser Gly Lys Thr Tyr Thr Leu Lys Leu Arg Val Lys Thr
            180                 185                 190

Ser Ala Ala Cys Asp Val Thr Val Trp Pro Gln Gly Asp Ala Thr Gln
        195                 200                 205

Tyr Trp Pro Thr Pro Ser Phe Lys Ser Thr Thr Glu Trp Thr Thr Val
    210                 215                 220

Ala Gln Ala Phe Glu Ala Lys Ser Ala Leu Lys Gln Leu Arg Phe Glu
225                 230                 235                 240

Leu Gly Thr Leu Gly Gly Asp Ile Trp Met Asp Asp Val Gln Leu Leu
                245                 250                 255

Asp Pro Asp Gly Asn Asn Leu Ile Ala Asn Gly Thr Phe Glu Glu Asn
            260                 265                 270

Ala Asp Gly Trp Thr Lys Pro Ser Trp His Glu Tyr Glu Ile Lys Thr
        275                 280                 285

Val Ala Asp Pro Asp Gln Glu Gly Gly Gly Gly Met Thr Glu Glu
    290                 295                 300

Val Lys Lys Asp Thr Leu Thr Trp Ala Leu Asn Asn Phe Ile Ser Gly
305                 310                 315                 320

Met Met Lys Ala Cys Asn Gly Lys Val Lys Ala Trp Asp Val Val Asn
                325                 330                 335

Glu Pro Met Ser Asp Ala Ala Pro Ala Glu Leu Lys Thr Ala Gly Arg
            340                 345                 350

Asp Gly Asp Pro Lys Lys Cys Phe Phe Trp Gln Asp His Leu Gly Lys
        355                 360                 365

Asp Tyr Ala Arg Leu Ala Val Lys Leu Ala Arg Lys Ala Ala Ser Asp
    370                 375                 380

Ser Val Gln Leu Lys Leu Phe Ile Asn Asp Tyr Asn Leu Glu Ala Ala
385                 390                 395                 400

Tyr Asn Lys Asn Ala Lys Leu Gln Gly Leu Ile Asp Met Ile Lys Tyr
                405                 410                 415

Trp Glu Ser Asp Gly Val Thr Lys Ile Asp Gly Ile Gly Ser Gln Met
            420                 425                 430

His Val Thr Tyr Ser Met Asn Pro Lys Thr Gln Ala Ala Asn Glu Glu
        435                 440                 445

Ala Tyr Val Asn His Leu Lys Met Met Ala Ala Thr Gly Lys Leu Val
    450                 455                 460

Arg Ile Ser Glu Leu Asp Met Gly Ile Ala Asp Ala Glu Gly Asn Thr
465                 470                 475                 480

Ile Asn Thr Ala Asp Val Thr Glu Glu Gln Gln Gln Leu Met Ala Gln
                485                 490                 495

Tyr Tyr Lys Phe Ile Val Ser Lys Tyr Phe Glu Ile Ile Pro Ala Asn
            500                 505                 510

Gln Gln Tyr Gly Ile Cys Asn Trp Gly Leu Gln Asp Ser Pro Lys Gly
        515                 520                 525

Ser Gly Trp Arg Ala Asp Glu Pro Ile Gly Leu Trp Asp Ala Asn Trp
    530                 535                 540

Val Arg Lys Pro Ala Tyr Val Gly Phe Cys Glu Gly Leu Lys Gln Glu
545                 550                 555                 560

<210> SEQ ID NO 44
<211> LENGTH: 1683
<212> TYPE: DNA
<213> ORGANISM: Prevotella bryantii

<400> SEQUENCE: 44
atgaaagtat taaattcttt attatacgtt gcagcaggac tctctcttac agcttgtgca      60
gaccaggata ttcctggttt cacaacggat gagcctgctg aggttatcgc tcaagacgaa     120
atcaattcat atggtacgtt gaagagctat gttaaccgtg ataaatatcc tcagtttgta     180
atggccggtg ccgttaatgc agaacagttt aaccaagtag gtcagcttta ttcgctggct     240
aaagctaact atgatgaagt ggtaacaggt aatgcgttta gtatgcttc tgttgttggt      300 tcagatggta ccttgaatac tgctacggta gagtcttttg tgaataatgc tacaaatgca     360
ggtcttactg ttttcggtca tactctctgt tggcactctc agcagcaagt agcttatctg     420
aatagcctta taacagaccc taatgctact aagcatgtgc tttatatcca catgggcgaa     480
cctaaaacca caactgggga tcgtgagtta tatgttaatc ctactactga attacagagc     540
ggcaaaactt acaccttaaa gttgcgtgta aaaacttctg ctgcttgtga tgtaacggta     600

```
tggcctcagg gtgatgcaac tcagtattgg ccaactcctt cattcaagtc tactacagag    660
tggactactg ttgcgcaggc tttcgaggct aagagtgctt tgaagcaact tcgtttcgag    720
ttgggtactc ttggtggtga tatttggatg gatgatgtac agctactcga tccagatgga    780
aataacttga tagccaatgg tacttttgag gaaaatgcag acggttggac caagccttct    840
tggcatgaat acgaaatcaa gacggtagcc gacccagacc aagaaggtgg tggcggtggt    900
atgaccgaag aagtaaagaa agatacccct acttgggcac tcaataactt tatctctggc    960
atgatgaagg cttgtaatgg taaagttaag gcttgggatg tcgtaaatga gcctatgagt   1020
gacgccgctc ctgcagaact taagaccgct ggtcgtgatg gtgatcctaa gaagtgtttc   1080
ttctggcaag atcatcttgg taaagattat gcccgtttag ctgtgaagtt ggctcgtaag   1140
gctgccagcg attcggtaca gttgaaactg tttatcaacg attataatct tgaagctgct   1200
tataataaga atgctaaact tcagggtctt atcgatatga taaaatattg ggaaagcgat   1260
ggtgttacca aaattgatgg tataggtagt cagatgcacg ttacttatag catgaatcct   1320
aaaactcagg ctgctaacga ggaagcttat gtaaaccatc tgaagatgat ggcagcaaca   1380
ggtaagttgg tgcgtatctc tgagctcgat atgggtatcg cagatgcaga aggcaatacc   1440
attaatactg ctgacgttac tgaagaacag cagcagttga tggctcaata ctataagttt   1500
attgtatcga gtactttga aatcattcct gctaaccagc agtatggtat ttgtaactgg   1560
ggtcttcagg atagtcctaa aggtagtggc tggagagctg atgaacctat cggtctttgg   1620
gatgcaaatt gggtacgtaa acctgcttat gtaggcttct gtgaaggttt gaaacaggag   1680
taa                                                                1683

<210> SEQ ID NO 45
<211> LENGTH: 1686
<212> TYPE: DNA
<213> ORGANISM: Prevotella bryantii

<400> SEQUENCE: 45
atgggcagca gccatcatca tcatcatcac agcagcggcc tggtgccgcg cggcagccat     60
atggaccagg atattcctgg tttcacaacg gatgagcctg ctgaggttat cgctcaagac    120
gaaatcaatt catacggtac gttgaagagc tatgttaacc gtgataaata tcctcagttt    180
gtaatggccg gtgccgttaa tgcagaacag tttaaccaag taggtcagct ttattcgctg    240
gctaaagcta actatgatga gtggtaaca ggtaatgcgt ttaagtatgc ttctgttgtt    300
ggttcagatg gtaccttgaa tactgctacg gtagagtctt ttgtgaataa tgctacaaat    360
gcaggtctta ctgttttcgg tcatactctc tgttggcact ctcagcagca gtagcttat    420 ctgaatagcc ttataacaga ccctaatgct actaagcatg tgctttatat ccacatgggc    480
gaacctaaaa ccaacaactg ggatcgtgag ttatatgtta atcctactac tgaattacag    540
agcggcaaaa cttacaccctt aaagttgcgt gtaaaaactt ctgctgcttg tgatgtaacg    600
gtatggcctc agggtgatgc aactcagtat tggccaactc cttcattcaa gtctactaca    660
gagtggacta ctgttgcgca ggctttcgag gctaagagtg ctttgaagca acttcgtttc    720 gagtgggta ctcttggtgg tgatatttgg atggatgatg tacagctact cgatccagat    780
ggaaataact tgatagccaa tggtactttt gaggaaaatg cagacggttg gaccaagcct    840
tcttggcatg aatacgaaat caagacggta gccgacccag accaagaagg tggtggcggt    900
ggtatgaccg aagaagtaaa gaaagatacc cttacttggg cactcaataa ctttatctct    960
ggcatgatga aggcttgtaa tggtaaagtt aaggcttggg atgtcgtaaa tgagcctatg   1020
```

```
agtgacgccg ctcctgcaga acttaagacc gctggtcgtg atggtgatcc taagaagtgt    1080
ttcttctggc aagatcatct tggtaaagat tatgcccgtt tagctgtgaa gttggctcgt    1140
aaggctgcca gcgattcggt acagttgaaa ctgtttatca acgattataa tcttgaagct    1200
gcttataata agaatgctaa acttcagggt cttatcgata tgataaaata tgggaaagc     1260 gatggtgtta ccaaaattga tggtataggt agtcagatgc acgttactta tagcatgaat    1320
cctaaaactc aggctgctaa cgaggaagct tatgtaaacc atctgaagat gatggcagca    1380
acaggtaagt tggtgcgtat ctctgagctc gatatgggta tcgcagatgc agaaggcaat    1440
accattaata ctgctgacgt tactgaagaa cagcagcagt tgatggctca atactataag    1500
tttattgtat cgaagtactt tgaaatcatt cctgctaacc agcagtatgg tatttgtaac    1560
tggggtcttc aggatagtcc taaaggtagt ggctggagag ctgatgaacc tatcggtctt    1620
tgggatgcaa attgggtacg taaacctgct tatgtaggct tctgtgaagg tttgaaacag    1680
gagtaa                                                                1686

<210> SEQ ID NO 46
<211> LENGTH: 561
<212> TYPE: PRT
<213> ORGANISM: Prevotella bryantii

<400> SEQUENCE: 46

Met Gly Ser Ser His His His His His Ser Ser Gly Leu Val Pro
1               5                   10                  15

Arg Gly Ser His Met Asp Gln Asp Ile Pro Gly Phe Thr Thr Asp Glu
            20                  25                  30

Pro Ala Glu Val Ile Ala Gln Asp Glu Ile Asn Ser Tyr Gly Thr Leu
        35                  40                  45

Lys Ser Tyr Val Asn Arg Asp Lys Tyr Pro Gln Phe Val Met Ala Gly
    50                  55                  60

Ala Val Asn Ala Glu Gln Phe Asn Gln Val Gly Gln Leu Tyr Ser Leu
65                  70                  75                  80

Ala Lys Ala Asn Tyr Asp Glu Val Val Thr Gly Asn Ala Phe Lys Tyr
                85                  90                  95

Ala Ser Val Val Gly Ser Asp Gly Thr Leu Asn Thr Ala Thr Val Glu
            100                 105                 110

Ser Phe Val Asn Asn Ala Thr Asn Ala Gly Leu Thr Val Phe Gly His
        115                 120                 125

Thr Leu Cys Trp His Ser Gln Gln Val Ala Tyr Leu Asn Ser Leu
    130                 135                 140

Ile Thr Asp Pro Asn Ala Thr Lys His Val Leu Tyr Ile His Met Gly
145                 150                 155                 160

Glu Pro Lys Thr Asn Asn Trp Asp Arg Glu Leu Tyr Val Asn Pro Thr
                165                 170                 175

Thr Glu Leu Gln Ser Gly Lys Thr Tyr Thr Leu Lys Leu Arg Val Lys
            180                 185                 190

Thr Ser Ala Ala Cys Asp Val Thr Val Trp Pro Gln Gly Asp Ala Thr
        195                 200                 205

Gln Tyr Trp Pro Thr Pro Ser Phe Lys Ser Thr Thr Glu Trp Thr Thr
    210                 215                 220

Val Ala Gln Ala Phe Glu Ala Lys Ser Ala Leu Lys Gln Leu Arg Phe
225                 230                 235                 240

Glu Leu Gly Thr Leu Gly Gly Asp Ile Trp Met Asp Asp Val Gln Leu
```

```
                245                 250                 255
Leu Asp Pro Asp Gly Asn Asn Leu Ile Ala Asn Gly Thr Phe Glu Glu
            260                 265                 270

Asn Ala Asp Gly Trp Thr Lys Pro Ser Trp His Glu Tyr Glu Ile Lys
            275                 280                 285

Thr Val Ala Asp Pro Asp Gln Glu Gly Gly Gly Met Thr Glu
            290                 295                 300

Glu Val Lys Lys Asp Thr Leu Thr Trp Ala Leu Asn Asn Phe Ile Ser
305                 310                 315                 320

Gly Met Met Lys Ala Cys Asn Gly Lys Val Lys Ala Trp Asp Val Val
                325                 330                 335

Asn Glu Pro Met Ser Asp Ala Ala Pro Ala Glu Leu Lys Thr Ala Gly
            340                 345                 350

Arg Asp Gly Asp Pro Lys Lys Cys Phe Phe Trp Gln Asp His Leu Gly
            355                 360                 365

Lys Asp Tyr Ala Arg Leu Ala Val Lys Leu Ala Arg Lys Ala Ala Ser
            370                 375                 380

Asp Ser Val Gln Leu Lys Leu Phe Ile Asn Asp Tyr Asn Leu Glu Ala
385                 390                 395                 400

Ala Tyr Asn Lys Asn Ala Lys Leu Gln Gly Leu Ile Asp Met Ile Lys
                405                 410                 415

Tyr Trp Glu Ser Asp Gly Val Thr Lys Ile Asp Gly Ile Gly Ser Gln
            420                 425                 430

Met His Val Thr Tyr Ser Met Asn Pro Lys Thr Gln Ala Ala Asn Glu
            435                 440                 445

Glu Ala Tyr Val Asn His Leu Lys Met Met Ala Ala Thr Gly Lys Leu
            450                 455                 460

Val Arg Ile Ser Glu Leu Asp Met Gly Ile Ala Asp Ala Glu Gly Asn
465                 470                 475                 480

Thr Ile Asn Thr Ala Asp Val Thr Glu Glu Gln Gln Leu Met Ala
                485                 490                 495

Gln Tyr Tyr Lys Phe Ile Val Ser Lys Tyr Phe Glu Ile Ile Pro Ala
            500                 505                 510

Asn Gln Gln Tyr Gly Ile Cys Asn Trp Gly Leu Gln Asp Ser Pro Lys
            515                 520                 525

Gly Ser Gly Trp Arg Ala Asp Glu Pro Ile Gly Leu Trp Asp Ala Asn
            530                 535                 540

Trp Val Arg Lys Pro Ala Tyr Val Gly Phe Cys Glu Gly Leu Lys Gln
545                 550                 555                 560

Glu

<210> SEQ ID NO 47
<211> LENGTH: 1686
<212> TYPE: DNA
<213> ORGANISM: Prevotella bryantii

<400> SEQUENCE: 47
atgggcagca gccatcatca tcatcatcac agcagcggcc tggtgccgcg cggcagccat    60
atggaccagg atattcctgg tttcacaacg gatgagcctg ctgaggttat cgctcaagac   120
gaaatcaatt catacggtac gttgaagagc tatgttaacc gtgataaata tcctcagttt   180
gtaatggccg gtgccgttaa tgcagaacag tttaaccaag taggtcagct ttattcgctg   240
gctaaagcta actatgatga agtggtaaca ggtaatgcgt taagtatgc ttctgttgtt   300
```

-continued

```
ggttcagatg gtaccttgaa tactgctacg gtagagtctt ttgtgaataa tgctacaaat    360
gcaggtctta ctgttttcgg tcatactctc tgttggcact ctcagcagca agtagcttat    420
ctgaatagcc ttataacaga ccctaatgct actaagcatg tgctttatat ccacatgggc    480
gaacctaaaa ccaacaactg ggatcgtgag ttatatgtta atcctactac tgaattacag    540
agcggcaaaa cttacacctt aaagttgcgt gtaaaaactt ctgctgcttg tgatgtaacg    600
gtatggcctc agggtgatgc aactcagtat tggccaactc cttcattcaa gtctactaca    660
gagtggacta ctgttgcgca ggctttcgag gctaagagtg ctttgaagca acttcgtttc    720
gagttgggta ctcttggtgg tgatatttgg atggatgatg tacagctact cgatccagat    780
ggaaataact tgatagccaa tggtactttt gaggaaaatg cagacggttg gaccaagcct    840
tcttggcatg aatacgaaat caagacggta gccgacccag accaagaagg tggtggcggt    900
ggtatgaccg aagaagtaaa gaaagatacc cttacttggg cactcaataa ctttatctct    960
ggcatgatga aggcttgtaa tggtaaagtt aaggcttggg atgtcgtaaa tgagcctatg   1020
agtgacgccg ctcctgcaga acttaagacc gctggtcgtg atggtgatcc taagaagtgt   1080
ttcttctggc aagatcatct tggtaaagat tatgcccgtt agctgtgaa gttggctcgt   1140
aaggctgcca gcgattcggt acagttgaaa ctgtttatca acgattataa tcttgaagct   1200
gcttataata agaatgctaa acttcagggt cttatcgata tgataaaata ttgggaaagc   1260
gatggtgtta ccaaaattga tggtataggt agtcagatgc acgttactta tagcatgaat   1320
cctaaaactc aggctgctaa cgaggaagct tatgtaaacc atctgaagat gatggcagca   1380
acaggtaagt tggtgcgtat ctctgagctc gatatgggta tcgcagatgc agaaggcaat   1440
accattaata ctgctgacgt tactgaagaa cagcagcagt tgatggctca atactataag   1500
tttattgtat cgaagtactt tgaaatcatt cctgctaacc agcagtatgg tatttgtaac   1560
tggggtcttc aggatagtcc taaaggtagt ggctggagag ctgatgaacc tatcggtctt   1620
tgggatgcaa attgggtacg taaacctgct tatgtaggct ctgtgaagg tttgaaacag   1680
gagtaa                                                             1686
```

<210> SEQ ID NO 48
<211> LENGTH: 561
<212> TYPE: PRT
<213> ORGANISM: Prevotella bryantii

<400> SEQUENCE: 48

```
Met Gly Ser Ser His His His His His His Ser Ser Gly Leu Val Pro
  1               5                  10                  15

Arg Gly Ser His Met Asp Gln Asp Ile Pro Gly Phe Thr Thr Asp Glu
             20                  25                  30

Pro Ala Glu Val Ile Ala Gln Asp Glu Ile Asn Ser Tyr Gly Thr Leu
         35                  40                  45

Lys Ser Tyr Val Asn Arg Asp Lys Tyr Pro Gln Phe Val Met Ala Gly
     50                  55                  60

Ala Val Asn Ala Glu Gln Phe Asn Gln Val Gly Gln Leu Tyr Ser Leu
 65                  70                  75                  80

Ala Lys Ala Asn Tyr Asp Glu Val Val Thr Gly Asn Ala Phe Lys Tyr
                 85                  90                  95

Ala Ser Val Val Gly Ser Asp Gly Thr Leu Asn Thr Ala Thr Val Glu
            100                 105                 110

Ser Phe Val Asn Asn Ala Thr Asn Ala Gly Leu Thr Val Phe Gly His
        115                 120                 125
```

```
Thr Leu Cys Trp His Ser Gln Gln Val Ala Tyr Leu Asn Ser Leu
        130                 135                 140

Ile Thr Asp Pro Asn Ala Thr Lys His Val Leu Tyr Ile His Met Gly
145                 150                 155                 160

Glu Pro Lys Thr Asn Asn Trp Asp Arg Glu Leu Tyr Val Asn Pro Thr
                165                 170                 175

Thr Glu Leu Gln Ser Gly Lys Thr Tyr Thr Leu Lys Leu Arg Val Lys
            180                 185                 190

Thr Ser Ala Ala Cys Asp Val Thr Val Trp Pro Gln Gly Asp Ala Thr
        195                 200                 205

Gln Tyr Trp Pro Thr Pro Ser Phe Lys Ser Thr Thr Glu Trp Thr Thr
210                 215                 220

Val Ala Gln Ala Phe Glu Ala Lys Ser Ala Leu Lys Gln Leu Arg Phe
225                 230                 235                 240

Glu Leu Gly Thr Leu Gly Gly Asp Ile Trp Met Asp Asp Val Gln Leu
                245                 250                 255

Leu Asp Pro Asp Gly Asn Asn Leu Ile Ala Asn Gly Thr Phe Glu Glu
            260                 265                 270

Asn Ala Asp Gly Trp Thr Lys Pro Ser Trp His Glu Tyr Glu Ile Lys
        275                 280                 285

Thr Val Ala Asp Pro Asp Gln Glu Gly Gly Gly Gly Met Thr Glu
        290                 295                 300

Glu Val Lys Lys Asp Thr Leu Thr Trp Ala Leu Asn Asn Phe Ile Ser
305                 310                 315                 320

Gly Met Met Lys Ala Cys Asn Gly Lys Val Lys Ala Trp Asp Val Val
                325                 330                 335

Asn Glu Pro Met Ser Asp Ala Ala Pro Ala Glu Leu Lys Thr Ala Gly
            340                 345                 350

Arg Asp Gly Asp Pro Lys Lys Cys Phe Phe Trp Gln Asp His Leu Gly
        355                 360                 365

Lys Asp Tyr Ala Arg Leu Ala Val Lys Leu Ala Arg Lys Ala Ala Ser
370                 375                 380

Asp Ser Val Gln Leu Lys Leu Phe Ile Asn Asp Tyr Asn Leu Glu Ala
385                 390                 395                 400

Ala Tyr Asn Lys Asn Ala Lys Leu Gln Gly Leu Ile Asp Met Ile Lys
                405                 410                 415

Tyr Trp Glu Ser Asp Gly Val Thr Lys Ile Asp Gly Ile Gly Ser Gln
            420                 425                 430

Met His Val Thr Tyr Ser Met Asn Pro Lys Thr Gln Ala Ala Asn Glu
        435                 440                 445

Glu Ala Tyr Val Asn His Leu Lys Met Met Ala Ala Thr Gly Lys Leu
450                 455                 460

Val Arg Ile Ser Glu Leu Asp Met Gly Ile Ala Asp Ala Glu Gly Asn
465                 470                 475                 480

Thr Ile Asn Thr Ala Asp Val Thr Glu Glu Gln Gln Leu Met Ala
                485                 490                 495

Gln Tyr Tyr Lys Phe Ile Val Ser Lys Tyr Phe Glu Ile Ile Pro Ala
            500                 505                 510

Asn Gln Gln Tyr Gly Ile Cys Asn Trp Gly Leu Gln Asp Ser Pro Lys
        515                 520                 525

Gly Ser Gly Trp Arg Ala Asp Glu Pro Ile Gly Leu Trp Asp Ala Asn
530                 535                 540
```

```
Trp Val Arg Lys Pro Ala Tyr Val Gly Phe Cys Glu Gly Leu Lys Gln
545                 550                 555                 560

Glu

<210> SEQ ID NO 49
<211> LENGTH: 1077
<212> TYPE: DNA
<213> ORGANISM: Prevotella bryantii

<400> SEQUENCE: 49
atgttgctgc caatagcagc agttgctcaa atcagcctta cgatgaagga tgtcttaggt    60
aaatacttct tggtcggaac agcacttaat agtcatcaga tttggacgca tgatcccaaa   120
atcgttcatg ctataactga taattttaat tcggttgtcg ctgaaaattg tatgaaaggt   180
gagattattc atccagaaga ggattattat gattggcatg atgctgacca gttggttaaa   240
tttgcggaac agcataagat gacagttcat ggccactgtt tggtttggca ctcacaggct   300
ccaaaatgga tgtttaccga taaggaaggt aaagaagtta cccgtgaggt gctcatcgac   360
cgtatgtatc atcacattac taatgtcgtt aagcgatata aaggtaaaat caagggttgg   420
gatgtcgtta acgaggctat ccttgataat ggtgaatatc gtcagtctcc ttattataag   480
atcattggtc ctgattttat caagcttgca tttattttg ctcatcaggc agatcctgat   540
gcagaattgt attataatga ctattcgatg tctattcctg ctaagcgtaa tgctgtagtc   600
aaactggtta aggagttgaa agctgcagga tgtcgtattg atgctgtagg tatgcagagc   660
cataacggtt ttaactatcc taatcttgag gattatgaaa attctatcaa ggctttcatt   720
gctgcaggtg tagatgttca gtttacagaa ctcgatgtca atatgctacc taatcctaag   780
agctttggtg gtgcagagat tagccagaac tataagtata ataaggaact taatccatat   840
gtaaatgggt tgactaaagc tgctcagaag actttcgatc agcagtatct gtcattcttt   900
aagatttatc gtaagtatgt agatcatatt aagcgtgtaa cgctttgggg tgtggacgac   960
ggaagcagct ggctgaatgg ttggcctgtg cctggtcgta ccaactatgg tctgcttatc  1020
gaccgcaact acaaggtaaa acctgtggtt aaagaaatta tcaaacttta tgagtaa    1077

<210> SEQ ID NO 50
<211> LENGTH: 358
<212> TYPE: PRT
<213> ORGANISM: Prevotella bryantii

<400> SEQUENCE: 50

Met Leu Leu Pro Ile Ala Ala Val Ala Gln Asn Gln Pro Thr Met Lys
  1               5                  10                  15

Asp Val Leu Gly Lys Tyr Phe Leu Val Gly Thr Ala Leu Asn Ser His
                 20                  25                  30

Gln Ile Trp Thr His Asp Pro Lys Ile Val His Ala Ile Thr Asp Asn
             35                  40                  45

Phe Asn Ser Val Val Ala Glu Asn Cys Met Lys Gly Glu Ile Ile His
         50                  55                  60

Pro Glu Glu Asp Tyr Tyr Asp Trp His Asp Ala Asp Gln Leu Val Lys
 65                  70                  75                  80

Phe Ala Glu Gln His Lys Met Thr Val His Gly His Cys Leu Val Trp
                 85                  90                  95

His Ser Gln Ala Pro Lys Trp Met Phe Thr Asp Lys Glu Gly Lys Glu
                100                 105                 110

Val Thr Arg Glu Val Leu Ile Asp Arg Met Tyr His His Ile Thr Asn
```

```
            115                 120                 125
Val Val Lys Arg Tyr Lys Gly Lys Ile Lys Gly Trp Asp Val Val Asn
130                 135                 140

Glu Ala Ile Leu Asp Asn Gly Glu Tyr Arg Gln Ser Pro Tyr Tyr Lys
145                 150                 155                 160

Ile Ile Gly Pro Asp Phe Ile Lys Leu Ala Phe Ile Phe Ala His Gln
                165                 170                 175

Ala Asp Pro Asp Ala Glu Leu Tyr Tyr Asn Asp Tyr Ser Met Ser Ile
            180                 185                 190

Pro Ala Lys Arg Asn Ala Val Val Lys Leu Val Lys Glu Leu Lys Ala
        195                 200                 205

Ala Gly Cys Arg Ile Asp Ala Val Gly Met Gln Ser His Asn Gly Phe
    210                 215                 220

Asn Tyr Pro Asn Leu Glu Asp Tyr Glu Asn Ser Ile Lys Ala Phe Ile
225                 230                 235                 240

Ala Ala Gly Val Asp Val Gln Phe Thr Glu Leu Asp Val Asn Met Leu
                245                 250                 255

Pro Asn Pro Lys Ser Phe Gly Gly Ala Glu Ile Ser Gln Asn Tyr Lys
            260                 265                 270

Tyr Asn Lys Glu Leu Asn Pro Tyr Val Asn Gly Leu Thr Lys Ala Ala
        275                 280                 285

Gln Lys Thr Phe Asp Gln Gln Tyr Leu Ser Phe Phe Lys Ile Tyr Arg
    290                 295                 300

Lys Tyr Val Asp His Ile Lys Arg Val Thr Leu Trp Gly Val Asp Asp
305                 310                 315                 320

Gly Ser Ser Trp Leu Asn Gly Trp Pro Val Pro Gly Arg Thr Asn Tyr
                325                 330                 335

Gly Leu Leu Ile Asp Arg Asn Tyr Lys Val Lys Pro Val Lys Glu
            340                 345                 350

Ile Ile Lys Leu Tyr Glu
        355

<210> SEQ ID NO 51
<211> LENGTH: 41
<212> TYPE: DNA
<213> ORGANISM: Artificial Sequence
<220> FEATURE:
<223> OTHER INFORMATION: Synthesized Construct

<400> SEQUENCE: 51
catatgcagg atgctgtttt ccagaatttt aagtatactg g                    41

<210> SEQ ID NO 52
<211> LENGTH: 36
<212> TYPE: DNA
<213> ORGANISM: Artificial Sequence
<220> FEATURE:
<223> OTHER INFORMATION: Synthesized Construct

<400> SEQUENCE: 52
ctcgagttat ttcacagcat aaagtccgat taccgc                          36

<210> SEQ ID NO 53
<211> LENGTH: 558
<212> TYPE: PRT
<213> ORGANISM: Prevotella bryantii

<400> SEQUENCE: 53
```

```
Met Lys Pro Ile Leu Ser Leu Leu Val Met Ala Ser Leu Ser Val Ser
 1               5                  10                  15

Ser Phe Ala Gln Asp Ala Val Phe Gln Asn Phe Lys Tyr Thr Gly Asn
            20                  25                  30

Glu Ser Arg Phe Ala Lys Asn Ile Asp Thr Ser Lys Glu Tyr Tyr Asn
        35                  40                  45

Pro Val Leu Ala Gly Phe Tyr Pro Asp Pro Ser Leu Cys Arg Lys Gly
    50                  55                  60

Asp Thr Tyr Tyr Leu Val Asn Ser Ser Phe Ser Phe Tyr Pro Gly Val
65                  70                  75                  80

Pro Leu Ser Thr Ser Lys Asp Leu Ile His Trp Lys Pro Ala Gly Tyr
                85                  90                  95

Val Leu Asn Arg Glu Ser Gln Leu Pro Leu Thr Arg Gln Asn Ile Ser
            100                 105                 110

Gly Gly Ile Phe Ala Pro Ala Ile Ser Tyr Asn Glu Lys Asn Lys Thr
            115                 120                 125

Phe Tyr Met Ile Thr Thr Asn Val Gly Ala Gly Asn Phe Phe Val Lys
        130                 135                 140

Ser Lys Asp Pro Glu Lys Gly Trp Ser Asp Pro Ile Tyr Leu Pro Lys
145                 150                 155                 160

Val Asn Gly Ile Asp Pro Ser Phe Phe Asp Lys Asp Gly Lys Gly
                165                 170                 175

Tyr Ile Val His Asn Gly Pro Val Thr Gly Lys Gln Glu Tyr Glu Gly
            180                 185                 190

Gln Arg Ala Ile Arg Leu Phe Glu Phe Asp Val Lys Gly Asp Ser Ile
        195                 200                 205

Lys Gly Asp Phe Thr Glu Ile Val Arg Gly Gly Thr His Val Gln Lys
210                 215                 220

Asn Pro Ile Trp Ile Glu Gly Pro His Leu Phe Arg Val Gly Lys Tyr
225                 230                 235                 240

Tyr Tyr Leu Met Cys Ala Glu Gly Gly Thr Cys Asp Trp His Ser Glu
            245                 250                 255

Val Ile Phe Arg Ala Lys Ser Pro Lys Gly Pro Trp Glu Glu Cys Pro
        260                 265                 270

Asp Asn Pro Ile Leu Thr Gln Arg Thr Gly Leu Asp Pro Asn Arg Pro
    275                 280                 285

Asp Ile Val Thr Ser Ala Gly His Ala Asp Ile Val Gln Ser Lys Glu
290                 295                 300

Gly Asp Trp Trp Ala Val Phe Leu Gly Cys Arg Pro Tyr Gln Asp Asp
305                 310                 315                 320

Phe Tyr Asn Thr Gly Arg Asp Thr Tyr Leu Leu Pro Val Thr Trp Lys
            325                 330                 335

Asn Gly Trp Pro Ile Ile Gln Pro Lys Asn Thr Ala Ile Pro Ala Val
        340                 345                 350

Ser Lys Met Thr Lys Trp Gln Glu Lys Leu Ser Ala Gly Leu Lys Asn
    355                 360                 365

Gln Gly Glu Phe Ser Gly Asn Phe Ser Tyr Glu Asp Lys Phe Asp Gly
    370                 375                 380

Glu Ser Leu Asn Gln Arg Trp Met Phe Leu Arg Asn Pro Ser Ala Phe
385                 390                 395                 400

Trp Lys Thr Ser Ser Glu Gly Leu Val Ile Ser Pro Lys His Ala Lys
            405                 410                 415

Ile Asn Glu Lys Glu Ser Pro Ser Val Ile Phe Thr Arg Gln Gln His
```

```
                420             425             430
Thr Asn Phe Thr Ala Glu Thr Thr Val Arg Phe Ala Pro Thr Ser Glu
            435             440             445
Lys Thr Gln Ala Gly Leu Val Leu Met Gln Lys Glu Asp His Asn Phe
        450             455             460
Val Phe Val Lys Thr Leu Arg Ala Gly Lys Pro Val Leu Val Leu Glu
465             470             475             480
Arg Ala Glu Arg Gly Asn Ala Val Ile Ala Ser Thr Glu Leu Thr Gly
                485             490             495
Val His Ala Ala Gly Asn Glu Pro Leu Arg Leu Lys Val Val Gly Asn
            500             505             510
Gly Arg Tyr Tyr Asp Phe Tyr Tyr Ala Glu Gly Asp Ala Asp Tyr Gln
        515             520             525
Leu Leu Ala Lys Gly Val Asp Ala Val Asn Leu Ser Thr His Gln Ser
        530             535             540
Gly Gly Phe Ile Gly Ala Val Ile Gly Leu Tyr Ala Val Lys
545             550             555
```

<210> SEQ ID NO 54
<211> LENGTH: 1677
<212> TYPE: DNA
<213> ORGANISM: Prevotella bryantii

<400> SEQUENCE: 54

```
atgaaaccta tattatctct tctcgttatg gcttctttga gtgtaagtag ttttgctcag    60
gatgctgttt tccagaattt taagtatact ggtaacgaaa gtcgttttgc taaaaatatc   120
gacaccagta agaatattta atccggtatt ggctggtt tttatccaga tccatcttta    180
tgccgtaagg gtgatcccta ttatttggta aactcttctt ttagttttta tcctggtgta   240
ccattgagta cgagtaagga tttgattcat tggaaaccgg ctggatatgt tctcaatcgt   300
gaatctcagt tgcctttgac tcgccaaaat atttcaggcg gtattttgc tccagcgatt   360
tcttataatg agaagaataa aactttttat atgattacca caaatgtggg cgcaggtaac   420
ttcttcgtaa agagtaagga tcctgagaag ggatggagtg acccgattta tcttcctaag   480
gtaaatggta ttgacccaag tttcttcttt gataaggatg gtaaaggcta tattgttcat   540
aatggtcctg taacaggtaa acaggaatat gagggtcagc gtgctattcg tcttttcgag   600
tttgatgtga agggtgatag cattaagggc gattttacag agattgttcg tggtggtacc   660
catgttcaga aaaatccgat ttggatagag ggtccacatc ttttccgtgt ggcaaatat   720
tattatctga tgtgtgctga aggtggtacc tgtgattggc attctgaagt aatcttccgt   780
gccaagagtc caaagggtcc ttgggaggaa tgtcctgata ccctatatt gactcagcgt   840
actggtcttg atcctaatcg tcctgatatc gtaaccagtg ccggtcatgc agatattgtg   900
cagagtaagg aaggtgattg gtgggctgta ttcctcggct gtcgcccata tcaggatgac   960
ttctataata caggtcgtga tacttatctt ttgcctgtaa cctggaaaaa tggttggcct  1020
attattcagc ctaagaatac tgcaattcct gctgttagca agatgacgaa gtggcaggaa  1080
aaactgagtg caggactgaa gaatcagggt gaattctctg gtaatttcag ctatgaagat  1140
aagtttgatg gtgaaagctt aaatcagcgt tggatgttcc ttcgtaatcc ttctgctttc  1200
tggaagacct cttccgaggg attggtgatt tctccaaaac atgctaagat taatgaaaag  1260
gagagtcctc ctgttatctt tactcgtcag cagcatacta actttactgc tgagactact  1320
gttcgtttcg ctcctacaag tgaaaaaaca caggctggtt tggttttgat gcagaaagag  1380
```

```
gatcataact tcgtgtttgt caaaactctt cgtgctggta aaccggtact tgttcttgaa    1440
agagctgaac gtggtaatgc ggttatagct tctacggaat tgacaggtgt acatgctgct    1500
ggtaacgaac ctcttcgtct caaggtggta ggtaacggtc gttactatga tttctattat    1560
gcagagggtg atgctgatta ccagctctta gctaaggggtg tcgatgctgt taatttgagt    1620
acacaccaga gtggtggttt cattggtgcg gtaatcggac tttatgctgt gaaataa      1677
```

```
<210> SEQ ID NO 55
<211> LENGTH: 560
<212> TYPE: PRT
<213> ORGANISM: Prevotella bryantii

<400> SEQUENCE: 55
```

```
Met Gly Ser Ser His His His His His Ser Ser Gly Leu Val Pro
 1               5                  10                  15

Arg Gly Ser His Met Gln Asp Ala Val Phe Gln Asn Phe Lys Tyr Thr
            20                  25                  30

Gly Asn Glu Ser Arg Phe Ala Lys Asn Ile Asp Thr Ser Lys Glu Tyr
        35                  40                  45

Tyr Asn Pro Val Leu Ala Gly Phe Tyr Pro Asp Pro Ser Leu Cys Arg
 50                  55                  60

Lys Gly Asp Thr Tyr Tyr Leu Val Asn Ser Ser Phe Ser Phe Tyr Pro
65                  70                  75                  80

Gly Val Pro Leu Ser Thr Ser Lys Asp Leu Ile His Trp Lys Pro Ala
                85                  90                  95

Gly Tyr Val Leu Asn Arg Glu Ser Gln Leu Pro Leu Thr Arg Gln Asn
           100                 105                 110

Ile Ser Gly Gly Ile Phe Ala Pro Ala Ile Ser Tyr Asn Glu Lys Asn
       115                 120                 125

Lys Thr Phe Tyr Met Ile Thr Thr Asn Val Gly Ala Gly Asn Phe Phe
130                 135                 140

Val Lys Ser Lys Asp Pro Glu Lys Gly Trp Ser Asp Pro Ile Tyr Leu
145                 150                 155                 160

Pro Lys Val Asn Gly Ile Asp Pro Ser Phe Phe Phe Asp Lys Asp Gly
                165                 170                 175

Lys Gly Tyr Ile Val His Asn Gly Pro Val Thr Gly Lys Gln Glu Tyr
           180                 185                 190

Glu Gly Gln Arg Ala Ile Arg Leu Phe Glu Phe Asp Val Lys Gly Asp
       195                 200                 205

Ser Ile Lys Gly Asp Phe Thr Glu Ile Val Arg Gly Gly Thr His Val
210                 215                 220

Gln Lys Asn Pro Ile Trp Ile Glu Gly Pro His Leu Phe Arg Val Gly
225                 230                 235                 240

Lys Tyr Tyr Tyr Leu Met Cys Ala Glu Gly Gly Thr Cys Asp Trp His
                245                 250                 255

Ser Glu Val Ile Phe Arg Ala Lys Ser Pro Lys Gly Pro Trp Glu Glu
           260                 265                 270

Cys Pro Asp Asn Pro Ile Leu Thr Gln Arg Thr Gly Leu Asp Pro Asn
       275                 280                 285

Arg Pro Asp Ile Val Thr Ser Ala Gly His Ala Asp Ile Val Gln Ser
   290                 295                 300

Lys Glu Gly Asp Trp Trp Ala Val Phe Leu Gly Cys Arg Pro Tyr Gln
305                 310                 315                 320
```

```
Asp Asp Phe Tyr Asn Thr Gly Arg Asp Thr Tyr Leu Leu Pro Val Thr
                325                 330                 335

Trp Lys Asn Gly Trp Pro Ile Ile Gln Pro Lys Asn Thr Ala Ile Pro
            340                 345                 350

Ala Val Ser Lys Met Thr Lys Trp Gln Glu Lys Leu Ser Ala Gly Leu
        355                 360                 365

Lys Asn Gln Gly Glu Phe Ser Gly Asn Phe Ser Tyr Glu Asp Lys Phe
    370                 375                 380

Asp Gly Glu Ser Leu Asn Gln Arg Trp Met Phe Leu Arg Asn Pro Ser
385                 390                 395                 400

Ala Phe Trp Lys Thr Ser Ser Glu Gly Leu Val Ile Ser Pro Lys His
                405                 410                 415

Ala Lys Ile Asn Glu Lys Glu Ser Pro Ser Val Ile Phe Thr Arg Gln
            420                 425                 430

Gln His Thr Asn Phe Thr Ala Glu Thr Thr Val Arg Phe Ala Pro Thr
        435                 440                 445

Ser Glu Lys Thr Gln Ala Gly Leu Val Leu Met Gln Lys Glu Asp His
    450                 455                 460

Asn Phe Val Phe Val Lys Thr Leu Arg Ala Gly Lys Pro Val Leu Val
465                 470                 475                 480

Leu Glu Arg Ala Glu Arg Gly Asn Ala Val Ile Ala Ser Thr Glu Leu
                485                 490                 495

Thr Gly Val His Ala Ala Gly Asn Glu Pro Leu Arg Leu Lys Val Val
            500                 505                 510

Gly Asn Gly Arg Tyr Tyr Asp Phe Tyr Tyr Ala Glu Gly Asp Ala Asp
        515                 520                 525

Tyr Gln Leu Leu Ala Lys Gly Val Asp Ala Val Asn Leu Ser Thr His
    530                 535                 540

Gln Ser Gly Gly Phe Ile Gly Ala Val Ile Gly Leu Tyr Ala Val Lys
545                 550                 555                 560

<210> SEQ ID NO 56
<211> LENGTH: 1683
<212> TYPE: DNA
<213> ORGANISM: Prevotella bryantii

<400> SEQUENCE: 56
atgggcagca gccatcatca tcatcatcac agcagcggcc tggtgccgcg cggcagccat      60
atgcaggatg ctgttttcca gaattttaag tatactggta acgaaagtcg ttttgctaaa     120
aatatcgaca ccagtaaaga atattataat ccggtattgg ctggttttta tccagatcca     180
tctttatgcc gtaagggtga tacctattat ttggtaaact cttcttttag tttttatcct     240
ggtgtaccat tgagtacgag taaggatttg attcattgga aaccggctgg atatgttctc     300
aatcgtgaat ctcagttgcc tttgactcgc caaaatattt caggcggtat ttttgctcca     360
gcgatttctt ataatgagaa gaataaaact ttttatatga ttaccacaaa tgtgggcgca     420
ggtaacttct tcgtaaagag taaggatcct gagaagggat ggagtgaccc gatttatctt     480
cctaaggtaa atggtattga cccaagtttc ttctttgata aggatggtaa aggctatatt     540
gttcataatg gtcctgtaac aggtaaacag gaatatgagg tcagcgtgc tattcgtctt      600 ttcgagtttg atgtgaaggg tgatagcatt aagggcgatt ttacagagat gttcgtggt      660 ggtacccatg ttcagaaaaa tccgatttgg atagagggtc acatctttt ccgtgttggc      720 aaatattatt atctgatgtg tgctgaaggt ggtacctgtg attggcattc tgaagtaatc     780
```

| | |
|---|---|
| ttccgtgcca agagtccaaa gggtccttgg gaggaatgtc ctgataaccc tatattgact | 840 |
| cagcgtactg gtcttgatcc taatcgtcct gatatcgtaa ccagtgccgg tcatgcagat | 900 |
| attgtgcaga gtaaggaagg tgattggtgg gctgtattcc tcggctgtcg cccatatcag | 960 |
| gatgacttct ataatacagg tcgtgatact tatcttttgc ctgtaacctg gaaaaatggt | 1020 |
| tggcctatta ttcagcctaa gaatactgca attcctgctg ttagcaagat gacgaagtgg | 1080 |
| caggaaaaac tgagtgcagg actgaagaat cagggtgaat tctctggtaa tttcagctat | 1140 |
| gaagataagt ttgatggtga aagcttaaat cagcgttgga tgttccttcg taatccttct | 1200 |
| gctttctgga agacctcttc cgagggattg gtgatttctc caaaacatgc taagattaat | 1260 |
| gaaaaggaga gtccttctgt tatctttact cgtcagcagc atactaactt tactgctgag | 1320 |
| actactgttc gtttcgctcc tacaagtgaa aaaacacagg ctggtttggt tttgatgcag | 1380 |
| aaagaggatc ataacttcgt gtttgtcaaa actcttcgtg ctggtaaacc ggtacttgtt | 1440 |
| cttgaaagag ctgaacgtgg taatgcggtt atagcttcta cggaattgac aggtgtacat | 1500 |
| gctgctggta acgaacctct tcgtctcaag gtggtaggta acggtcgtta ctatgatttc | 1560 |
| tattatgcag agggtgatgc tgattaccag ctccttagcta agggtgtcga tgctgttaat | 1620 |
| ttgagtacac accagagtgg tggtttcatt ggtgcggtaa tcggactttta tgctgtgaaa | 1680 |
| taa | 1683 |

<210> SEQ ID NO 57
<211> LENGTH: 1683
<212> TYPE: DNA
<213> ORGANISM: Prevotella bryantii

<400> SEQUENCE: 57

| | |
|---|---|
| atgggcagca gccatcatca tcatcatcac agcagcggcc tggtgccgcg cggcagccat | 60 |
| atgcaggatg ctgttttcca gaattttaag tatactggta acgaaagtcg ttttgctaaa | 120 |
| aatatcgaca ccagtaaaga atattataat ccggtattgg ctggttttta tccagatcca | 180 |
| tctttatgcc gtaagggtga tacctattat ttggtaaact cttcttttag ttttttatcct | 240 |
| ggtgtaccat tgagtacgag taaggatttg attcattgga aaccggctgg atatgttctc | 300 |
| aatcgtgaat ctcagttgcc tttgactcgc caaaatattt caggcggtat ttttgctcca | 360 |
| gcgatttctt ataatgagaa gaataaaact ttttatatga ttaccacaaa tgtgggcgca | 420 |
| ggtaacttct tcgtaaagag taaggatcct gagaagggat ggagtgaccc gatttatctt | 480 |
| cctaaggtaa atggtattga cccaagtttc ttctttgata aggatggtaa aggctatatt | 540 |
| gttcataatg gtcctgtaac aggtaaacag gaatatgagg gtcagcgtgc tattcgtctt | 600 |
| ttcgagtttg atgtgaaggg tgatagcatt aagggcgatt ttacagagat tgttcgtggt | 660 |
| ggtacccatg ttcagaaaaa tccgatttgg atagagggtc cacatctttt ccgtgttggc | 720 |
| aaatattatt atctgatgtg tgctgaaggt ggtacctgtg attggcattc tgaagtaatc | 780 |
| ttccgtgcca agagtccaaa gggtccttgg gaggaatgtc ctgataaccc tatattgact | 840 |
| cagcgtactg gtcttgatcc taatcgtcct gatatcgtaa ccagtgccgg tcatgcagat | 900 |
| attgtgcaga gtaaggaagg tgattggtgg gctgtattcc tcggctgtcg cccatatcag | 960 |
| gatgacttct ataatacagg tcgtgatact tatcttttgc ctgtaacctg gaaaaatggt | 1020 |
| tggcctatta ttcagcctaa gaatactgca attcctgctg ttagcaagat gacgaagtgg | 1080 |
| caggaaaaac tgagtgcagg actgaagaat cagggtgaat tctctggtaa tttcagctat | 1140 |
| gaagataagt ttgatggtga aagcttaaat cagcgttgga tgttccttcg taatccttct | 1200 |

-continued

```
gctttctgga agacctcttc cgagggattg gtgatttctc caaaacatgc taagattaat    1260
gaaaaggaga gtccttctgt tatcttact cgtcagcagc atactaactt tactgctgag    1320
actactgttc gtttcgctcc tacaagtgaa aaaacacagg ctggtttggt tttgatgcag    1380
aaagaggatc ataacttcgt gtttgtcaaa actcttcgtg ctggtaaacc ggtacttgtt    1440
cttgaaagag ctgaacgtgg taatgcggtt atagcttcta cggaattgac aggtgtacat    1500
gctgctggta acgaacctct tcgtctcaag gtggtaggta acggtcgtta ctatgatttc    1560
tattatgcag agggtgatgc tgattaccag ctcttagcta agggtgtcga tgctgttaat    1620
ttgagtacac accagagtgg tggtttcatt ggtgcggtaa tcggacttta tgctgtgaaa    1680
taa                                                                 1683
```

<210> SEQ ID NO 58
<211> LENGTH: 560
<212> TYPE: PRT
<213> ORGANISM: Prevotella bryantii

<400> SEQUENCE: 58

```
Met Gly Ser Ser His His His His His His Ser Ser Gly Leu Val Pro
  1               5                  10                  15

Arg Gly Ser His Met Gln Asp Ala Val Phe Gln Asn Phe Lys Tyr Thr
             20                  25                  30

Gly Asn Glu Ser Arg Phe Ala Lys Asn Ile Asp Thr Ser Lys Glu Tyr
         35                  40                  45

Tyr Asn Pro Val Leu Ala Gly Phe Tyr Pro Asp Pro Ser Leu Cys Arg
     50                  55                  60

Lys Gly Asp Thr Tyr Tyr Leu Val Asn Ser Ser Phe Ser Phe Tyr Pro
 65                  70                  75                  80

Gly Val Pro Leu Ser Thr Ser Lys Asp Leu Ile His Trp Lys Pro Ala
                 85                  90                  95

Gly Tyr Val Leu Asn Arg Glu Ser Gln Leu Pro Leu Thr Arg Gln Asn
            100                 105                 110

Ile Ser Gly Gly Ile Phe Ala Pro Ala Ile Ser Tyr Asn Glu Lys Asn
        115                 120                 125

Lys Thr Phe Tyr Met Ile Thr Thr Asn Val Gly Ala Gly Asn Phe Phe
    130                 135                 140

Val Lys Ser Lys Asp Pro Glu Lys Gly Trp Ser Asp Pro Ile Tyr Leu
145                 150                 155                 160

Pro Lys Val Asn Gly Ile Asp Pro Ser Phe Phe Asp Lys Asp Gly
                165                 170                 175

Lys Gly Tyr Ile Val His Asn Gly Pro Val Thr Gly Lys Gln Glu Tyr
            180                 185                 190

Glu Gly Gln Arg Ala Ile Arg Leu Phe Glu Phe Asp Val Lys Gly Asp
        195                 200                 205

Ser Ile Lys Gly Asp Phe Thr Glu Ile Val Arg Gly Gly Thr His Val
    210                 215                 220

Gln Lys Asn Pro Ile Trp Ile Glu Gly Pro His Leu Phe Arg Val Gly
225                 230                 235                 240

Lys Tyr Tyr Tyr Leu Met Cys Ala Glu Gly Thr Cys Asp Trp His
                245                 250                 255

Ser Glu Val Ile Phe Arg Ala Lys Ser Pro Lys Gly Pro Trp Glu Glu
            260                 265                 270

Cys Pro Asp Asn Pro Ile Leu Thr Gln Arg Thr Gly Leu Asp Pro Asn
```

```
              275                 280                 285
Arg Pro Asp Ile Val Thr Ser Ala Gly His Ala Asp Ile Val Gln Ser
290                 295                 300

Lys Glu Gly Asp Trp Trp Ala Val Phe Leu Gly Cys Arg Pro Tyr Gln
305                 310                 315                 320

Asp Asp Phe Tyr Asn Thr Gly Arg Asp Thr Tyr Leu Leu Pro Val Thr
                325                 330                 335

Trp Lys Asn Gly Trp Pro Ile Ile Gln Pro Lys Asn Thr Ala Ile Pro
            340                 345                 350

Ala Val Ser Lys Met Thr Lys Trp Gln Glu Lys Leu Ser Ala Gly Leu
        355                 360                 365

Lys Asn Gln Gly Glu Phe Ser Gly Asn Phe Ser Tyr Glu Asp Lys Phe
370                 375                 380

Asp Gly Glu Ser Leu Asn Gln Arg Trp Met Phe Leu Arg Asn Pro Ser
385                 390                 395                 400

Ala Phe Trp Lys Thr Ser Ser Glu Gly Leu Val Ile Ser Pro Lys His
                405                 410                 415

Ala Lys Ile Asn Glu Lys Glu Ser Pro Ser Val Ile Phe Thr Arg Gln
            420                 425                 430

Gln His Thr Asn Phe Thr Ala Glu Thr Thr Val Arg Phe Ala Pro Thr
        435                 440                 445

Ser Glu Lys Thr Gln Ala Gly Leu Val Leu Met Gln Lys Glu Asp His
450                 455                 460

Asn Phe Val Phe Val Lys Thr Leu Arg Ala Gly Lys Pro Val Leu Val
465                 470                 475                 480

Leu Glu Arg Ala Glu Arg Gly Asn Ala Val Ile Ala Ser Thr Glu Leu
                485                 490                 495

Thr Gly Val His Ala Ala Gly Asn Glu Pro Leu Arg Leu Lys Val Val
            500                 505                 510

Gly Asn Gly Arg Tyr Tyr Asp Phe Tyr Tyr Ala Glu Gly Asp Ala Asp
        515                 520                 525

Tyr Gln Leu Leu Ala Lys Gly Val Asp Ala Val Asn Leu Ser Thr His
530                 535                 540

Gln Ser Gly Gly Phe Ile Gly Ala Val Ile Gly Leu Tyr Ala Val Lys
545                 550                 555                 560

<210> SEQ ID NO 59
<211> LENGTH: 35
<212> TYPE: DNA
<213> ORGANISM: Artificial Sequence
<220> FEATURE:
<223> OTHER INFORMATION: Synthesized Construct

<400> SEQUENCE: 59
gcgccatatg caaactatac ttattaatca gcagg                              35

<210> SEQ ID NO 60
<211> LENGTH: 27
<212> TYPE: DNA
<213> ORGANISM: Artificial Sequence
<220> FEATURE:
<223> OTHER INFORMATION: Synthesized Construct

<400> SEQUENCE: 60
cgcgctcgag tcacttgatg acttcag                                       27

<210> SEQ ID NO 61
```

```
<211> LENGTH: 776
<212> TYPE: PRT
<213> ORGANISM: Prevotella bryantii

<400> SEQUENCE: 61
```

| | | | | | | | | | | | | | | |
|---|---|---|---|---|---|---|---|---|---|---|---|---|---|---|
| Met | Arg | Lys | Lys | Ile | Leu | Leu | Met | Cys | Ala | Ser | Ile | Ala | Leu | Val | Ser |
| 1 | | | | 5 | | | | | 10 | | | | | 15 | |

Cys Asn Asn Gln Thr Ile Leu Ile Asn Gln Gln Val Asp Ala Leu Tyr
            20                  25                  30

Asp Arg Met Ser Gln Glu Glu Arg Ile Asn Gln Leu Arg Ser Gly Tyr
        35                  40                  45

Met Asp Asp Leu Phe Asp Glu Gln Gly Asn Leu Asp Thr Val Lys Cys
 50                  55                  60

Lys Glu Leu Ile Pro Phe Gly Ile Gly His Phe Ser Gln Tyr Ala Ser
65                  70                  75                  80

Gln Lys Pro Leu Asp Ala Asn Ile Leu Arg Asp Arg Val Ala Ala Val
                85                  90                  95

Gln Asp Trp Leu Ile His His Thr Pro Asn Gly Ile Pro Ala Leu Phe
            100                 105                 110

His Glu Glu Val Leu Ser Gly Val Asn Thr Lys Asp Ala Thr Ile Tyr
        115                 120                 125

Pro Gln Gln Ile Gly Gln Ala Cys Ser Phe Asn Pro Glu Leu Ala Glu
130                 135                 140

Arg Lys Thr Leu Gln Thr Gly Ile Asp Met Arg Lys Met Gly Gly Val
145                 150                 155                 160

Leu Ser Leu Ser Pro Met Val Asp Val Cys Arg Asn Pro Ser Phe Asn
                165                 170                 175

Arg Leu Glu Glu Ser Tyr Gly Glu Asp Gly Tyr Leu Ser Ala Val Met
            180                 185                 190

Gly Thr Ala Phe Val Lys Gly Leu Gln Gln Gly Asp Leu Thr Lys Gly
        195                 200                 205

Val Gly Ala Cys Ser Lys His Tyr Leu Gly Tyr Gly Gly Gly Gly Asp
210                 215                 220

Ala Lys Glu Lys Glu Met Met Glu Glu Ile Leu Leu Pro His Glu Thr
225                 230                 235                 240

Met Ile Arg Leu Ala Gly Ser Lys Ala Leu Met Pro Gly Tyr His Ala
                245                 250                 255

Val His Gly Thr Asn Cys Val Ala Asn His Glu Ile Leu Thr Asp Ile
            260                 265                 270

Leu Arg Gly Tyr Leu Gly Phe Asp Gly Met Val Val Ser Asp Tyr Thr
        275                 280                 285

Ala Ile Asp Gln Ile Pro Gly Leu Asp Thr Pro Leu Gln Lys Ala Thr
290                 295                 300

Ala Ala Ile Asn Ala Gly Asn Asp Val Asp Phe Pro His Gly Ala Asn
305                 310                 315                 320

Tyr Lys Phe Leu Gln Gly Leu Asp Lys Gly Met Val Lys Ser Glu
                325                 330                 335

Ala Phe Glu Arg Ala Val Lys Asp Val Leu Arg His Lys Tyr Arg Gln
            340                 345                 350

Gly Leu Phe Asp Lys Asn Ala Tyr Leu Tyr Ser Lys Asp Pro Ile Gln
        355                 360                 365

Leu Asp Ser Lys Glu Glu Arg Gln Thr Ala Tyr Asp Ile Ala Thr Gln
370                 375                 380

Ser Val Val Leu Leu Glu Asn Lys Gly Ile Leu Pro Leu Arg Gly Lys

```
             385                 390                 395                 400
Gln Asn Ile Phe Val Thr Gly Pro Asn Ala Asn Thr Met Trp Ala Met
                    405                 410                 415

Cys Gly Asp Tyr Ser Phe Pro Ala Met Thr Tyr Phe Trp Lys Lys Val
                420                 425                 430

Thr Glu Asp Leu Asp His Pro His Ile Val Lys Leu Leu Glu Gly Met
            435                 440                 445

Lys Asp Arg Lys Pro Ala Gly Ile Asn Ile Ser Tyr Ser Arg Gly Cys
450                 455                 460

Asp Trp Thr Asp Thr Ile Glu Thr Lys Tyr Ala Val Ser Gly Asp Glu
465                 470                 475                 480

Arg Ala Trp Glu Tyr Glu Val Leu His Arg Lys Val Asp Ser Gly Glu
                485                 490                 495

Lys Ala Asp Glu Thr Glu Ala Leu Ala Met Ala Lys Glu Ala Asp Val
                500                 505                 510

Ile Ile Ala Ala Val Gly Glu Asn Val Met Leu Cys Gly Glu Asn Arg
            515                 520                 525

Asp Arg Gln Gly Leu Cys Leu Pro Gly His Gln Glu Gln Tyr Val Glu
530                 535                 540

Arg Leu Leu Ala Thr Gly Lys Pro Val Val Leu Val Val Phe Gly Gly
545                 550                 555                 560

Arg Ala Gln Val Ile Ser Asn Ile Ala Asn Arg Cys Ala Ala Val Ile
                565                 570                 575

Gln Ala Trp Tyr Pro Gly Glu Glu Gly His Ala Val Ala Asp Ile
                580                 585                 590

Leu Tyr Gly Asn Val Ser Pro Ser Ala Lys Leu Ser Val Ser Tyr Pro
            595                 600                 605

Asn Val Glu Leu Asn Glu Pro Ile Cys Tyr Asn Tyr Ser Ala Lys Gln
            610                 615                 620

Asp Ser Arg Val Ala Trp Pro Phe Gly Tyr Gly Leu Ser Tyr Thr Thr
625                 630                 635                 640

Phe Asp Tyr Ser Asn Leu Glu Val Pro Thr Glu Val Lys Thr Ser Asp
                645                 650                 655

Glu Ser Leu His Ile Ala Phe Glu Val Ala Asn Thr Gly Lys Met Asp
            660                 665                 670

Ala Asp Glu Ile Ala Gln Val Tyr Leu Ser Pro Thr Gln Glu Asn Gln
            675                 680                 685

Asn Ile Arg Pro Ile Gln Leu Gln Gly Phe Ala Arg Ile Ser Leu Lys
690                 695                 700

Ala Gly Glu Arg Lys Lys Val Lys Val Lys Leu Tyr Thr Glu Gln Phe
705                 710                 715                 720

Gly Tyr Tyr Ser Asn Asn Gly Lys Arg Gln Trp Asn Ile Ala Pro Gly
                725                 730                 735

Thr Phe Thr Val Lys Ile Gly Ala Ser Ser Gln Asp Ile Lys Leu Gln
            740                 745                 750

Lys Asn Ile Thr Val Lys Gly Asp Ile Val Val Lys Pro Leu Arg Asp
            755                 760                 765

Phe Tyr Phe Ser Glu Val Ile Lys
            770                 775

<210> SEQ ID NO 62
<211> LENGTH: 2331
<212> TYPE: DNA
<213> ORGANISM: Prevotella bryantii
```

<400> SEQUENCE: 62

```
atgagaaaaa aaatattgct tatgtgtgct tctatagctc ttgtcagttg taataaccaa    60
actatactta ttaatcagca ggttgacgct ctttacgata gaatgtcgca ggaagaacgc   120
attaaccaat tacgtagtgg atatatggat gacttgtttg atgaacaggg taatctggat   180
accgtaaaat gtaaagagtt gattccgttt ggtatcggtc acttctctca atatgccagc   240
caaaaaccgc tcgatgcaaa tattcttcga gaccgcgttg ctgctgtaca agactggctc   300
atacatcata ctcctaacgg aattcctgct ctattccacg aagaagtgct ctcgggtgtt   360
aacacgaaag atgctacgat ctatccacaa caaataggac aagcatgctc ttttaatccc   420
gaactagctg agcgaaagac cttacaaacg ggtatcgata tgcgcaaaat gggaggcgta   480
ctctccttat cgcctatggt agacgtatgc cgaaatccaa gtttcaaccg gctcgaagag   540
tcgtatggcg aagatgggta tctgtcagct gtaatgggta ctgcctttgt caagggattg   600
caacagggcg acttaaccaa gggtgtgggg gcttgcagca agcactatct cggatatggt   660
ggcggaggcg atgctaagga aaaggagatg atggaagaaa ttctacttcc tcacgaaaca   720
atgattcgac tggctggaag caaagcgctg atgcctggtt atcacgctgt acatggtact   780
aactgtgtag ctaatcatga gatactgacc gatattcttc gtggctatct cggcttcgat   840
ggtatggtgg ttagtgacta tacagccata gaccaaattc ctggtcttga tactcctctt   900
cagaaggcta ctgcagcgat caacgctggc aacgatgtgg attttccgca tggggccaac   960
tataagttcc tgcaggaagg tctcgataaa ggtatggtta agtccgaggc ttttgagcgt  1020
gctgtaaaag atgttcttcg ccataaatat cgccaagggc tcttcgacaa gaacgcttat  1080
ctctacagca aagatcctat tcagctcgat agtaaggagg agcgacagac tgcctacgat  1140
atcgctacac aaagtgtcgt tttacttgaa aataaaggga tattaccgct tcgaggcaaa  1200
cagaatatct tcgtcacagg tccgaatgcg aatacaatgt gggccatgtg tggtgactat  1260
tcgttcccgg caatgactta tttctggaag aaggtaactg aagatcttga ccatcctcat  1320
atcgtgaaac tcctcgaagg tatgaaagac cgaaagcctg cggggataaa tatttcttat  1380
tcccgcggat gtgactggac tgatactatc gaaaccaagt atgctgtatc tggtgatgaa  1440
cgtgcttggg aatacgaggt attacatcgt aaggtcgatt ctggtgaaaa ggctgatgaa  1500
actgaagctc tggccatggc aaaggaggcg atgttatca tcgcagctgt tggtgagaat  1560
gtaatgctat gtggcgaaaa tcgtgatcga caggggcttt gcctcccggg acatcaggaa  1620
caatatgtag aacgacttct ggctacagga aaacctgttg tgctggttgt ttttggtgga  1680
agagcgcaag tcatctctaa cattgccaac cgttgtgctg ctgttatcca ggcttggtat  1740
cctggtgagg aaggtggtca tgctgttgca gatattctct acggtaacgt gtctccatca  1800
gctaaacttt ctgtaagtta tccgaatgta gaactgaacg agcctatctg ctataactat  1860
tctgccaaac aggattcacg tgtggcttgg ccttttcggct atggtctgag ctataccact  1920
ttcgactata gtaatcttga agttcctaca gaagtgaaga cttctgatga aagcttgcat  1980
atcgcattcg aagtagcaaa tacgggaaaa atggatgctg atgaaatcgc tcaggtttac  2040
ttgtctccta ctcaagagaa tcagaatatc cgccctatcc aactgcaggg ctttgcccgc  2100
atatcactca aggctggtga gcgtaagaaa gtaaaggtaa aactctacac tgaacagttt  2160
ggctattatt ctaacaacgg taaacgacaa tggaatatcg cccctggcac atttacggtc  2220
aagataggag cctcatcaca ggatatcaaa ttgcaaaaaa atataaccgt caagggagat  2280
```

```
atcgtagtga aacctttgcg tgattttttac ttctctgaag tcatcaagtg a          2331
```

<210> SEQ ID NO 63
<211> LENGTH: 2343
<212> TYPE: DNA
<213> ORGANISM: Prevotella bryantii

<400> SEQUENCE: 63

```
atgggcagca gccatcatca tcatcatcac agcagcggcc tggtgccgcg cggcagccat    60
atgcaaacta tacttattaa tcagcaggtt gacgctcttt acgatagaat gtcgcaggaa   120
gaacgcatta accaattacg tagtggatat atggatgact tgtttgatga acagggtaat   180
ctggataccg taaaatgtaa agagttgatt ccgtttggta tcggtcactt ctctcaatat   240
gccagccaaa aaccgctcga tgcaaatatt cttcgagacc gcgttgctgc tgtacaagac   300
tggctcatac atcatactcc taacggaatt cctgctctat tccacgaaga agtgctctcg   360
ggtgttaaca cgaaagatgc tacgatctat ccacaacaaa taggacaagc atgctctttt   420
aatcccgaac tagctgagcg aaagacctta caaacgggta tcgatatgcg caaaatggga   480
ggcgtactct ccttatcgcc tatggtagac gtatgccgaa atccaagttt caaccggctc   540
gaagagtcgt atgcgaagaa tgggtatctg tcagctgtaa tgggtactgc ctttgtcaag   600
ggattgcaac agggcgactt aaccaagggt gtggggctt gcagcaagca ctatctcgga   660
tatggtggtg gaggcgatgc taaggaaaag gagatgatgg aagaaattct acttcctcac   720
gaaacaatga ttcgactggc tggaagcaaa gcgctgatgc ctggttatca cgctgtacat   780
ggtactaact gtgtagctaa tcatgagata ctgaccgata ttcttcgtgg ctatctcggc   840
ttcgatggta tggtggttag tgactataca gccatagacc aaattcctgg tcttgatact   900
cctcttcaga aggctactgc agcgatcaac gctggcaacg atgtggattt ccgcatgggg   960
gccaactata agttcctgca ggaaggtctc gataaggta tggttaagtc cgaggctttt  1020
gagcgtgctg taaagatgt tcttcgccat aaatatcgcc aagggctctt cgacaagaac  1080
gcttatctct acagcaaaga tcctattcag ctcgatagta aggaggagcg acagactgcc  1140
tacgatatcg ctacacaaag tgtcgtttta cttgaaaata aagggatatt accgcttcga  1200
ggcaaacaga atatcttcgt cacaggtccg aatgcgaata caatgtgggc catgtgtggt  1260
gactattcgt tcccggcaat gacttatttc tggaagaagg taactgaaga tcttgaccat  1320
cctcatatcg tgaaactcct cgaaggtatg aaagaccgaa agcctgcggg gataaatatt  1380
tcttattccc gcggatgtga ctggactgat actatcgaaa ccaagtatgc tgtatctggt  1440
gatgaacgtg cttgggaata cgaggtatta catcgtaagg tcgattctgg tgaaaaggct  1500
gatgaaactg aagctctggc catggcaaag gaggcggatg ttatcatcgc agctgttggt  1560
gagaatgtaa tgctatgtgg cgaaaatcgt gatcgacagg ggctttgcct cccgggacat  1620
caggaacaat atgtagaacg acttctggct acaggaaaac tgttgtgct ggttgttttt  1680
ggtggaagag cgcaagtcat ctctaacatt gccaaccgtt gtgctgctgt taccaggct  1740
tggtatcctg gtgaggaagg tggtcatgct gttgcagata ttctctacgg taacgtgtct  1800
ccatcagcta aactttctgt aagttatccg aatgtagaac tgaacgagcc tatctgctat  1860
aactattctg ccaaacagga ttcacgtgtg gcttggcctt tcggctatgg tctgagctat  1920
accactttcg actatagtaa tcttgaagtt cctacagaag tgaagacttc tgatgaaagc  1980
ttgcatatcg cattcgaagt agcaaatacg ggaaaaatgg atgctgatga aatcgctcag  2040
gtttacttgt ctcctactca agagaatcag aatatccgcc ctatccaact gcagggcttt  2100
```

-continued

```
gcccgcatat cactcaaggc tggtgagcgt aagaaagtaa aggtaaaact ctacactgaa    2160
cagtttggct attattctaa caacggtaaa cgacaatgga atatcgcccc tggcacattt    2220
acggtcaaga taggagcctc atcacaggat atcaaattgc aaaaaaatat aaccgtcaag    2280
ggagatatcg tagtgaaacc tttgcgtgat ttttacttct ctgaagtcat caagtgactc    2340
gag                                                                  2343
```

<210> SEQ ID NO 64
<211> LENGTH: 778
<212> TYPE: PRT
<213> ORGANISM: Prevotella bryantii

<400> SEQUENCE: 64

```
Met Gly Ser Ser His His His His His His Ser Gly Leu Val Pro
 1               5                  10                  15

Arg Gly Ser His Met Gln Thr Ile Leu Ile Asn Gln Gln Val Asp Ala
            20                  25                  30

Leu Tyr Asp Arg Met Ser Gln Glu Glu Arg Ile Asn Gln Leu Arg Ser
        35                  40                  45

Gly Tyr Met Asp Asp Leu Phe Asp Glu Gln Gly Asn Leu Asp Thr Val
    50                  55                  60

Lys Cys Lys Glu Leu Ile Pro Phe Gly Ile Gly His Phe Ser Gln Tyr
65                  70                  75                  80

Ala Ser Gln Lys Pro Leu Asp Ala Asn Ile Leu Arg Asp Arg Val Ala
                85                  90                  95

Ala Val Gln Asp Trp Leu Ile His Thr Pro Asn Gly Ile Pro Ala
            100                 105                 110

Leu Phe His Glu Glu Val Leu Ser Gly Val Asn Thr Lys Asp Ala Thr
        115                 120                 125

Ile Tyr Pro Gln Gln Ile Gly Gln Ala Cys Ser Phe Asn Pro Glu Leu
    130                 135                 140

Ala Glu Arg Lys Thr Leu Gln Thr Gly Ile Asp Met Arg Lys Met Gly
145                 150                 155                 160

Gly Val Leu Ser Leu Ser Pro Met Val Asp Val Cys Arg Asn Pro Ser
                165                 170                 175

Phe Asn Arg Leu Glu Glu Ser Tyr Gly Glu Asp Gly Tyr Leu Ser Ala
            180                 185                 190

Val Met Gly Thr Ala Phe Val Lys Gly Leu Gln Gln Gly Asp Leu Thr
        195                 200                 205

Lys Gly Val Gly Ala Cys Ser Lys His Tyr Leu Gly Tyr Gly Gly Gly
    210                 215                 220

Gly Asp Ala Lys Glu Lys Glu Met Met Glu Glu Ile Leu Leu Pro His
225                 230                 235                 240

Glu Thr Met Ile Arg Leu Ala Gly Ser Lys Ala Leu Met Pro Gly Tyr
                245                 250                 255

His Ala Val His Gly Thr Asn Cys Val Ala Asn His Glu Ile Leu Thr
            260                 265                 270

Asp Ile Leu Arg Gly Tyr Leu Gly Phe Asp Gly Met Val Val Ser Asp
        275                 280                 285

Tyr Thr Ala Ile Asp Gln Ile Pro Gly Leu Asp Thr Pro Leu Gln Lys
    290                 295                 300

Ala Thr Ala Ala Ile Asn Ala Gly Asn Asp Val Asp Phe Pro His Gly
305                 310                 315                 320
```

```
Ala Asn Tyr Lys Phe Leu Gln Glu Gly Leu Asp Lys Gly Met Val Lys
                325                 330                 335

Ser Glu Ala Phe Glu Arg Ala Val Lys Asp Val Leu Arg His Lys Tyr
            340                 345                 350

Arg Gln Gly Leu Phe Asp Lys Asn Ala Tyr Leu Tyr Ser Lys Asp Pro
        355                 360                 365

Ile Gln Leu Asp Ser Lys Glu Arg Gln Thr Ala Tyr Asp Ile Ala
    370                 375                 380

Thr Gln Ser Val Val Leu Glu Asn Lys Gly Ile Leu Pro Leu Arg
385                 390                 395                 400

Gly Lys Gln Asn Ile Phe Val Thr Gly Pro Asn Ala Asn Thr Met Trp
                405                 410                 415

Ala Met Cys Gly Asp Tyr Ser Phe Pro Ala Met Thr Tyr Phe Trp Lys
            420                 425                 430

Lys Val Thr Glu Asp Leu Asp His Pro His Ile Val Lys Leu Leu Glu
        435                 440                 445

Gly Met Lys Asp Arg Lys Pro Ala Gly Ile Asn Ile Ser Tyr Ser Arg
    450                 455                 460

Gly Cys Asp Trp Thr Asp Thr Ile Glu Thr Lys Tyr Ala Val Ser Gly
465                 470                 475                 480

Asp Glu Arg Ala Trp Glu Tyr Glu Val Leu His Arg Lys Val Asp Ser
                485                 490                 495

Gly Glu Lys Ala Asp Glu Thr Glu Ala Leu Ala Met Ala Lys Glu Ala
            500                 505                 510

Asp Val Ile Ile Ala Ala Val Gly Glu Asn Val Met Leu Cys Gly Glu
        515                 520                 525

Asn Arg Asp Arg Gln Gly Leu Cys Leu Pro Gly His Gln Glu Gln Tyr
    530                 535                 540

Val Glu Arg Leu Leu Ala Thr Gly Lys Pro Val Val Leu Val Val Phe
545                 550                 555                 560

Gly Gly Arg Ala Gln Val Ile Ser Asn Ile Ala Asn Arg Cys Ala Ala
                565                 570                 575

Val Ile Gln Ala Trp Tyr Pro Gly Glu Glu Gly Gly His Ala Val Ala
            580                 585                 590

Asp Ile Leu Tyr Gly Asn Val Ser Pro Ser Ala Lys Leu Ser Val Ser
        595                 600                 605

Tyr Pro Asn Val Glu Leu Asn Glu Pro Ile Cys Tyr Asn Tyr Ser Ala
    610                 615                 620

Lys Gln Asp Ser Arg Val Ala Trp Pro Phe Gly Tyr Gly Leu Ser Tyr
625                 630                 635                 640

Thr Thr Phe Asp Tyr Ser Asn Leu Glu Val Pro Thr Glu Val Lys Thr
                645                 650                 655

Ser Asp Glu Ser Leu His Ile Ala Phe Glu Val Ala Asn Thr Gly Lys
            660                 665                 670

Met Asp Ala Asp Glu Ile Ala Gln Val Tyr Leu Ser Pro Thr Gln Glu
        675                 680                 685

Asn Gln Asn Ile Arg Pro Ile Gln Leu Gln Gly Phe Ala Arg Ile Ser
    690                 695                 700

Leu Lys Ala Gly Glu Arg Lys Lys Val Lys Val Lys Leu Tyr Thr Glu
705                 710                 715                 720

Gln Phe Gly Tyr Tyr Ser Asn Asn Gly Lys Arg Gln Trp Asn Ile Ala
                725                 730                 735

Pro Gly Thr Phe Thr Val Lys Ile Gly Ala Ser Ser Gln Asp Ile Lys
```

Leu Gln Lys Asn Ile Thr Val Lys Gly Asp Ile Val Val Lys Pro Leu
    740                 745                 750
Arg Asp Phe Tyr Phe Ser Glu Val Ile Lys
    755                 760                 765
        770                 775

<210> SEQ ID NO 65
<211> LENGTH: 2343
<212> TYPE: DNA
<213> ORGANISM: Prevotella bryantii

<400> SEQUENCE: 65

| | | | | | |
|---|---|---|---|---|---|
| atgggcagca | gccatcatca | tcatcatcac | agcagcggcc | tggtgccgcg | cggcagccat | 60 |
| atgcaaacta | tacttattaa | tcagcaggtt | gacgctcttt | acgatagaat | gtcgcaggaa | 120 |
| gaacgcatta | accaattacg | tagtggatat | atggatgact | tgtttgatga | acagggtaat | 180 |
| ctggataccg | taaaatgtaa | agagttgatt | ccgtttggta | tcggtcactt | ctctcaatat | 240 |
| gccagccaaa | aaccgctcga | tgcaaatatt | cttcgagacc | gcgttgctgc | tgtacaagac | 300 |
| tggctcatac | atcatactcc | taacggaatt | cctgctctat | ccacgaaga | agtgctctcg | 360 |
| ggtgttaaca | cgaaagatgc | tacgatctat | ccacaacaaa | taggacaagc | atgctctttt | 420 |
| aatcccgaac | tagctgagcg | aaagaccta | caaacgggta | tcgatatgcg | caaaatggga | 480 |
| ggcgtactct | ccttatcgcc | tatggtagac | gtatgccgaa | atccaagttt | caaccggctc | 540 |
| gaagagtcgt | atgcgaaga | tgggtatctg | tcagctgtaa | tgggtactgc | ctttgtcaag | 600 |
| ggattgcaac | agggcgactt | aaccaagggt | gtggggggctt | gcagcaagca | ctatctcgga | 660 |
| tatggtggtg | gaggcgatgc | taaggaaaag | gagatgatgg | aagaaattct | acttcctcac | 720 |
| gaaacaatga | ttcgactggc | tggaagcaaa | gcgctgatgc | tggttatca | cgctgtacat | 780 |
| ggtactaact | gtgtagctaa | tcatgagata | ctgaccgata | ttcttcgtgg | ctatctcggc | 840 |
| ttcgatggta | tggtggttag | tgactataca | gccatagacc | aaattcctgg | tcttgatact | 900 |
| cctcttcaga | aggctactgc | agcgatcaac | gctggcaacg | atgtggattt | ccgcatgggg | 960 |
| gccaactata | agttcctgca | ggaaggtctc | gataaaggta | tggttaagtc | cgaggctttt | 1020 |
| gagcgtgctg | taaagatgt | tcttcgccat | aaatatcgcc | aagggctctt | cgacaagaac | 1080 |
| gcttatctct | acagcaaaga | tcctattcag | ctcgatagta | aggaggagcg | acagactgcc | 1140 |
| tacgatatcg | ctacacaaag | tgtcgttta | cttgaaaata | aagggatatt | accgcttcga | 1200 |
| ggcaaacaga | atatcttcgt | cacaggtccg | aatgcgaata | caatgtgggc | catgtgtggt | 1260 |
| gactattcgt | tcccggcaat | gacttatttc | tggaagaagg | taactgaaga | tcttgaccat | 1320 |
| cctcatatcg | tgaaactcct | cgaaggtatg | aaagaccgaa | agcctgcggg | gataaatatt | 1380 |
| tcttattccc | gcggatgtga | ctggactgat | actatcgaaa | ccaagtatgc | tgtatctggt | 1440 |
| gatgaacgtg | cttgggaata | cgaggtatta | catcgtaagg | tcgattctgg | tgaaaaggct | 1500 |
| gatgaaactg | aagctctggc | catggcaaag | gaggcggatg | ttatcatcgc | agctgttggt | 1560 |
| gagaatgtaa | tgctatgtgg | cgaaaatcgt | gatcgacagg | ggctttgcct | cccgggacat | 1620 |
| caggaacaat | atgtagaacg | acttctggct | acaggaaaac | ctgttgtgct | ggttgttttt | 1680 |
| ggtggaagag | cgcaagtcat | ctctaacatt | gccaaccgtt | gtgctgctgt | tatccaggct | 1740 |
| tggtatcctg | gtgaggaagg | tggtcatgct | gttgcagata | ttctctacgg | taacgtgtct | 1800 |
| ccatcagcta | aactttctgt | aagttatccg | aatgtagaac | tgaacgagcc | tatctgctat | 1860 |
| aactattctg | ccaaacagga | ttcacgtgtg | gcttggcctt | tcggctatgg | tctgagctat | 1920 |

-continued

```
accactttcg actatagtaa tcttgaagtt cctacagaag tgaagacttc tgatgaaagc    1980
ttgcatatcg cattcgaagt agcaaatacg ggaaaaatgg atgctgatga aatcgctcag    2040
gtttacttgt ctcctactca agagaatcag aatatccgcc ctatccaact gcagggcttt    2100
gcccgcatat cactcaaggc tggtgagcgt aagaaagtaa aggtaaaact ctacactgaa    2160
cagtttggct attattctaa caacggtaaa cgacaatgga atatcgcccc tggcacattt    2220
acggtcaaga taggagcctc atcacaggat atcaaattgc aaaaaaatat aaccgtcaag    2280
ggagatatcg tagtgaaacc tttgcgtgat ttttacttct ctgaagtcat caagtgactc    2340
gag                                                                  2343
```

<210> SEQ ID NO 66
<211> LENGTH: 778
<212> TYPE: PRT
<213> ORGANISM: Prevotella bryantii

<400> SEQUENCE: 66

```
Met Gly Ser Ser His His His His His His Ser Ser Gly Leu Val Pro
 1               5                  10                  15

Arg Gly Ser His Met Gln Thr Ile Leu Ile Asn Gln Gln Val Asp Ala
            20                  25                  30

Leu Tyr Asp Arg Met Ser Gln Glu Arg Ile Asn Gln Leu Arg Ser
        35                  40                  45

Gly Tyr Met Asp Asp Leu Phe Asp Glu Gln Gly Asn Leu Asp Thr Val
    50                  55                  60

Lys Cys Lys Glu Leu Ile Pro Phe Gly Ile Gly His Phe Ser Gln Tyr
65                  70                  75                  80

Ala Ser Gln Lys Pro Leu Asp Ala Asn Ile Leu Arg Asp Arg Val Ala
                85                  90                  95

Ala Val Gln Asp Trp Leu Ile His His Thr Pro Asn Gly Ile Pro Ala
            100                 105                 110

Leu Phe His Glu Glu Val Leu Ser Gly Val Asn Thr Lys Asp Ala Thr
        115                 120                 125

Ile Tyr Pro Gln Gln Ile Gly Gln Ala Cys Ser Phe Asn Pro Glu Leu
    130                 135                 140

Ala Glu Arg Lys Thr Leu Gln Thr Gly Ile Asp Met Arg Lys Met Gly
145                 150                 155                 160

Gly Val Leu Ser Leu Ser Pro Met Val Asp Val Cys Arg Asn Pro Ser
                165                 170                 175

Phe Asn Arg Leu Glu Glu Ser Tyr Gly Glu Asp Gly Tyr Leu Ser Ala
            180                 185                 190

Val Met Gly Thr Ala Phe Val Lys Gly Leu Gln Gln Gly Asp Leu Thr
        195                 200                 205

Lys Gly Val Gly Ala Cys Ser Lys His Tyr Leu Gly Tyr Gly Gly Gly
    210                 215                 220

Gly Asp Ala Lys Glu Lys Glu Met Met Glu Glu Ile Leu Leu Pro His
225                 230                 235                 240

Glu Thr Met Ile Arg Leu Ala Gly Ser Lys Ala Leu Met Pro Gly Tyr
                245                 250                 255

His Ala Val His Gly Thr Asn Cys Val Ala Asn His Glu Ile Leu Thr
            260                 265                 270

Asp Ile Leu Arg Gly Tyr Leu Gly Phe Asp Gly Met Val Val Ser Asp
        275                 280                 285
```

```
Tyr Thr Ala Ile Asp Gln Ile Pro Gly Leu Asp Thr Pro Leu Gln Lys
    290                 295                 300

Ala Thr Ala Ala Ile Asn Ala Gly Asn Asp Val Asp Phe Pro His Gly
305                 310                 315                 320

Ala Asn Tyr Lys Phe Leu Gln Glu Gly Leu Asp Lys Gly Met Val Lys
                325                 330                 335

Ser Glu Ala Phe Glu Arg Ala Val Lys Asp Val Leu Arg His Lys Tyr
            340                 345                 350

Arg Gln Gly Leu Phe Asp Lys Asn Ala Tyr Leu Tyr Ser Lys Asp Pro
                355                 360                 365

Ile Gln Leu Asp Ser Lys Glu Glu Arg Gln Thr Ala Tyr Asp Ile Ala
    370                 375                 380

Thr Gln Ser Val Val Leu Leu Glu Asn Lys Gly Ile Leu Pro Leu Arg
385                 390                 395                 400

Gly Lys Gln Asn Ile Phe Val Thr Gly Pro Asn Ala Asn Thr Met Trp
                405                 410                 415

Ala Met Cys Gly Asp Tyr Ser Phe Pro Ala Met Thr Tyr Phe Trp Lys
                420                 425                 430

Lys Val Thr Glu Asp Leu Asp His Pro His Ile Val Lys Leu Leu Glu
            435                 440                 445

Gly Met Lys Asp Arg Lys Pro Ala Gly Ile Asn Ile Ser Tyr Ser Arg
    450                 455                 460

Gly Cys Asp Trp Thr Asp Thr Ile Glu Thr Lys Tyr Ala Val Ser Gly
465                 470                 475                 480

Asp Glu Arg Ala Trp Glu Tyr Glu Val Leu His Arg Lys Val Asp Ser
                485                 490                 495

Gly Glu Lys Ala Asp Glu Thr Glu Ala Leu Ala Met Ala Lys Glu Ala
            500                 505                 510

Asp Val Ile Ile Ala Ala Val Gly Glu Asn Val Met Leu Cys Gly Glu
            515                 520                 525

Asn Arg Asp Arg Gln Gly Leu Cys Leu Pro Gly His Gln Glu Gln Tyr
    530                 535                 540

Val Glu Arg Leu Leu Ala Thr Gly Lys Pro Val Val Leu Val Val Phe
545                 550                 555                 560

Gly Gly Arg Ala Gln Val Ile Ser Asn Ile Ala Asn Arg Cys Ala Ala
                565                 570                 575

Val Ile Gln Ala Trp Tyr Pro Gly Glu Gly Gly His Ala Val Ala
                580                 585                 590

Asp Ile Leu Tyr Gly Asn Val Ser Pro Ser Ala Lys Leu Ser Val Ser
    595                 600                 605

Tyr Pro Asn Val Glu Leu Asn Glu Pro Ile Cys Tyr Asn Tyr Ser Ala
610                 615                 620

Lys Gln Asp Ser Arg Val Ala Trp Pro Phe Gly Tyr Gly Leu Ser Tyr
625                 630                 635                 640

Thr Thr Phe Asp Tyr Ser Asn Leu Glu Val Pro Thr Glu Val Lys Thr
            645                 650                 655

Ser Asp Glu Ser Leu His Ile Ala Phe Glu Val Ala Asn Thr Gly Lys
            660                 665                 670

Met Asp Ala Asp Glu Ile Ala Gln Val Tyr Leu Ser Pro Thr Gln Glu
            675                 680                 685

Asn Gln Asn Ile Arg Pro Ile Gln Leu Gln Gly Phe Ala Arg Ile Ser
    690                 695                 700

Leu Lys Ala Gly Glu Arg Lys Lys Val Lys Val Lys Leu Tyr Thr Glu
```

```
                705                 710                 715                 720

Gln Phe Gly Tyr Tyr Ser Asn Asn Gly Lys Arg Gln Trp Asn Ile Ala
                         725                 730                 735

Pro Gly Thr Phe Thr Val Lys Ile Gly Ala Ser Ser Gln Asp Ile Lys
                         740                 745                 750

Leu Gln Lys Asn Ile Thr Val Lys Gly Asp Ile Val Lys Pro Leu
                         755                 760                 765

Arg Asp Phe Tyr Phe Ser Glu Val Ile Lys
                 770                 775

<210> SEQ ID NO 67
<211> LENGTH: 33
<212> TYPE: DNA
<213> ORGANISM: Artificial Sequence
<220> FEATURE:
<223> OTHER INFORMATION: Synthesized Construct

<400> SEQUENCE: 67
gacgacgaca agatggaaga tggccatcag ctg                                    33

<210> SEQ ID NO 68
<211> LENGTH: 33
<212> TYPE: DNA
<213> ORGANISM: Artificial Sequence
<220> FEATURE:
<223> OTHER INFORMATION: Synthesized Construct

<400> SEQUENCE: 68
gaggagaagc ccggtttatt caatcggcat ttt                                    33

<210> SEQ ID NO 69
<211> LENGTH: 638
<212> TYPE: PRT
<213> ORGANISM: Prevotella bryantii

<400> SEQUENCE: 69

Met His Tyr His Phe Lys Gln Ser Lys Met Lys Lys Thr Leu Val Leu
         1                 5                   10                  15

Ile Ile Thr Leu Ile Leu Cys Leu Gly Ala Ser Ala Glu Asp Gly His
                         20                  25                  30

Gln Leu Trp Leu Arg Tyr Gln Gln Thr His Ala Gln Val Asn Ala Pro
                     35                  40                  45

Gln Gly Gly Glu Ile Leu Asn Thr Ala Cys Arg Glu Leu Arg Asn Tyr
                 50                  55                  60

Trp Leu Gly Gln Ala Ile Asn Leu Gln Leu Val Ser Gln Asn Ile Val
         65                  70                  75                  80

Ala Pro Glu Gly Tyr Thr Phe Asp Gly Lys Thr Leu Lys Ala Ser Thr
                         85                  90                  95

Glu Ser Gly Leu Leu Tyr Gly Ala Tyr Ala Leu Leu Arg Glu Gln Thr
                         100                 105                 110

Val Arg Gly Thr Ala Lys Gly Ile Ile Leu Lys Ser Thr Pro Lys Ser
                     115                 120                 125

Lys Tyr Arg Ile Leu Asn His Trp Asp Asn Leu Asp Gly Ser Ile Glu
                 130                 135                 140

Arg Gly Tyr Ala Gly Lys Ser Ile Phe Trp Asn Ser Pro Ile Lys Gly
         145                 150                 155                 160

Glu Ala Tyr Asp Thr Arg Leu Lys Glu Tyr Ala Arg Ala Asn Ala Ser
                         165                 170                 175
```

```
Val Gly Ile Asn Gly Thr Val Leu Asp Asn Val Asn Ala Ser Pro Lys
            180                 185                 190

Met Leu Thr His Thr Tyr Leu Asp Ser Val Ala His Ile Ala Asn Ile
        195                 200                 205

Leu Arg Pro Tyr Gly Leu Arg Val Tyr Leu Ser Val Asn Phe Gly Thr
    210                 215                 220

Pro Lys Ala Leu Gly Ala Thr Asn Thr Ala Asp Pro Leu Asn Lys Arg
225                 230                 235                 240

Val Ile Ser Trp Trp Asn Lys Lys Ala Lys Glu Ile Tyr Lys Leu Ile
                245                 250                 255

Pro Asp Phe Gly Gly Phe Cys Val Lys Ala Asn Ser Glu Gly Gln Pro
            260                 265                 270

Gly Pro Phe Asp Tyr Gly Arg Thr His Ala Gln Gly Ala Asn Met Leu
        275                 280                 285

Ala Asp Ala Leu Lys Pro Tyr Gly Gly Leu Val Phe Trp Arg Ser Phe
    290                 295                 300

Val Tyr Gly Ser Lys His Lys Gly Glu Asp Arg Val Lys Gln Ala Val
305                 310                 315                 320

Ser Glu Phe Ala Asp Leu Asp Gly Thr Phe Arg Glu Asn Val Ile Leu
                325                 330                 335

Gln Ser Lys Asn Gly Pro Leu Asp Phe Gln Pro Arg Glu Pro Tyr Ala
            340                 345                 350

Pro Ile Phe Asp Gln Met His Arg Thr Thr Gln Ala Val Glu Leu Gln
        355                 360                 365

Ile Thr Gln Glu Tyr Leu Gly His Asp Lys His Leu Val Tyr Leu Ala
    370                 375                 380

Pro Met Trp Gln Glu Phe Phe Ser Phe Val Ser Val Asn Arg Leu Lys
385                 390                 395                 400

Gly Val Val Gly Val Ala Asn Ile Gly Asp His Ile Asn Trp Cys Gly
                405                 410                 415

His Pro Phe Ala Gln Ser Asn Trp Tyr Ala Phe Gly Arg Leu Ala Trp
            420                 425                 430

Asp Ala Ser Leu Asn Ser Lys Thr Ile Gly Glu Glu Trp Leu Ile Gln
        435                 440                 445

Thr Tyr Thr Asp Lys Tyr Gln Phe Val Ala Pro Val Leu Asp Met Met
    450                 455                 460

Leu Ser Ser Arg Glu Ala Cys Val Asp Tyr Met Glu Pro Leu Gly Leu
465                 470                 475                 480

His His Ile Met Ala Phe Asp His His Tyr Gly Pro Glu Pro Asp Gly
                485                 490                 495

Phe Ile Ala Ser Tyr Pro Ile Glu Trp Cys Pro Val Tyr Tyr His Lys
            500                 505                 510

Ala Asp Ala His Gly Leu Gly Phe Glu Arg Ser Ser Lys Gly Thr Asn
        515                 520                 525

Ala Thr Ala Gln Tyr Pro Glu Pro Tyr Arg Ser Leu Tyr Asp Asn Leu
    530                 535                 540

Ala Thr Cys Pro Pro Glu Tyr Leu Leu Trp Phe His His Val Ala Trp
545                 550                 555                 560

Asn Tyr Arg Met Pro Ser Gly Arg Thr Met Trp Gln Glu Leu Asn Ala
                565                 570                 575

His Tyr Asn Lys Gly Val Lys Thr Val Gln Asn Tyr Glu Asn Leu Trp
            580                 585                 590

Gln Gln Met Lys Pro Tyr Ile Asp Glu Ala Arg Trp Gln His Thr Ala
```

```
                      595                 600                 605
Asn Leu Leu His Leu Gln Glu Gln Asn Ala Glu Leu Trp Arg Asn Thr
    610                 615                 620

Cys Leu Lys Tyr Phe Ala Thr Phe Ser Lys Met Pro Ile Glu
625                 630                 635

<210> SEQ ID NO 70
<211> LENGTH: 625
<212> TYPE: PRT
<213> ORGANISM: Prevotella bryantii

<400> SEQUENCE: 70

Met Ala His His His His His Val Asp Asp Asp Lys Met Glu
1               5                   10                  15

Asp Gly His Gln Leu Trp Leu Arg Tyr Gln Gln Thr His Ala Gln Val
                20                  25                  30

Asn Ala Pro Gln Gly Gly Glu Ile Leu Asn Thr Ala Cys Arg Glu Leu
            35                  40                  45

Arg Asn Tyr Trp Leu Gly Gln Ala Ile Asn Leu Gln Leu Val Ser Gln
    50                  55                  60

Asn Ile Val Ala Pro Glu Gly Tyr Thr Phe Asp Gly Lys Thr Leu Lys
65                  70                  75                  80

Ala Ser Thr Glu Ser Gly Leu Leu Tyr Gly Ala Tyr Ala Leu Leu Arg
                85                  90                  95

Glu Gln Thr Val Arg Gly Thr Ala Lys Gly Ile Ile Leu Lys Ser Thr
                100                 105                 110

Pro Lys Ser Lys Tyr Arg Ile Leu Asn His Trp Asp Asn Leu Asp Gly
            115                 120                 125

Ser Ile Glu Arg Gly Tyr Ala Gly Lys Ser Ile Phe Trp Asn Ser Pro
130                 135                 140

Ile Lys Gly Glu Ala Tyr Asp Thr Arg Leu Lys Glu Tyr Ala Arg Ala
145                 150                 155                 160

Asn Ala Ser Val Gly Ile Asn Gly Thr Val Leu Asp Asn Val Asn Ala
                165                 170                 175

Ser Pro Lys Met Leu Thr His Thr Tyr Leu Asp Ser Val Ala His Ile
                180                 185                 190

Ala Asn Ile Leu Arg Pro Tyr Gly Leu Arg Val Tyr Leu Ser Val Asn
            195                 200                 205

Phe Gly Thr Pro Lys Ala Leu Gly Ala Thr Asn Thr Ala Asp Pro Leu
    210                 215                 220

Asn Lys Arg Val Ile Ser Trp Trp Asn Lys Lys Ala Lys Glu Ile Tyr
225                 230                 235                 240

Lys Leu Ile Pro Asp Phe Gly Phe Cys Val Lys Ala Asn Ser Glu
                245                 250                 255

Gly Gln Pro Gly Pro Phe Asp Tyr Gly Arg Thr His Ala Gln Gly Ala
                260                 265                 270

Asn Met Leu Ala Asp Ala Leu Lys Pro Tyr Gly Gly Leu Val Phe Trp
            275                 280                 285

Arg Ser Phe Val Tyr Gly Ser Lys His Lys Gly Glu Asp Arg Val Lys
    290                 295                 300

Gln Ala Val Ser Glu Phe Ala Asp Leu Asp Gly Thr Phe Arg Glu Asn
305                 310                 315                 320

Val Ile Leu Gln Ser Lys Asn Gly Pro Leu Asp Phe Gln Pro Arg Glu
                325                 330                 335
```

```
Pro Tyr Ala Pro Ile Phe Asp Gln Met His Arg Thr Thr Gln Ala Val
            340                 345                 350

Glu Leu Gln Ile Thr Gln Glu Tyr Leu Gly His Asp Lys His Leu Val
        355                 360                 365

Tyr Leu Ala Pro Met Trp Gln Glu Phe Phe Ser Phe Val Ser Val Asn
    370                 375                 380

Arg Leu Lys Gly Val Val Gly Val Ala Asn Ile Gly Asp His Ile Asn
385                 390                 395                 400

Trp Cys Gly His Pro Phe Ala Gln Ser Asn Trp Tyr Ala Phe Gly Arg
                405                 410                 415

Leu Ala Trp Asp Ala Ser Leu Asn Ser Lys Thr Ile Gly Glu Glu Trp
            420                 425                 430

Leu Ile Gln Thr Tyr Thr Asp Lys Tyr Gln Phe Val Ala Pro Val Leu
        435                 440                 445

Asp Met Met Leu Ser Ser Arg Glu Ala Cys Val Asp Tyr Met Glu Pro
    450                 455                 460

Leu Gly Leu His His Ile Met Ala Phe Asp His Tyr Gly Pro Glu
465                 470                 475                 480

Pro Asp Gly Phe Ile Ala Ser Tyr Pro Ile Glu Trp Cys Pro Val Tyr
                485                 490                 495

Tyr His Lys Ala Asp Ala His Gly Leu Gly Phe Glu Arg Ser Ser Lys
            500                 505                 510

Gly Thr Asn Ala Thr Ala Gln Tyr Pro Glu Pro Tyr Arg Ser Leu Tyr
        515                 520                 525

Asp Asn Leu Ala Thr Cys Pro Pro Glu Tyr Leu Leu Trp Phe His His
    530                 535                 540

Val Ala Trp Asn Tyr Arg Met Pro Ser Gly Arg Thr Met Trp Gln Glu
545                 550                 555                 560

Leu Asn Ala His Tyr Asn Lys Gly Val Lys Thr Val Gln Asn Tyr Glu
                565                 570                 575

Asn Leu Trp Gln Gln Met Lys Pro Tyr Ile Asp Glu Ala Arg Trp Gln
            580                 585                 590

His Thr Ala Asn Leu Leu His Leu Gln Glu Gln Asn Ala Glu Leu Trp
        595                 600                 605

Arg Asn Thr Cys Leu Lys Tyr Phe Ala Thr Phe Ser Lys Met Pro Ile
    610                 615                 620

Glu
625

<210> SEQ ID NO 71
<211> LENGTH: 1878
<212> TYPE: DNA
<213> ORGANISM: Prevotella bryantii

<400> SEQUENCE: 71
atggcacatc accaccacca tcacgtggat gacgacgaca agatggaaga tggccatcag      60
ctgtggctgc gctatcagca gacccatgcg caggtgaacg cgccgcaggg cggcgaaatt     120
ctgaacaccg cgtgccgcga actgcgcaac tattggctgg gccaggcgat taacctgcag     180
ctggtgagcc agaacattgt ggcgccggaa ggctataccc ttgatggcaa aaccctgaaa     240
gcgagcaccg aaagcggcct gctgtatggc gcgtatgcgc tgctgcgcga cagaccgtg      300 cgcggcaccg cgaaaggcat tattctgaaa agcacccccga aaagcaaata tcgcattctg     360
aaccattggg ataacctgga tggcagcatt gaacgcggct atgcgggcaa aagcattttt     420
```

```
tggaacagcc cgattaaagg cgaagcgtat gatacccgcc tgaaagaata tgcgcgcgcg    480
aacgcgagcg tgggcattaa cggcaccgtg ctggataacg tgaacgcgag cccgaaaatg    540
ctgacccata cctatctgga tagcgtggcg catattgcga acattctgcg cccgtatggc    600
ctgcgcgtgt atctgagcgt gaactttggc accccgaaag cgctgggcgc gaccaacacc    660
gcggatccgc tgaacaaacg cgtgattagc tggtggaaca aaaaagcgaa agaaatttat    720
aaactgattc cggattttgg cggcttttgc gtgaaagcga acagcgaagg ccagccgggc    780
ccgtttgatt atggccgcac ccatgcgcag ggcgcgaaca tgctggcgga tgcgctgaaa    840
ccgtatggcg gcctggtgtt ttggcgcagc tttgtgtatg cagcaaaaca taaaggcgaa    900
gatcgcgtga acaggcggt gagcgaattt gcggatctgg atggcacctt tcgcgaaaac    960
gtgattctgc agagcaaaaa cggcccgctg gattttcagc cgcgcgaacc gtatgcgccg   1020
atttttgatc agatgcatcg caccacccag gcggtggaac tgcagattac ccaggaatat   1080
ctgggccatg ataaacatct ggtgtatctg gcgccgatgt ggcaggaatt ttttagcttt   1140
gtgagcgtga accgcctgaa aggcgtggtg ggcgtggcga cattggcga tcatattaac   1200 tggtgcggcc atccgtttgc gcagagcaac tggtatgcgt ttggccgcct ggcgtgggat   1260
gcgagcctga cagcaaaaac cattggcgaa gaatggctga ttcagaccta ccgataaaa   1320 tatcagtttg tggcgccggt gctggatatg atgctgagca gccgcgaagc gtgcgtggat   1380
tatatggaac cgctgggcct gcatcatatt atggcgtttg atcatcatta tggccccgga   1440
ccggatggct ttattgcgag ctatccgatt gaatggtgcc cggtgtatta tcataaagcg   1500
gatgcgcatg gcctgggctt tgaacgcagc agcaaaggca ccaacgcgac cgcgcagtat   1560
ccggaaccgt atcgcagcct gtatgataac ctggcgacct gcccgccgga atatctgctg   1620
tggtttcatc atgtggcgtg gaactatcgc atgccgagcg ccgcaccat gtggcaggaa   1680 ctgaacgcgc attataacaa aggcgtgaaa accgtgcaga actatgaaaa cctgtggcag   1740
cagatgaaac cgtatattga tgaagcgcgc tggcagcata ccgcgaacct gctgcatctg   1800
caggaacaga acgcggaact gtggcgcaac acctgcctga atatttttgc gacctttagc   1860
aaaatgccga ttgaataa                                                 1878
```

<210> SEQ ID NO 72
<211> LENGTH: 1878
<212> TYPE: DNA
<213> ORGANISM: Prevotella bryantii

<400> SEQUENCE: 72

```
atggcacatc accaccacca tcacgtggat gacgacgaca gatggaaga tggccatcag     60 ctgtggctgc gctatcagca gacccatgcg caggtgaacg cgccgcaggg cggcgaaatt    120
ctgaacaccg cgtgccgcga actgcgcaac tattggctgg gccaggcgat taacctgcag    180
ctggtgagcc agaacattgt ggcgccggaa ggctatacct ttgatggcaa aaccctgaaa    240
gcgagcaccg aaagcggcct gctgtatggc gcgtatgcgc tgctgcgcga acagaccgtg    300
cgcggcaccg cgaaaggcat tattctgaaa agcacccccga aaagcaaata tcgcattctg    360
aaccattggg ataaccctgga tggcagcatt gaacgcggct atgcgggcaa aagcattttt    420
tggaacagcc cgattaaagg cgaagcgtat gatacccgcc tgaaagaata tgcgcgcgcg    480
aacgcgagcg tgggcattaa cggcaccgtg ctggataacg tgaacgcgag cccgaaaatg    540
ctgacccata cctatctgga tagcgtggcg catattgcga acattctgcg cccgtatggc    600
ctgcgcgtgt atctgagcgt gaactttggc accccgaaag cgctgggcgc gaccaacacc    660
```

```
gcggatccgc tgaacaaacg cgtgattagc tggtggaaca aaaaagcgaa agaaatttat    720
aaactgattc cggattttgg cggcttttgc gtgaaagcga acagcgaagg ccagccgggc    780
ccgtttgatt atggccgcac ccatgcgcag ggcgcgaaca tgctggcgga tgcgctgaaa    840
ccgtatggcg gcctggtgtt ttggcgcagc tttgtgtatg cagcaaaca taaaggcgaa    900 gatcgcgtga acaggcggt gagcgaattt gcggatctgg atggcaccct tcgcgaaaac    960
gtgattctgc agagcaaaaa cggcccgctg gattttcagc cgcgcgaacc gtatgcgccg   1020
atttttgatc agatgcatcg caccacccag gcggtggaac tgcagattac ccaggaatat   1080
ctgggccatg ataaacatct ggtgtatctg gcgccgatgt ggcaggaatt ttttagcttt   1140
gtgagcgtga accgcctgaa aggcgtggtg ggcgtggcga cattggcga tcatattaac   1200 tggtgcggcc atccgtttgc gcagagcaac tggtatgcgt ttggccgcct ggcgtgggat   1260
gcgagcctga acagcaaaac cattggcgaa gaatggctga ttcagaccta taccgataaa   1320
tatcagtttg tggcgccggt gctggatatg atgctgagca gccgcgaagc gtgcgtggat   1380
tatatggaac cgctgggcct gcatcatatt atggcgtttg atcatcatta tggcccggaa   1440
ccggatggct ttattgcgag ctatccgatt gaatggtgcc cggtgtatta tcataaagcg   1500
gatgcgcatg gcctgggctt tgaacgcagc agcaaaggca ccaacgcgac cgcgcagtat   1560
ccggaaccgt atcgcagcct gtatgataac ctggcgacct gccgccgga atatctgctg   1620 tggtttcatc atgtggcgtg gaactatcgc atgccgagcg gccgcaccat gtggcaggaa   1680
ctgaacgcgc attataacaa aggcgtgaaa accgtgcaga actatgaaaa cctgtggcag   1740
cagatgaaac cgtatattga tgaagcgcgc tggcagcata ccgcgaacct gctgcatctg   1800
caggaacaga cgcggaact gtggcgcaac acctgcctga atatttttgc gacctttagc   1860
aaaatgccga ttgaataa                                                  1878
```

<210> SEQ ID NO 73
<211> LENGTH: 625
<212> TYPE: PRT
<213> ORGANISM: Prevotella bryantii

<400> SEQUENCE: 73

```
Met Ala His His His His His Val Asp Asp Asp Lys Met Glu
  1               5                  10                  15

Asp Gly His Gln Leu Trp Leu Arg Tyr Gln Gln Thr His Ala Gln Val
                 20                  25                  30

Asn Ala Pro Gln Gly Gly Glu Ile Leu Asn Thr Ala Cys Arg Glu Leu
             35                  40                  45

Arg Asn Tyr Trp Leu Gly Gln Ala Ile Asn Leu Gln Leu Val Ser Gln
         50                  55                  60

Asn Ile Val Ala Pro Glu Gly Tyr Thr Phe Asp Gly Lys Thr Leu Lys
 65                  70                  75                  80

Ala Ser Thr Glu Ser Gly Leu Leu Tyr Gly Ala Tyr Ala Leu Leu Arg
                 85                  90                  95

Glu Gln Thr Val Arg Gly Thr Ala Lys Gly Ile Ile Leu Lys Ser Thr
            100                 105                 110

Pro Lys Ser Lys Tyr Arg Ile Leu Asn His Trp Asp Asn Leu Asp Gly
        115                 120                 125

Ser Ile Glu Arg Gly Tyr Ala Gly Lys Ser Ile Phe Trp Asn Ser Pro
    130                 135                 140

Ile Lys Gly Glu Ala Tyr Asp Thr Arg Leu Lys Glu Tyr Ala Arg Ala
```

-continued

```
            145                 150                 155                 160
        Asn Ala Ser Val Gly Ile Asn Gly Thr Val Leu Asp Asn Val Asn Ala
                        165                 170                 175
        Ser Pro Lys Met Leu Thr His Thr Tyr Leu Asp Ser Val Ala His Ile
                        180                 185                 190
        Ala Asn Ile Leu Arg Pro Tyr Gly Leu Arg Val Tyr Leu Ser Val Asn
                        195                 200                 205
        Phe Gly Thr Pro Lys Ala Leu Gly Ala Thr Asn Thr Ala Asp Pro Leu
            210                 215                 220
        Asn Lys Arg Val Ile Ser Trp Trp Asn Lys Ala Lys Glu Ile Tyr
        225                 230                 235                 240
        Lys Leu Ile Pro Asp Phe Gly Phe Cys Val Lys Ala Asn Ser Glu
                        245                 250                 255
        Gly Gln Pro Gly Pro Phe Asp Tyr Gly Arg Thr His Ala Gln Gly Ala
                        260                 265                 270
        Asn Met Leu Ala Asp Ala Leu Lys Pro Tyr Gly Gly Leu Val Phe Trp
                        275                 280                 285
        Arg Ser Phe Val Tyr Gly Ser Lys His Lys Gly Glu Asp Arg Val Lys
            290                 295                 300
        Gln Ala Val Ser Glu Phe Ala Asp Leu Asp Gly Thr Phe Arg Glu Asn
        305                 310                 315                 320
        Val Ile Leu Gln Ser Lys Asn Gly Pro Leu Asp Phe Gln Pro Arg Glu
                        325                 330                 335
        Pro Tyr Ala Pro Ile Phe Asp Gln Met His Arg Thr Gln Ala Val
                        340                 345                 350
        Glu Leu Gln Ile Thr Gln Glu Tyr Leu Gly His Asp Lys His Leu Val
                        355                 360                 365
        Tyr Leu Ala Pro Met Trp Gln Glu Phe Phe Ser Phe Val Ser Val Asn
            370                 375                 380
        Arg Leu Lys Gly Val Val Gly Val Ala Asn Ile Gly Asp His Ile Asn
        385                 390                 395                 400
        Trp Cys Gly His Pro Phe Ala Gln Ser Asn Trp Tyr Ala Phe Gly Arg
                        405                 410                 415
        Leu Ala Trp Asp Ala Ser Leu Asn Ser Lys Thr Ile Gly Glu Glu Trp
                        420                 425                 430
        Leu Ile Gln Thr Tyr Thr Asp Lys Tyr Gln Phe Val Ala Pro Val Leu
                        435                 440                 445
        Asp Met Met Leu Ser Ser Arg Glu Ala Cys Val Asp Tyr Met Glu Pro
            450                 455                 460
        Leu Gly Leu His His Ile Met Ala Phe Asp His His Tyr Gly Pro Glu
        465                 470                 475                 480
        Pro Asp Gly Phe Ile Ala Ser Tyr Pro Ile Glu Trp Cys Pro Val Tyr
                        485                 490                 495
        Tyr His Lys Ala Asp Ala His Gly Leu Gly Phe Glu Arg Ser Ser Lys
                        500                 505                 510
        Gly Thr Asn Ala Thr Ala Gln Tyr Pro Glu Pro Tyr Arg Ser Leu Tyr
                        515                 520                 525
        Asp Asn Leu Ala Thr Cys Pro Pro Glu Tyr Leu Leu Trp Phe His His
                        530                 535                 540
        Val Ala Trp Asn Tyr Arg Met Pro Ser Gly Arg Thr Met Trp Gln Glu
        545                 550                 555                 560
        Leu Asn Ala His Tyr Asn Lys Gly Val Lys Thr Val Gln Asn Tyr Glu
                        565                 570                 575
```

```
Asn Leu Trp Gln Gln Met Lys Pro Tyr Ile Asp Glu Ala Arg Trp Gln
            580                 585                 590

His Thr Ala Asn Leu Leu His Leu Gln Glu Gln Asn Ala Glu Leu Trp
        595                 600                 605

Arg Asn Thr Cys Leu Lys Tyr Phe Ala Thr Phe Ser Lys Met Pro Ile
    610                 615                 620

Glu
625
```

<210> SEQ ID NO 74
<211> LENGTH: 33
<212> TYPE: DNA
<213> ORGANISM: Artificial Sequence
<220> FEATURE:
<223> OTHER INFORMATION: Synthesized Construct

<400> SEQUENCE: 74
gcgccatatg atgaaaagta acaactaat aac                              33

<210> SEQ ID NO 75
<211> LENGTH: 38
<212> TYPE: DNA
<213> ORGANISM: Artificial Sequence
<220> FEATURE:
<223> OTHER INFORMATION: Synthesized Construct

<400> SEQUENCE: 75
cgcgctcgag ttattttagg taaataatta attttttc                        38

<210> SEQ ID NO 76
<211> LENGTH: 857
<212> TYPE: PRT
<213> ORGANISM: Prevotella bryantii

<400> SEQUENCE: 76

```
Met Lys Ser Lys Gln Leu Ile Thr Leu Phe Ile Val Ser Thr Ser Ile
 1               5                  10                  15

Leu Ser Leu His Ala Gln His Leu Pro Tyr Gln Asn Pro Ser Leu Ser
            20                  25                  30

Ala Glu Gln Arg Ala Glu Asp Leu Cys Ser Arg Leu Thr Leu Glu Glu
        35                  40                  45

Lys Cys Lys Leu Met Gln Asn Gly Ser Pro Ala Ile Lys Arg Leu Asn
    50                  55                  60

Ile Pro Ala Phe Glu Trp Trp Ser Glu Ala Leu His Gly Thr Ala Arg
65                  70                  75                  80

Asn Gly Phe Ala Thr Val Phe Pro Asn Thr Thr Gly Met Ala Ala Ser
                85                  90                  95

Trp Asn Asp Gln Leu Leu Leu Gln Ile Phe Ser Ala Ile Gly Asn Glu
            100                 105                 110

Ser Arg Ile Lys Asn Thr Leu Ala Arg Lys Ser Gly Asn Ile Lys Arg
        115                 120                 125

Tyr Gln Gly Leu Ser Ile Trp Thr Pro Asn Ile Asn Ile Phe Arg Asp
    130                 135                 140

Pro Arg Trp Gly Arg Gly Gln Glu Thr Tyr Gly Glu Asp Pro Tyr Leu
145                 150                 155                 160

Thr Gly Lys Met Gly Leu Ala Val Val Glu Gly Leu Gln Gly Pro Lys
                165                 170                 175

Asn Ser Lys Tyr Tyr Lys Leu Leu Ala Cys Ala Lys His Phe Ala Val
```

```
                180                 185                 190
His Ser Gly Pro Glu Tyr Leu Arg His Ser Phe Asn Ile Glu Asn Leu
        195                 200                 205

Pro Ala Arg Asp Leu Trp Glu Thr Tyr Leu Pro Ala Phe Lys Thr Leu
        210                 215                 220

Ile Gln Glu Gly Asn Val Ala Glu Val Met Cys Ala Tyr His Ser Met
225                 230                 235                 240

Asp Gly Leu Pro Cys Cys Gly Ser Asn Lys Tyr Leu Gln Gln Ile Leu
                245                 250                 255

Arg Gln Asp Leu Gly Phe Lys Gly Met Val Val Ser Asp Cys Gly Ala
        260                 265                 270

Ile Gly Asp Phe Trp Ile Gln Gly Arg His Glu Val Ala Gln Asp Ala
        275                 280                 285

Ala Gln Ala Ser Ala Gln Ala Val Leu Ala Gly Thr Asp Val Glu Cys
        290                 295                 300

Gly Ala Asn Tyr Asp Lys Leu Pro Glu Ala Val Lys Arg Gly Glu Ile
305                 310                 315                 320

Ser Glu Glu Lys Ile Asn Val Ser Val Met Arg Leu Leu Lys Ala Arg
                325                 330                 335

Phe Lys Leu Gly Asp Phe Asp Ser Asp Asn Met Val Glu Trp Thr Gln
        340                 345                 350

Leu Pro Glu Ser Leu Ile Ala Cys Ser Lys His Lys Gln Leu Ala Tyr
        355                 360                 365

Gln Met Ala Gln Glu Ser Met Thr Leu Leu Lys Asn Asn Gly Ile Leu
        370                 375                 380

Pro Leu Gln Lys Asn Ala Arg Ile Ala Val Met Gly Ala Asn Ala Asn
385                 390                 395                 400

Asp Ser Ile Met Leu Trp Gly Asn Tyr Asn Gly Tyr Pro Thr Lys Thr
                405                 410                 415

Ile Ser Ile Leu Glu Gly Leu Gln Asn Lys Ser Lys His Ile Ser Tyr
        420                 425                 430

Ile Pro Gly Cys Gly Leu Thr Lys Asn Glu Phe Ile Asp Ser Arg Phe
        435                 440                 445

Ser Gln Phe Lys Thr Pro Asp Gly Lys Val Gly Met Arg Ala Thr Tyr
        450                 455                 460

Trp Asn Asn Thr Lys Met Asn Gly Thr Pro Ala Thr Thr Met Asp Ile
465                 470                 475                 480

Thr Glu Pro Ile Asn Leu Ser Asn Gly Gly Ala Thr Val Phe Ala Pro
                485                 490                 495

Gly Val Asn Leu Glu His Phe Ser Ala Lys Tyr Glu Gly Thr Phe His
        500                 505                 510

Ala Asn Lys Ser Glu Asp Ile His Leu Lys Leu Ser Ser Asp Asp Leu
        515                 520                 525

Ala Arg Ile Ile Ile Asp Gly Asp Thr Ile Ile Asn Ser Trp Lys Ala
        530                 535                 540

Arg Glu Arg Val Asn Val Ser Asp Lys Ile Val His Val Glu Ala Asn
545                 550                 555                 560

Lys Asp Tyr Lys Ile Gln Ile Asp Tyr Val Gln Asn Asp Ala Ala Ala
                565                 570                 575

Ile Ile Gln Phe Asp Leu Gly Pro Leu Val Lys Met Thr Glu Lys Glu
        580                 585                 590

Leu Leu Gln Lys Val Gly Asp Ala Gln Val Val Ile Tyr Val Gly Gly
        595                 600                 605
```

Ile Ser Pro Arg Leu Glu Gly Glu Met Lys Val Asn Glu Leu Gly
610                 615                 620

Phe Lys Gly Gly Asp Arg Thr Thr Ile Glu Leu Pro Gln Ser Gln Arg
625                 630                 635                 640

Asp Met Ile Ala Leu Leu His Asn Ser Gly Lys Lys Val Ile Phe Val
            645                 650                 655

Asn Cys Ser Gly Gly Ala Ile Ala Leu Glu Pro Glu Ser Arg Asn Ala
            660                 665                 670

Asp Ala Ile Leu Gln Ala Trp Tyr Gly Glu Met Gly Gly Gln Ala
            675                 680                 685

Val Ala Asp Val Leu Phe Gly Asp Tyr Asn Pro Asn Gly Lys Leu Pro
690                 695                 700

Val Thr Phe Tyr Lys Asn Asp Ser Gln Leu Pro Asp Tyr Asn Asp Tyr
705                 710                 715                 720

Thr Met Lys Gly Arg Thr Tyr Arg Tyr Leu His Gln Ala Pro Leu Tyr
                725                 730                 735

Pro Phe Gly Tyr Gly Leu Ser Tyr Thr Thr Phe Ala Tyr Asp Asn Ala
            740                 745                 750

Lys Tyr Asp Arg Arg Lys Gly Asn Leu Ser Leu Glu Val Thr Asn Thr
            755                 760                 765

Gly Lys Cys Glu Gly Thr Thr Thr Ile Gln Val Tyr Ile Arg Arg Thr
770                 775                 780

Ala Asp Ile Asn Gly Pro Ile Lys Thr Leu Lys Ala Phe Gln Lys Val
785                 790                 795                 800

Ser Leu Gln Ala Asn Glu Lys Lys Arg Val Thr Ile Asn Leu Pro Arg
                805                 810                 815

Glu Arg Phe Glu Gly Trp Asp Glu Thr Thr Asn Thr Met Arg Ile Val
            820                 825                 830

Pro Gly Lys Tyr Glu Ile Met Val Gly Gln His Ser Asp Asp Pro Asp
            835                 840                 845

Met Lys Lys Leu Ile Ile Tyr Leu Lys
850                 855

<210> SEQ ID NO 77
<211> LENGTH: 2574
<212> TYPE: DNA
<213> ORGANISM: Prevotella bryantii

<400> SEQUENCE: 77
atgaaaagta acaactaat aactttattt attgtcagca caagtatatt gagcttacat      60
gcacaacatt taccttatca aaatccttct ttatcggcag aacaaagagc agaagatctc     120
tgtagtcgat taacattaga agaaaaatgt aaactcatgc aaaatggttc tccagccatc     180
aaaagactca acataccagc attcgaatgg tggagcgaag ccctgcatgg cacagcccgc     240
aacggatttg ctactgtatt tcctaataca acaggcatgg cggcttcatg gaatgatcag     300
ttacttctgc agatttttc agctataggt aatgaatcac gtattaaaaa tacactggct     360
cgcaaatcag gaaacataaa aagatatcaa ggcctttcta tctggacacc aaatatcaat     420
attttcagag atccacgttg gggaagaggt caagaaactt atggtgaaga tccgtatctg     480
acaggtaaga tgggactagc tgttgtagaa ggtttacaag gacctaaaaa tagcaaatat     540 tataaaactac ttgcttgtgc caaacatttt gccgtacata gtggtcccga atatctccga     600
cattcattta acatcgaaaa tctgcccgca agagatcttt gggaaaccta tctaccagca     660

```
ttcaagacat taatacaaga aggcaatgta gccgaagtta tgtgtgcata tcatagtatg    720
gatggtctac cttgctgtgg tagtaacaag tatcttcaac aaatattacg tcaagactta    780
ggattcaaag gaatggttgt tagtgattgt ggtgctattg gtgatttctg gatacaaggc    840
agacatgaag ttgctcaaga cgcagcacaa gcatcagctc aagcagtact ggcaggaaca    900
gacgtagaat gtggagcaaa ctatgataaa ttaccagaag ctgtaaaaag aggagaaata    960
tcagaagaaa aaattaatgt aagcgtaatg cgtctgctta aagctagatt taaactcggt    1020
gactttgatt ctgataacat ggtggaatgg acacaactac cagaaagcct cattgcttgc    1080
tctaaacata acagcttgc ctaccaaatg gctcaagaat caatgacact tcttaaaaat    1140
aatggtatac ttcccctcca aaagaatgca agaattgcag ttatgggagc aaatgccaac    1200
gattcaatca tgctttgggg caactataac ggctatccta caaaaactat cagtatacta    1260
gaaggcttgc aaaataaaag caaacatata tcatatattc caggatgtgg tctgaccaaa    1320
aacgaattca ttgacagtag attcagccaa ttcaaaactc ctgatggcaa agttggtatg    1380
cgcgcaactt actggaacaa tactaaaatg aatggtacac cagccactac tatggatatt    1440
actgagccta tcaatctcag taacggtgga gcaaccgttt cgcccctgg tgtaaattta    1500 gaacactttt ctgctaaata tgaaggaacc ttccatgcaa ataaatcaga agatattcac    1560
ctaaaacttt caagtgatga tttggctcgc ataattatag acggtgacac cataatcaat    1620
agttggaaag cacgcgaaag agtcaatgta agtgataaaa ttgtacatgt agaagccaac    1680
aaagattata agatacaaat agattatgta cagaatgacg cagctgctat catacaattc    1740
gaccttgggc cattagtaaa gatgaccgaa aaagagctct tacaaaaagt aggggatgcc    1800
caggttgtca tctatgttgg tggtatatca ccaagattag aaggtgaaga atgaaagta    1860 aacgaacttg gatttaaagg aggcgatcga accactatag aacttccaca atctcagcgt    1920
gatatgatag ctttacttca caactctggt aaaaaagtaa tatttgtaaa ctgttcgggt    1980
ggcgcaatag ctcttgaacc ggaaagcaga aatgcagatg ccattttaca agcttggtat    2040
ggaggagaga tgggtggaca agcagtcgct gatgttctct ttggtgatta taatccaaat    2100
ggaaaattac ctgtaacctt ctacaagaat gatagtcagc tacctgacta taatgattat    2160
acaatgaaag gtagaacgta tcgttatctg caccaagctc ctctttatcc tttcggatat    2220
ggattaagct ataccacatt tgcatacgat aatgccaaat atgaccgtcg aaagggcaac    2280
ctctctctag aagttaccaa tactggtaaa tgcgaaggca ctacaacgat acaagtatac    2340
atacgacgga ctgcagatat aaatggacct ataaaaacat taaaagcttt ccaaaaagtt    2400
tcattgcaag ctaatgaaaa gaaagagtt acaataaatc tacctcgcga acgttttgaa    2460
ggatgggatg aaacgactaa cacgatgcga atagtccctg gaaaatacga atcatggtt    2520 ggccaacata gtgacgatcc tgatatgaaa aaattaatta tttacctaaa ataa          2574
```

<210> SEQ ID NO 78
<211> LENGTH: 857
<212> TYPE: PRT
<213> ORGANISM: Prevotella bryantii

<400> SEQUENCE: 78

Met Gly Ser Ser His His His His His His Ser Ser Gly Leu Val Pro
1               5                   10                  15

Arg Gly Ser His Met Gln His Leu Pro Tyr Gln Asn Pro Ser Leu Ser
            20                  25                  30

Ala Glu Gln Arg Ala Glu Asp Leu Cys Ser Arg Leu Thr Leu Glu Glu

```
               35                  40                  45
Lys Cys Lys Leu Met Gln Asn Gly Ser Pro Ala Ile Lys Arg Leu Asn
 50                  55                  60

Ile Pro Ala Phe Glu Trp Trp Ser Glu Ala Leu His Gly Thr Ala Arg
 65                  70                  75                  80

Asn Gly Phe Ala Thr Val Phe Pro Asn Thr Thr Gly Met Ala Ala Ser
                     85                  90                  95

Trp Asn Asp Gln Leu Leu Leu Gln Ile Phe Ser Ala Ile Gly Asn Glu
                100                 105                 110

Ser Arg Ile Lys Asn Thr Leu Ala Arg Lys Ser Gly Asn Ile Lys Arg
                115                 120                 125

Tyr Gln Gly Leu Ser Ile Trp Thr Pro Asn Ile Asn Ile Phe Arg Asp
     130                 135                 140

Pro Arg Trp Gly Arg Gly Gln Glu Thr Tyr Gly Glu Asp Pro Tyr Leu
145                 150                 155                 160

Thr Gly Lys Met Gly Leu Ala Val Val Glu Gly Leu Gln Gly Pro Lys
                    165                 170                 175

Asn Ser Lys Tyr Tyr Lys Leu Leu Ala Cys Ala Lys His Phe Ala Val
                180                 185                 190

His Ser Gly Pro Glu Tyr Leu Arg His Ser Phe Asn Ile Glu Asn Leu
                195                 200                 205

Pro Ala Arg Asp Leu Trp Glu Thr Tyr Leu Pro Ala Phe Lys Thr Leu
    210                 215                 220

Ile Gln Glu Gly Asn Val Ala Glu Val Met Cys Ala Tyr His Ser Met
225                 230                 235                 240

Asp Gly Leu Pro Cys Cys Gly Ser Asn Lys Tyr Leu Gln Gln Ile Leu
                    245                 250                 255

Arg Gln Asp Leu Gly Phe Lys Gly Met Val Val Ser Asp Cys Gly Ala
                260                 265                 270

Ile Gly Asp Phe Trp Ile Gln Gly Arg His Glu Val Ala Gln Asp Ala
                275                 280                 285

Ala Gln Ala Ser Ala Gln Ala Val Leu Ala Gly Thr Asp Val Glu Cys
    290                 295                 300

Gly Ala Asn Tyr Asp Lys Leu Pro Glu Ala Val Lys Arg Gly Glu Ile
305                 310                 315                 320

Ser Glu Glu Lys Ile Asn Val Ser Val Met Arg Leu Leu Lys Ala Arg
                325                 330                 335

Phe Lys Leu Gly Asp Phe Asp Ser Asp Asn Met Val Glu Trp Thr Gln
                340                 345                 350

Leu Pro Glu Ser Leu Ile Ala Cys Ser Lys His Lys Gln Leu Ala Tyr
                355                 360                 365

Gln Met Ala Gln Glu Ser Met Thr Leu Leu Lys Asn Asn Gly Ile Leu
    370                 375                 380

Pro Leu Gln Lys Asn Ala Arg Ile Ala Val Met Gly Ala Asn Ala Asn
385                 390                 395                 400

Asp Ser Ile Met Leu Trp Gly Asn Tyr Asn Gly Tyr Pro Thr Lys Thr
                    405                 410                 415

Ile Ser Ile Leu Glu Gly Leu Gln Asn Lys Ser Lys His Ile Ser Tyr
                420                 425                 430

Ile Pro Gly Cys Gly Leu Thr Lys Asn Glu Phe Ile Asp Ser Arg Phe
                435                 440                 445

Ser Gln Phe Lys Thr Pro Asp Gly Lys Val Gly Met Arg Ala Thr Tyr
    450                 455                 460
```

Trp Asn Asn Thr Lys Met Asn Gly Thr Pro Ala Thr Thr Met Asp Ile
465                 470                 475                 480

Thr Glu Pro Ile Asn Leu Ser Asn Gly Gly Ala Thr Val Phe Ala Pro
            485                 490                 495

Gly Val Asn Leu Glu His Phe Ser Ala Lys Tyr Glu Gly Thr Phe His
        500                 505                 510

Ala Asn Lys Ser Glu Asp Ile His Leu Lys Leu Ser Ser Asp Asp Leu
        515                 520                 525

Ala Arg Ile Ile Ile Asp Gly Asp Thr Ile Ile Asn Ser Trp Lys Ala
530                 535                 540

Arg Glu Arg Val Asn Val Ser Asp Lys Ile Val His Val Glu Ala Asn
545                 550                 555                 560

Lys Asp Tyr Lys Ile Gln Ile Asp Tyr Val Gln Asn Asp Ala Ala Ala
            565                 570                 575

Ile Ile Gln Phe Asp Leu Gly Pro Leu Val Lys Met Thr Glu Lys Glu
            580                 585                 590

Leu Leu Gln Lys Val Gly Asp Ala Gln Val Val Ile Tyr Val Gly Gly
        595                 600                 605

Ile Ser Pro Arg Leu Glu Gly Glu Met Lys Val Asn Glu Leu Gly
        610                 615                 620

Phe Lys Gly Gly Asp Arg Thr Thr Ile Glu Leu Pro Gln Ser Gln Arg
625                 630                 635                 640

Asp Met Ile Ala Leu Leu His Asn Ser Gly Lys Lys Val Ile Phe Val
            645                 650                 655

Asn Cys Ser Gly Gly Ala Ile Ala Leu Glu Pro Glu Ser Arg Asn Ala
            660                 665                 670

Asp Ala Ile Leu Gln Ala Trp Tyr Gly Gly Glu Met Gly Gly Gln Ala
            675                 680                 685

Val Ala Asp Val Leu Phe Gly Asp Tyr Asn Pro Asn Gly Lys Leu Pro
        690                 695                 700

Val Thr Phe Tyr Lys Asn Asp Ser Gln Leu Pro Asp Tyr Asn Asp Tyr
705                 710                 715                 720

Thr Met Lys Gly Arg Thr Tyr Arg Tyr Leu His Gln Ala Pro Leu Tyr
            725                 730                 735

Pro Phe Gly Tyr Gly Leu Ser Tyr Thr Thr Phe Ala Tyr Asp Asn Ala
        740                 745                 750

Lys Tyr Asp Arg Arg Lys Gly Asn Leu Ser Leu Glu Val Thr Asn Thr
        755                 760                 765

Gly Lys Cys Glu Gly Thr Thr Thr Ile Gln Val Tyr Ile Arg Arg Thr
        770                 775                 780

Ala Asp Ile Asn Gly Pro Ile Lys Thr Leu Lys Ala Phe Gln Lys Val
785                 790                 795                 800

Ser Leu Gln Ala Asn Glu Lys Lys Arg Val Thr Ile Asn Leu Pro Arg
            805                 810                 815

Glu Arg Phe Glu Gly Trp Asp Glu Thr Thr Asn Thr Met Arg Ile Val
            820                 825                 830

Pro Gly Lys Tyr Glu Ile Met Val Gly Gln His Ser Asp Asp Pro Asp
        835                 840                 845

Met Lys Lys Leu Ile Ile Tyr Leu Lys
    850                 855

<210> SEQ ID NO 79
<211> LENGTH: 2580

<212> TYPE: DNA
<213> ORGANISM: Prevotella bryantii

<400> SEQUENCE: 79

```
atgggcagca gccatcatca tcatcatcac agcagcggcc tggtgccgcg cggcagccat      60
atgcaacatt taccttatca aaatccttct ttatcggcag aacaaagagc agaagatctc     120
tgtagtcgat taacattaga agaaaaatgt aaactcatgc aaaatggttc tccagccatc     180
aaaagactca acataccagc attcgaatgg tggagcgaag ccctgcatgg cacagcccgc     240
aacggatttg ctactgtatt tcctaataca acaggcatgg cggcttcatg gaatgatcag     300
ttacttctgc agattttttc agctataggt aatgaatcac gtattaaaaa tacactggct     360
cgcaaatcag gaaacataaa aagatatcaa ggcctttcta tctggacacc aaatatcaat     420
attttcagag atccacgttg gggaagaggt caagaaactt atggtgaaga tccgtatctg     480
acaggtaaga tgggactagc tgttgtagaa ggtttacaag gacctaaaaa tagcaaatat     540
tataaactac ttgcttgtgc caaacatttt gccgtacata gtggtcccga atatctccga     600
cattcattta acatcgaaaa tctgcccgca agagatcttt gggaaccta tctaccagca     660
ttcaagacat taatacaaga aggcaatgta gccgaagtta tgtgtgcata tcatagtatg     720
gatggtctac cttgctgtgg tagtaacaag tatcttcaac aaatattacg tcaagactta     780
ggattcaaag gaatggttgt tagtgattgt ggtgctattg tgatttctg gatcaaggc      840
agacatgaag ttgctcaaga cgcagcacaa gcatcagctc aagcagtact ggcaggaaca     900
gacgtagaat gtggagcaaa ctatgataaa ttaccagaag ctgtaaaaag aggagaaata     960
tcagaagaaa aaattaatgt aagcgtaatg cgtctgctta aagctagatt taaactcggt    1020
gactttgatt ctgataacat ggtggaatgg acacaactac cagaaagcct cattgcttgc    1080
tctaaacata acagcttgc ctaccaaatg gctcaagaat caatgacact tcttaaaaat    1140
aatggtatac ttccccctcca aaagaatgca agaattgcag ttatgggagc aaatgccaac    1200
gattcaatca tgctttgggg caactataac ggctatccta caaaaactat cagtatacta    1260
gaaggcttgc aaaataaaag caaacatata tcatatattc caggatgtgg tctgaccaaa    1320
aacgaattca ttgacagtag attcagccaa ttcaaaactc ctgatggcaa agttggtatg    1380
cgcgcaactt actggaacaa tactaaaatg aatggtacac cagccactac tatgatatt    1440
actgagccta tcaatctcag taacggtgga gcaaccgttt tcgcccctgg tgtaaattta    1500
gaacactttt ctgctaaata tgaaggaacc ttccatgcaa ataaatcaga agatattcac    1560
ctaaaacttt caagtgatga tttggctcgc ataattatag acggtgacac cataatcaat    1620
agttggaaag cacgcgaaag agtcaatgta agtgataaaa ttgtacatgt agaagccaac    1680
aaagattata agatacaaat agattatgta cagaatgacg cagctgctat catacaattc    1740
gaccttgggc cattagtaaa gatgacagaa aaagagctct acaaaaagt aggggatgcc    1800
caggttgtca tctatgttgg tggtatatca ccaagattag aaggtgaaga atgaaagta    1860
aacgaacttg gatttaaagg aggcgatcga accactatag aacttccaca atctcagcgt    1920
gatatgatag cttacttca caactctggt aaaaaagtaa tatttgtaaa ctgttcgggt    1980
ggcgcaatag ctcttgaacc ggaaagcaga atgcagatg ccatttaca agcttggtat    2040
ggaggagaga tgggtggaca agcagtcgct gatgttctct ttggtgatta taatccaaat    2100
ggaaaattac ctgtaaccctt ctacaagaat gatagtcagc tacctgacta atgattat     2160
acaatgaaag gtagaacgta tcgttatctg caccaagctc ctctttatcc tttcggatat    2220
```

-continued

| | |
|---|---|
| ggattaagct ataccacatt tgcatacgat aatgccaaat atgaccgtcg aaagggcaac | 2280 |
| ctctctctag aagttaccaa tactggtaaa tgcgaaggca ctacaacgat acaagtatac | 2340 |
| atacgacgga ctgcagatat aaatggacct ataaaaacat aaaagctttt ccaaaaagtt | 2400 |
| tcattgcaag ctaatgaaaa gaaagagtt acaataaatc tacctcgcga acgttttgaa | 2460 |
| ggatgggatg aaacgactaa cacgatgcga atagtccctg gaaaatacga atcatggtt | 2520 |
| ggccaacata gtgacgatcc tgatatgaaa aaattaatta tttacctaaa ataactcgag | 2580 |

<210> SEQ ID NO 80
<211> LENGTH: 2580
<212> TYPE: DNA
<213> ORGANISM: Prevotella bryantii

<400> SEQUENCE: 80

| | |
|---|---|
| atgggcagca gccatcatca tcatcatcac agcagcggcc tggtgccgcg cggcagccat | 60 |
| atgcaacatt taccttatca aaatccttct ttatcggcag aacaaagagc agaagatctc | 120 |
| tgtagtcgat taacattaga agaaaatgt aaactcatgc aaaatggttc tccagccatc | 180 |
| aaaagactca acataccagc attcgaatgg tggagcgaag ccctgcatgg cacagcccgc | 240 |
| aacggatttg ctactgtatt tcctaataca acaggcatgg cggcttcatg gaatgatcag | 300 |
| ttacttctgc agatttttc agctataggt aatgaatcac gtattaaaaa tacactggct | 360 |
| cgcaaatcag gaaacataaa aagatatcaa ggcctttcta tctggacacc aaatatcaat | 420 |
| attttcagag atccacgttg gggaagaggt caagaaactt atggtgaaga tccgtatctg | 480 |
| acaggtaaga tgggactagc tgttgtagaa ggtttacaag gacctaaaaa tagcaaatat | 540 |
| tataaactac ttgcttgtgc caaacatttt gccgtacata gtggtcccga atatctccga | 600 |
| cattcattta catcgaaaaa tctgcccgca agagatcttt gggaaaccta tctaccagca | 660 |
| ttcaagacat taatacaaga aggcaatgta gccgaagtta tgtgtgcata tcatagtatg | 720 |
| gatggtctac cttgctgtgg tagtaacaag tatcttcaac aaatattacg tcaagactta | 780 |
| ggattcaaag aatggttgt tagtgattgt ggtgctattg gtgatttctg gatacaaggc | 840 |
| agacatgaag ttgctcaaga cgcagcacaa gcatcagctc aagcagtact ggcaggaaca | 900 |
| gacgtagaat gtggagcaaa ctatgataaa ttaccagaag ctgtaaaaag aggagaaata | 960 |
| tcagaagaaa aaattaatgt aagcgtaatg cgtctgctta aagctagatt taaactcggt | 1020 |
| gactttgatt ctgataacat ggtggaatgg acacaactac cagaaagcct cattgcttgc | 1080 |
| tctaaacata aacagcttgc ctaccaaatg gctcaagaat caatgacact tcttaaaaat | 1140 |
| aatggtatac ttccccctcca aaagaatgca agaattgcag ttatgggagc aaatgccaac | 1200 |
| gattcaatca tgctttgggg caactataac ggctatccta caaaaactat cagtatacta | 1260 |
| gaaggcttgc aaaataaaag caaacatata tcatatattc caggatgtgg tctgaccaaa | 1320 |
| aacgaattca ttgacagtag attcagccaa ttcaaaactc ctgatggcaa agttggtatg | 1380 |
| cgcgcaactt actggaacaa tactaaaatg aatggtacac cagccactac tatggatatt | 1440 |
| actgagccta tcaatctcag taacggtgga gcaaccgttt tcgcccctgg tgtaaattta | 1500 |
| gaacactttt ctgctaaata tgaaggaacc ttccatgcaa ataaatcaga agatattcac | 1560 |
| ctaaaacttt caagtgatga tttggctcgc ataattatag acggtgacac cataatcaat | 1620 |
| agttggaaag cacgcgaaag agtcaatgta agtgataaaa ttgtacatgt agaagccaac | 1680 |
| aaagattata agatacaaat agattatgta cagaatgacg cagctgctat catacaattc | 1740 |
| gaccttgggc cattagtaaa gatgacagaa aaagagctct acaaaaagt aggggatgcc | 1800 |

```
caggttgtca tctatgttgg tggtatatca ccaagattag aaggtgaaga aatgaaagta    1860
aacgaacttg gatttaaagg aggcgatcga accactatag aacttccaca atctcagcgt    1920
gatatgatag ctttacttca caactctggt aaaaaagtaa tatttgtaaa ctgttcgggt    1980
ggcgcaatag ctcttgaacc ggaaagcaga aatgcagatg ccattttaca agcttggtat    2040
ggaggagaga tgggtggaca agcagtcgct gatgttctct ttggtgatta taatccaaat    2100
ggaaaattac ctgtaacctt ctacaagaat gatagtcagc tacctgacta taatgattat    2160
acaatgaaag gtagaacgta tcgttatctg caccaagctc ctctttatcc tttcggatat    2220
ggattaagct ataccacatt tgcatacgat aatgccaaat atgaccgtcg aaagggcaac    2280
ctctctctag aagttaccaa tactggtaaa tgcgaaggca ctacaacgat acaagtatac    2340
atacgacgga ctgcagatat aaatggacct ataaaaacat aaaagctttc caaaaagtt    2400 tcattgcaag ctaatgaaaa gaaaagagtt acaataaatc tacctcgcga acgttttgaa    2460
ggatgggatg aaacgactaa cacgatgcga atagtccctg gaaaatacga atcatggtt    2520 ggccaacata gtgacgatcc tgatatgaaa aaattaatta tttacctaaa ataactcgag    2580
```

<210> SEQ ID NO 81
<211> LENGTH: 857
<212> TYPE: PRT
<213> ORGANISM: Prevotella bryantii

<400> SEQUENCE: 81

```
Met Gly Ser Ser His His His His His Ser Ser Gly Leu Val Pro
 1               5                  10                  15

Arg Gly Ser His Met Gln His Leu Pro Tyr Gln Asn Pro Ser Leu Ser
            20                  25                  30

Ala Glu Gln Arg Ala Glu Asp Leu Cys Ser Arg Leu Thr Leu Glu Glu
        35                  40                  45

Lys Cys Lys Leu Met Gln Asn Gly Ser Pro Ala Ile Lys Arg Leu Asn
    50                  55                  60

Ile Pro Ala Phe Glu Trp Trp Ser Glu Ala Leu His Gly Thr Ala Arg
65                  70                  75                  80

Asn Gly Phe Ala Thr Val Phe Pro Asn Thr Thr Gly Met Ala Ala Ser
                85                  90                  95

Trp Asn Asp Gln Leu Leu Leu Gln Ile Phe Ser Ala Ile Gly Asn Glu
            100                 105                 110

Ser Arg Ile Lys Asn Thr Leu Ala Arg Lys Ser Gly Asn Ile Lys Arg
        115                 120                 125

Tyr Gln Gly Leu Ser Ile Trp Thr Pro Asn Ile Asn Ile Phe Arg Asp
    130                 135                 140

Pro Arg Trp Gly Arg Gly Gln Glu Thr Tyr Gly Glu Asp Pro Tyr Leu
145                 150                 155                 160

Thr Gly Lys Met Gly Leu Ala Val Val Glu Gly Leu Gln Gly Pro Lys
                165                 170                 175

Asn Ser Lys Tyr Tyr Lys Leu Leu Ala Cys Ala Lys His Phe Ala Val
            180                 185                 190

His Ser Gly Pro Glu Tyr Leu Arg His Ser Phe Asn Ile Glu Asn Leu
        195                 200                 205

Pro Ala Arg Asp Leu Trp Glu Thr Tyr Leu Pro Ala Phe Lys Thr Leu
    210                 215                 220

Ile Gln Glu Gly Asn Val Ala Glu Val Met Cys Ala Tyr His Ser Met
225                 230                 235                 240
```

```
Asp Gly Leu Pro Cys Cys Gly Ser Asn Lys Tyr Leu Gln Gln Ile Leu
            245                 250                 255

Arg Gln Asp Leu Gly Phe Lys Gly Met Val Val Ser Asp Cys Gly Ala
        260                 265                 270

Ile Gly Asp Phe Trp Ile Gln Gly Arg His Glu Val Ala Gln Asp Ala
        275                 280                 285

Ala Gln Ala Ser Ala Gln Ala Val Leu Ala Gly Thr Asp Val Glu Cys
        290                 295                 300

Gly Ala Asn Tyr Asp Lys Leu Pro Glu Ala Val Lys Arg Gly Glu Ile
305                 310                 315                 320

Ser Glu Glu Lys Ile Asn Val Ser Val Met Arg Leu Leu Lys Ala Arg
                325                 330                 335

Phe Lys Leu Gly Asp Phe Asp Ser Asp Asn Met Val Glu Trp Thr Gln
                340                 345                 350

Leu Pro Glu Ser Leu Ile Ala Cys Ser Lys His Lys Gln Leu Ala Tyr
            355                 360                 365

Gln Met Ala Gln Glu Ser Met Thr Leu Leu Lys Asn Asn Gly Ile Leu
        370                 375                 380

Pro Leu Gln Lys Asn Ala Arg Ile Ala Val Met Gly Ala Asn Ala Asn
385                 390                 395                 400

Asp Ser Ile Met Leu Trp Gly Asn Tyr Asn Gly Tyr Pro Thr Lys Thr
                405                 410                 415

Ile Ser Ile Leu Glu Gly Leu Gln Asn Lys Ser Lys His Ile Ser Tyr
                420                 425                 430

Ile Pro Gly Cys Gly Leu Thr Lys Asn Glu Phe Ile Asp Ser Arg Phe
            435                 440                 445

Ser Gln Phe Lys Thr Pro Asp Gly Lys Val Gly Met Arg Ala Thr Tyr
        450                 455                 460

Trp Asn Asn Thr Lys Met Asn Gly Thr Pro Ala Thr Thr Met Asp Ile
465                 470                 475                 480

Thr Glu Pro Ile Asn Leu Ser Asn Gly Gly Ala Thr Val Phe Ala Pro
                485                 490                 495

Gly Val Asn Leu Glu His Phe Ser Ala Lys Tyr Glu Gly Thr Phe His
                500                 505                 510

Ala Asn Lys Ser Glu Asp Ile His Leu Lys Leu Ser Ser Asp Asp Leu
            515                 520                 525

Ala Arg Ile Ile Ile Asp Gly Asp Thr Ile Ile Asn Ser Trp Lys Ala
        530                 535                 540

Arg Glu Arg Val Asn Val Ser Asp Lys Ile Val His Val Glu Ala Asn
545                 550                 555                 560

Lys Asp Tyr Lys Ile Gln Ile Asp Tyr Val Gln Asn Asp Ala Ala Ala
                565                 570                 575

Ile Ile Gln Phe Asp Leu Gly Pro Leu Val Lys Met Thr Glu Lys Glu
                580                 585                 590

Leu Leu Gln Lys Val Gly Asp Ala Gln Val Val Ile Tyr Val Gly Gly
            595                 600                 605

Ile Ser Pro Arg Leu Glu Gly Glu Met Lys Val Asn Glu Leu Gly
        610                 615                 620

Phe Lys Gly Gly Asp Arg Thr Thr Ile Glu Leu Pro Gln Ser Gln Arg
625                 630                 635                 640

Asp Met Ile Ala Leu Leu His Asn Ser Gly Lys Lys Val Ile Phe Val
                645                 650                 655
```

```
Asn Cys Ser Gly Gly Ala Ile Ala Leu Glu Pro Glu Ser Arg Asn Ala
            660                 665                 670

Asp Ala Ile Leu Gln Ala Trp Tyr Gly Gly Glu Met Gly Gly Gln Ala
        675                 680                 685

Val Ala Asp Val Leu Phe Gly Asp Tyr Asn Pro Asn Gly Lys Leu Pro
    690                 695                 700

Val Thr Phe Tyr Lys Asn Asp Ser Gln Leu Pro Asp Tyr Asn Asp Tyr
705                 710                 715                 720

Thr Met Lys Gly Arg Thr Tyr Arg Tyr Leu His Gln Ala Pro Leu Tyr
                725                 730                 735

Pro Phe Gly Tyr Gly Leu Ser Tyr Thr Thr Phe Ala Tyr Asp Asn Ala
            740                 745                 750

Lys Tyr Asp Arg Arg Lys Gly Asn Leu Ser Leu Glu Val Thr Asn Thr
        755                 760                 765

Gly Lys Cys Glu Gly Thr Thr Thr Ile Gln Val Tyr Ile Arg Arg Thr
    770                 775                 780

Ala Asp Ile Asn Gly Pro Ile Lys Thr Leu Lys Ala Phe Gln Lys Val
785                 790                 795                 800

Ser Leu Gln Ala Asn Glu Lys Lys Arg Val Thr Ile Asn Leu Pro Arg
                805                 810                 815

Glu Arg Phe Glu Gly Trp Asp Glu Thr Thr Asn Thr Met Arg Ile Val
            820                 825                 830

Pro Gly Lys Tyr Glu Ile Met Val Gly Gln His Ser Asp Asp Pro Asp
        835                 840                 845

Met Lys Lys Leu Ile Ile Tyr Leu Lys
    850                 855

<210> SEQ ID NO 82
<211> LENGTH: 35
<212> TYPE: DNA
<213> ORGANISM: Artificial Sequence
<220> FEATURE:
<223> OTHER INFORMATION: Synthesized Construct

<400> SEQUENCE: 82
catatgaaga cgactattga tgaacattgg gtagg                          35

<210> SEQ ID NO 83
<211> LENGTH: 35
<212> TYPE: DNA
<213> ORGANISM: Artificial Sequence
<220> FEATURE:
<223> OTHER INFORMATION: Synthesized Construct

<400> SEQUENCE: 83
ctcgagctat cgcagaattt cagcagcata ctgtc                          35

<210> SEQ ID NO 84
<211> LENGTH: 1197
<212> TYPE: DNA
<213> ORGANISM: Prevotella bryantii

<400> SEQUENCE: 84
atgaaaagaa tattattagc ttggtttttg ttgtgtgccc tgtttactca ggcacgggtt    60
aagacgacta ttgatgaaca ttgggtaggt acttgggcaa cggctcagca gatacctgta   120
aaatcgtata tgccatacaa taatgacatg tctaatcgtt cggttcgtca gatcgttaaa   180
gtctcaatag gtggtgatat gattcgcctt caattgtcaa atgaattaag ttctgaaccg   240
```

```
gtatatatac gttccgtata tgtcgctact tctgtagatt cttttacgat tctgccaaag    300
acggcaaaat atctaaagtt tggtaatcag tataaggctg ttattcctgc aggtaagact    360
ttaacaagtg atgctttgct ctttaaactg gccccactgc aaaaacttgc tattaccatc    420
aattacacga aagctccttc taaacctacg gtacacatgg ggtctcgcac tacttcttat    480
atcatgaagg gtgtaaccaa tgcgcacagc aattttgcac catcttttcg cgaaaatcac    540
tggtttaata tctcggccat agatgtctat tctaccaaag ctcatgctat cggtattatt    600
ggcaattcga ttacagacgg aaagggtagt accgataatg cgcaaaatcg ctggccggat    660
atgctttctg aatatctaca gttaaaacat aaagtagata acgtgggtat tctgaatatg    720
ggcattggta ataatcgtgt agctactacc ggtggcttcg gaacaatggc caagttgcgc    780
ttcaatcgtg atattttaga gcagcagggc ttagagagcg tggtaatctt tgagggtgtg    840
aatgatatcg gcaatagcaa aggtaatagt gaggctgtag cggcgttgct tattgctacc    900
tacgaagaaa tgataaaaaa atgcaaagcc cgtaaactga agtgtatct aggtaccata    960 actccgttta agggagctgg ctactattct ccattccacg aggccgcccg acttacggtg   1020
aacgaatgga taagaagtca gagaggtaag gtggatggta tactcgattt cgacgaactg   1080
ctacgcgatc cggtagagac cgacagaatg atgaaaaact atcagagtga ctggctacat   1140
ccgaatgcag aaggctataa actgatggga cagtatgctg ctgaaattct gcgatag      1197
```

<210> SEQ ID NO 85
<211> LENGTH: 398
<212> TYPE: PRT
<213> ORGANISM: Prevotella bryantii

<400> SEQUENCE: 85

```
Met Lys Arg Ile Leu Leu Ala Trp Phe Leu Leu Cys Ala Leu Phe Thr
 1               5                  10                  15

Gln Ala Arg Val Lys Thr Thr Ile Asp Glu His Trp Val Gly Thr Trp
                20                  25                  30

Ala Thr Ala Gln Gln Ile Pro Val Lys Ser Tyr Met Pro Tyr Asn Asn
            35                  40                  45

Asp Met Ser Asn Arg Ser Val Arg Gln Ile Val Lys Val Ser Ile Gly
        50                  55                  60

Gly Asp Met Ile Arg Leu Gln Leu Ser Asn Glu Leu Ser Ser Glu Pro
 65                  70                  75                  80

Val Tyr Ile Arg Ser Val Tyr Val Ala Thr Ser Val Asp Ser Phe Thr
                85                  90                  95

Ile Leu Pro Lys Thr Ala Lys Tyr Leu Lys Phe Gly Asn Gln Tyr Lys
               100                 105                 110

Ala Val Ile Pro Ala Gly Lys Thr Leu Thr Ser Asp Ala Leu Leu Phe
           115                 120                 125

Lys Leu Ala Pro Leu Gln Lys Leu Ala Ile Thr Ile Asn Tyr Thr Lys
       130                 135                 140

Ala Pro Ser Lys Pro Thr Val His Met Gly Ser Arg Thr Thr Ser Tyr
145                 150                 155                 160

Ile Met Lys Gly Val Thr Asn Ala His Ser Asn Phe Ala Pro Ser Phe
               165                 170                 175

Arg Glu Asn His Trp Phe Asn Ile Ser Ala Ile Asp Val Tyr Ser Thr
           180                 185                 190

Lys Ala His Ala Ile Gly Ile Ile Gly Asn Ser Ile Thr Asp Gly Lys
       195                 200                 205
```

Gly Ser Thr Asp Asn Ala Gln Asn Arg Trp Pro Asp Met Leu Ser Glu
    210                 215                 220

Tyr Leu Gln Leu Lys His Lys Val Asp Asn Val Gly Ile Leu Asn Met
225                 230                 235                 240

Gly Ile Gly Asn Asn Arg Val Ala Thr Thr Gly Gly Phe Gly Thr Met
                245                 250                 255

Ala Lys Leu Arg Phe Asn Arg Asp Ile Leu Glu Gln Gln Gly Leu Glu
            260                 265                 270

Ser Val Val Ile Phe Glu Gly Val Asn Asp Ile Gly Asn Ser Lys Gly
        275                 280                 285

Asn Ser Glu Ala Val Ala Ala Leu Leu Ile Ala Thr Tyr Glu Glu Met
    290                 295                 300

Ile Lys Lys Cys Lys Ala Arg Lys Leu Lys Val Tyr Leu Gly Thr Ile
305                 310                 315                 320

Thr Pro Phe Lys Gly Ala Gly Tyr Tyr Ser Pro Phe His Glu Ala Ala
                325                 330                 335

Arg Leu Thr Val Asn Glu Trp Ile Arg Ser Gln Arg Gly Lys Val Asp
            340                 345                 350

Gly Ile Leu Asp Phe Asp Glu Leu Leu Arg Asp Pro Val Glu Thr Asp
        355                 360                 365

Arg Met Met Lys Asn Tyr Gln Ser Asp Trp Leu His Pro Asn Ala Glu
    370                 375                 380

Gly Tyr Lys Leu Met Gly Gln Tyr Ala Ala Glu Ile Leu Arg
385                 390                 395

<210> SEQ ID NO 86
<211> LENGTH: 1200
<212> TYPE: DNA
<213> ORGANISM: Prevotella bryantii

<400> SEQUENCE: 86

```
atgggcagca gccatcatca tcatcatcac agcagcggcc tggtgccgcg cggcagccat      60
atgaagacga ctattgatga acattgggta ggtacttggg caacggctca gcagatacct     120
gtaaaatcgt atatgccata caataatgac atgtctaatc gttcggttcg tcagatcgtt     180
aaagtctcaa taggtggtga tatgattcgc cttcaattgt caaatgaatt aagttctgaa     240
ccggtatata tacgttccgt atatgtcgct acttctgtag attctttac gattctgcca      300
aagacggcaa atatctaaa gtttggtaat cagtataagg ctgttattcc tgcaggtaag     360
acttaacaa gtgatgcttt gctctttaaa ctggccccac tgcaaaaact tgctattacc     420
atcaattaca cgaaagctcc ttctaaacct acggtacaca tggggtctcg cactacttct     480
tatatcatga agggtgtaac caatgcgcac agcaattttg caccatcttt tcgcgaaaat     540
cactggttta atatctcggc catagatgtc tattctacca agctcatgc tatcggtatt      600
attggcaatt cgattacaga cggaaagggt agtaccgata tgcgcaaaa tcgctggccg     660
gatatgcttt ctgaatatct acagttaaaa cataaagtag ataacgtggg tattctgaat     720
atgggcattg gtaataatcg tgtagctact accggtggct tcggaacaat ggccaagttg     780
cgcttcaatc gtgatatttt agagcagcag ggcttagaga gcgtggtaat ctttgagggt     840
gtgaatgata tcggcaatag caaaggtaat agtgaggctg tagcggcgtt gcttattgct     900
acctacgaag aaatgataaa aaatgcaaa gcccgtaaac tgaaagtgta tctaggtacc      960
ataactccgt ttaagggagc tggctactat tctccattcc acgaggccgc cgacttacg     1020
gtgaacgaat ggataagaag tcagagaggt aaggtggatg gtatactcga tttcgacgaa    1080
```

-continued

```
ctgctacgcg atccggtaga gaccgacaga atgatgaaaa actatcagag tgactggcta    1140
catccgaatg cagaaggcta taaactgatg ggacagtatg ctgctgaaat tctgcgatag    1200
```

<210> SEQ ID NO 87
<211> LENGTH: 423
<212> TYPE: PRT
<213> ORGANISM: Prevotella bryantii

<400> SEQUENCE: 87

| | | | | | | | | | | | | | | |
|---|---|---|---|---|---|---|---|---|---|---|---|---|---|---|
| Met | Gly | Ser | Ser | His | His | His | His | His | Ser | Ser | Gly | Leu | Val | Pro |
| 1 | | | | 5 | | | | | 10 | | | | | 15 |
| Arg | Gly | Ser | His | Met | Lys | Thr | Thr | Ile | Asp | Glu | His | Trp | Val | Gly | Thr |
| | | | 20 | | | | | 25 | | | | | 30 | | |
| Trp | Ala | Thr | Ala | Gln | Gln | Ile | Pro | Val | Lys | Ser | Tyr | Met | Glu | Thr | Pro |
| | | 35 | | | | | 40 | | | | | 45 | | | |
| Tyr | Asn | Asn | Asp | Met | Glu | Thr | Ser | Asn | Arg | Ser | Val | Arg | Gln | Ile | Val |
| 50 | | | | | 55 | | | | | 60 | | | | | |
| Lys | Val | Ser | Ile | Gly | Gly | Asp | Met | Glu | Thr | Ile | Arg | Leu | Gln | Leu | Ser |
| 65 | | | | 70 | | | | | 75 | | | | | 80 | |
| Asn | Glu | Leu | Ser | Ser | Glu | Pro | Val | Tyr | Ile | Arg | Ser | Val | Tyr | Val | Ala |
| | | | | 85 | | | | | 90 | | | | | 95 | |
| Thr | Ser | Val | Asp | Ser | Phe | Thr | Ile | Leu | Pro | Lys | Thr | Ala | Lys | Tyr | Leu |
| | | | 100 | | | | | 105 | | | | | 110 | | |
| Lys | Phe | Gly | Asn | Gln | Tyr | Lys | Ala | Val | Ile | Pro | Ala | Gly | Lys | Thr | Leu |
| | | | 115 | | | | | 120 | | | | | 125 | | |
| Thr | Ser | Asp | Ala | Leu | Leu | Phe | Lys | Leu | Ala | Pro | Leu | Gln | Lys | Leu | Ala |
| | | | 130 | | | | | 135 | | | | | 140 | | |
| Ile | Thr | Ile | Asn | Tyr | Thr | Lys | Ala | Pro | Ser | Lys | Pro | Thr | Val | His | Met |
| 145 | | | | | 150 | | | | | 155 | | | | | 160 |
| Glu | Thr | Gly | Ser | Arg | Thr | Thr | Ser | Tyr | Ile | Met | Glu | Thr | Lys | Gly | Val |
| | | | | 165 | | | | | 170 | | | | | 175 | |
| Thr | Asn | Ala | His | Ser | Asn | Phe | Ala | Pro | Ser | Phe | Arg | Glu | Asn | His | Trp |
| | | | 180 | | | | | 185 | | | | | 190 | | |
| Phe | Asn | Ile | Ser | Ala | Ile | Asp | Val | Tyr | Ser | Thr | Lys | Ala | His | Ala | Ile |
| | | | 195 | | | | | 200 | | | | | 205 | | |
| Gly | Ile | Ile | Gly | Asn | Ser | Ile | Thr | Asp | Gly | Lys | Gly | Ser | Thr | Asp | Asn |
| | | 210 | | | | | 215 | | | | | 220 | | | |
| Ala | Gln | Asn | Arg | Trp | Pro | Asp | Met | Glu | Thr | Leu | Ser | Glu | Tyr | Leu | Gln |
| 225 | | | | | 230 | | | | | 235 | | | | | 240 |
| Leu | Lys | His | Lys | Val | Asp | Asn | Val | Gly | Ile | Leu | Asn | Met | Glu | Thr | Gly |
| | | | | 245 | | | | | 250 | | | | | 255 | |
| Ile | Gly | Asn | Asn | Arg | Val | Ala | Thr | Thr | Gly | Gly | Phe | Gly | Thr | Met | Glu |
| | | | 260 | | | | | 265 | | | | | 270 | | |
| Thr | Ala | Lys | Leu | Arg | Phe | Asn | Arg | Asp | Ile | Leu | Glu | Gln | Gln | Gly | Leu |
| | | | 275 | | | | | 280 | | | | | 285 | | |
| Glu | Ser | Val | Val | Ile | Phe | Glu | Gly | Val | Asn | Asp | Ile | Gly | Asn | Ser | Lys |
| | | 290 | | | | | 295 | | | | | 300 | | | |
| Gly | Asn | Ser | Glu | Ala | Val | Ala | Ala | Leu | Leu | Ile | Ala | Thr | Tyr | Glu | Glu |
| 305 | | | | | 310 | | | | | 315 | | | | | 320 |
| Met | Glu | Thr | Ile | Lys | Lys | Cys | Lys | Ala | Arg | Lys | Leu | Lys | Val | Tyr | Leu |
| | | | | 325 | | | | | 330 | | | | | 335 | |
| Gly | Thr | Ile | Thr | Pro | Phe | Lys | Gly | Ala | Gly | Tyr | Tyr | Ser | Pro | Phe | His |
| | | | 340 | | | | | 345 | | | | | 350 | | |

Glu Ala Ala Arg Leu Thr Val Asn Glu Trp Ile Arg Ser Gln Arg Gly
            355                 360                 365

Lys Val Asp Gly Ile Leu Asp Phe Asp Glu Leu Leu Arg Asp Pro Val
        370                 375                 380

Glu Thr Asp Arg Met Glu Thr Met Glu Thr Lys Asn Tyr Gln Ser Asp
385                 390                 395                 400

Trp Leu His Pro Asn Ala Glu Gly Tyr Lys Leu Met Glu Thr Gly Gln
                405                 410                 415

Tyr Ala Ala Glu Ile Leu Arg
            420

<210> SEQ ID NO 88
<211> LENGTH: 1200
<212> TYPE: DNA
<213> ORGANISM: Prevotella bryantii

<400> SEQUENCE: 88

```
atgggcagca gccatcatca tcatcatcac agcagcggcc tggtgccgcg cggcagccat      60
atgaagacga ctattgatga acattgggta ggtacttggg caacggctca gcagatacct     120
gtaaaatcgt atatgccata caataatgac atgtctaatc gttcggttcg tcagatcgtt     180
aaagtctcaa taggtggtga tatgattcgc cttcaattgt caaatgaatt aagttctgaa     240
ccggtatata tacgttccgt atatgtcgct acttctgtag attcttttac gattctgcca     300
aagacggcaa atatctaaa gtttggtaat cagtataagg ctgttattcc tgcaggtaag     360
actttaacaa gtgatgcttt gctctttaaa ctggccccac tgcaaaaact tgctattacc     420
atcaattaca cgaaagctcc ttctaaacct acggtacaca tggggtctcg cactacttct     480
tatatcatga agggtgtaac caatgcgcac agcaattttg caccatcttt tcgcgaaaat     540
cactggttta atatctcggc catagatgtc tattctacca aagctcatgc tatcggtatt     600
attggcaatt cgattacaga cggaaagggt agtaccgata tgcgcaaaa tcgctggccg     660
gatatgcttt ctgaatatct acagttaaaa cataaagtag ataacgtggg tattctgaat     720
atgggcattg gtaataatcg tgtagctact accggtggct tcggaacaat ggccaagttg     780
cgcttcaatc gtgatatttt agagcagcag ggcttagaga gcgtggtaat ctttgagggt     840
gtgaatgata tcggcaatag caaaggtaat agtgaggctg tagcggcgtt gcttattgct     900
acctacgaag aaatgataaa aaatgcaaa gcccgtaaac tgaaagtgta tctaggtacc     960
ataactccgt ttaagggagc tggctactat tctccattcc acgaggccgc ccgacttacg    1020
gtgaacgaat ggataagaag tcagagaggt aaggtggatg gtatactcga tttcgacgaa    1080
ctgctacgcg atccggtaga gaccgacaga atgatgaaaa actatcagag tgactggcta    1140
catccgaatg cagaaggcta taaactgatg ggacagtatg ctgctgaaat tctgcgataga   1200
```

<210> SEQ ID NO 89
<211> LENGTH: 399
<212> TYPE: PRT
<213> ORGANISM: Prevotella bryantii

<400> SEQUENCE: 89

Met Gly Ser Ser His His His His His His Ser Ser Gly Leu Val Pro
1               5                   10                  15

Arg Gly Ser His Met Lys Thr Thr Ile Asp Glu His Trp Val Gly Thr
            20                  25                  30

Trp Ala Thr Ala Gln Gln Ile Pro Val Lys Ser Tyr Met Pro Tyr Asn
        35                  40                  45

Asn Asp Met Ser Asn Arg Ser Val Arg Gln Ile Val Lys Val Ser Ile
 50                  55                  60

Gly Gly Asp Met Ile Arg Leu Gln Leu Ser Asn Glu Leu Ser Ser Glu
 65                  70                  75                  80

Pro Val Tyr Ile Arg Ser Val Tyr Val Ala Thr Ser Val Asp Ser Phe
             85                  90                  95

Thr Ile Leu Pro Lys Thr Ala Lys Tyr Leu Lys Phe Gly Asn Gln Tyr
            100                 105                 110

Lys Ala Val Ile Pro Ala Gly Lys Thr Leu Thr Ser Asp Ala Leu Leu
        115                 120                 125

Phe Lys Leu Ala Pro Leu Gln Lys Leu Ala Ile Thr Ile Asn Tyr Thr
        130                 135                 140

Lys Ala Pro Ser Lys Pro Thr Val His Met Gly Ser Arg Thr Thr Ser
145                 150                 155                 160

Tyr Ile Met Lys Gly Val Thr Asn Ala His Ser Asn Phe Ala Pro Ser
                165                 170                 175

Phe Arg Glu Asn His Trp Phe Asn Ile Ser Ala Ile Asp Val Tyr Ser
            180                 185                 190

Thr Lys Ala His Ala Ile Gly Ile Ile Gly Asn Ser Ile Thr Asp Gly
        195                 200                 205

Lys Gly Ser Thr Asp Asn Ala Gln Asn Arg Trp Pro Asp Met Leu Ser
210                 215                 220

Glu Tyr Leu Gln Leu Lys His Lys Val Asp Asn Val Gly Ile Leu Asn
225                 230                 235                 240

Met Gly Ile Gly Asn Asn Arg Val Ala Thr Thr Gly Gly Phe Gly Thr
                245                 250                 255

Met Ala Lys Leu Arg Phe Asn Arg Asp Ile Leu Glu Gln Gln Gly Leu
            260                 265                 270

Glu Ser Val Val Ile Phe Glu Gly Val Asn Asp Ile Gly Asn Ser Lys
        275                 280                 285

Gly Asn Ser Glu Ala Val Ala Ala Leu Leu Ile Ala Thr Tyr Glu Glu
        290                 295                 300

Met Ile Lys Lys Cys Lys Ala Arg Lys Leu Lys Val Tyr Leu Gly Thr
305                 310                 315                 320

Ile Thr Pro Phe Lys Gly Ala Gly Tyr Tyr Ser Pro Phe His Glu Ala
                325                 330                 335

Ala Arg Leu Thr Val Asn Glu Trp Ile Arg Ser Gln Arg Gly Lys Val
            340                 345                 350

Asp Gly Ile Leu Asp Phe Asp Glu Leu Leu Arg Asp Pro Val Glu Thr
        355                 360                 365

Asp Arg Met Met Lys Asn Tyr Gln Ser Asp Trp Leu His Pro Asn Ala
        370                 375                 380

Glu Gly Tyr Lys Leu Met Gly Gln Tyr Ala Ala Glu Ile Leu Arg
385                 390                 395

<210> SEQ ID NO 90
<211> LENGTH: 31
<212> TYPE: DNA
<213> ORGANISM: Artificial Sequence
<220> FEATURE:
<223> OTHER INFORMATION: Synthesized Construct

<400> SEQUENCE: 90
gacgacgaca agatgcaaag cggcgaaaca g                          31

<210> SEQ ID NO 91
<211> LENGTH: 34
<212> TYPE: DNA
<213> ORGANISM: Artificial Sequence
<220> FEATURE:
<223> OTHER INFORMATION: Synthesized Construct

<400> SEQUENCE: 91
gaggagaagc ccggttattt gaaaagcaac tgtg                                34

<210> SEQ ID NO 92
<211> LENGTH: 725
<212> TYPE: PRT
<213> ORGANISM: Bacteroides intestinalis

<400> SEQUENCE: 92

```
Met Lys Asn Leu Leu Asn Asn Tyr Gln Met Lys His Leu Phe Lys Phe
  1               5                  10                  15

Ser Leu Cys Ala Leu Ala Phe Ala Met Ser Ala Asn Asn Gly Phe Ala
             20                  25                  30

Gln Ser Gly Glu Thr Gly Leu Lys Asp Ala Tyr Lys Asp Tyr Phe Ser
         35                  40                  45

Ile Gly Val Ala Val Asn Met Arg Asn Ile Ala Asn Pro Glu Gln Ile
     50                  55                  60

Ala Ile Ile Lys Lys Asp Phe Asn Ser Ile Thr Ala Glu Asn Asp Met
 65                  70                  75                  80

Lys Pro Gln Pro Thr Glu Pro Ala Tyr Gly Gln Phe Asn Trp Glu Asn
                 85                  90                  95

Ala Asp Lys Ile Ala Asn Phe Cys Arg Ser Asn Gly Ile Lys Leu Arg
            100                 105                 110

Gly His Cys Leu Met Trp His Ala Gln Ile Gly Glu Trp Met Tyr Lys
        115                 120                 125

Asp Glu Lys Gly Asp Phe Val Ser Lys Glu Lys Leu Phe Gln Asn Met
    130                 135                 140

Lys His His Ile Thr Ala Ile Val Glu Arg Tyr Lys Asp Val Ile Tyr
145                 150                 155                 160

Ala Trp Asp Val Val Asn Glu Ala Ile Ser Asp Gly Trp Gln Gly
                165                 170                 175

Gly Arg Arg Gly Met Gly Glu Gln Pro Ser Pro Tyr Arg Asn Ser Pro
            180                 185                 190

Leu Tyr Gln Ile Ala Gly Asp Glu Phe Ile Lys Lys Ala Phe Ile Tyr
        195                 200                 205

Ala Arg Glu Ala Asp Pro Asn Val Leu Leu Phe Tyr Asn Asp Tyr Asn
    210                 215                 220

Ala Ala Asp Pro Gly Lys Arg Asp Arg Ile Tyr Asn Met Val Lys Ser
225                 230                 235                 240

Met Lys Glu Glu Gly Val Pro Ile Asp Gly Ile Gly Met Gln Gly His
                245                 250                 255

Tyr Asn Val Tyr Gly Pro Ser Met Glu Asp Val Asp Ala Ala Leu Thr
            260                 265                 270

Lys Tyr Ser Thr Ile Val Lys His Ile His Ile Thr Glu Leu Asp Ile
        275                 280                 285

Arg Ala Asn Gln Glu Met Gly Gly Gln Leu Asn Phe Ser Arg Asp Gly
    290                 295                 300

Gly Asn Ile Ser Gln Val Val Lys Thr Leu Gln Glu Asp Gln Tyr Ala
305                 310                 315                 320
```

```
Arg Leu Phe Lys Val Leu Arg Lys His Lys Asp Val Val Asp Asn Val
                325                 330                 335

Thr Phe Trp Asn Leu Ser Asp Arg Asp Ser Trp Leu Gly Ala Arg Asn
                340                 345                 350

Tyr Pro Leu Pro Tyr Asp Glu Asn Tyr Lys Pro Lys Arg Val Tyr Ser
                355                 360                 365

Ile Ile Lys Asp Phe Asp Pro Ala His Asp Asn Ala Val Val Lys Glu
                370                 375                 380

Asp Phe Arg Pro Ser Val Leu Asn Gln Pro Gly Arg Gln Tyr Pro Met
385                 390                 395                 400

Val Asn Ser Gln Gly Tyr Ala Arg Phe Arg Val Val Ala Pro Asp Ala
                405                 410                 415

Lys Ser Val Ile Val Ser Leu Gly Leu Gly Arg Gly Gly Thr Val
                420                 425                 430

Leu Arg Lys Asp Lys Glu Gly Val Trp Val Gly Thr Thr Asp Gly Pro
                435                 440                 445

Met Asp Glu Gly Phe His Tyr Tyr His Leu Thr Ile Asp Gly Gly Val
                450                 455                 460

Phe Asn Asp Pro Gly Ala Lys Asn Tyr Tyr Gly Ser Cys Arg Trp Glu
465                 470                 475                 480

Ser Gly Ile Glu Ile Pro Ala His Asp Glu Asp Phe Tyr Ala Met Lys
                485                 490                 495

Gln Val Pro His Gly Asn Val Gln Gln Val Tyr Phe Tyr Ser Lys Ser
                500                 505                 510

Thr Asp Thr His Arg Arg Ala Phe Val Tyr Thr Pro Pro Thr Tyr Gly
                515                 520                 525

Lys Asp Lys Lys Lys Tyr Pro Val Leu Tyr Leu Gln His Gly Trp Gly
                530                 535                 540

Glu Asp Glu Thr Ala Trp Ser Asn Gln Gly His Ala Asn Leu Ile Met
545                 550                 555                 560

Asp Asn Leu Ile Ala Glu Gly Lys Ile Glu Pro Phe Ile Ile Val Met
                565                 570                 575

Thr Tyr Gly Met Thr Asn Asp Val Lys Phe Gly His Ile Lys Glu Phe
                580                 585                 590

Thr Ala Lys Glu Phe Glu Thr Val Leu Val Asp Glu Leu Ile Pro Tyr
                595                 600                 605

Ile Asp Ser Asn Phe Arg Thr Gln Ala Asp Lys Lys His Arg Ala Met
                610                 615                 620

Ala Gly Leu Ser Met Gly Gly Phe Glu Thr Lys Leu Ile Thr Leu Arg
625                 630                 635                 640

Arg Pro Glu Val Phe Asn Tyr Tyr Gly Leu Leu Ser Gly Gly Thr Tyr
                645                 650                 655

Ala Pro Asp Asp Ile Lys Asp Lys Gln Val Glu Ser Ile Phe Ile
                660                 665                 670

Ser Cys Gly Ser Lys Glu Asn Pro Asp Gly Val Thr Lys Ala Val Asn
                675                 680                 685

Asp Leu Lys Ala Ala Gly Phe Lys Ala Thr Ser Phe Val Ser Pro Asp
                690                 695                 700

Thr Ala His Glu Phe Leu Thr Trp Arg Arg Ser Leu Tyr His Met Ala
705                 710                 715                 720

Gln Leu Leu Phe Lys
                725
```

<210> SEQ ID NO 93
<211> LENGTH: 2178
<212> TYPE: DNA
<213> ORGANISM: Bacteroides intestinalis

<400> SEQUENCE: 93

| | | | | | |
|---|---|---|---|---|---|
| atgaaaaacc | ttttaaataa | ttatcagatg | aaacatttat | tcaaattttc | cctttgcgcg | 60 |
| ttggcatttg | ccatgagcgc | aaataacggg | ttcgcacaaa | gcggcgaaac | aggactgaag | 120 |
| gatgcttata | aagattactt | ctctattggc | gtggctgtta | atatgcgtaa | tatcgcaaat | 180 |
| cccgaacaga | ttgccatcat | caaaaaagac | tttaacagta | ttacggcgga | aaacgacatg | 240 |
| aagccgcaac | ccaccgagcc | tgcctacgga | cagttcaact | gggagaatgc | cgacaagatc | 300 |
| gccaactttt | gccgtagcaa | cggtatcaaa | cttcgcgggc | attgcttgat | gtggcatgcc | 360 |
| cagataggag | aatggatgta | taaggatgaa | aaaggcgatt | ttgtgtcgaa | agagaaatta | 420 |
| ttccagaata | tgaagcatca | tatcacagcc | atcgtggaac | gttataaaga | cgtgatatat | 480 |
| gcgtgggacg | tggtgaacga | agctatctcc | gatggtggct | ggcagggtgg | ccggcgaggc | 540 |
| atgggagagc | aaccaagtcc | atatcgcaat | tcccccctttt | atcagattgc | cggtgacgag | 600 |
| ttcattaaga | agcctttat | ttatgcccgt | gaggccgacc | ctaatgtact | ccttttctat | 660 |
| aatgactata | atgctgccga | tcccggaaag | cgcgaccgca | tctataatat | ggtgaaatcc | 720 |
| atgaaggaag | aaggtgtgcc | cattgatggt | atcggcatgc | agggacatta | caatgtctac | 780 |
| ggtccgagta | tggaagatgt | agatgctgcc | ttgacaaaat | actctacgat | agtgaaacat | 840 |
| attcatatta | ccgagttgga | tattcgtgcc | aatcaggaga | tggggaggaca | gctcaacttc | 900 |
| agccgtgacg | gcggcaatat | cagtcaggtg | gtgaaaacgc | ttcaggaaga | tcagtatgct | 960 |
| cgcctgttta | aagtgcttcg | caagcataag | gatgtggtag | acaatgttac | tttctggaat | 1020 |
| cttccgacc | gcgactcatg | gctcggcgca | cgcaattatc | cgttgcctta | cgatgagaat | 1080 |
| tataagccga | aacgtgtcta | tagcatcatt | aaggattttg | atccggcaca | cgataatgct | 1140 |
| gtggtgaaag | aagatttccg | tccttctgtg | cttaatcagc | ccggacggca | gtatcctatg | 1200 |
| gttaattcgc | agggatatgc | ccgcttccgt | gtagttgctc | ctgatgccaa | atcagtcatt | 1260 |
| gtcagccttg | gactgggagg | tcgtggcggc | acagttctcc | gtaaggataa | agaaggtgta | 1320 |
| tgggtgggta | ctacagatgg | ccctatggac | gagggattcc | attattacca | cctcactatc | 1380 |
| gacggtggcg | tgtttaatga | cccgggcgcc | aagaattatt | acggttcttg | ccgatgggaa | 1440 |
| agcggcattg | agattccggc | tcatgacgaa | gatttctatg | ccatgaaaca | agtgcctcac | 1500 |
| ggcaatgttc | agcaggttta | tttctattcc | aagagtacgg | acactcaccg | tcgtgcattt | 1560 |
| gtttatacac | cgcccactta | tggcaaggat | aagaagaagt | atccggttct | ttatttacag | 1620 |
| cacggatggg | gagaagatga | aacggcatgg | tccaaccagg | ggcatgcgaa | tctgattatg | 1680 |
| gacaacctga | ttgccgaagg | caagattgaa | ccgttcatca | ttgtaatgac | gtatggcatg | 1740 |
| acgaatgatg | tgaaatttgg | gcatatcaaa | gagttcacgg | ctaaggagtt | tgaaacggtg | 1800 |
| ctggtggacg | aactaatacc | ttatattgat | agtaacttcc | gtacacaggc | cgacaagaag | 1860 |
| caccgtgcta | tggcaggact | ttctatggt | ggctttgaga | cgaaactgat | tactctgcga | 1920 |
| cgtccggaag | tattcaatta | ctatggactg | ttgagcggtg | gcacttatgc | accggacgac | 1980 |
| atcaaggata | aaaagcaggt | ggaatccatc | ttcatcagtt | gcggaagcaa | ggagaatccg | 2040 |
| gatggtgtga | ctaaggctgt | gaacgacctc | aaggctgccg | gtttcaaggc | tacgtcgttc | 2100 |
| gtttctcccg | atacggcgca | tgaattcctg | acttggcgta | gaagtttgta | tcacatggca | 2160 |

-continued

```
cagttgcttt tcaaataa                                                      2178

<210> SEQ ID NO 94
<211> LENGTH: 36
<212> TYPE: DNA
<213> ORGANISM: Artificial Sequence
<220> FEATURE:
<223> OTHER INFORMATION: Synthesized Construct

<400> SEQUENCE: 94
gacgacgaca agatgctcat ctgcgctgct gaaaag                                     36

<210> SEQ ID NO 95
<211> LENGTH: 38
<212> TYPE: DNA
<213> ORGANISM: Artificial Sequence
<220> FEATURE:
<223> OTHER INFORMATION: Synthesized Construct

<400> SEQUENCE: 95
gaggagaagc ccggttaatt taacgtataa tgtatctg                                   38

<210> SEQ ID NO 96
<211> LENGTH: 885
<212> TYPE: PRT
<213> ORGANISM: Prevotella bryantii

<400> SEQUENCE: 96
```

Met Lys Leu Phe Thr Lys Tyr Ala Val Val Ala Ile Leu Thr Leu Pro
1               5                   10                  15

Ser Thr Ala Thr Tyr Ser Leu Ile Cys Ala Ala Glu Lys Ser Ala Gln
            20                  25                  30

Asn Thr His Thr Thr Ser Arg Thr Ser Asp Lys Thr Ser Thr Leu Leu
        35                  40                  45

Pro Tyr Gln Asn Pro Asn Leu Ser Ala Tyr Glu Arg Ala Ile Asp Leu
    50                  55                  60

Cys His Arg Leu Thr Leu Glu Glu Lys Ala Leu Leu Met Gln Asp Glu
65                  70                  75                  80

Ser Pro Ala Ile Pro Arg Leu Gly Ile Lys Lys Phe Phe Trp Trp Ser
                85                  90                  95

Glu Ala Leu His Gly Ala Ala Asn Met Gly Asn Val Thr Asn Phe Pro
            100                 105                 110

Glu Pro Ile Ala Met Ala Ser Ser Phe Asn Pro Thr Leu Leu Lys Ser
        115                 120                 125

Val Phe Ser Ala Ala Ser Asp Glu Met Arg Ala Gln Tyr His His Arg
    130                 135                 140

Met Asp Asn Gly Gly Glu Asp Glu Lys Phe His Ser Leu Ser Val Trp
145                 150                 155                 160

Thr Pro Asn Val Asn Ile Phe Arg Asp Pro Arg Trp Gly Arg Gly Gln
                165                 170                 175

Glu Thr Tyr Gly Glu Asp Pro Tyr Leu Thr Ser Val Met Gly Cys Ala
            180                 185                 190

Val Val Glu Gly Leu Gln Gly Pro Glu Ser Ser Lys Tyr Arg Lys Leu
        195                 200                 205

Trp Ala Cys Ala Lys His Phe Ala Val His Ser Gly Pro Glu Ser Thr
    210                 215                 220

Arg His Thr Ala Asn Leu Asn Asn Ile Ser Pro Arg Asp Leu Tyr Glu
225                 230                 235                 240

```
Thr Tyr Leu Pro Ala Phe Gln Ser Thr Val Gln Asp Gly His Val Arg
            245                 250                 255

Glu Val Met Cys Ala Tyr Gln Arg Leu Asp Asp Glu Pro Cys Cys Ser
            260                 265                 270

Asn Asn Arg Leu Leu Gln Gln Ile Leu Arg Glu Glu Trp Gly Phe Lys
            275                 280                 285

Tyr Leu Val Val Ser Asp Cys Gly Ala Val Ser Asp Ile Trp Gln Ser
            290                 295                 300

His Lys Thr Ser Ser Asp Ala Val His Ala Ser Arg Gln Ala Thr Leu
305                 310                 315                 320

Ala Gly Thr Asp Val Glu Cys Gly Tyr Gly Tyr Thr Tyr Ala Lys Ile
            325                 330                 335

Pro Glu Ala Val Lys Arg Gly Leu Leu Thr Glu Glu Ile Asp Lys
            340                 345                 350

His Val Ile Arg Leu Leu Glu Gly Arg Phe Asp Leu Gly Glu Met Asp
            355                 360                 365

Asp Ser Lys Leu Val Glu Trp Ser Lys Ile Pro Tyr Ser Ile Met Ser
            370                 375                 380

Cys Lys Ala His Ala Gln Leu Ala Leu Asp Met Ala Arg Gln Ser Ile
385                 390                 395                 400

Val Leu Leu Gln Asn Lys Gly Asn Ile Leu Pro Leu Gln Leu Lys Lys
            405                 410                 415

Asn Glu Arg Ile Ala Val Ile Gly Pro Asn Ala Asp Asn Lys Pro Met
            420                 425                 430

Met Trp Gly Asn Tyr Asn Gly Thr Pro Asn His Thr Val Ser Ile Leu
            435                 440                 445

Glu Gly Ile Arg Lys Gln Tyr Lys Asn Val Val Tyr Leu Pro Ala Cys
450                 455                 460

Asp Leu Thr Asp Lys Met Val Val Lys Pro Leu Phe Asn Gln Cys Lys
465                 470                 475                 480

Val Ala Asn Lys Thr Gly Leu Lys Gly Thr Phe Trp Asn Asn Thr Lys
            485                 490                 495

Met Ser Gly Lys Pro Val Thr Thr Gln Tyr Tyr Asn Ala Pro Leu Ala
            500                 505                 510

Val Thr Thr Ala Gly Met His Asn Phe Ala Pro Gly Val Lys Val Glu
            515                 520                 525

Asp Phe Ser Ala Lys Tyr Glu Thr Thr Phe Thr Pro Gln Lys Asn Gly
            530                 535                 540

Glu Val Val Ile Asn Val Glu Gly Cys Gly Asp Phe Ala Leu Tyr Val
545                 550                 555                 560

Asn Gly Lys Glu Met Gln Lys Phe His Thr Trp Arg Thr Thr Pro Thr
            565                 570                 575

Arg Thr Pro Leu Gln Val Lys Ser Gly Glu Gln Tyr Leu Ile Glu Val
            580                 585                 590

Arg Phe Thr Tyr Val Lys Thr Trp Gly Ala Asn Leu Lys Ile Asn Ile
            595                 600                 605

Gly Glu Glu His Pro Val Asp Tyr Ala Ala Asn Ile Ala Gln Leu Lys
            610                 615                 620

Gly Ile Asp Lys Val Ile Phe Val Gly Gly Ile Ala Pro Ser Leu Glu
625                 630                 635                 640

Gly Glu Glu Met Pro Val Asn Ile Pro Gly Phe Lys Gly Gly Asp Arg
            645                 650                 655
```

```
Thr Asp Ile Glu Met Pro Gln Val Gln Arg Asp Phe Ile Lys Ala Leu
            660                 665                 670

Ala Glu Ala Gly Lys Gln Ile Ile Leu Val Asn Cys Ser Gly Ser Ala
        675                 680                 685

Ile Ala Leu Thr Pro Glu Ala Gln Arg Cys Gln Ala Ile Ile Gln Ala
        690                 695                 700

Trp Tyr Pro Gly Gln Glu Gly Thr Ala Val Ala Asp Ile Leu Met
705             710                 715                 720

Gly Lys Val Asn Pro Met Gly Lys Leu Pro Val Thr Phe Tyr Lys Ser
                725                 730                 735

Thr Gln Gln Leu Pro Asp Phe Glu Asp Tyr Ser Met Lys Asn Arg Thr
            740                 745                 750

Tyr Arg Tyr Phe Glu Asp Ala Leu Tyr Pro Phe Gly Tyr Gly Leu Ser
        755                 760                 765

Tyr Thr Ser Phe Glu Ile Gly Thr Ala Lys Leu Gln Thr Leu Thr Asn
        770                 775                 780

Asn Ser Ile Thr Leu Gln Ile Pro Val Thr Asn Thr Gly Lys Arg Glu
785             790                 795                 800

Gly Thr Glu Leu Val Gln Val Tyr Leu Arg Arg Asp Asp Val Glu
            805                 810                 815

Gly Pro Ser Lys Thr Leu Arg Ser Phe Ala His Ile Thr Leu Lys Ala
        820                 825                 830

Gly Glu Thr Lys Lys Ala Ile Leu Lys Leu Asn Arg Asn Gln Phe Glu
        835                 840                 845

Cys Trp Asp Ala Ser Thr Asn Thr Met Arg Val Ile Pro Gly Lys Tyr
850             855                 860

Thr Ile Phe Tyr Gly Asn Ser Ser Lys Lys Glu Asp Leu Lys Gln Ile
865             870                 875                 880

His Tyr Thr Leu Asn
            885
```

```
<210> SEQ ID NO 97
<211> LENGTH: 2658
<212> TYPE: DNA
<213> ORGANISM: Prevotella bryantii

<400> SEQUENCE: 97
atgaaactat tcacaaaata cgctgttgtg gcaatattaa ctttaccctc tacagctaca     60
tactcactca tctgcgctgc tgaaaagtct gctcaaaata cccatactac aagcagaaca    120
tcggacaaga cttcaactct attaccttat cagaatccaa atctttcagc ctacgaagaa    180
gccatagatc tctgccatag acttaccttag aagaaaagg ctttacttat gcaggatgaa    240
tcacctgcaa taccaagact tggcattaaa aaattttttct ggtggagcga agcattacat    300
ggtgctgcca atatgggcaa tgtaaccaat tttccagaac ccatagctat ggcctcatcc    360
tttaatccca ctttgctcaa atctgttttt tctgctgcaa gcgatgagat gcgtgcacaa    420
tatcatcatc gtatggataa tggtggagaa gatgaaaaat tcatagcct ctctgtttgg    480 acaccaaacg taaatatctt tagagacccg agatggggac gtggacaaga gacatacggt    540 gaggacccctt atctcacttc ggttatggga tgtgccgtag tcgaagggtt gcagggacct    600
gaaagcagta aatatcgaaa actgtgggcc tgtgccaagc actttgccgt acatagtggc    660
ccagaatcta ctcgccatac agccaaccta ataacatct cgccacgcga tctctatgaa    720
acctatctac ctgctttcca gtccacagta caggatggtc atgtgcgtga ggtaatgtgt    780
```

```
gcctatcagc gtctcgatga cgaaccatgc tgtagtaata atcgtttgct acaacaaatt    840
ctccgcgaag aatggggttt caaatatctc gtcgtaagcg actgcggtgc tgtaagtgat    900
atttggcaga gtcataagac atcaagtgat gctgtacatg cttcacgaca agctacactt    960
gcaggtacag atgtggaatg tggctatggc tatacctatg caaaaatacc tgaagcggta   1020
aaacgaggcc ttctcacaga agaagaaatc gacaaacatg tcataagact acttgaagga   1080
cgtttcgatt taggcgaaat ggatgattct aaacttgtgg aatggagtaa gatacccttat  1140
tccatcatgt catgcaaagc tcatgcacaa ctggctctcg acatggcacg acagagtatt   1200
gtattacttc agaacaaggg aaatatcttg ccattacaac tcaaaaaaaa tgaacgtatc   1260
gccgttattg gtccaaatgc agataataaa ccgatgatgt ggggcaacta taatggtaca   1320
cctaaccata cagtatcgat tctcgaaggt attcgcaagc aatataaaaa tgtagtatat   1380
cttcctgcct gcgacttaac agataaaatg gtcgttaaac cactgttcaa tcaatgtaaa   1440
gtagcaaata agaccggttt gaagggtact ttttggaata atactaagat gagtggcaaa   1500
cctgtaacca ctcagtatta taatgcccct ttggctgtaa cgacagcagg tatgcacaat   1560
tttgccccag gtgtaaaagt agaagacttt tctgcaaaat acgaaactac tttcactcct   1620
caaaaaaatg gtgaagtcgt catcaacgta gaaggttgcg gagatttcgc tctctatgta   1680
aatggcaaag aaatgcaaaa attccatact tggcgtacta cacctacccg cacaccgcta   1740
caggtaaaaa gtggcgaaca gtatttgata gaggtacgtt ttacctacgt aaaaacctgg   1800
ggggctaatc ttaagattaa tatcggtgaa gaacatcctg tcgattatgc tgctaatatc   1860
gctcaactca gggtatagaa taaggtcatc tttgtgggtg gtattgctcc ttcactggaa   1920
ggtgaagaga tgccggtgaa tattcctgga tttaaaggtg gagatcgcac tgatattgaa   1980
atgccacaag tacagagaga ctttatcaaa gctttagctg aagcaggtaa acagattatt   2040
ttagtaaact gctctggttc tgctatcgct ctaacacctg aagcacagcg ttgtcaggct   2100
attattcagg cgtggtatcc tgggcaagaa ggaggtacgg ctgttgccga tatacttatg   2160
ggtaaggtaa atcctatggg aaaaactaccg gtaaccttct ataagagtac ccaacagtta   2220
cctgattttg aggattattc tatgaagaac cgtacatatc ggtattttga agatgctctc   2280
tatcccttcg gatatggttt gagctatact tcgttcgaaa taggaacagc taaactgcaa   2340
acacttacga caatagcat aactcttcag attccggtaa ccaatacggg gaaacgggag   2400
ggcacagaac tagttcaagt atatctccgc agagatgatg acgtagaagg accatctaaa   2460
acactgaggt cttttgctca tatcacactg aaagctgggg aaacaaaaaa ggctattctc   2520
aaactaaacc gaaatcagtt tgaatgctgg gacgcgtcta ccaatactat gcgggtaata   2580
cccggtaaat ataccatctt ttatggtaac agttcgaaaa aagaagattt aaaacagata   2640
cattatacgt taaattag                                                 2658
```

<210> SEQ ID NO 98
<211> LENGTH: 2637
<212> TYPE: DNA
<213> ORGANISM: Prevotella bryantii

<400> SEQUENCE: 98

```
atggcacatc accaccacca tcacgtggat gacgacgaca agatgctcat ctgcgctgct     60
gaaaagtctg ctcaaaatac ccatactaca agcagaacat cggacaagac ttcaactcta    120
ttaccttatc agaatccaaa tctttcagcc tacgaaagag ccatagatct ctgccataga    180
cttacccttag aagaaaaggc tttacttatg caggatgaat cacctgcaat accaagactt    240
```

```
ggcattaaaa aatttttctg gtggagcgaa gcattacatg gtgctgccaa tatgggcaat    300
gtaaccaatt ttccagaacc catagctatg gcctcatcct ttaatcccac tttgctcaaa    360
tctgtttttt ctgctgcaag cgatgagatg cgtgcacaat atcatcatcg tatggataat    420
ggtggagaag atgaaaaatt tcatagcctc tctgtttgga caccaaacgt aaatatcttt    480
agagacccga gatggggacg tggacaagag acatacggtg aggaccctta tctcacttcg    540
gttatgggat gtgccgtagt cgaagggttg cagggacctg aaagcagtaa atatcgaaaa    600
ctgtgggcct gtgccaagca ctttgccgta catagtggcc cagaatctac tcgccataca    660
gccaacctaa ataacatctc gccacgcgat ctctatgaaa cctatctacc tgctttccag    720
tccacagtac aggatggtca tgtgcgtgag gtaatgtgtg cctatcagcg tctcgatgac    780
gaaccatgct gtagtaataa tcgtttgcta caacaaattc tccgcgaaga atggggtttc    840
aaatatctcg tcgtaagcga ctgcggtgct gtaagtgata tttggcagag tcataagaca    900
tcaagtgatg ctgtacatgc ttcacgacaa gctacacttg caggtacaga tgtggaatgt    960
ggctatggct ataccatgc aaaaatacct gaagcggtaa aacgaggcct tctcacagaa    1020
gaagaaatcg acaaacatgt cataagacta cttgaaggac gtttcgattt aggcgaaatg    1080
gatgattcta aacttgtgga atggagtaag atacct tatt ccatcatgtc atgcaaagct    1140
catgcacaac tggctctcga catggcacga cagagtattg tattacttca gaacaaggga    1200
aatatcttgc cattacaact caaaaaaaat gaacgtatcg ccgttattgg tccaaatgca    1260
gataataaac cgatgatgtg gggcaactat aatggtacac ctaaccatac agtatcgatt    1320
ctcgaaggta ttcgcaagca atataaaaat gtagtatatc ttcctgcctg cgacttaaca    1380
gataaaatgg tcgttaaacc actgttcaat caatgtaaag tagcaaataa gaccggtttg    1440
aagggtactt tttggaataa tactaagatg agtggcaaac ctgtaaccac tcagtattat    1500 aatgccccctt tggctgtaac gacagcaggt atgcacaatt ttgccccagg tgtaaaagta    1560
gaagactttt ctgcaaaata cgaaactact ttcactcctc aaaaaaatgg tgaagtcgtc    1620
atcaacgtag aaggttgcgg agatttcgct ctctatgtaa atggcaaaga aatgcaaaaa    1680
ttccatactt ggcgtactac acctacccgc acaccgctac aggtaaaaag tggcgaacag    1740
tatttgatag aggtacgttt tacctacgta aaaacctggg gggctaatct taagattaat    1800
atcggtgaag aacatcctgt cgattatgct gctaatatcg ctcaactcaa gggtatagat    1860
aaggtcatct ttgtgggtgg tattgctcct tcactggaag gtgaagagat gccggtgaat    1920
attcctggat ttaaaggtgg agatcgcact gatattgaaa tgccacaagt acagagagac    1980
tttatcaaag ctttagctga agcaggtaaa cagattattt tagtaaactg ctctggttct    2040
gctatcgctc taacacctga agcacagcgt tgtcaggcta ttattcaggc gtggtatcct    2100
gggcaagaag gaggtacggc tgttgccgat atacttatgg gtaaggtaaa tcctatggga    2160
aaactaccgg taaccttcta taagagtacc caacagttac ctgattttga ggattattct    2220
atgaagaacc gcacatatcg gtattttgaa gatgctctct atcccttcgg atatggtttg    2280
agctatactt cgttcgaaat aggaacagct aaactgcaaa cacttacgaa caatagcata    2340
actcttcaga ttccggtaac caatacgggg aaacgggagg gcacagaact agttcaagta    2400
tatctccgca gagatgatga cgtagaagga ccatccaaaa cactgaggtc ttttgctcat    2460
atcacactga aagctgggga aacaaaaaag gctattctca aactaaaccg aaatcagttt    2520
gaatgctggg acgcgtctac caatactatg cgggtaatac ccggtaaata taccatcttt    2580
```
tatggtaaca gttcgaaaaa agaagattta aaacagatac attatacgtt aaattaa      2637

<210> SEQ ID NO 99
<211> LENGTH: 878
<212> TYPE: PRT
<213> ORGANISM: Prevotella bryantii

<400> SEQUENCE: 99

```
Met Ala His His His His His Val Asp Asp Asp Lys Met Leu
1               5                   10                  15

Ile Cys Ala Ala Glu Lys Ser Ala Gln Asn Thr His Thr Thr Ser Arg
            20                  25                  30

Thr Ser Asp Lys Thr Ser Thr Leu Leu Pro Tyr Gln Asn Pro Asn Leu
        35                  40                  45

Ser Ala Tyr Glu Arg Ala Ile Asp Leu Cys His Arg Leu Thr Leu Glu
    50                  55                  60

Glu Lys Ala Leu Leu Met Gln Asp Glu Ser Pro Ala Ile Pro Arg Leu
65                  70                  75                  80

Gly Ile Lys Lys Phe Phe Trp Trp Ser Glu Ala Leu His Gly Ala Ala
                85                  90                  95

Asn Met Gly Asn Val Thr Asn Phe Pro Glu Pro Ile Ala Met Ala Ser
            100                 105                 110

Ser Phe Asn Pro Thr Leu Leu Lys Ser Val Phe Ser Ala Ala Ser Asp
        115                 120                 125

Glu Met Arg Ala Gln Tyr His His Arg Met Asp Asn Gly Gly Glu Asp
    130                 135                 140

Glu Lys Phe His Ser Leu Ser Val Trp Thr Pro Asn Val Asn Ile Phe
145                 150                 155                 160

Arg Asp Pro Arg Trp Gly Arg Gly Gln Glu Thr Tyr Gly Glu Asp Pro
                165                 170                 175

Tyr Leu Thr Ser Val Met Gly Cys Ala Val Val Glu Gly Leu Gln Gly
            180                 185                 190

Pro Glu Ser Ser Lys Tyr Arg Lys Leu Trp Ala Cys Ala Lys His Phe
        195                 200                 205

Ala Val His Ser Gly Pro Glu Ser Thr Arg His Thr Ala Asn Leu Asn
    210                 215                 220

Asn Ile Ser Pro Arg Asp Leu Tyr Glu Thr Tyr Leu Pro Ala Phe Gln
225                 230                 235                 240

Ser Thr Val Gln Asp Gly His Val Arg Glu Val Met Cys Ala Tyr Gln
                245                 250                 255

Arg Leu Asp Asp Glu Pro Cys Cys Ser Asn Asn Arg Leu Leu Gln Gln
            260                 265                 270

Ile Leu Arg Glu Glu Trp Gly Phe Lys Tyr Leu Val Val Ser Asp Cys
        275                 280                 285

Gly Ala Val Ser Asp Ile Trp Gln Ser His Lys Thr Ser Ser Asp Ala
    290                 295                 300

Val His Ala Ser Arg Gln Ala Thr Leu Ala Gly Thr Asp Val Glu Cys
305                 310                 315                 320

Gly Tyr Gly Tyr Thr Tyr Ala Lys Ile Pro Glu Ala Val Lys Arg Gly
                325                 330                 335

Leu Leu Thr Glu Glu Glu Ile Asp Lys His Val Ile Arg Leu Leu Glu
            340                 345                 350

Gly Arg Phe Asp Leu Gly Glu Met Asp Asp Ser Lys Leu Val Glu Trp
        355                 360                 365
```

```
Ser Lys Ile Pro Tyr Ser Ile Met Ser Cys Lys Ala His Ala Gln Leu
    370             375                 380

Ala Leu Asp Met Ala Arg Gln Ser Ile Val Leu Leu Gln Asn Lys Gly
385                 390                 395                 400

Asn Ile Leu Pro Leu Gln Leu Lys Lys Asn Glu Arg Ile Ala Val Ile
                405                 410                 415

Gly Pro Asn Ala Asp Asn Lys Pro Met Met Trp Gly Asn Tyr Asn Gly
            420                 425                 430

Thr Pro Asn His Thr Val Ser Ile Leu Glu Gly Ile Arg Lys Gln Tyr
        435                 440                 445

Lys Asn Val Val Tyr Leu Pro Ala Cys Asp Leu Thr Asp Lys Met Val
    450                 455                 460

Val Lys Pro Leu Phe Asn Gln Cys Lys Val Ala Asn Lys Thr Gly Leu
465                 470                 475                 480

Lys Gly Thr Phe Trp Asn Asn Thr Lys Met Ser Gly Lys Pro Val Thr
                485                 490                 495

Thr Gln Tyr Tyr Asn Ala Pro Leu Ala Val Thr Thr Ala Gly Met His
            500                 505                 510

Asn Phe Ala Pro Gly Val Lys Val Glu Asp Phe Ser Ala Lys Tyr Glu
        515                 520                 525

Thr Thr Phe Thr Pro Gln Lys Asn Gly Glu Val Val Ile Asn Val Glu
    530                 535                 540

Gly Cys Gly Asp Phe Ala Leu Tyr Val Asn Gly Lys Glu Met Gln Lys
545                 550                 555                 560

Phe His Thr Trp Arg Thr Thr Pro Thr Arg Thr Pro Leu Gln Val Lys
                565                 570                 575

Ser Gly Glu Gln Tyr Leu Ile Glu Val Arg Phe Thr Tyr Val Lys Thr
            580                 585                 590

Trp Gly Ala Asn Leu Lys Ile Asn Ile Gly Glu Glu His Pro Val Asp
        595                 600                 605

Tyr Ala Ala Asn Ile Ala Gln Leu Lys Gly Ile Asp Lys Val Ile Phe
    610                 615                 620

Val Gly Gly Ile Ala Pro Ser Leu Glu Gly Glu Glu Met Pro Val Asn
625                 630                 635                 640

Ile Pro Gly Phe Lys Gly Gly Asp Arg Thr Asp Ile Glu Met Pro Gln
                645                 650                 655

Val Gln Arg Asp Phe Ile Lys Ala Leu Ala Glu Ala Gly Lys Gln Ile
            660                 665                 670

Ile Leu Val Asn Cys Ser Gly Ser Ala Ile Ala Leu Thr Pro Glu Ala
        675                 680                 685

Gln Arg Cys Gln Ala Ile Ile Gln Ala Trp Tyr Pro Gly Gln Glu Gly
    690                 695                 700

Gly Thr Ala Val Ala Asp Ile Leu Met Gly Lys Val Asn Pro Met Gly
705                 710                 715                 720

Lys Leu Pro Val Thr Phe Tyr Lys Ser Thr Gln Gln Leu Pro Asp Phe
                725                 730                 735

Glu Asp Tyr Ser Met Lys Asn Arg Thr Tyr Arg Tyr Phe Glu Asp Ala
            740                 745                 750

Leu Tyr Pro Phe Gly Tyr Gly Leu Ser Tyr Thr Ser Phe Glu Ile Gly
        755                 760                 765

Thr Ala Lys Leu Gln Thr Leu Thr Asn Asn Ser Ile Thr Leu Gln Ile
    770                 775                 780

Pro Val Thr Asn Thr Gly Lys Arg Glu Gly Thr Glu Leu Val Gln Val
```

```
                785                 790                 795                 800
Tyr Leu Arg Arg Asp Asp Val Glu Gly Pro Ser Lys Thr Leu Arg
                    805                 810                 815

Ser Phe Ala His Ile Thr Leu Lys Ala Gly Glu Thr Lys Lys Ala Ile
                820                 825                 830

Leu Lys Leu Asn Arg Asn Gln Phe Glu Cys Trp Asp Ala Ser Thr Asn
            835                 840                 845

Thr Met Arg Val Ile Pro Gly Lys Tyr Thr Ile Phe Tyr Gly Asn Ser
    850                 855                 860

Ser Lys Lys Glu Asp Leu Lys Gln Ile His Tyr Thr Leu Asn
865                 870                 875

<210> SEQ ID NO 100
<211> LENGTH: 2637
<212> TYPE: DNA
<213> ORGANISM: Prevotella bryantii

<400> SEQUENCE: 100
atggcacatc accaccacca tcacgtggat gacgacgaca agatgctcat ctgcgctgct      60
gaaaagtctg ctcaaaatac ccatactaca agcagaacat cggacaagac ttcaactcta     120
ttaccttatc agaatccaaa tctttcagcc tacgaaagag ccatagatct ctgccataga     180
cttaccttag aagaaaaggc tttacttatg caggatgaat cacctgcaat accaagactt     240
ggcattaaaa aattttttctg gtggagcgaa gcattacatg gtgctgccaa tatgggcaat     300
gtaaccaatt ttccagaacc catagctatg gcctcatcct taatcccac tttgctcaaa      360 tctgttttt ctgctgcaag cgatgagatg cgtgcacaat atcatcatcg tatggataat      420
ggtggagaag atgaaaaatt tcatagcctc tctgtttgga caccaaacgt aaatatcttt     480
agagacccga gatggggacg tggacaagag acatacggtg aggacccta tctcacttcg      540 gttatgggat gtgccgtagt cgaagggttg cagggacctg aaagcagtaa atatcgaaaa     600
ctgtgggcct gtgccaagca ctttgccgta catagtggcc cagaatctac tcgccataca     660
gccaacctaa ataacatctc gccacgcgat ctctatgaaa cctatctacc tgctttccag     720
tccacagtac aggatggtca tgtgcgtgag gtaatgtgtg cctatcagcg tctcgatgac     780
gaaccatgct gtagtaataa tcgtttgcta caacaaattc tccgcgaaga atggggtttc     840
aaatatctcg tcgtaagcga ctgccgtgct gtaagtgata tttggcagag tcataagaca     900
tcaagtgatg ctgtacatgc ttcacgacaa gctacacttg caggtacaga tgtggaatgt     960
ggctatggct ataccatgc aaaaatacct gaagcggtaa aacgaggcct ctctcacagaa    1020 gaagaaatcg acaaacatgt cataagacta cttgaaggac gtttcgattt aggcgaaatg    1080
gatgattcta aacttgtgga atggagtaag ataccttatt ccatcatgtc atgcaaagct    1140
catgcacaac tggctctcga catggcacga cagagtattg tattacttca gaacaaggga    1200
aatatcttgc cattacaact caaaaaaaat gaacgtatcg ccgttattgg tccaaatgca    1260
gataataaac gatgatgtgg gcaactat aatggtacac ctaaccatac agtatcgatt      1320
ctcgaaggta ttcgcaagca atataaaaat gtagtatatc ttcctgcctg cgacttaaca    1380
gataaaatgg tcgttaaacc actgttcaat caatgtaaag tagcaaataa gaccggtttg    1440
aagggtactt tttggaataa tactaagatg agtggcaaac ctgtaaccac tcagtattat    1500
aatgcccctt tggctgtaac gacagcaggt atgcacaatt ttgccccagg tgtaaaagta    1560 gaagacttt ctgcaaaata cgaaactact ttcactcctc aaaaaaatgg tgaagtcgtc    1620
```

-continued

```
atcaacgtag aaggttgcgg agatttcgct ctctatgtaa atggcaaaga aatgcaaaaa    1680
ttccatactt ggcgtactac acctacccgc acaccgctac aggtaaaaag tggcgaacag    1740
tatttgatag aggtacgttt tacctacgta aaaacctggg gggctaatct taagattaat    1800
atcggtgaag aacatcctgt cgattatgct gctaatatcg ctcaactcaa gggtatagat    1860
aaggtcatct tgtgggtgg tattgctcct tcactggaag gtgaagagat gccggtgaat    1920
attcctggat ttaaaggtgg agatcgcact gatattgaaa tgccacaagt acagagagac    1980
tttatcaaag ctttagctga agcaggtaaa cagattattt tagtaaactg ctctggttct    2040
gctatcgctc taacacctga agcacagcgt tgtcaggcta ttattcaggc gtggtatcct    2100
gggcaagaag gaggtacggc tgttgccgat atacttatgg gtaaggtaaa tcctatggga    2160
aaactaccgg taaccttcta taagagtacc caacagttac ctgattttga ggattattct    2220
atgaagaacc gcacatatcg gtattttgaa gatgctctct atcccttcgg atatggtttg    2280
agctatactt cgttcgaaat aggaacagct aaactgcaaa cacttacgaa caatagcata    2340
actcttcaga ttccggtaac caatacgggg aaacgggagg gcacagaact agttcaagta    2400
tatctccgca gagatgatga cgtagaagga ccatccaaaa cactgaggtc ttttgctcat    2460
atcacactga aagctgggga acaaaaaag gctattctca aactaaaccg aaatcagttt    2520
gaatgctggg acgcgtctac caatactatg cgggtaatac ccggtaaata taccatcttt    2580
tatggtaaca gttcgaaaaa agaagattta aacagatac attatacgtt aaattaa      2637
```

<210> SEQ ID NO 101
<211> LENGTH: 878
<212> TYPE: PRT
<213> ORGANISM: Prevotella bryantii

<400> SEQUENCE: 101

```
Met Ala His His His His His Val Asp Asp Asp Lys Met Leu
 1               5                  10                  15

Ile Cys Ala Ala Glu Lys Ser Ala Gln Asn Thr His Thr Thr Ser Arg
                20                  25                  30

Thr Ser Asp Lys Thr Ser Thr Leu Leu Pro Tyr Gln Asn Pro Asn Leu
            35                  40                  45

Ser Ala Tyr Glu Arg Ala Ile Asp Leu Cys His Arg Leu Thr Leu Glu
        50                  55                  60

Glu Lys Ala Leu Leu Met Gln Asp Glu Ser Pro Ala Ile Pro Arg Leu
 65                  70                  75                  80

Gly Ile Lys Lys Phe Phe Trp Trp Ser Glu Ala Leu His Gly Ala Ala
                85                  90                  95

Asn Met Gly Asn Val Thr Asn Phe Pro Glu Pro Ile Ala Met Ala Ser
                100                 105                 110

Ser Phe Asn Pro Thr Leu Leu Lys Ser Val Phe Ser Ala Ala Ser Asp
            115                 120                 125

Glu Met Arg Ala Gln Tyr His His Arg Met Asp Asn Gly Gly Glu Asp
        130                 135                 140

Glu Lys Phe His Ser Leu Ser Val Trp Thr Pro Asn Val Asn Ile Phe
145                 150                 155                 160

Arg Asp Pro Arg Trp Gly Arg Gly Gln Glu Thr Tyr Gly Glu Asp Pro
                165                 170                 175

Tyr Leu Thr Ser Val Met Gly Cys Ala Val Val Glu Gly Leu Gln Gly
            180                 185                 190

Pro Glu Ser Ser Lys Tyr Arg Lys Leu Trp Ala Cys Ala Lys His Phe
```

-continued

```
            195                 200                 205
Ala Val His Ser Gly Pro Glu Ser Thr Arg His Thr Ala Asn Leu Asn
210                 215                 220

Asn Ile Ser Pro Arg Asp Leu Tyr Glu Thr Tyr Leu Pro Ala Phe Gln
225                 230                 235                 240

Ser Thr Val Gln Asp Gly His Val Arg Glu Val Met Cys Ala Tyr Gln
                245                 250                 255

Arg Leu Asp Asp Glu Pro Cys Cys Ser Asn Asn Arg Leu Leu Gln Gln
            260                 265                 270

Ile Leu Arg Glu Glu Trp Gly Phe Lys Tyr Leu Val Val Ser Asp Cys
        275                 280                 285

Gly Ala Val Ser Asp Ile Trp Gln Ser His Lys Thr Ser Ser Asp Ala
290                 295                 300

Val His Ala Ser Arg Gln Ala Thr Leu Ala Gly Thr Asp Val Glu Cys
305                 310                 315                 320

Gly Tyr Gly Tyr Thr Tyr Ala Lys Ile Pro Glu Ala Val Lys Arg Gly
                325                 330                 335

Leu Leu Thr Glu Glu Ile Asp Lys His Val Ile Arg Leu Leu Glu
            340                 345                 350

Gly Arg Phe Asp Leu Gly Glu Met Asp Asp Ser Lys Leu Val Glu Trp
        355                 360                 365

Ser Lys Ile Pro Tyr Ser Ile Met Ser Cys Lys Ala His Ala Gln Leu
370                 375                 380

Ala Leu Asp Met Ala Arg Gln Ser Ile Val Leu Leu Gln Asn Lys Gly
385                 390                 395                 400

Asn Ile Leu Pro Leu Gln Leu Lys Lys Asn Glu Arg Ile Ala Val Ile
                405                 410                 415

Gly Pro Asn Ala Asp Asn Lys Pro Met Met Trp Gly Asn Tyr Asn Gly
            420                 425                 430

Thr Pro Asn His Thr Val Ser Ile Leu Glu Gly Ile Arg Lys Gln Tyr
        435                 440                 445

Lys Asn Val Val Tyr Leu Pro Ala Cys Asp Leu Thr Asp Lys Met Val
450                 455                 460

Val Lys Pro Leu Phe Asn Gln Cys Lys Val Ala Asn Lys Thr Gly Leu
465                 470                 475                 480

Lys Gly Thr Phe Trp Asn Asn Thr Lys Met Ser Gly Lys Pro Val Thr
                485                 490                 495

Thr Gln Tyr Tyr Asn Ala Pro Leu Ala Val Thr Thr Ala Gly Met His
            500                 505                 510

Asn Phe Ala Pro Gly Val Lys Val Glu Asp Phe Ser Ala Lys Tyr Glu
        515                 520                 525

Thr Thr Phe Thr Pro Gln Lys Asn Gly Glu Val Val Ile Asn Val Glu
530                 535                 540

Gly Cys Gly Asp Phe Ala Leu Tyr Val Asn Gly Lys Glu Met Gln Lys
545                 550                 555                 560

Phe His Thr Trp Arg Thr Thr Pro Thr Arg Thr Pro Leu Gln Val Lys
                565                 570                 575

Ser Gly Glu Gln Tyr Leu Ile Glu Val Arg Phe Thr Tyr Val Lys Thr
            580                 585                 590

Trp Gly Ala Asn Leu Lys Ile Asn Ile Gly Glu Glu His Pro Val Asp
        595                 600                 605

Tyr Ala Ala Asn Ile Ala Gln Leu Lys Gly Ile Asp Lys Val Ile Phe
610                 615                 620
```

-continued

```
Val Gly Gly Ile Ala Pro Ser Leu Glu Gly Glu Met Pro Val Asn
625                 630                 635                 640

Ile Pro Gly Phe Lys Gly Gly Asp Arg Thr Asp Ile Glu Met Pro Gln
            645                 650                 655

Val Gln Arg Asp Phe Ile Lys Ala Leu Ala Glu Ala Gly Lys Gln Ile
            660                 665                 670

Ile Leu Val Asn Cys Ser Gly Ser Ala Ile Ala Leu Thr Pro Glu Ala
            675                 680                 685

Gln Arg Cys Gln Ala Ile Ile Gln Ala Trp Tyr Pro Gly Gln Glu Gly
        690             695             700

Gly Thr Ala Val Ala Asp Ile Leu Met Gly Lys Val Asn Pro Met Gly
705                 710                 715                 720

Lys Leu Pro Val Thr Phe Tyr Lys Ser Thr Gln Gln Leu Pro Asp Phe
                725                 730                 735

Glu Asp Tyr Ser Met Lys Asn Arg Thr Tyr Arg Tyr Phe Glu Asp Ala
            740                 745                 750

Leu Tyr Pro Phe Gly Tyr Gly Leu Ser Tyr Thr Ser Phe Glu Ile Gly
        755                 760                 765

Thr Ala Lys Leu Gln Thr Leu Thr Asn Asn Ser Ile Thr Leu Gln Ile
        770                 775                 780

Pro Val Thr Asn Thr Gly Lys Arg Glu Gly Thr Glu Leu Val Gln Val
785                 790                 795                 800

Tyr Leu Arg Arg Asp Asp Val Glu Gly Pro Ser Lys Thr Leu Arg
                805                 810                 815

Ser Phe Ala His Ile Thr Leu Lys Ala Gly Glu Thr Lys Lys Ala Ile
            820                 825                 830

Leu Lys Leu Asn Arg Asn Gln Phe Glu Cys Trp Asp Ala Ser Thr Asn
        835                 840                 845

Thr Met Arg Val Ile Pro Gly Lys Tyr Thr Ile Phe Tyr Gly Asn Ser
    850                 855                 860

Ser Lys Lys Glu Asp Leu Lys Gln Ile His Tyr Thr Leu Asn
865                 870                 875
```